(12) United States Patent
Choi et al.

(10) Patent No.: US 12,281,352 B2
(45) Date of Patent: Apr. 22, 2025

(54) ULTRASENSITIVE MOLECULAR DETECTION VIA HYBRIDIZATION CHAIN REACTION

(71) Applicants: California Institute of Technology, Pasadena, CA (US); Molecular Instruments, Inc., Los Angeles, CA (US)

(72) Inventors: Harry M T Choi, South Pasadena, CA (US); Chun Hao R. Chen, Los Angeles, CA (US); Mike C. Liu, Los Angeles, CA (US); Aneesh Acharya, Altadena, CA (US); Niles A. Pierce, Pasadena, CA (US)

(73) Assignees: California Institute of Technology, Pasadena, CA (US); Molecular Instruments, Inc., Los Angeles, CA (US)

( * ) Notice: Subject to any disclaimer, the term of this patent is extended or adjusted under 35 U.S.C. 154(b) by 0 days.

(21) Appl. No.: 18/635,474

(22) Filed: Apr. 15, 2024

(65) Prior Publication Data
US 2024/0336957 A1    Oct. 10, 2024

Related U.S. Application Data

(63) Continuation of application No. 18/625,726, filed on Apr. 3, 2024.

(60) Provisional application No. 63/457,043, filed on Apr. 4, 2023.

(51) Int. Cl.
*C12Q 1/682*    (2018.01)
*C12Q 1/6818*   (2018.01)
*C12Q 1/6841*   (2018.01)

(52) U.S. Cl.
CPC .......... *C12Q 1/682* (2013.01); *C12Q 1/6818* (2013.01); *C12Q 1/6841* (2013.01)

(58) Field of Classification Search
CPC ..... C12Q 1/682; C12Q 1/6818; C12Q 1/6841
See application file for complete search history.

(56) References Cited

U.S. PATENT DOCUMENTS

| 7,632,641 | B2 | 12/2009 | Dirks et al. |
| 7,727,721 | B2 | 6/2010 | Pierce et al. |
| 7,960,357 | B2 | 6/2011 | Dirks et al. |
| 8,241,854 | B2 | 8/2012 | Yin et al. |
| 8,318,921 | B2 | 11/2012 | Pierce et al. |
| 8,478,543 | B2 | 7/2013 | Pierce et al. |
| 8,497,364 | B2 | 7/2013 | Pierce et al. |
| 8,658,780 | B2 | 2/2014 | Pierce et al. |

(Continued)

OTHER PUBLICATIONS

Wu et al., "Hybridization chain reaction and its applications in biosensing," Talenta, vol. 234, pp. 1-17. (Year: 2021).*

(Continued)

*Primary Examiner* — Angela M. Bertagna
*Assistant Examiner* — Francesca Filippa Giammona
(74) *Attorney, Agent, or Firm* — Knobbe, Martens, Olson & Bear, LLP

(57) ABSTRACT

The present application relates to hybridization chain reaction (HCR). In particular, compositions and methods are presented for ultrasensitive molecular detection using HCR signal amplification. Some embodiments and methods involve cooperative probe junctions, reporter-labeled probes, and nonlinear HCR signal amplification.

17 Claims, 102 Drawing Sheets

Specification includes a Sequence Listing.

(56) References Cited

U.S. PATENT DOCUMENTS

| | | |
|---|---|---|
| 8,877,438 B2 | 11/2014 | Yin |
| 8,962,241 B2 | 2/2015 | Yin et al. |
| 9,217,151 B2 | 12/2015 | Yin et al. |
| 9,834,439 B2 | 12/2017 | Yin et al. |
| 9,856,472 B2 | 1/2018 | Pierce et al. |
| 10,450,599 B2 | 10/2019 | Pierce et al. |
| 10,815,519 B2 | 10/2020 | Husain et al. |
| 11,873,485 B2 | 1/2024 | Hochrein et al. |
| 2006/0234261 A1 | 10/2006 | Pierce et al. |
| 2010/0021901 A1 | 1/2010 | Yin et al. |
| 2010/0021904 A1 | 1/2010 | Pierce et al. |
| 2017/0009278 A1 | 1/2017 | Soderberg et al. |
| 2018/0010166 A1 | 1/2018 | Pierce et al. |
| 2018/0066303 A1* | 3/2018 | Husain ............ C12Q 1/6825 |
| 2018/0362944 A1 | 12/2018 | Hanewich-Hollatz et al. |
| 2020/0087726 A1 | 3/2020 | Lei et al. |
| 2020/0256867 A1 | 8/2020 | Hennek et al. |
| 2022/0090163 A1* | 3/2022 | Pierce ............ C12Q 1/6816 |
| 2022/0235353 A1 | 7/2022 | Hochrein et al. |
| 2022/0282300 A1 | 9/2022 | Pierce et al. |
| 2024/0091762 A1 | 3/2024 | Schulte et al. |

OTHER PUBLICATIONS

Zeng et al., "Nonlinear hybridization chain reaction-based functional DNA nanostructure assembly for biosensing, bioimaging applications," Biosensors and Bioelectronics, vol. 173, pp. 1-15. (Year: 2021).*

Wang et al., "DNA Nanofirecrackers Assembled through Hybridization Chain Reaction for Ultrasensitive SERS Immunoassay of Prostate Specific Antigen," Anal. Chem., pp. 4046-4052. (Year: 2020).*

Chai et al., "Recent Progress in DNA Hybridization Chain Reaction Strategies for Amplified Biosensing," ACS Appl. Mater. Interfaces, vol. 31, pp. 38931-38946. (Year: 2021).*

Dirks, R. M.; Pierce, N. A. Triggered Amplification by Hybridization Chain Reaction. Proc. Natl. Acad. Sci. U. S. A. 2004, 101 (43), 15275-15278.

Choi, H. M. T.; Chang, J. Y.; Trinh, L. A.; Padilla, J. E.; Fraser, S. E.; Pierce, N. A. Programmable in Situ Amplification for Multiplexed Imaging of mRNA Expression. Nat. Biotechnol. 2010, 28 (11), 1208-1212.

Choi, H. M. T.; Beck, V. A.; Pierce, N. A. Next-Generation in Situ Hybridization Chain Reaction: Higher Gain, Lower Cost, Greater Durability. ACS Nano 2014, 8 (5), 4284-4294.

Choi, H. M. T.; Schwarzkopf, M.; Fornace, M. E.; Acharya, A.; Artavanis, G.; Stegmaier, J.; Cunha, A.; Pierce, N. A. Third-Generation in Situ Hybridization Chain Reaction: Multiplexed, Quantitative, Sensitive, Versatile, Robust. Development 2018, 145, dev165753.

Schwarzkopf, M.; Liu, M. C.; Schulte, S. J.; Ives, R.; Husain, N.; Choi, H. M. T.; Pierce, N. A. Hybridization Chain Reaction Enables a Unified Approach to Multiplexed, Quantitative, High-Resolution Immunohistochemistry and in Situ Hybridization. Development 2021, 148 (22), dev199847.

Choi, H. M. T.; Calvert, C. R.; Husain, N.; Huss, D.; Barsi, J. C.; Deverman, B. E.; Hunter, R. C.; Kato, M.; Lee, S. M.; Abelin, A. C. T.; Rosenthal, A. Z.; Akbari, O. S.; Li, Y.; Hay, B. A.; Sternberg, P. W.; Patterson, P. H.; Davidson, E. H.; Mazmanian, S. K.; Prober, D. A.; van de Rijn, M.; Leadbetter, J. R.; Newman, D. K.; Readhead, C.; Bronner, M. E.; Wold, B.; Lansford, R.; Sauka-Spengler, T.; Fraser, S. E.; Pierce, N. A. Mapping a Multiplexed Zoo of mRNA Expression. Development 2016, 143, 3632- 3637.

Schulte, S. J.; Shin, B.; Rothenberg, E. V.; Pierce, N. A. Multiplex, Quantitative, High-Resolution Imaging of Protein: Protein Complexes via Hybridization Chain Reaction. ACS Chem. Biol. 2024, 19 (2), 280-288.

Schulte, S. J.; Fornace, M. E.; Hall, J. K.; Shin, G. J.; Pierce, N. A. HCR Spectral Imaging: 10-Plex, Quantitative, High-Resolution RNA and Protein Imaging in Highly Autofluorescent Samples. Development 2024, 151, dev202307.

Tao, Y.; Zhou, X.; Sun, L.; Lin, D.; Cai, H.; Chen, X.; Zhou, W.; Yang, B.; Hu, Z.; Yu, J.; Zhang, J.; Yang, X.; Yang, F.; Shen, B.; Qi, W.; Fu, Z.; Dai, J.; Cao, G. Highly Efficient and Robust π-FISH Rainbow for Multiplexed in Situ Detection of Diverse Biomolecules. Nat. Commun. 2023, 14 (1), 443.

Player, A. N.; Shen, L.- P.; Kenny, D.; Antao, V. P.; Kolberg, J. A. Single-Copy Gene Detection Using Branched DNA (bDNA) in Situ Hybridization. J. Histochem. Cytochem. 2001, 49 (5), 603-611.

Wang, F.; Flanagan, J.; Su, N.; Wang, L.-C.; Bui, S.; Nielson, A.; Wu, X. Y.; Vo, H.-T.; Ma, X.-J.; Luo, Y. L. RNAscope: A Novel in Situ RNA Analysis Platform for Formalin-Fixed, Paraffin-Embedded Tissues. J. Mol. Diagn. 2012, 14 (1), 22-29.

Kenny, D.; Shen, L.-P.; Kolberg, J. A. Detection of Viral Infection and Gene Expression in Clinical Tissue Specimens Using Branched DNA (bDNA) in Situ Hybridization. J. Histochem. Cytochem. 2002, 50 (9), 1219-1227.

Zadeh, J. N.; Steenberg, C. D.; Bois, J. S.; Wolfe, B. R.; Pierce, M. B.; Khan, A. R.; Dirks, R. M.; Pierce, N. A. Nupack: Analysis and Design of Nucleic Acid Systems. J. Comput. Chem. 2011, 32 (1), 170-173.

International Search Report and Written Opinion, re PCT Application No. PCT/US2024/022859, mailed Jul. 18, 2024.

* cited by examiner

Protocol summary: HCR RNA-FISH with fractional-initiator probes

Experimental timeline: HCR RNA-FISH with fractional-initiator probes

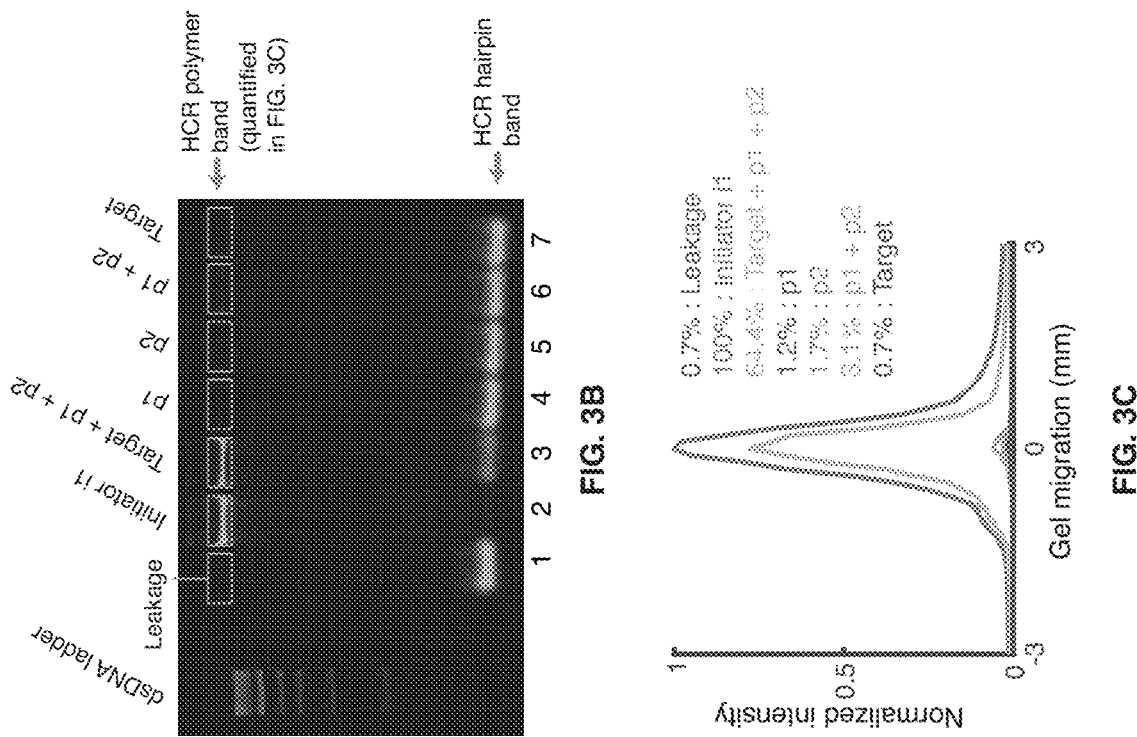
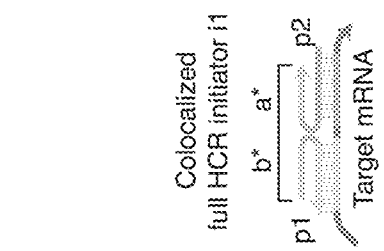
FIG. 3A
Fractional-initiator probes p1 and p2 each carry a fraction of HCR initiator i1; selective binding of probes p1 and p2 to the target mRNA colocalizes full HCR initiator i1

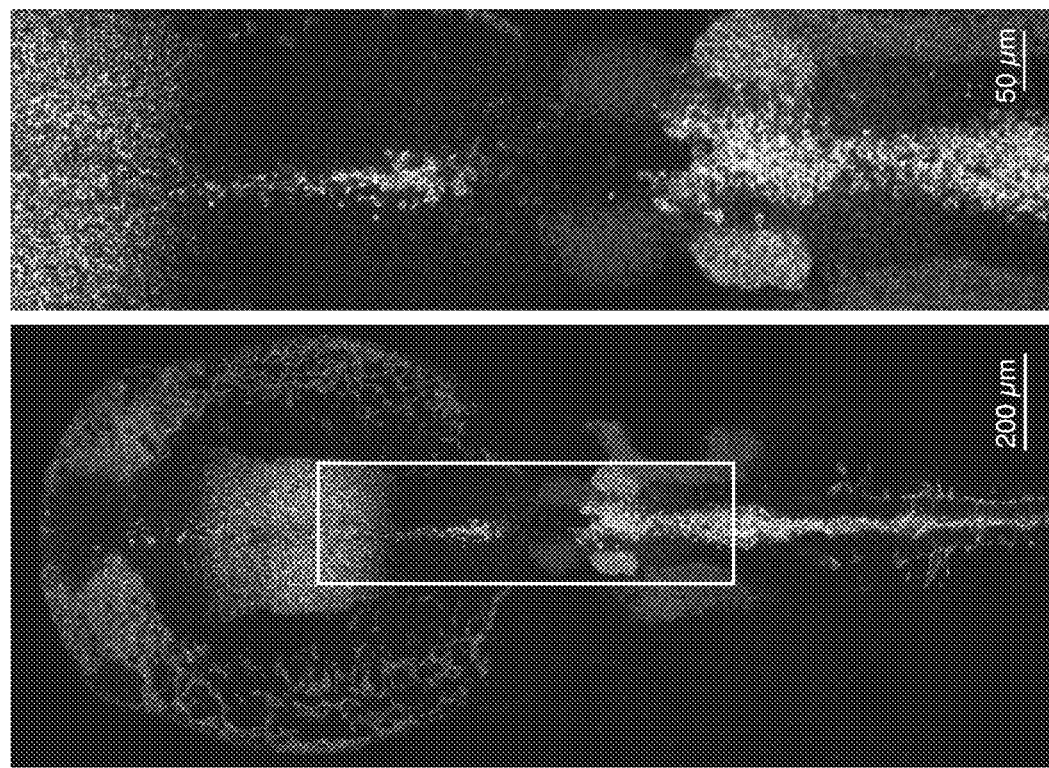
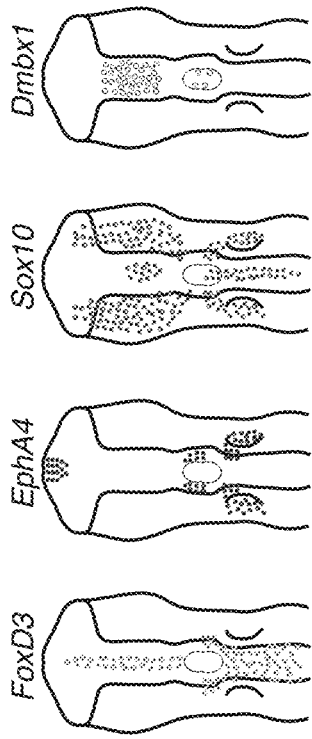
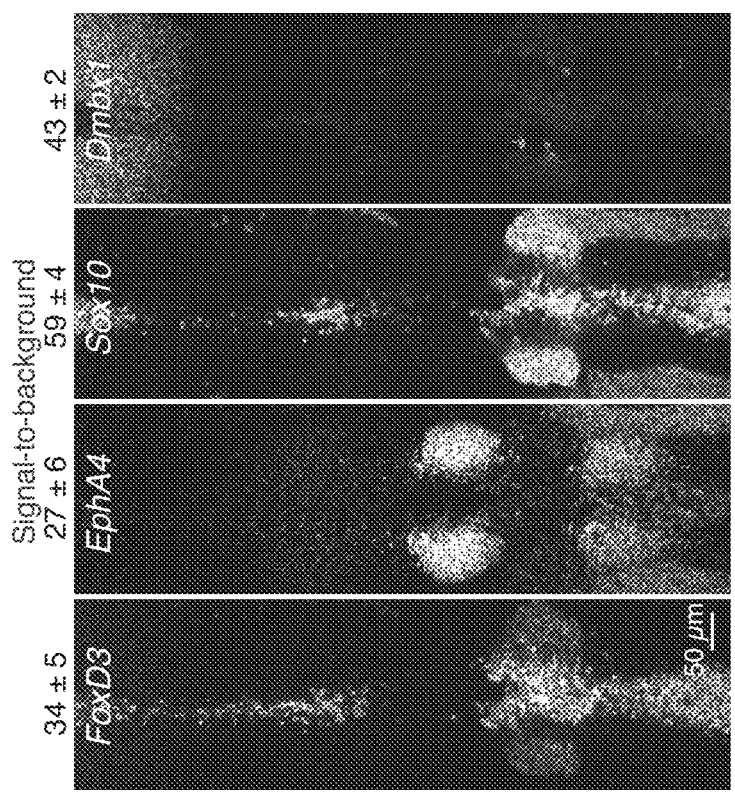
FIG. 5A  FIG. 5B  FIG. 5C  FIG. 5D

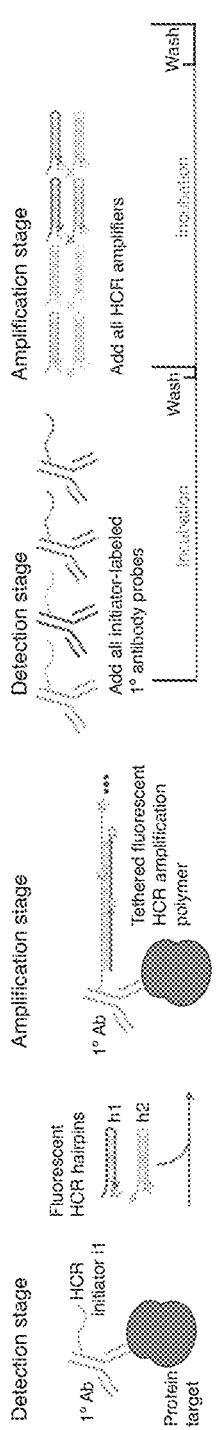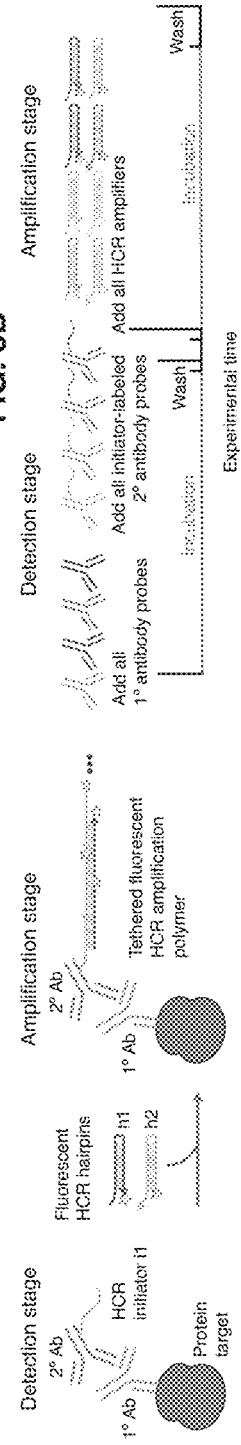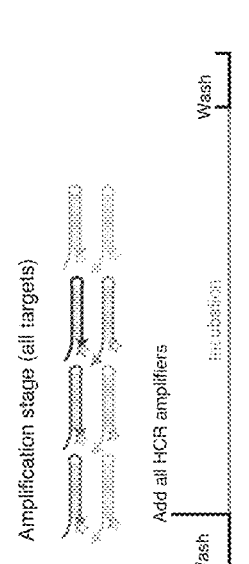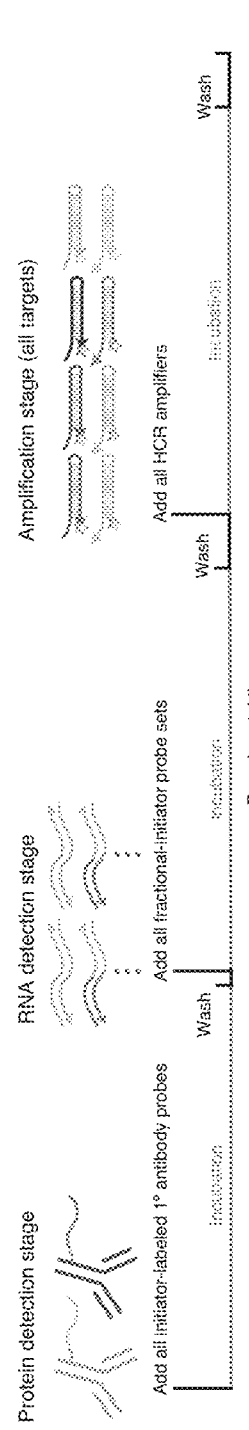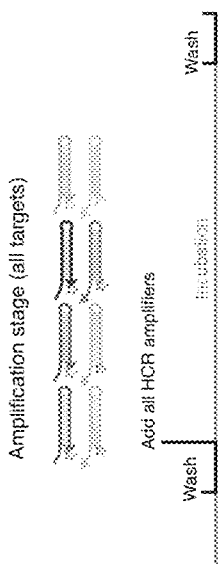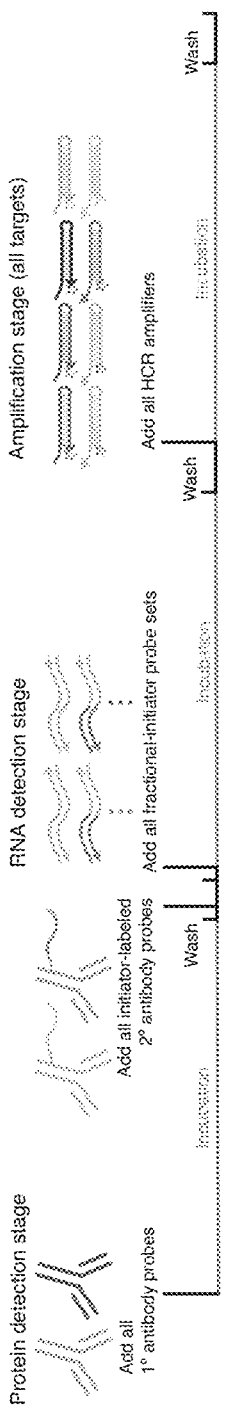

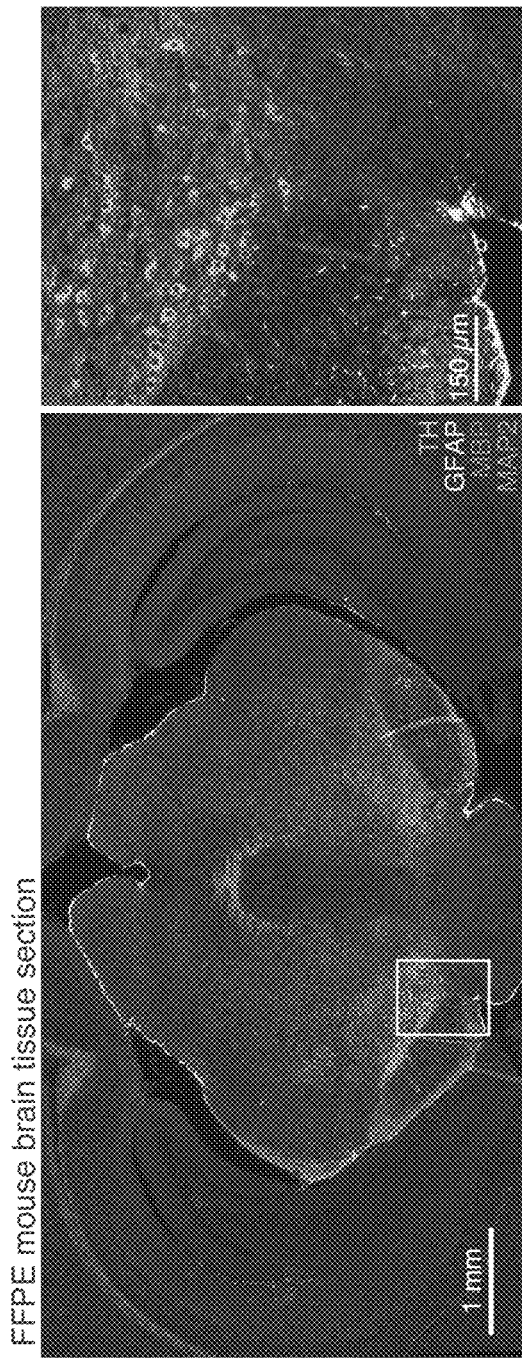

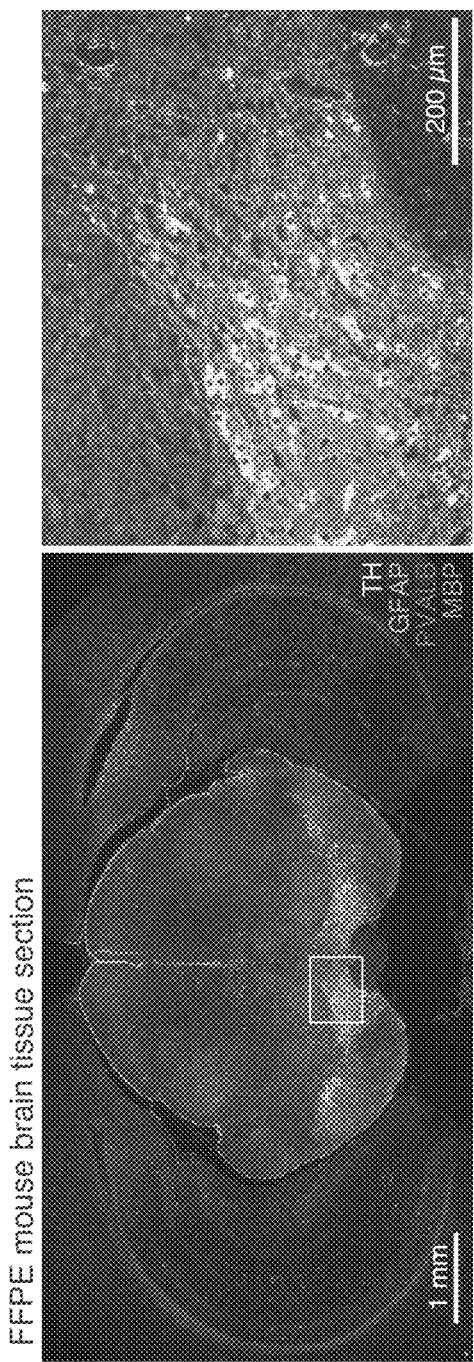

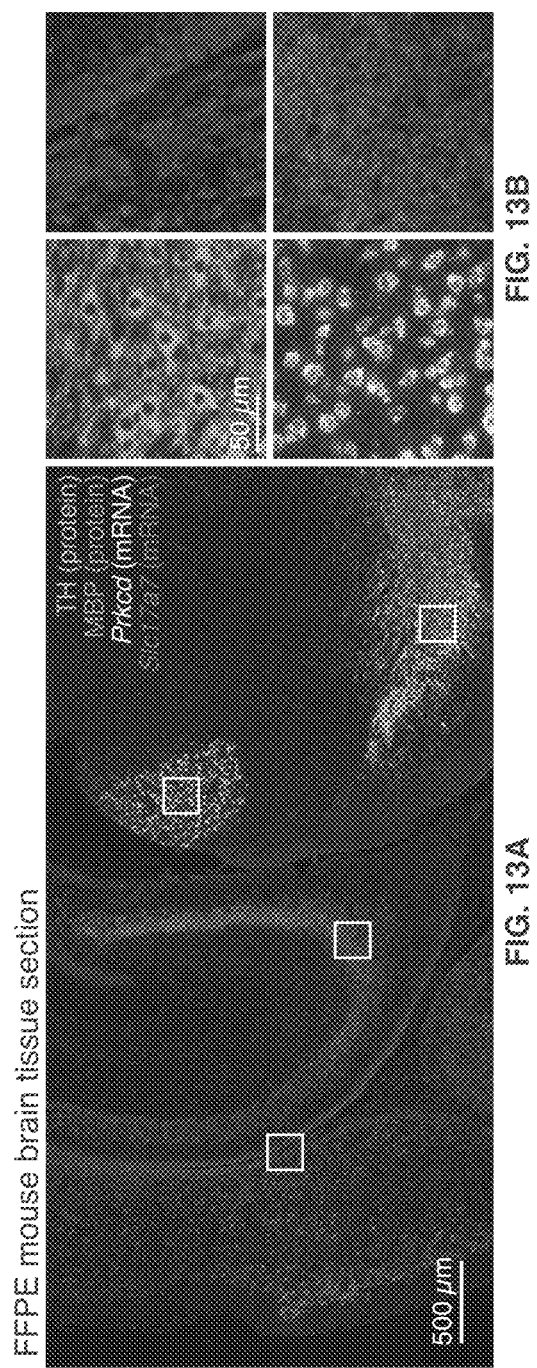

Unlabeled HCR hairpins

Reporter-labeled HCR hairpins

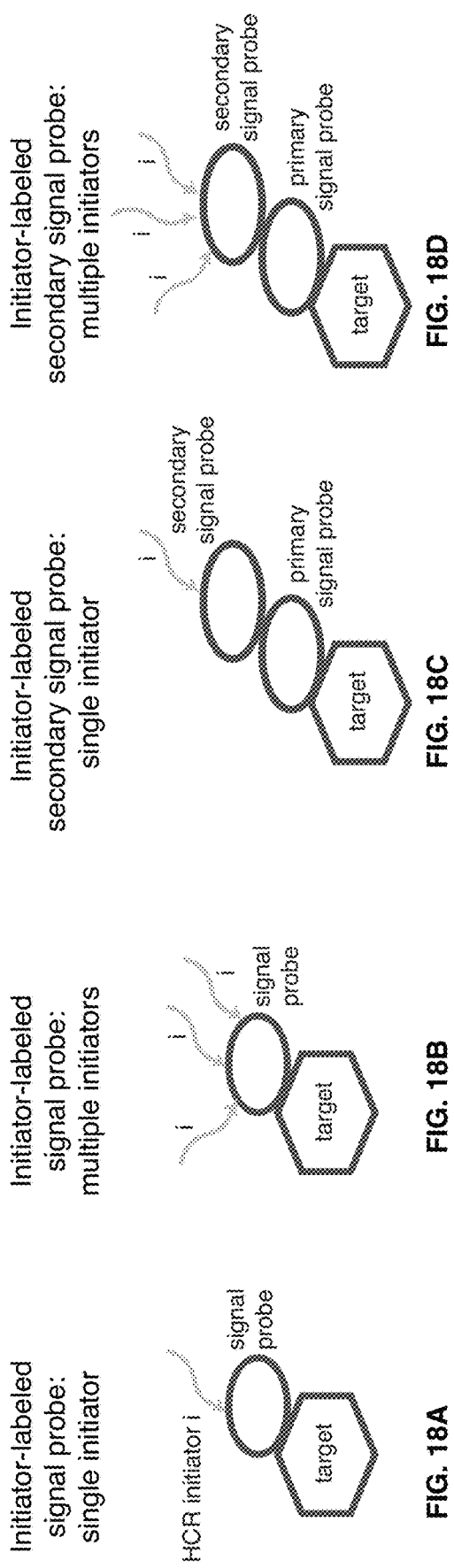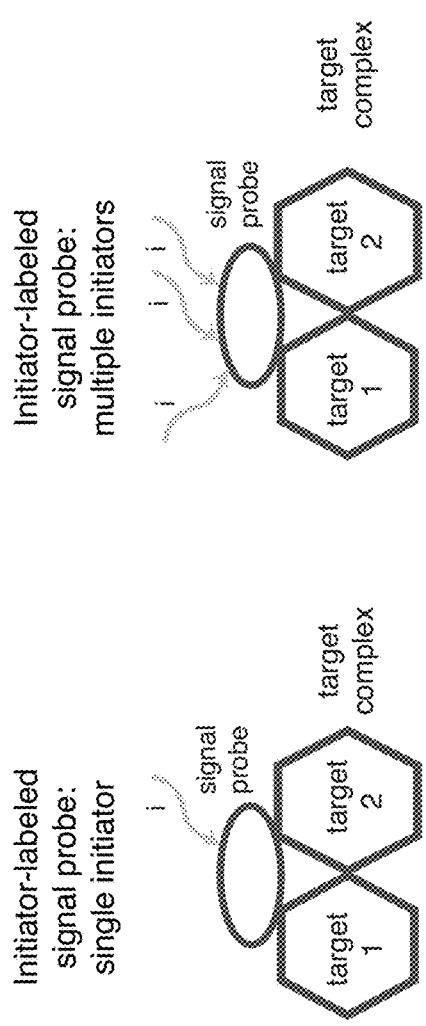

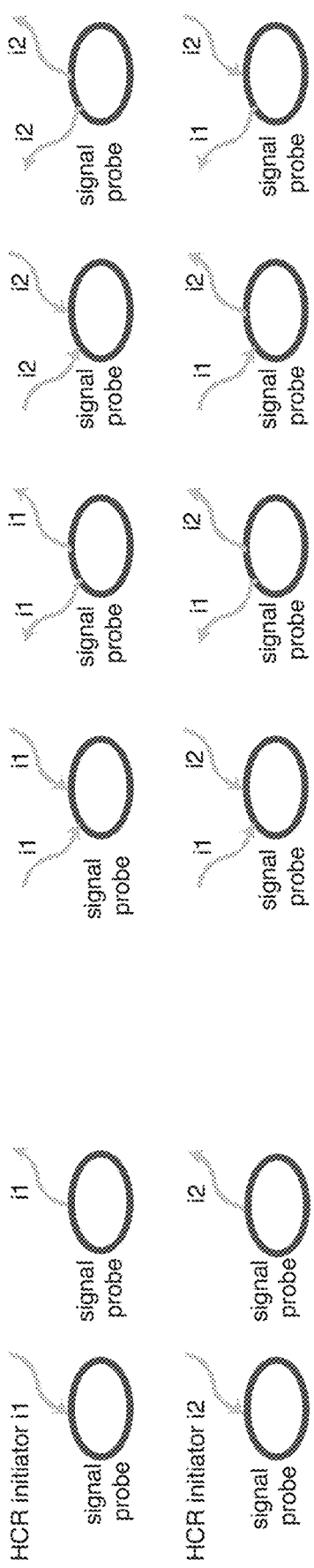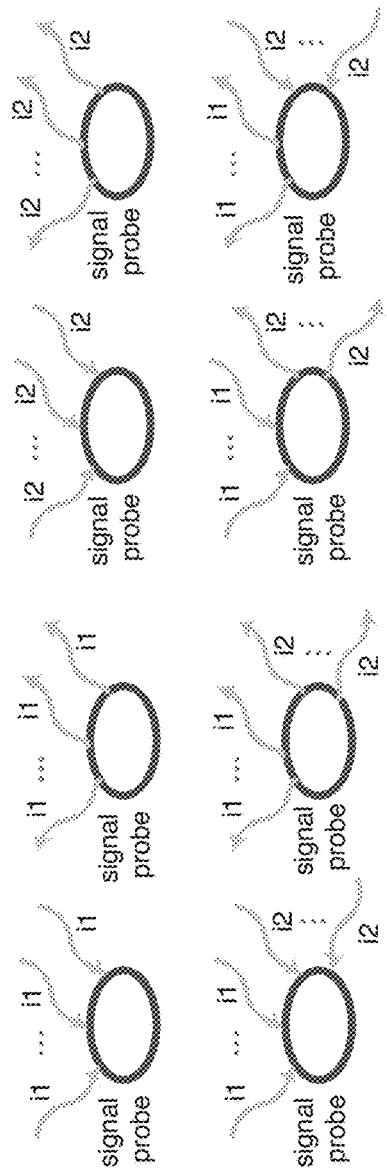
FIG. 19A
FIG. 19B
FIG. 19C

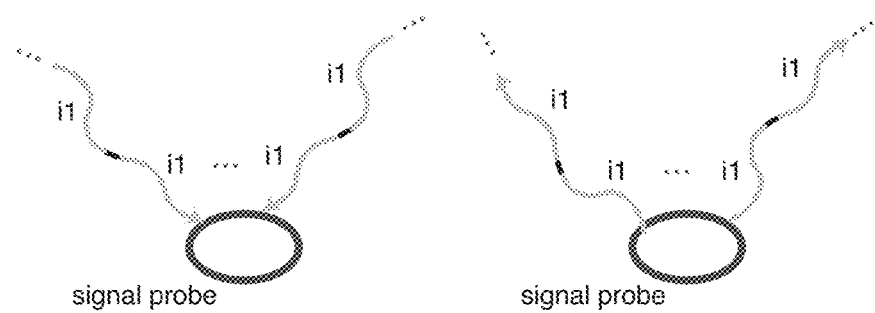
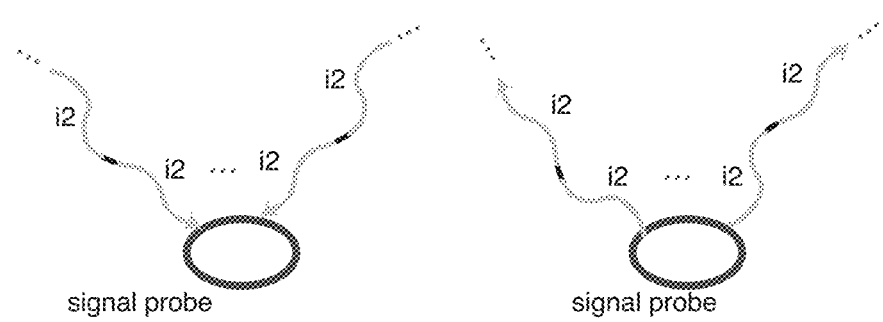
FIG. 19E
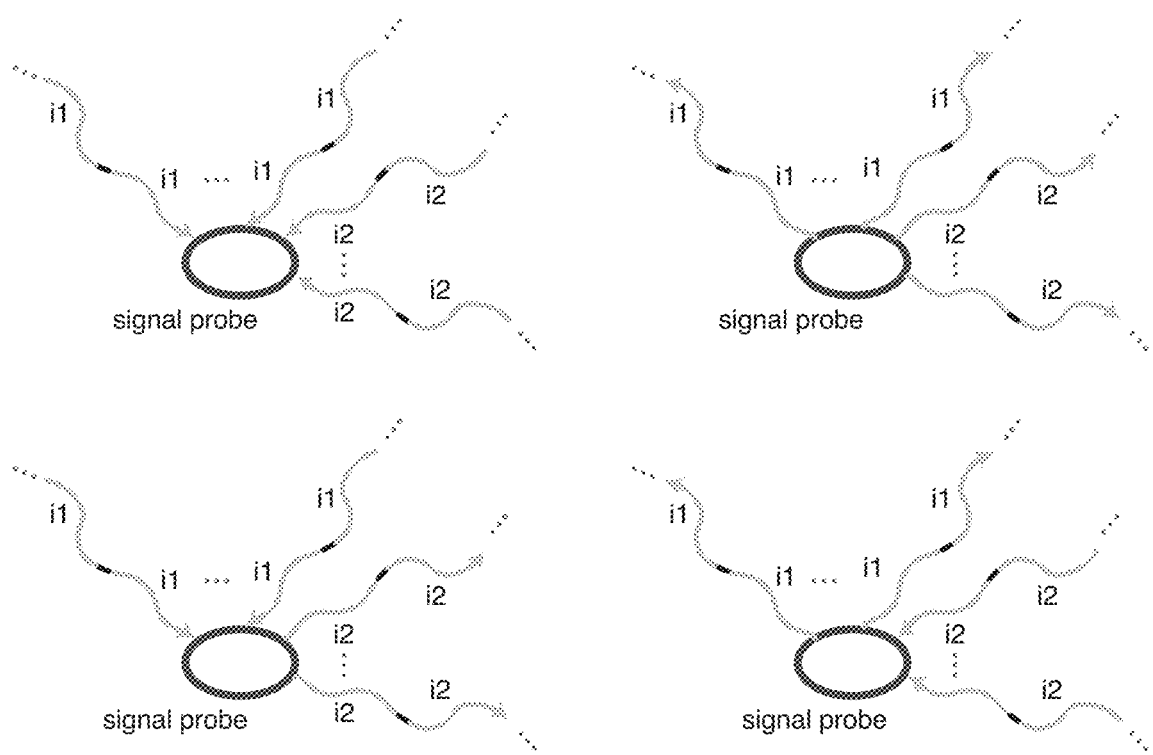
FIG. 19F

Arrangement 1

Arrangement 2

Arrangement 3

Arrangement 4

Arrangement 5

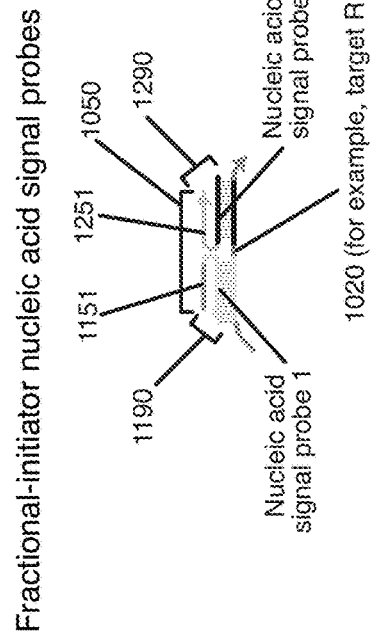
FIG. 21A Fractional-initiator signal probes
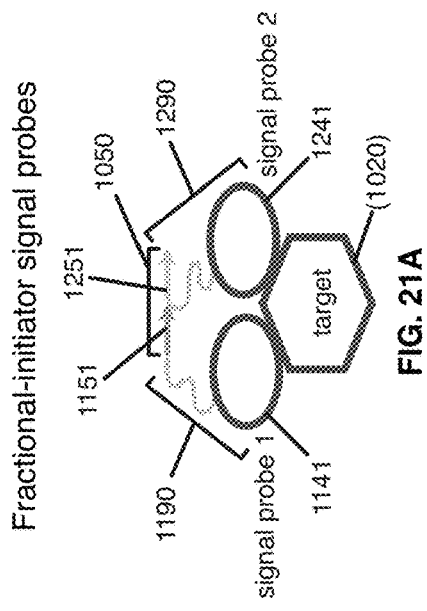
FIG. 21B Fractional-initiator nucleic acid signal probes
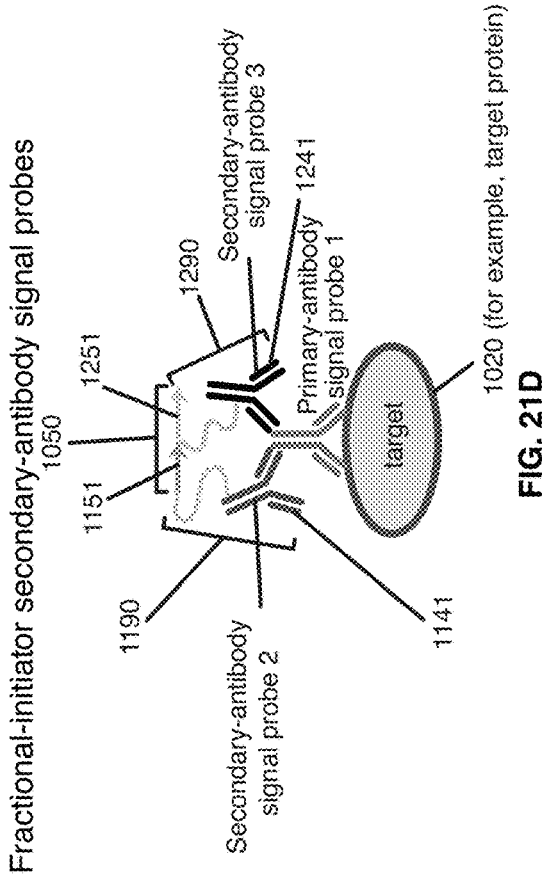
FIG. 21C Fractional-initiator primary-antibody signal probes
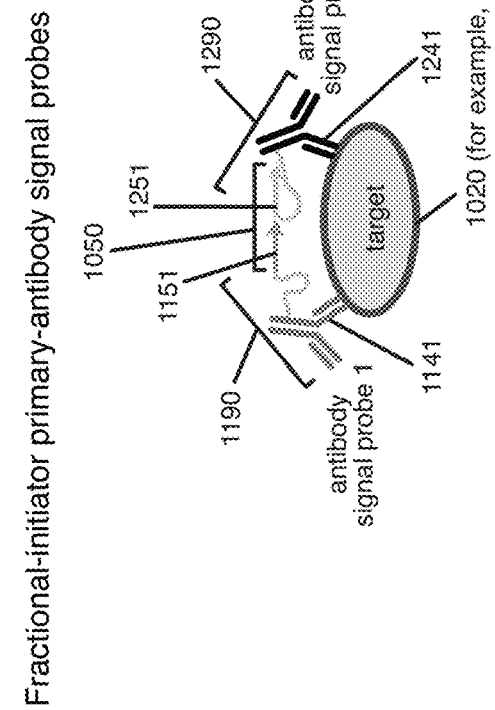
FIG. 21D Fractional-initiator secondary-antibody signal probes

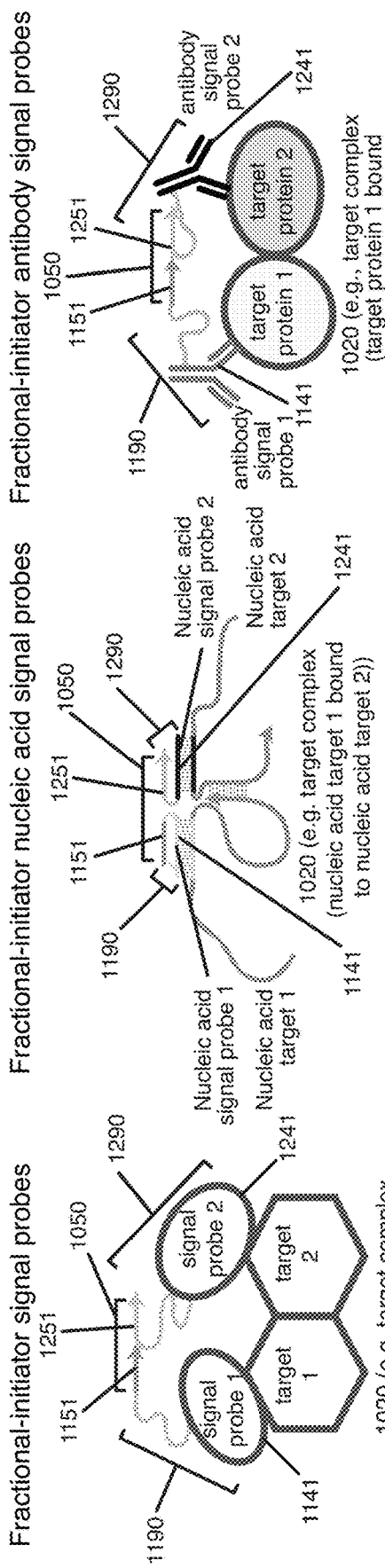
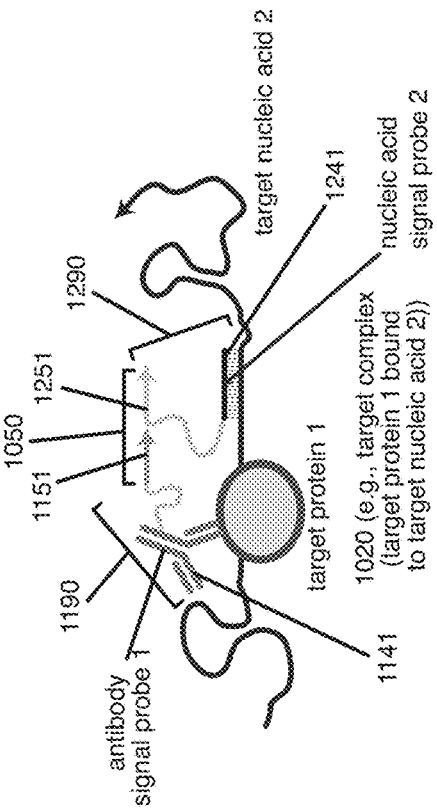
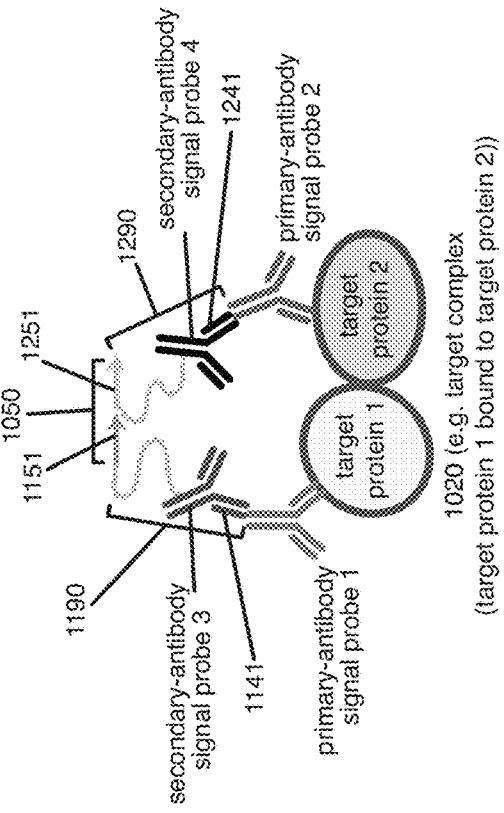
FIG. 22A Fractional-initiator signal probes
FIG. 22B Fractional-initiator nucleic acid signal probes
FIG. 22C Fractional-initiator antibody signal probes
FIG. 22D Fractional-initiator antibody signal probes
FIG. 22E Fractional-initiator antibody and nucleic acid signal probes Fractional-initiator signal probes Fractional-initiator signal probes Fractional-initiator signal probes

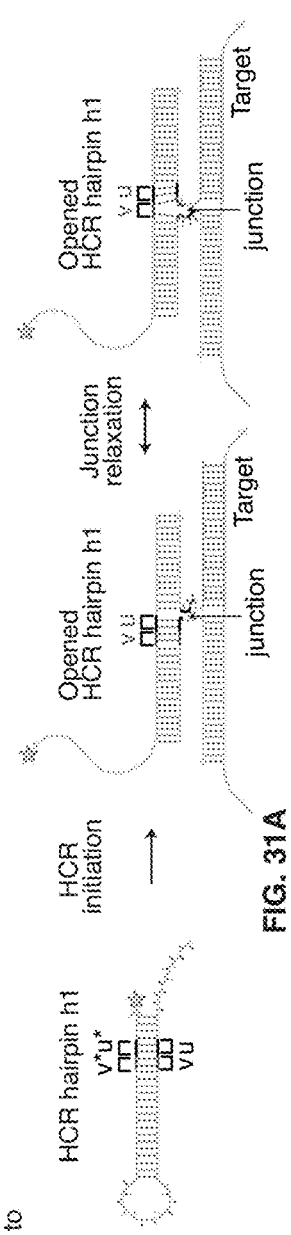
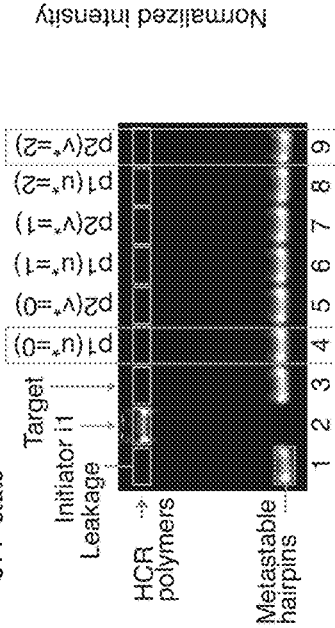
FIG. 31A
FIG. 31B
FIG. 31C

HCR RNA-CISH with CARD

Enhanced sensitivity with HCR RNA-CISH vs bDNA CARD

Better-preserved tissue morphology with HCR RNA-CISH vs bDNA CARD

HCR RNA-CISH with CARD

4-plex HCR RNA-CISH reagents

Multiplex HCR RNA-CISH with CARD

FFPE mouse duodenum tissue section miRNA detection (Approach 1)

miRNA detection (Approach 2)

Splice junction detection

HCR IHC with CARD (Approach 1)
- Anti-target initiator-labeled 1° Ab signal probe
- Reporter-labeled amplifier
- Anti-reporter enzyme-labeled readout probe
- Enzyme-mediated CARD

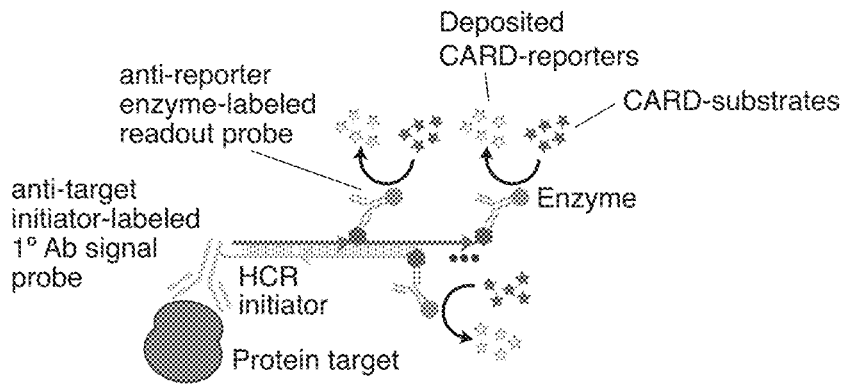

FIG. 39A

HCR IHC with CARD (Approach 2)
- Anti-target 1° Ab signal probe
- Anti-primary initiator-labeled 2° Ab signal probe
- Reporter-labeled amplifier
- Anti-reporter enzyme-labeled readout probe
- Enzyme-mediated CARD

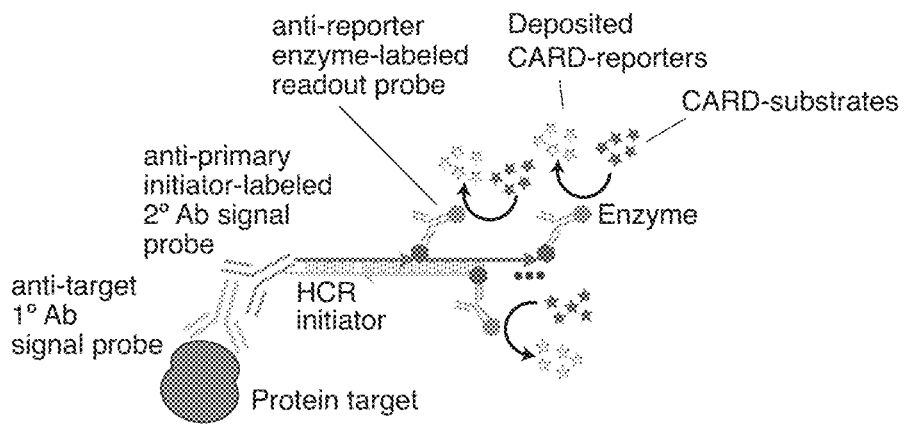

FIG. 39B

Multiplex HCR IHC with CARD

FFPE human tonsil tissue section

Enhanced sensitivity using enzyme-free nonlinear HCR RNA-FISH
(see Approach 1 of FIG. 45)

Multiplex Enzyme-Free Nonlinear HCR RNA-FISH

FFPE mouse duodenum tissue sections

Enzyme-Free Nonlinear HCR RNA-FISH (Approach 2)
- Fractional-initiator signal probes
- Reporter-labeled amplifier during linear stage
- Anti-reporter initiator-labeled primary bridging probe
- Fluorphore-labeled amplifier during nonlinear stage

HCR RNA-FISH for microRNA targets

Enzyme-Free Nonlinear HCR IF

Enzyme-Free Linear HCR IF

Multiplex enzyme-free HCR IF

FFPE human tonsil tissue section

Enzyme-free HCR RNA-FISH/IF

FFPE human breast cancer tissue section

Reporter-Labeled Signal Probes

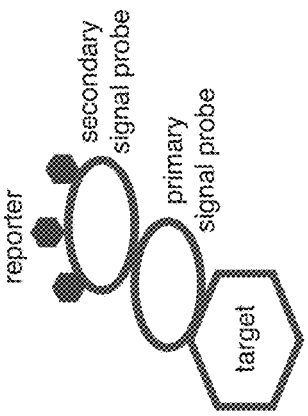

anti-primary reporter-labeled secondary signal probe: multiple reporters

FIG. 56D

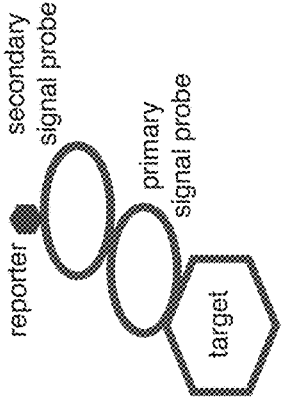

anti-primary reporter-labeled secondary signal probe: single reporter

FIG. 56C

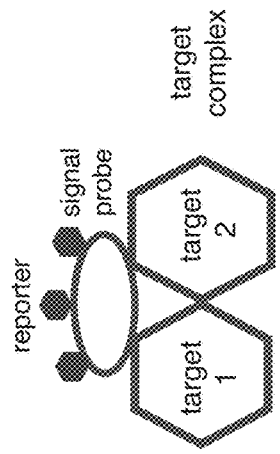

anti-target1:target2 reporter-labeled signal probe: multiple reporters

FIG. 56F anti-target reporter-labeled signal probe: multiple reporters

FIG. 56B

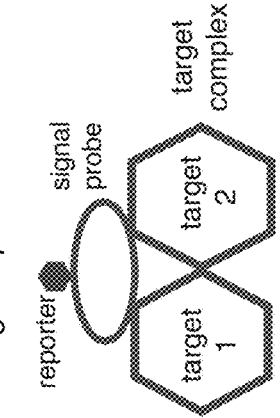

anti-target1:target2 reporter-labeled signal probe: single reporter

FIG. 56E

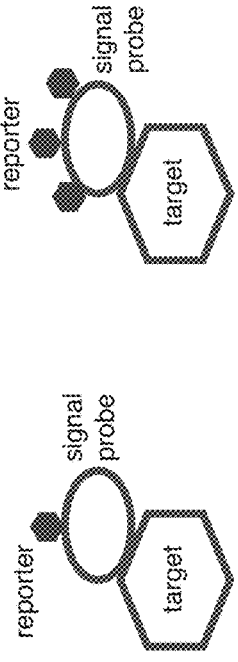

anti-target reporter-labeled signal probe: single reporter

FIG. 56A

Reporter-Labeled Signal Probes

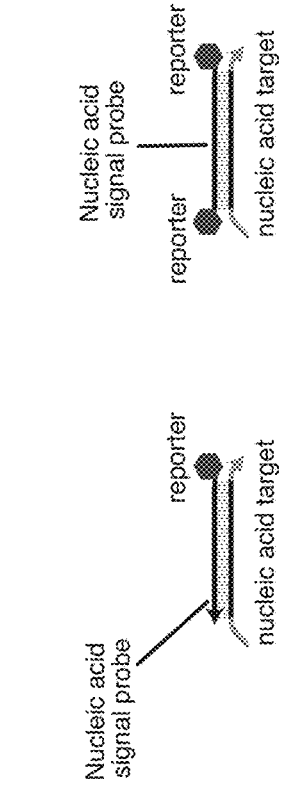

Nucleic acid signal probe: single reporter

FIG. 56G

Nucleic acid signal probe: multiple reporters

FIG. 56H

Anti-primary secondary-antibody signal probe: single reporter

FIG. 56K

Anti-primary secondary-antibody signal probe: multiple reporters

FIG. 56L

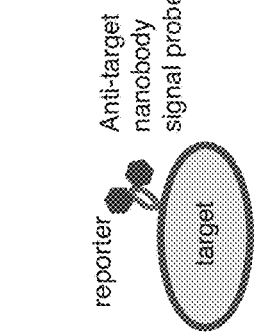

Anti-target primary-antibody signal probe: single reporter

FIG. 56I

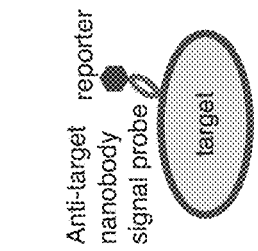

Anti-target primary-antibody signal probe: multiple reporters

FIG. 56J

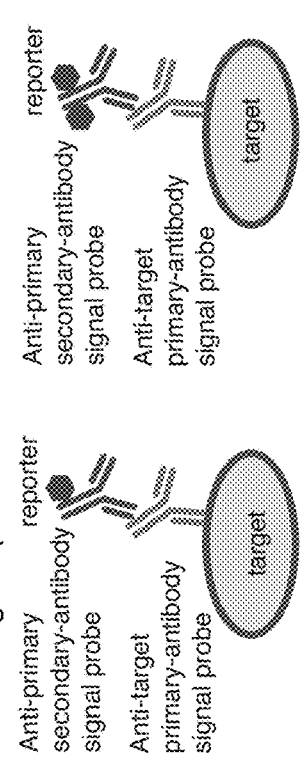

Anti-target nanobody signal probe: single reporter

FIG. 56M

Anti-target nanobody signal probe: multiple reporters

FIG. 56N

Poly-Reporter-Labeled Signal Probes

Detection of a target using a reporter-labeled signal probe and either an anti-reporter initiator-labeled signal probe or a pair of anti-reporter fractional-initiator signal probes

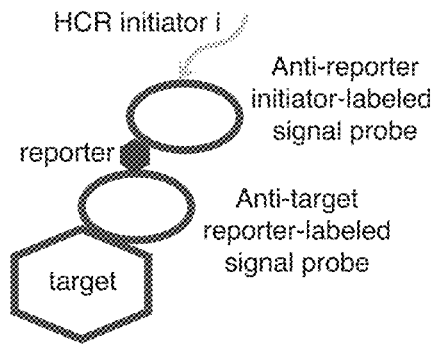

FIG. 58A

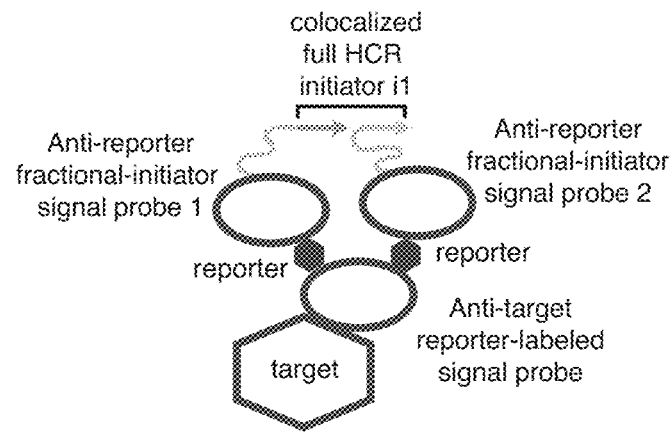

FIG. 58B

Detection of targets in a complex or in proximity using a pair of anti-target reporter-labeled signal probes and a pair of anti-reporter fractional-initiator signal probes and a proximity probe

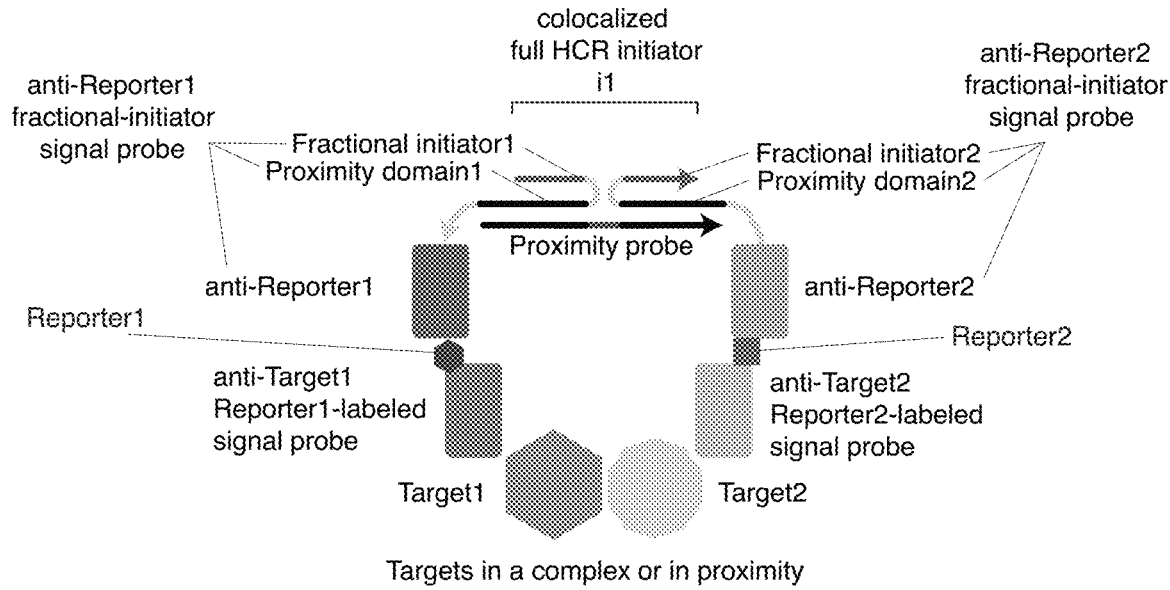

FIG. 58C

Reporter-labeled signal probes and initiator-labeled signal probes
FIG. 59A
FIG. 59C
FIG. 59E
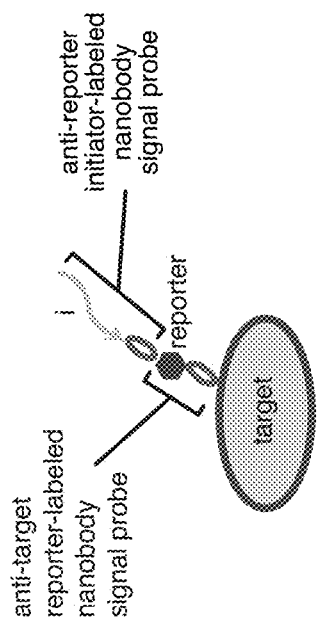
FIG. 59B
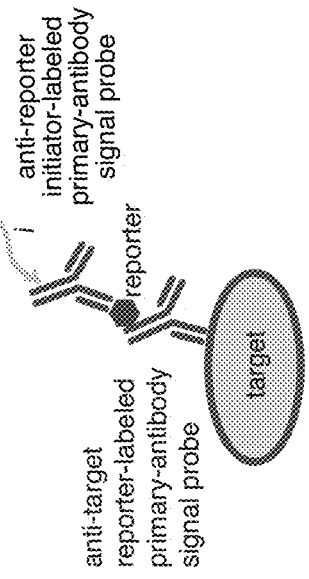
FIG.59D
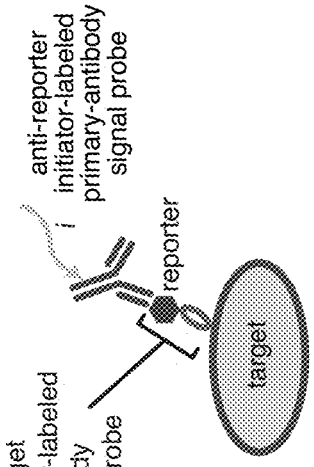
FIG. 59F

HCR IHC with CARD

4-plex HCR IHC reagents

Cooperative probe junctions for fractional-initiator signal probes

Cooperative probe junctions for fractional-initiator signal probes

Fractional-initiator nucleic acid signal probes

Fractional-initiator secondary-antibody signal probes

Fractional-initiator signal probes

Fractional-initiator primary-antibody signal probes

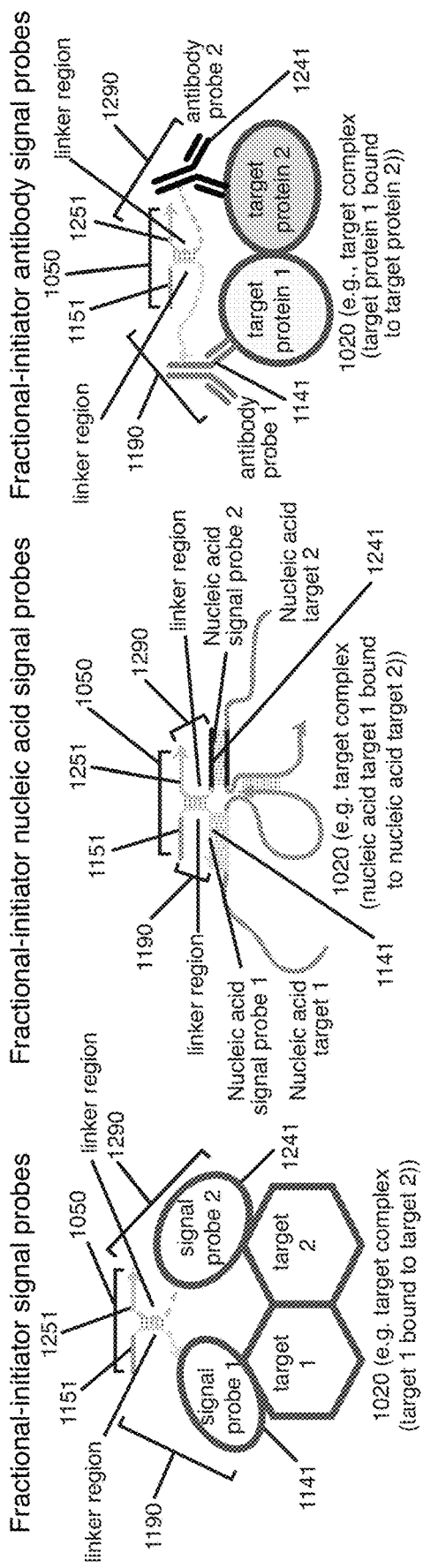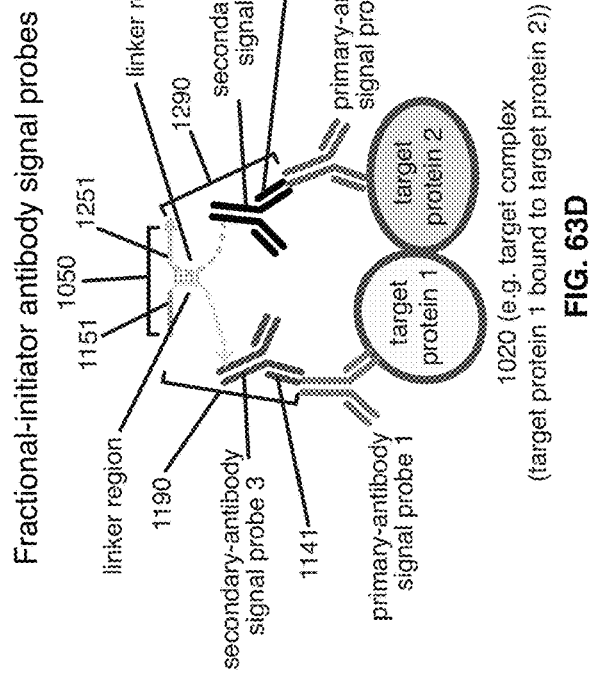
FIG. 63A Fractional-initiator signal probes
FIG. 63B Fractional-initiator nucleic acid signal probes
FIG. 63C Fractional-initiator antibody signal probes
FIG. 63D Fractional-initiator antibody signal probes
FIG. 63E Fractional-initiator antibody and nucleic acid signal probes Probe set comprising one probe unit Probe set comprising multiple probe units Probe set comprising mutliple probe units including some probes that comprise two fractional initiators and participate in two probe units Probe set comprising mutliple probe units as well as helper probes Probe unit comprising two fractional initiator probes Probe unit comprising N fractional initiator probes Probes that comprise two fractional initiators and participate in two probe units

Multiplex HCR IF using reporter-labeled probes
- anti-target reporter-labeled 1°Ab signal probe
- anti-reporter initiator-labeled 1° Ab signal probe
- fluorophore-labeled amplifier

Enhanced sensitivity using enzyme-free nonlinear HCR RNA-FISH
(see Approach 2 of FIG. 49A)

**Detection of targets in a complex or in proximity
using anti-target fractional-initiator signal probes
and a proximity probe**

**Detection of targets in a complex or in proximity
using anti-target signal probes,
anti-anti-target fractional-initiator signal probes,
and a proximity probe**

**Detection of a target
using anti-target signal probes,
anti-anti-target fractional-initiator signal probes,
and a proximity probe**

Detection of targets in a complex or in proximity using anti-target reporter-labeled signal probes, anti-reporter fractional-initiator signal probes, and a proximity probe

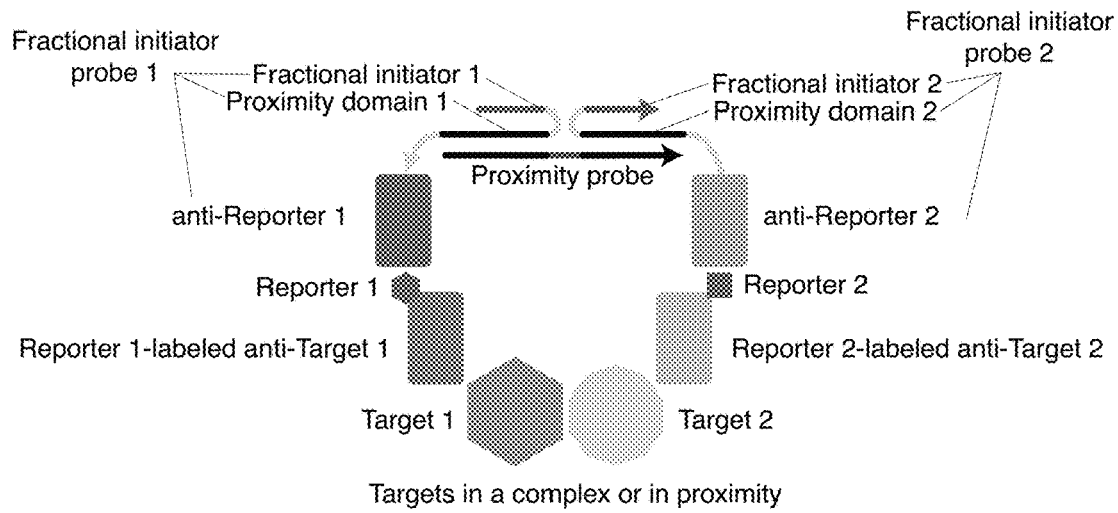

FIG. 68D

Detection of targets in a complex or in proximity
- Target 1: anti-Target 1 fractional-initiator signal probe
- Target 2: anti-Target 2 signal probe, anti-anti-Target 2 fractional-initiator signal probe
- Proximity probe

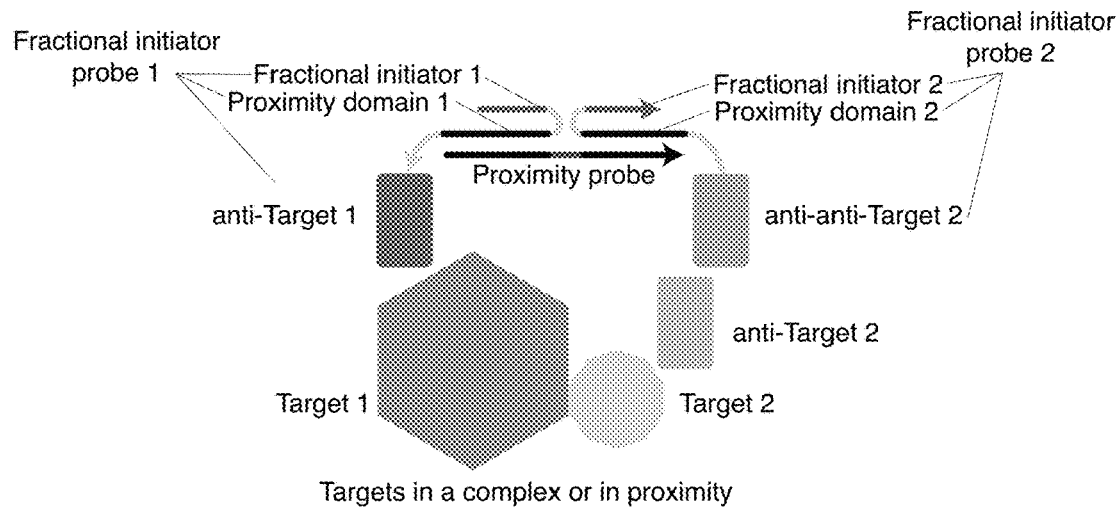

FIG. 68E

Detection of targets in a complex or in proximity
- Target 1: anti-Target 1 signal probe, anti-anti-Target 1 fractional-initiator signal probe
- Target 2: anti-Target 2 Reporter 2-labeled signal probe, anti-Reporter 2 fractional-initiator signal probe
- Proximity probe

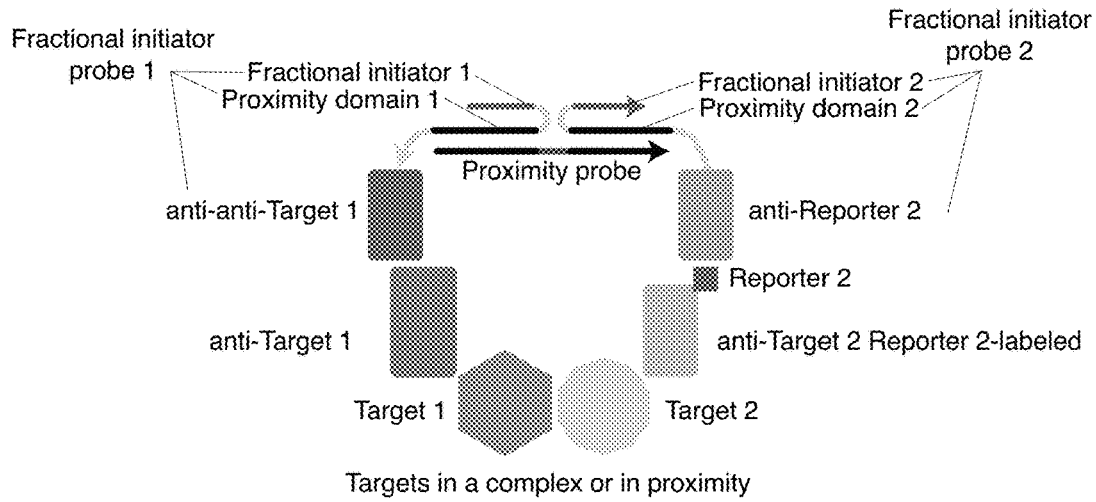

FIG. 68F

Detection of targets in a complex or in proximity
- Target 1: anti-Target 1 fractional-initiator signal probe
- Target 2: anti-Target 2 Reporter 2-labeled signal probe, anti-Reporter 2 fractional-initiator signal probe
- Proximity probe

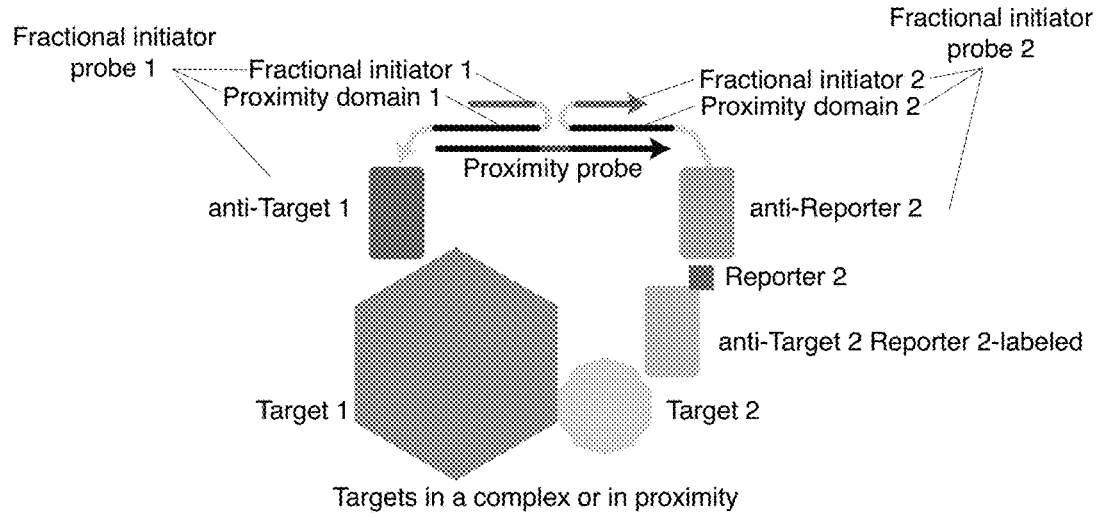

FIG. 68G

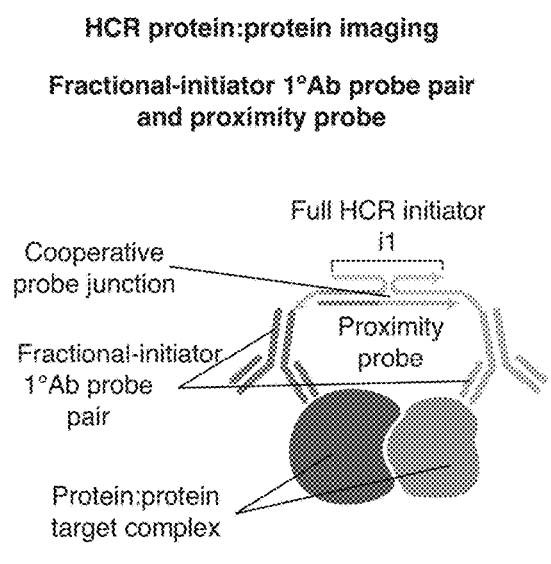
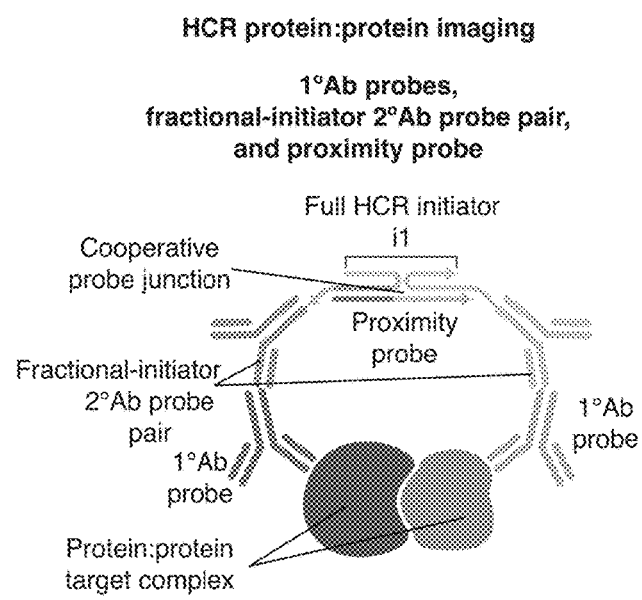
FIG. 69A
FIG. 69B

Enhanced sensitivity using enzyme-free nonlinear HCR RNA-FISH
(see approach of FIG. 71)

Target Detection with Enzyme-Free Nonlinear HCR Signal Amplification

- Anti-target initiator-labeled signal probe
- Reporter-labeled HCR amplifier during 1st amplification stage
- Anti-reporter initiator-labeled bridging probe
- Reporter-labeled HCR amplifier during 2nd amplification stage
- Anti-reporter initiator-labeled bridging probe
- Fluorphore-labeled HCR amplifier during 3rd amplification stage

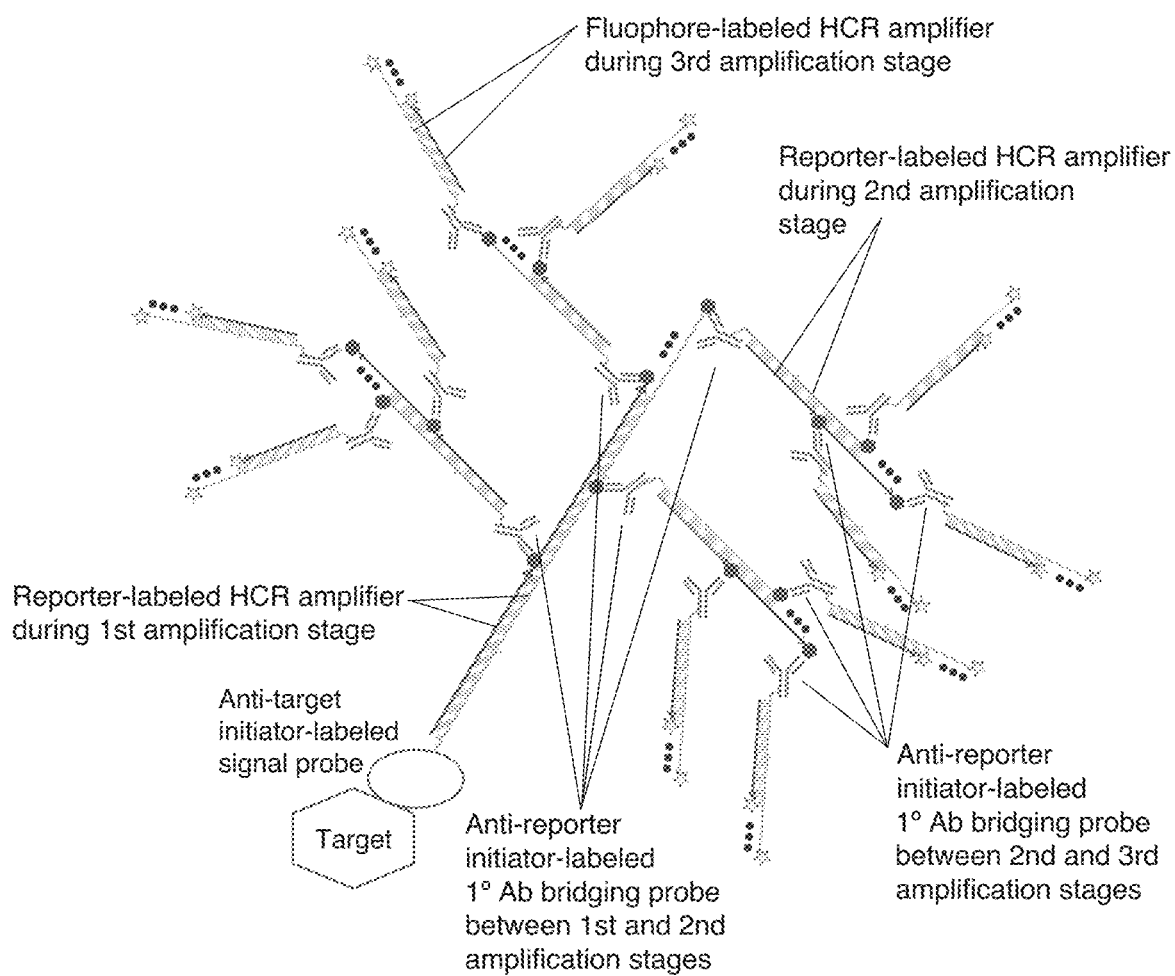

FIG. 73

ULTRASENSITIVE MOLECULAR DETECTION VIA HYBRIDIZATION CHAIN REACTION

REFERENCE TO RELATED APPLICATIONS

This application is a continuation of U.S. patent application Ser. No. 18/625,726, filed Apr. 3, 2024 and claims priority to U.S. Provisional Patent Application No. 63/457,043, filed Apr. 4, 2023. The disclosures of the above-referenced applications are hereby expressly incorporated by reference herein in their entireties.

STATEMENT REGARDING FEDERALLY SPONSORED R&D

This invention was made with government support under Grant Nos. R01EB006192 and R44GM140796 awarded by the National Institutes of Health. The government has certain rights in the invention.

INCORPORATION BY REFERENCE OF MATERIAL IN SEQUENCE LISTING FILE

This application incorporates the material in the XML sequence listing provided herewith, entitled CALTE.163C1seqlist.xml, was created on Apr. 10, 2024, and is 4,818 bytes in size.

BACKGROUND

Field

The present application relates to hybridization chain reaction (HCR). In particular, compositions and methods are provided for ultrasensitive molecular detection using HCR signal amplification.

SUMMARY

Compositions and methods are provided for ultrasensitive molecular detection using HCR signal amplification. Some embodiments and methods involve one, two, or three of the following aspects: 1) cooperative probe junctions, 2) reporter-labeled probes, 3) nonlinear HCR signal amplification. In some embodiments related to cooperative probe junctions, a target is detected using a probe set comprising one or more probe units each comprising two or more fractional-initiator probes, wherein a fractional-initiator probe comprises a target-binding region, a linker region, and a fractional-initiator, wherein the target-binding regions on the probes within a probe unit are configured to bind to overlapping or non-overlapping binding sites on the target, wherein the linker regions on the probes within a probe unit are optionally configured to bind to each other, wherein the fractional-initiators on the probes within each probe unit are configured to bind to overlapping or non-overlapping binding sites on an HCR hairpin, and wherein binding of the probes within a probe unit to cognate binding sites on the target and cognate binding sites on an HCR hairpin leads to formation of a cooperative probe junction that mutually facilitates target binding and colocalization of a full HCR initiator to efficiently trigger HCR signal amplification. In some embodiments related to reporter-labeled probes, the target is detected by an anti-target reporter-labeled probe (for example, an anti-target hapten-labeled primary antibody), which in turn is detected by an anti-reporter initiator-labeled probe (for example, an anti-hapten initiator-labeled primary antibody) or by one or more fractional-initiator probes (for example, one or more anti-hapten fractional-initiator primary antibodies), avoiding the need to conjugate an initiator to the target-binding probe and also avoiding the need to use secondary antibodies; in some contexts, conjugating an initiator to a target-binding probe can sometimes interfere with probe/target binding, and in some contexts, use of secondary antibodies can sometimes interfere with multiplexing. In some embodiments related to nonlinear HCR signal amplification, ultrasensitive detection is achieved using multiple rounds of HCR signal amplification to grow branched HCR amplification polymers. In some embodiments, during a linear amplification stage, an anti-target initiator-labeled signal probe triggers reporter-labeled HCR hairpins to grow a reporter-decorated first HCR amplification polymer tethered to the target. In some embodiments, anti-reporter initiator-labeled bridging probes bind to the reporters decorating the first HCR amplification polymer to decorate the first HCR amplification polymer with HCR initiators. In some embodiments, during a nonlinear amplification stage, each HCR initiator decorating the first HCR amplification polymer triggers auxiliary-reporter-labeled HCR hairpins to grow an auxiliary-reporter-decorated HCR amplification polymer that branches off of the first HCR amplification polymer tethered to the target. In some embodiments, multiple rounds of bridging and nonlinear HCR signal amplification are performed to grow multiple generations of HCR amplification polymers tethered to each other and to the target. In some embodiments, the reporters and/or the auxiliary reporters on the HCR amplification polymer directly or indirectly mediate catalytic reporter deposition (CARD) in the vicinity of the target.

In accordance with some implementations, methods of HCR are provided involving cooperative probe junctions. In some embodiments, the methods comprise: a) providing a sample possibly containing a target, b) contacting the sample with a probe set comprising one or more probe units each comprising two or more fractional-initiator probes, c) contacting the sample with an HCR amplifier labeled with a reporter; d) detecting a signal directly or indirectly from the reporter. In accordance with some implementations, each of the two or more fractional-initiator probes comprises: a target-binding region, a linker region, and a fractional initiator. In accordance with some implementations, the target-binding region on the probes within each probe unit are configured to bind to different binding sites on the target. In accordance with some implementations, the linker regions on the two or more fractional initiator probes are configured to bind to each other. In accordance with some implementations, the fractional initiators on the two or more fractional initiator probes are configured to bind to different binding sites on an HCR hairpin. In accordance with some implementations, the probes within each probe unit are configured to form a cooperative probe junction when they bind the target, each other, and an HCR hairpin. In accordance with some implementations, an HCR amplifier comprises two or more HCR hairpins. In accordance with some implementations, an HCR hairpin comprises an input domain comprising a single-stranded toehold and a stem section, and further comprises an output domain comprising a single-stranded loop and a complement to the stem section. In accordance with some implementations, at least one HCR hairpin further comprises a reporter. In accordance with some implementations, a wash step is performed between any of steps (b)-(d). In accordance with some implementations, each of the two or more fractional-initiator probes further comprises a proximity domain. In accordance with some implementations, the proximity domains are configured to bind to a proximity probe. In accordance with some implementations, the sample is contacted with one or more proximity probes following step (b) and before step (c). In accordance with some implementations, a wash step is performed following the providing of one or more proximity probes to remove unbound proximity probes. In accordance with some implementations, the cooperative probe junction further comprises the one or more proximity probes. In accordance with some implementations, one or more auxiliary-reporter-labeled readout probes are provided following step (c). In accordance with some implementations, a wash step is performed following the providing of one or more auxiliary-reporter-labeled readout probes to remove unbound auxiliary-reporter-labeled readout probes. In accordance with some implementations, a signal is detected form the auxiliary reporter. In accordance with some implementations, after step (d), the method further comprises a step (e) in which the signal is removed. In accordance with some implementations, the method further comprises repeating any of the steps of the method to detect another target in the sample, wherein the target binding domains are for a different target. In accordance with some implementations, the target-binding regions on the two or more fractional initiator probes are configured to bind overlapping binding sites on the target. In accordance with some implementations, the target-binding regions on the two or more fractional initiator probes are configured to bind non-overlapping binding sites on the target. In accordance with some implementations, the fractional initiators on the two or more fractional initiator probes are configured to bind overlapping binding sites on the HCR hairpin. In accordance with some implementations, the fractional initiators on the two or more fractional initiator probes are configured to bind non-overlapping binding sites on the HCR hairpin. In accordance with some implementations, the target comprises an RNA molecule, a DNA molecule, a protein, a small molecule, a chemical, a biological molecule, a pathogen, a complex of molecules, or a set of molecules in proximity. In accordance with some implementations, the reporter and the auxiliary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

In accordance with some implementations, compositions are provided for detecting a target within a sample, comprising: a) an anti-target reporter-labeled signal probe configured to bind to the target; b) an anti-reporter initiator-labeled signal probe configured to bind to the reporter; c) an auxiliary-reporter-labeled HCR amplifier configured to be triggered by the initiator to grow an auxiliary-reporter-decorated HCR amplification polymer tethered to the target; wherein the auxiliary reporter directly or indirectly mediates generation of a signal. In accordance with some implementations, the composition further comprises an anti-auxiliary-reporter tertiary-reporter-labeled readout probe configured to bind to the auxiliary-reporter-decorated amplification polymer. In accordance with some implementations, the tertiary reporters directly or indirectly mediate generation of a signal. In accordance with some implementations, target comprises an RNA molecule, a DNA molecule, a protein, a small molecule, a chemical, a biological molecule, a pathogen, a complex of molecules, or a set of molecules in proximity. In accordance with some implementations, the reporter, the auxiliary reporter, and the tertiary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

In accordance with some implementations, compositions are provided for detection of N targets within a sample (where N is a positive integer), comprising: a) a jth anti-target signal probe comprising a jth reporter and configured to bind to the jth target (for j=1, . . . , N where j is a positive integer); b) a jth anti-reporter signal probe comprising a jth HCR initiator and configured to bind to the jth reporter; c) a jth HCR amplifier comprising a jth auxiliary reporter and configured to be triggered by the jth HCR initiator to grow a jth auxiliary-reporter-decorated HCR amplification polymer tethered to the jth target; wherein the jth auxiliary reporters directly or indirectly mediate generation of a signal for the jth target. In accordance with some implementations, the composition further comprises a jth anti-auxiliary-reporter readout probe comprising a jth tertiary reporter and configured to bind to the jth auxiliary-reporter-decorated amplification polymer. In accordance with some implementations, the jth tertiary reporter directly or indirectly mediates generation of a signal for the jth target. In accordance with some implementations, the jth target comprises an RNA molecule, a DNA molecule, a protein, a small molecule, a chemical, a biological molecule, a pathogen, a complex of molecules, or a set of molecules in proximity. In accordance with some implementations, the jth reporter, the jth auxiliary reporter, and the jth tertiary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

In accordance with some implementations, methods of HCR are provided involving reporter-labeled probes. In accordance with some implementations, the method comprises: providing a sample containing a target; contacting the sample with at least one reporter-labeled signal probe comprising a target-binding region and at least one reporter; contacting the sample with at least one anti-reporter initiator-labeled signal probe comprising a reporter-binding region and at least one initiator; contacting the sample with a first HCR hairpin, comprising a first input domain comprising a first toehold and a first stem section, and a first output domain comprising a first hairpin loop and a complement to the first stem section; contacting the sample with a second HCR hairpin, comprising a second input domain, comprising a second toehold and a second stem section, and a second output domain, comprising a second hairpin loop and a complement to the second stem section; wherein at least one of the first HCR hairpin and the second HCR hairpin further comprises an auxiliary reporter; and detecting a signal directly or indirectly from the reporter and/or the auxiliary reporter. In accordance with some implementations, a wash step is performed between any of the above steps. In accordance with some implementations, the signal is removed following detection. In accordance with some implementations, the first HCR hairpin comprises a first auxiliary reporter. In accordance with some implementations, the first auxiliary reporter directly or indirectly mediates generation of a signal. In accordance with some implementations, the second HCR hairpin comprises a second auxiliary reporter. In accordance with some implementations, the second auxiliary reporter directly or indirectly mediates generation of a signal. In accordance with some implementations, (a) the reporter-labeled signal probe comprises an anti-target primary antibody or nanobody, (b) the reporter comprises a hapten, and (c) the anti-reporter initiator-labeled signal probe comprises an anti-hapten primary antibody or nanobody. In accordance with some implementations, the method further comprises: binding the first HCR hairpin to the at least one initiator; binding the second HCR hairpin to the first HCR hairpin; contacting the sample with an anti-auxiliary-reporter readout probe comprising an enzyme that mediates CARD; contacting the sample with one or more CARD-substrates; and measuring a signal from one or more deposited CARD-reporters generated from the CARD-substrate by the enzyme that mediates CARD. In accordance with some implementations, the anti-auxiliary-reporter readout probe comprises a primary antibody or nanobody that binds the auxiliary reporter and further comprises a secondary antibody or nanobody (labeled with one or more enzymes that mediate CARD) that binds the primary antibody or nanobody. In accordance with some implementations, the method further comprises repeating any of the steps of the method to detect another target in the sample. In accordance with some implementations, the target comprises an RNA molecule, a DNA molecule, a protein, a small molecule, a chemical, a biological molecule, a pathogen, a complex of molecules, or a set of molecules in proximity. In accordance with some implementations, the reporter and the auxiliary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

In accordance with some implementations, compositions are provided for nonlinear HCR signal amplification comprising: a) a first HCR initiator; b) a first HCR amplifier comprising two or more HCR hairpins, at least one of which comprises a reporter; c) an anti-reporter bridging probe comprising a reporter-binding domain and a second HCR initiator; d) a second HCR amplifier comprising two or more HCR hairpins, at least one of which comprises an auxiliary reporter. In accordance with some implementations, the first HCR initiator is configured to trigger the HCR hairpins comprising the first HCR amplifier to grow a reporter-decorated first HCR amplification polymer tethered to the first HCR initiator. In accordance with some implementations, the anti-reporter bridging probe is configured to bind the reporters decorating the first HCR amplification polymer so as to decorate it with second HCR initiators. In accordance with some implementations, the second HCR initiator is configured to trigger the HCR hairpins comprising the second HCR amplifier to grow an auxiliary-reporter decorated second HCR amplification polymer tethered to the first HCR amplification polymer. In accordance with some implementations, the reporters and/or auxiliary reporters are configured to directly or indirectly mediate generation of an amplified signal. In accordance with some implementations the first HCR initiator is attached to a signal probe configured to bind directly or indirectly to a target. In accordance with some implementations, the first HCR initiator is a colocalized full first HCR initiator formed when two or more fractional-initiator probes are bound specifically to their cognate binding sites on a target. In accordance with some implementations, the first HCR initiator is a colocalized full first HCR initiator formed when two or more fractional-initiator probes are bound specifically to their cognate binding sites on two or more targets that are complexed or in proximity. In accordance with some implementations, the composition additional comprises one or more proximity probes configured to bind to the two or more fractional-initiator probes. In accordance with some implementations, (a) the auxiliary reporter is the same as the reporter, (b) the first HCR initiator has the same sequence as the second HCR initiator and the first HCR amplifier has the same sequence as the second HCR amplifier, and/or (c) the reporter and the auxiliary reporter can be the same or different, each comprising a hapten, a fluorophore, a chromophore, or a rare-earth element or compound. In accordance with some implementations, a) the auxiliary reporter is configured to mediate catalytic reporter deposition (CARD), b) the composition further comprises an anti-auxiliary-reporter readout probe comprising a tertiary reporter, c) the tertiary reporter comprises an enzyme, and/or d) the enzyme is configured to act on CARD-substrates to catalytically deposit CARD-reporters that directly or indirectly generate a fluorescent or chromogenic signal in the vicinity of the target. In accordance with some implementations, the target comprises an RNA molecule, a DNA molecule, a protein, a small molecule, a chemical, a biological molecule, a pathogen, a complex of molecules, or a set of molecules in proximity. In accordance with some implementations, the reporter, the auxiliary reporter, and the tertiary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

In accordance with some implementations, compositions are provided for detection of N targets in a sample (where N is a positive integer) using nonlinear HCR signal amplification, comprising: (a) a jth signal probe set (for j=1, . . . , N where j is a positive integer) configured to bind the jth target, comprising: i) a jth initiator-labeled signal probe comprising a jth first HCR initiator, or ii) a jth fractional-initiator signal probe set configured to colocalize a jth full first HCR initiator when the probes within a probe unit bind specifically to their cognate binding sites on the jth target, or iii) a jth fractional-initiator signal probe set configured to colocalize a jth full first HCR initiator when the probes within a probe unit bind specifically to the jth target complex or jth set of proximal targets and are bound by one or more jth proximity probes, or iv) a jth anti-target reporter-labeled primary signal probe comprising a jth reporter; and a jth anti-reporter initiator-labeled secondary signal probe comprising a jth first HCR initiator; (b) a jth first HCR amplifier comprising two or more HCR hairpins, at least one of which comprises a jth auxiliary reporter; (c) a jth anti-auxiliary-reporter bridging probe comprising a jth auxiliary-reporter-binding domain and a jth second HCR initiator; (d) a jth second HCR amplifier comprising two or more HCR hairpins, at least one of which comprises a jth tertiary reporter. In accordance with some implementations, the jth first HCR initiator is configured to trigger the HCR hairpins comprising the jth first HCR amplifier to grow a jth auxiliary-reporter-decorated first HCR amplification polymer tethered to the jth target. In accordance with some implementations, the jth anti-auxiliary-reporter bridging probe is configured to bind the jth auxiliary reporters decorating the jth first HCR amplification polymer so as to decorate it with jth second HCR initiators. In accordance with some implementations, the jth second HCR initiator decorating the jth first HCR amplification polymer is configured to trigger the HCR hairpins comprising the jth second HCR amplifier to grow a jth tertiary-reporter decorated second HCR amplification polymer tethered to the jth first HCR amplification polymer. In accordance with some implementations, the jth reporters, jth auxiliary reporters, and/or jth tertiary reporters are configured to directly or indirectly mediate generation of a jth amplified signal at the site of the jth target. In accordance with some implementations, the jth target comprises an RNA molecule, a DNA molecule, a protein, a small molecule, a chemical, a biological molecule, a pathogen, a complex of molecules, or a set of molecules in proximity. In accordance with some implementations, the jth reporter, the jth auxiliary reporter, and the jth tertiary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

In accordance with some implementations, compositions are provided for nonlinear HCR signal amplification comprising: a) a first HCR initiator; b) a self-bridging first HCR amplifier comprising two or more HCR hairpins each comprising one split-initiator tail; c) a second HCR amplifier comprising two or more HCR hairpins, at least one of which comprises a reporter. In accordance with some implementations, the first HCR initiator is configured to trigger the HCR hairpins comprising the first HCR amplifier to grow a first HCR amplification polymer tethered to the first HCR initiator; wherein the split-initiator tails on the two or more self-bridging HCR hairpins comprising the first HCR amplification polymer are configured to colocalize a full second HCR initiator within the polymer. In accordance with some implementations, each colocalized full second HCR initiator within the first HCR amplification polymer is configured to trigger the HCR hairpins comprising the second HCR amplifier to grow a reporter-decorated second HCR amplification polymer tethered to the first HCR amplification polymer. In accordance with some implementations, the reporters are configured to directly or indirectly mediate generation of an amplified signal. In accordance with some implementations, the target comprises an RNA molecule, a DNA molecule, a protein, a small molecule, a chemical, a biological molecule, a pathogen, a complex of molecules, or a set of molecules in proximity. In accordance with some implementations, the reporter comprises a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

In accordance with some implementations, methods for target detection with nonlinear HCR signal amplification are provided. In accordance with some implementations, the method comprises: a) providing a sample containing one or more targets; b) contacting the sample with a probe set comprising one or more initiator-labeled probes or one or more probe units each comprising two or more fractional-initiator probes; c) contacting the sample with a reporter-labeled first HCR amplifier, such that a linear amplification stage is initiated; d) contacting the sample with an anti-reporter initiator-labeled bridging probe comprising one or more HCR initiators; e) contacting the sample with an auxiliary-reporter-labeled second HCR amplifier, such that a nonlinear HCR amplification stage is initiated; f) detecting one or more signals from the reporter and/or the auxiliary reporter. In accordance with some implementations, the probe set comprises one or more initiator-labeled probes wherein an initiator-labeled probe comprises a target-binding region and one or more HCR initiators. In accordance with some implementations, the probe set comprises one or more probe units each comprising two or more fractional-initiator probes, wherein a fractional-initiator probe comprises a target-binding region and a fractional initiator. In accordance with some implementations, the method comprises additional rounds of HCR signal amplification, each additional round comprising repeating steps (c) through (d). In accordance with some implementations, the reporter comprises a hapten and the bridging probe comprises an anti-hapten primary antibody or nanobody. In accordance with some implementations, the auxiliary reporter is a fluorophore, a chromophore, or a rare-earth element or compound. In accordance with some implementations, the anti-reporter bridging probe comprises a primary antibody or nanobody that binds the reporter and further comprises an initiator-labeled secondary antibody or nanobody that binds the primary antibody or nanobody. In accordance with some implementations, the first HCR amplifier and the second HCR amplifier have the same sequence. In accordance with some implementations, the reporter and the auxiliary reporter are the same. In accordance with some implementations, the method further comprises contacting the sample with an anti-auxiliary-reporter readout probe comprising an enzyme that mediates CARD, contacting the sample with one or more CARD-substrates, and measuring a signal from one or more catalytically deposited CARD-reporters. In accordance with some implementations, the method further comprises performing a wash step between any of steps (b)-(f). In accordance with some implementations, after step (f), the method further comprises a step (g) in which the signal is removed. In accordance with some implementations, an HCR amplifier comprises two or more HCR hairpins. In accordance with some implementations, an HCR hairpin comprises an input domain comprising a single-stranded toehold and a stem section. In accordance with some implementations, an HCR hairpin further comprises an output domain comprising a single-stranded loop and a complement to the stem section. In accordance with some implementations, at least one HCR hairpin of the first HCR amplifier further comprises one or more reporters, and at least one HCR hairpin of the second HCR amplifier further comprises one or more auxiliary reporters. In accordance with some, the method further comprises repeating any of the steps of the method to detect another target in the sample. In accordance with some implementations, the target comprises an RNA molecule, a DNA molecule, a protein, a small molecule, a chemical, a biological molecule, a pathogen, a complex of molecules, or a set of molecules in proximity. In accordance with some implementations, the reporter and the auxiliary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

In accordance with some implementations, methods for nonlinear HCR signal amplification are provided. In accordance with some implementations, the method comprises: a) contacting a sample with a first HCR initiator or two or more fractional initiators that together comprise a full first HCR initiator; b) contacting the sample with a first-reporter-labeled HCR amplifier and incubating to initiate growth of a first-reporter-decorated HCR amplification polymer tethered to the first HCR initiator; c) contacting the sample with an anti-first-reporter bridging probe comprising a second HCR initiator and incubating so that the first HCR amplification polymer is decorated with second HCR initiators; d) contacting the sample with a second-reporter-labeled HCR amplifier and incubating to initiate growth of a second-reporter-decorated HCR amplification polymer tethered to each second HCR initiator decorating the first HCR amplification polymer tethered to the first HCR initiator; e) detecting a signal generated directly or indirectly by the first reporter and/or the second reporter, wherein at least one HCR hairpin of the first-reporter-labeled HCR amplifier comprises one or more first reporters, and wherein at least one HCR hairpin of the second-reporter-labeled HCR amplifier comprises one or more second reporters. In accordance with some implementations, the method further comprises providing an anti-second-reporter bridging probe comprising a third HCR initiator and incubating so that the second HCR amplification polymer is decorated with third HCR initiators. In accordance with some implementations, the method further comprises providing a third-reporter-labeled HCR amplifier and incubating to initiate growth of a third-reporter-decorated HCR amplification polymer tethered to each third HCR initiator decorating the second HCR amplification polymer tethered to a second HCR initiator decorating the first HCR amplification polymer tethered to the first HCR initiator, wherein at least one HCR hairpin of the third-reporter-labeled HCR amplifier comprises one or more third reporters. In accordance with some implementations, the third reporter directly or indirectly mediates generation of a signal. In accordance with some implementations: (a) some or all of the first reporter, the second reporter, and the third reporter are the same, (b) some or all of the first-reporter-decorated HCR amplifier, the second-reporter-decorated HCR amplifier, and the third-reporter-decorated HCR amplifier have the same sequence, and/or (c) the first, second and third reporters can be the same or different, each comprising a hapten, fluorophore, a chromophore, or a rare-earth element or compound. In accordance with some implementations, the third reporter is used to mediate CARD signal amplification. In accordance with some implementations, the anti-reporter initiator-labeled bridging probes used to bridge between different rounds of HCR signal amplification are the same. In accordance with some implementations, the method further comprises performing a wash step between any of steps (a)-(e). In accordance with some implementations, the method further comprises removing the signal following step (e). In accordance with some implementations, the method further comprises repeating any of steps (a)-(f). In accordance with some implementations, an HCR amplifier comprises two or more HCR hairpins. In accordance with some implementations, an HCR hairpin comprises an input domain comprising a single-stranded toehold and a stem section. In accordance with some implementations, an HCR hairpin further comprises an output domain comprising a single-stranded loop and a complement to the stem section. In accordance with some implementations, the target comprises an RNA molecule, a DNA molecule, a protein, a small molecule, a chemical, a biological molecule, a pathogen, a complex of molecules, or a set of molecules in proximity. In accordance with some implementations, the first reporter, the second reporter, and the third reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

BRIEF DESCRIPTION OF THE DRAWINGS

FIG. 3A depicts some embodiments of fractional-initiator probes colocalized by a target and FIGS. 3B-3C display test tube data demonstrating triggering HCR using fractional-initiator probes colocalized by a target.

FIGS. 5A-5D depict multiplex imaging of mRNA expression with high signal-to-background in a fixed whole-mount chicken embryo using fractional-initiator probes without probe set optimization.

FIGS. 8A-8D depict some embodiments of HCR IF using initiator-labeled probes and FIGS. 8E-8F depict some embodiments of HCR RNA-FISH/IF using fractional-initiator probes for RNA targets and initiator-labeled probes for protein targets.

FIGS. 9A-9B depict HCR IF for multiplex imaging of protein expression with high signal-to-background in an FFPE mouse brain tissue section using initiator-labeled primary antibody probes.

FIGS. 10A-10B depict HCR IF for multiplex imaging of protein expression with high signal-to-background in an FFPE mouse brain tissue section using primary antibody probes and initiator-labeled secondary antibody probes.

FIGS. 13A-13B depict HCR RNA-FISH/IF for simultaneous multiplex imaging of RNA and protein targets with high signal-to-background in an FFPE mouse brain tissue section using fractional-initiator probes to detect RNA targets and primary antibody probes and initiator-labeled secondary antibody probes to detect protein targets, with HCR signal amplification performed for all targets simultaneously.

FIGS. 19A-19F depict some embodiments of initiator-labeled probes.

FIGS. 21A-21D depict some embodiments of fractional-initiator probes colocalized by a target.

FIGS. 22A-22E depict some embodiments of fractional-initiator probes colocalized by a target complex.

FIGS. 31A-31C depict some embodiments of an example of in vitro optimization of cooperative probe junctions to enhance fractional-initiator HCR suppression (OFF state) and conversion (ON state).

FIG. 39A-39B depict some embodiments of ultrasensitive HCR IHC for chromogenic staining of protein targets using HCR to mediate CARD.

FIG. 56A-56N depict some embodiments of reporter-labeled signal probes.

FIGS. 58A-58C depict some embodiments of reporter-labeled signal probes, initiator-labeled signal probes, fractional-initiator signal probes, and proximity probes.

FIGS. 59A-59F depict some embodiments of reporter-labeled signal probes and initiator-labeled signal probes.

FIGS. 63A-63E depict some embodiments of cooperative probe junctions for fractional-initiator probes.

FIG. 68D depicts some embodiments of detection of targets in a complex or in proximity using anti-target reporter-labeled primary probes, anti-reporter fractional-initiator secondary probes, and a proximity probe.

FIGS. 68E-68I depict some embodiments of detection of targets in a complex or in proximity using a proximity probe and different signal probe compositions for each of the two targets that are in a complex or are in proximity.

FIGS. 69A-69B depict some embodiments for HCR imaging of protein:protein target complexes using primary antibody probes with or without secondary antibody probes.

FIG. 73 depicts some embodiments of nonlinear HCR signal amplification comprising: an anti-target signal probe comprising a first HCR initiator triggering a first round of HCR signal amplification; bridging to a second HCR initiator and triggering a second round of HCR signal amplification; and bridging to a third HCR initiator and triggering a third round of HCR signal amplification.

DETAILED DESCRIPTION

Figure 1A:
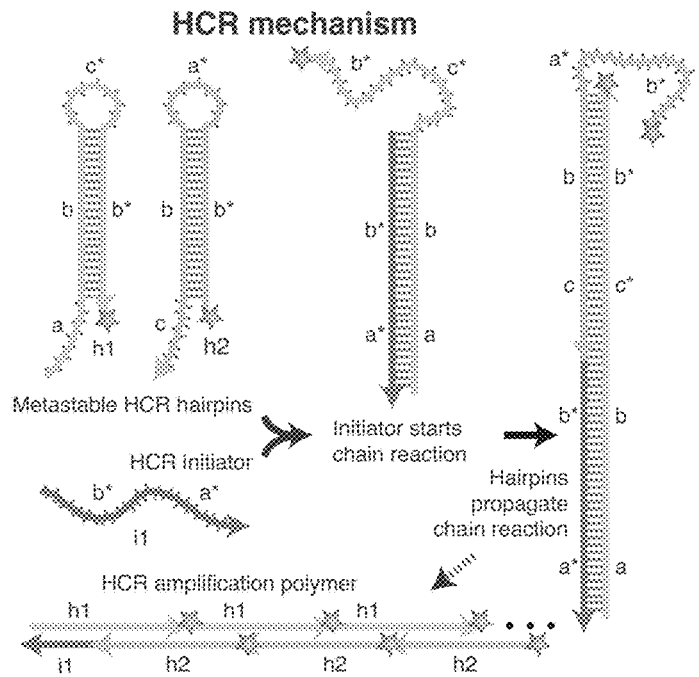
FIGS. 1A-1C depicts some embodiments of HCR RNA-FISH using initiator-labeled probes.
Figure 1B:
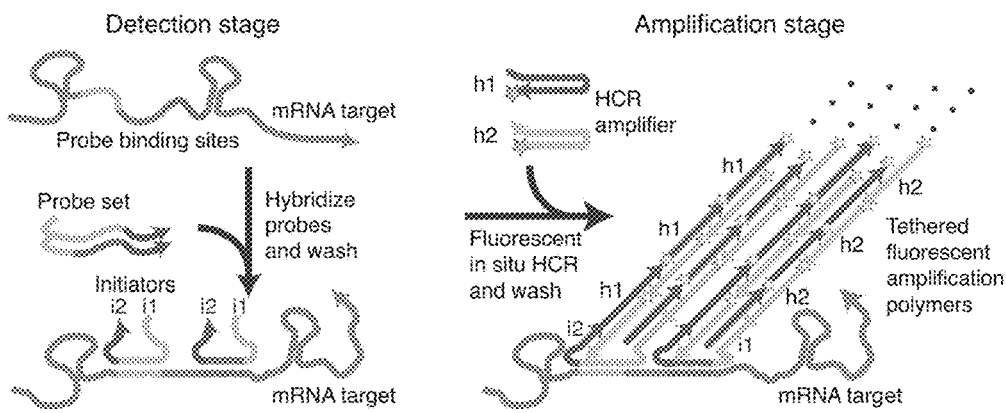
Figure 1C:
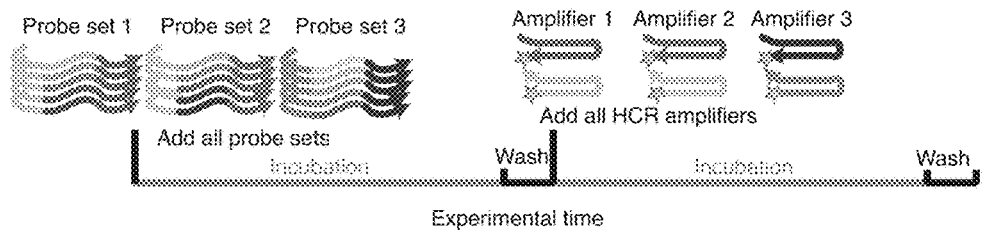
Figure 2A:
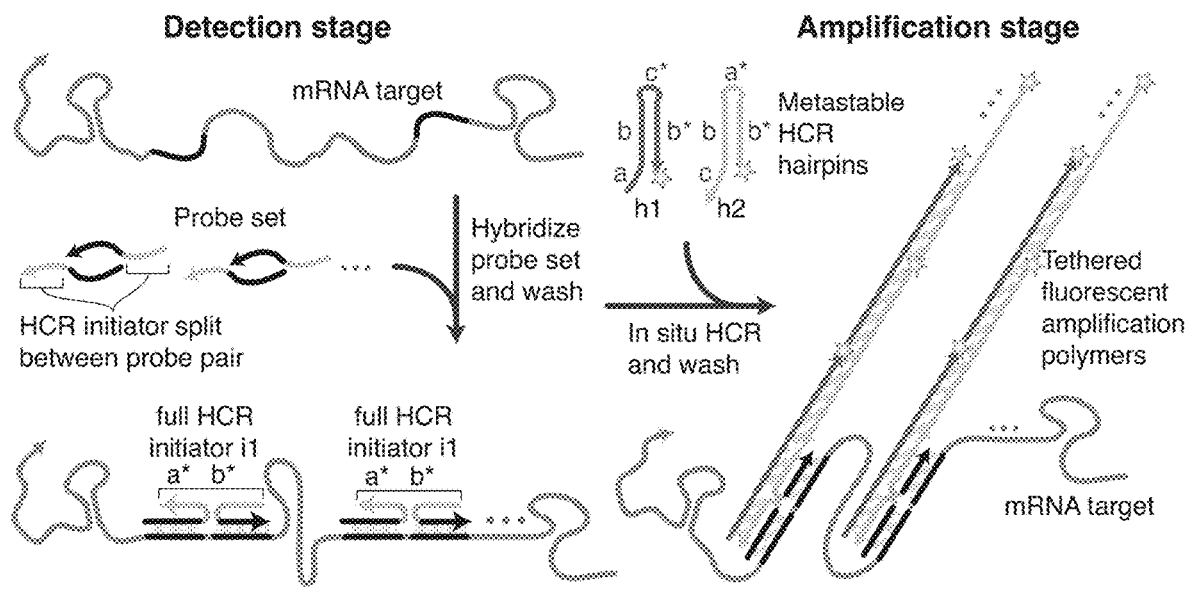
FIGS. 2A-2B depict some embodiments of HCR RNA-FISH using fractional-initiator probes.
Figure 2B:
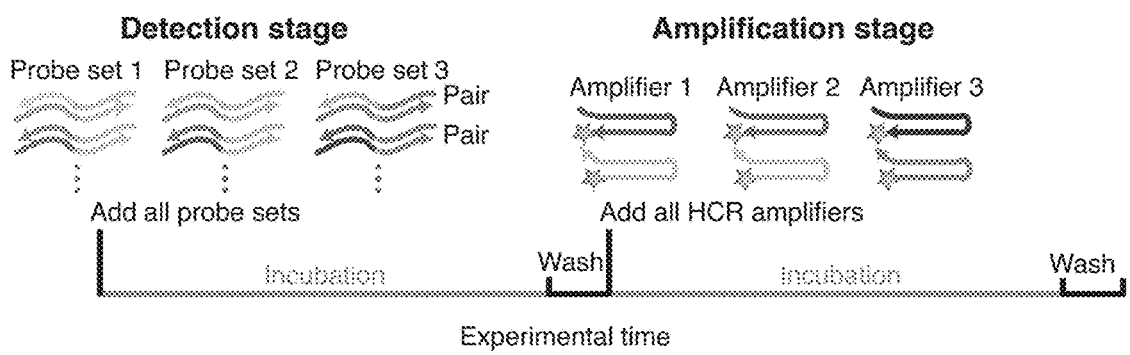

Signal amplification based on the mechanism of hybridization chain reaction (HCR)[1] enables detection of molecular targets within fixed biological samples, for example cells or tissues.[2-8] Target molecules are detected within the fixed sample using probes that trigger chain reactions in which reporter-labeled HCR hairpins self-assemble into tethered reporter-decorated HCR amplification polymers, generating amplified signals at the locations of target molecules or target complexes in situ within a sample (for example, see FIGS. 1B and 2A).[2-9] RNA targets can be imaged within fixed samples using fluorescent staining with HCR RNA fluorescence in situ hybridization (HCR RNA-FISH) or with chromogenic staining using HCR RNA chromogenic in situ hybridization (HCR RNA-CISH). DNA targets can be imaged within fixed samples using fluorescent staining with HCR DNA fluorescence in situ hybridization (HCR DNA-FISH) or with chromogenic staining using HCR DNA chromogenic in situ hybridization (HCR DNA-CISH). Protein targets can be imaged within fixed samples using fluorescent staining with HCR immunofluorescence (HCR IF) or with chromogenic staining with HCR immunohistochemistry (IHC). Target molecules that are bound to each other in a complex or are in proximity can be imaged within fixed samples using either fluorescent or chromogenic staining. In contrast to branched DNA in situ hybridization methods[10-12], which require use of long preamplifier and amplifier strands in order to achieve strong signal amplification, making it challenging for bDNA amplification reagents to penetrate deep into fixed samples, HCR signal amplification is performed using small HCR hairpins that penetrate deep into fixed samples before growing a long HCR amplification polymer at the site of the target, thus enabling strong signal amplification while also achieving deep sample penetration.[2-8]

Hybridization Chain Reaction (HCR) Signal Amplification

In some embodiments, a target is detected using a signal probe set comprising one or more initiator-labeled probes each comprising a target-binding domain and an amplification domain comprising one or more HCR initiators (for example, FIGS. 18A-18N, 19A-19F, 52A, 54, 60C, 71). In some embodiments, a target is detected using a signal probe set comprising one or more primary probes each comprising a target-binding domain and one or more reporters and one or more secondary probes each comprising a reporter-binding domain and an amplification domain comprising one or more HCR initiators (for example, FIGS. 58A-58C, 59A-59F, and 60A-60D). In some embodiments, a target is detected within a sample using a signal probe set comprising one or more probe units (for example see the probe sets of FIGS. 2A-2B and 64A-64D), where a probe unit comprises two or more fractional-initiator probes (for example see the probe units of FIGS. 20A-20E, 21A-21D, 22A-22E, 47A, 65A-65C, and 71), where each fractional-initiator probe comprises a target-binding domain and an amplification domain comprising a fractional initiator (for example, see the fractional-initiator probes of FIGS. 23, 47A, 65A-65C, and 71). In some embodiments, binding of each probe within a probe unit to adjacent cognate binding sites on the target colocalizes the fractional initiators to form a colocalized full HCR initiator (for example, see the colocalized full HCR initiators of FIGS. 2A, 20A-20E, 21A-21D, 22A-22E, 24A-24R, 37C, 38A-38B, 47A, 61A-61-E, 64A-64D, and 71) capable of triggering HCR signal amplification. In some embodiments, each fractional-initiator probe within a probe unit further comprises a proximity domain (for example, see FIGS. 58C, 68A-68I, and 69A-69C). In some embodiments, binding of each fractional-initiator probe within a probe unit to cognate binding sites on proximal targets enables binding of one or more proximity probes to the proximity domains within the probe unit to colocalize the fractional initiators to form a colocalized full HCR initiator (for example, see FIGS. 58C, 68A-68B, 68D-68I, and 69A-69C) capable of triggering HCR signal amplification.

In some embodiments, HCR signal amplification increases the signal strength by a factor of 2, 5, 10, 15, 20, 25, 30, 40, 50, 75, 100, 500, 1000, 2000, 5000, 10,000, 20,000, 50,000, or 100,000-fold, or a value within a range defined by any two of the aforementioned values.

In some embodiments, the target-binding domains within a probe unit are configured to bind to overlapping or non-overlapping regions of the target (for example, see FIGS. 2A-2B, 28, 29, and 30). In some embodiments, the fractional-initiators within a probe unit are designed to hybridize to overlapping or non-overlapping regions of an HCR hairpin (for example, see FIGS. 2A-2B, 28, 29, and 30). In some embodiments, individual fractional-initiator probes that bind non-specifically do not colocalize a full HCR initiator, suppressing spurious generation of amplified HCR background.

In some embodiments, an HCR amplifier comprises two or more HCR hairpins (for example, see the HCR amplifiers of FIGS. 1A-1B, 17A-17F, and 16A-16B). In some embodiments, each HCR hairpin (also known as an HCR monomer or an HCR hairpin monomer or a hairpin monomer) comprises an input domain comprising a single-stranded toehold and a stem section, and an output domain comprising a single-stranded loop and a complement to the stem section (for example, see the HCR hairpins of FIGS. 1A-1B, 14, 15, 16A-16B, and 17A-17F). In some embodiments, the one or more HCR initiators on an initiator-labeled probe each initiate a chain reaction of polymerization steps in which the initiator hybridizes to the input domain of a first HCR hairpin, opening the first hairpin to expose its output domain, which in turn hybridizes to the input domain of a second HCR hairpin, opening the second hairpin to expose its output domain, and so on and so forth, leading to a chain reaction in which hairpins polymerize to yield an HCR amplification polymer tethered to the target (for example, see the amplification polymers of FIGS. 14, 15, 16A-16B, 25A, 25C-25E, 26A, 39A-39B, 41A, and 60A). In some embodiments, in the absence of an HCR initiator of a colocalized full HCR initiator, HCR hairpins are kinetically trapped and do not polymerize, suppressing background. However, if the fractional-initiator probes within a probe unit bind to their adjacent cognate binding sites on the target to colocalize a full HCR initiator, the colocalized full HCR initiator (also known as a colocalized full initiator or a full HCR initiator or a full initiator) initiates a chain reaction of polymerization steps in which the colocalized full HCR initiator hybridizes to the input domain of a first HCR hairpin, opening the first hairpin to expose its output domain, which in turn hybridizes to the input domain of a second HCR hairpin, opening the second hairpin to expose its output domain, which in turn hybridizes to the input domain of second copy of the first HCR hairpin, opening the second copy of the first hairpin to expose its output domain, which in turn hybridizes to the input domain of second copy of the second HCR hairpin, opening the second copy of the second hairpin to expose its output domain, and so on and so forth, leading to a chain reaction in which first and second HCR hairpins polymerize in alternating fashion to yield an HCR amplification polymer tethered to the target (for example, see the amplification polymers of FIGS. 2A, 17C-17F, 16A-16B, 33, 35A, 47A).

In some embodiments, an HCR hairpin further comprises zero, one, or more reporters that directly or indirectly lead to generation of an amplified signal (for example, see FIG. 17A-17F). In some embodiments, the zero, one, or more reporters on an HCR hairpin serve to mediate an additional layer of signal amplification via HCR (see for example, FIGS. 45, 47A-47B, 49A-49B, 51A, 52A-52B, 60C-60D, 71) or via catalytic reporter deposition (CARD) (see for example, FIGS. 25A-25E, 26A-26C, 33, 35A, 39A-39B, 41A, 43, 60A-60B) or via both HCR and CARD (see for example, FIGS. 38A-38B). In some embodiments, a reporter on an HCR hairpin comprises a fractional reporter such that an auxiliary-reporter-labeled readout probe does not strongly bind the fractional reporter on an individual hairpin, but such that following HCR polymerization, neighboring hairpins in the HCR amplification polymer colocalize a full reporter such that the colocalized full reporter (also known as a full reporter) strongly binds an auxiliary-reporter-labeled readout probe (for example, FIGS. 17D and 27B). In some embodiments, a readout probe comprises one or more auxiliary reporters and further comprises a reporter-binding domain configured to bind a reporter on an HCR amplification polymer or configured to bind a colocalized full reporter (also known as a full reporter) within an HCR amplification polymer (for example, see the readout probes of FIGS. 27A-27B). In some embodiments, amplified signal is generated by one or more reporters or auxiliary reporters associated with an HCR amplification polymer tethered to the target within the sample. In some embodiments, signal is removed from the sample. In some embodiments, HCR signal is generated, detected, and removed from the sample one or more times.

In some embodiments, an HCR amplifier comprises (for example, see FIGS. 1A and 15): 1) a first HCR hairpin (h1) comprising a first input domain (sequence domains "a-b") comprising a first toehold (sequence domain "a") and a first stem section (sequence domain "b"), and a first output domain (sequence domains "c*-b*") comprising a first loop (sequence domain "c*") and a partner to the first stem section (sequence domain "b*") that is configured to bind the first stem section, and 2) a second HCR hairpin (h2) comprising a second input domain (sequence domains "b-c") comprising a second toehold (sequence domain "c") and a second stem section (sequence domain "b"), and a second output domain (sequence domains "b*-a*") comprising a second loop (sequence domain "a*") and a partner to the second stem section (sequence domain "b*") that is configured to bind the second stem section. In some embodiments, a first initiator (i1; sequence domains "b*-a*") comprises a partner to the first toehold (sequence domain "a*") and a partner to the first stem section (sequence domain "b*"). In some embodiments, the first initiator is configured to bind the first input domain. In some embodiments, binding of the first initiator to the first input domain opens the first HCR hairpin to expose the first output domain. In some embodiments, the exposed first output domain is configured to bind the second input domain. In some embodiments, binding of the exposed first output domain to the second input domain opens the second HCR hairpin to expose the second output domain. In some embodiments, the exposed second output domain is configured to bind the first input domain. In some embodiments, binding of the exposed second output domain to the first input domain leads to HCR polymerization in which first and second HCR hairpins are successively opened and added to the growing polymer in alternating fashion.

In some embodiments, a second initiator (i2; domains "c*-b*") is configured to bind the second input domain. In some embodiments, binding of the second initiator to the second input domain opens the second HCR hairpin to expose the second output domain. In some embodiments, the exposed second output domain is configured to bind the first input domain. In some embodiments, binding of the exposed second output domain to the first input domain opens the first HCR hairpin to expose the first output domain. In some embodiments, the exposed first output domain is configured to bind the second input domain. In some embodiments, binding of the exposed first output domain to the second input domain leads to HCR polymerization in which second and first HCR hairpins are opened and add to the growing polymer in alternating fashion.

In some embodiments, the first and second HCR hairpins are kinetically trapped so that they do not polymerize except in the presence of the first or second HCR initiators.

Additional information about HCR, fractional initiators, and uses thereof can be found in U.S. Pat. No. 10,450,599, filed on Jun. 30, 2017, with the title "Fractional Initiator Hybridization Chain Reaction" hereby expressly incorporated by reference in its entirety. Further information about HCR and uses thereof can be found in US20220282300A1, filed on Feb. 22, 2022, with the title "Analysis of Target Molecules within a Sample via Hybridization Chain Reaction", and PCT/US2024/017915, filed on Feb. 29, 2024, with the title "Probes for Measuring Molecular Proximity in a Sample", each hereby expressly incorporated by reference in its entirety.

HCR initiators. In some embodiments, an initiator-labeled probe comprises one or more HCR initiators capable of initiating an HCR polymerization cascade leading to growth of an HCR amplification polymer tethered to the initiator. In some embodiments, an initiator is fully complementary to the input domain of an HCR hairpin such that it hybridizes to the input domain of the hairpin to open the hairpin and initiate the HCR polymerization cascade. In some embodiments, the initiator is partially complementary to the input domain of an HCR hairpin, but sufficiently complementary such that it hybridizes to the input domain of the hairpin to open the hairpin and initiate the HCR polymerization cascade. In some embodiments, the initiator is shorter or longer than the input domain of an HCR hairpin and/or has incomplete complementarity to the input domain of the hairpin, but is able to hybridize to the input domain of the hairpin to open the hairpin and initiate the HCR polymerization cascade. In some embodiments, an HCR initiator might have 50%, 60%, 70%, 80%, 90%, or 100% (or any intermediate value between any of these values) complementarity to the input domain of an HCR hairpin, and hybridize to the input domain of the hairpin to open the hairpin and initiate the HCR polymerization cascade. In some situations, initiator-labeled probes comprising one or more initiators may cause increased background due to non-specific binding of initiators to DNA, RNA, proteins, or other molecules within the sample. In some embodiments, the initiators on an initiator-labeled probe are shielded by base-pairing to reduce non-specific binding of the probe within the sample (and thereby to reduce background). In some embodiments, the initiator can be shielded by a hairpin structure. In some embodiments, the initiator can be shielded by one or more auxiliary oligos. In some embodiments, the initiator can be shielded by self-complementarity within the oligo comprising an initiator and/or complementarity to one or more auxiliary strands.

Automatic background suppression with HCR fractional-initiator probes. In some embodiments, fractional-initiator probes automatically suppress background because the HCR initiator is split between a pair of probes (for example, see FIGS. 2-4, 33, 38, 45, 49, 58C, 61-63, and 68A-68I). In some embodiments, if probes bind specifically to the target at proximal cognate binding sites, the target colocalizes the two probes within a probe pair to form a colocalized full HCR initiator (also known as a full HCR initiator or a full initiator or a colocalized full initiator). In some embodiments, individual fractional-initiator probes that bind non-specifically do not trigger HCR since each probe carries only a fraction of an HCR initiator, and HCR signal amplification is triggered only if the full HCR initiator is colocalized.

Automatic background suppression with HCR hairpins. In some embodiments, HCR hairpins automatically suppress background because HCR hairpins are kinetically trapped so they do not polymerize in the absence of an HCR initiator. In some embodiments, if both probes within a fractional-initiator probe pair bind specifically to their proximal cognate binding sites on the target, the resulting colocalized full HCR initiator triggers growth of a tethered HCR amplification polymer (for example, see FIG. 2A). In some embodiments, individual HCR hairpins that bind non-specifically do not trigger HCR as they are kinetically trapped.

Automatic background suppression with HCR fractional-initiator probes and HCR hairpins. In some embodiments, the combination of HCR fractional-initiator probes for target detection and HCR amplification hairpins for signal amplification provide automatic background suppression throughout the protocol, ensuring that reagents will not generate amplified background even if they bind non-specifically.

HCR with Cooperative Probe Junctions

Some embodiments of cooperative probe junctions are depicted in FIGS. 28A-28B, 29, 30, 61A-61E, 62A-62D, 63A-63E, 68A-68C, 69A-69B. In some embodiments, a target is detected using a probe set comprising one or more probe units each comprising two or more fractional-initiator probes. In some embodiments, a fractional-initiator probe comprises a target-binding region, a linker region, and a fractional-initiator. In some embodiments, the target-binding regions on the probes within a probe unit are configured to bind to overlapping or non-overlapping binding sites on the target (FIGS. 28A-28B, 29, and 30). In some embodiments, the linker regions on the probes within a probe unit are configured to bind to each other (FIGS. 61A-61E, 62A-62D, 63A-63E). In some embodiments, the fractional-initiators on the probes within each probe unit are configured to bind to overlapping or non-overlapping binding sites on an HCR hairpin (FIGS. 28A-28B, 29, and 30). In some embodiments, binding of the probes within a probe unit to cognate binding sites on the target and optionally of the linker regions on the probes within a probe unit to each other leads to formation of a cooperative probe junction that facilitates target binding and colocalization of a full HCR initiator to efficiently trigger HCR signal amplification. In some embodiments, the colocalized full initiator initiates polymerization of the HCR monomers thereby generating a signal. In some embodiments, the cooperative probe junction increases the strength of HCR signal amplification.

In some embodiments, a cooperative probe junction comprises two or more fractional-initiator probes that are bound by a proximity probe at their proximity domains (for example, see FIGS. 68A-68I and 69A-69B). In some embodiments, a cooperative probe junction is utilized to conduct proximity measurements within a sample. In some embodiments, a fractional-initiator probe comprises a fractional initiator (also known as an HCR fractional initiator), a proximity domain, and a target-binding domain configured to bind directly to a target (for example, see FIGS. 68A, 68E, 68G, and 69A). In some embodiments, a fractional-initiator probe comprises a fractional initiator (also known as an HCR fractional initiator), a proximity domain, and a target-binding domain configured to bind indirectly to a target (for example, see FIGS. 68B, 68C-68I, and 69B). In some embodiments, different probe compositions are used for different targets in a complex or in proximity (for example, FIGS. 68E-68I). In some embodiments, a proximity domain is a sequence within a fractional-initiator probe that is configured to be bound by a proximity probe. In some embodiments, a fractional initiator is a sequence within a fractional-initiator probe that is unable on its own to trigger HCR signal amplification, but that when colocalized with one or more fractional initiators from one or more other fractional-initiator probes, for example, via binding of the fractional-initiator probes to one or more proximity probes, can form a cooperative probe junction that facilitates formation of a colocalized full HCR initiator (also known as a full HCR initiator, also known as a full initiator, also known as a colocalized full initiator) capable of triggering HCR signal amplification. In some embodiments, the colocalized full initiator initiates polymerization of the HCR monomers thereby generating a signal. In some embodiments, a fractional-initiator probe further comprises a linker region, wherein the linker regions on the probes within a probe unit are optionally configured to bind to each other.

In some embodiments: a first fractional-initiator signal probe comprises a first target-binding domain configured to bind directly or indirectly to a first target, a first proximity domain, and a first fractional initiator; a second fractional-initiator signal probe comprises a second target-binding domain configured to bind directly or indirectly to a second target, a second proximity domain, and a second fractional initiator; a proximity probe is configured to bind the first proximity domain and the second proximity domain (for example, see FIGS. 68A-68I and 69A-69B). In some embodiments, the first fractional initiator probe may additionally comprise a first linker region and the second fractional-initiator probe can additionally comprise a second linker region. In some embodiments, the first linker region is configured to bind to second linker region. In some embodiments, the first linker region binds the second linker region when the first and second linker region are in proximity to one another. In some embodiments, binding of the proximity probe to the first proximity domain and the second proximity domain colocalizes the first fractional initiator and the second fractional initiator. In some embodiments, binding of the proximity probe to the first proximity domain and the second proximity domain forms a cooperative probe junction that facilitates colocalization of the first fractional initiator and the second fractional initiator, colocalizing a full HCR initiator (also known as a full initiator) capable of triggering HCR signal amplification.

In some embodiments the first target and second target are in close enough proximity to each other that upon binding of a first fractional-initiator probe to the first target and binding of the second fractional-initiator probe to the second target, the proximity probe is able to bind to both the first proximity domain of the first fractional-initiator probe and the second proximity domain of the second fractional-initiator probe to form a cooperative probe junction. In some embodiments, the first target and the second target are bound to one another in a target complex (for example, see FIGS. 68A-68B, 68D-68I, and 69A-69B). In some embodiments, the first target and second target are not in a complex with each another but are in a complex with a third target. In some embodiments, the first target and second target are proximal but are not bound to each other. In some embodiments, the first target and the second target are the same molecule (for example, see FIG. 68C).

In some embodiments, the first fractional-initiator probe, the second fractional-initiator probe, and the proximity probe form a cooperative probe junction (for example, see FIGS. 69A-69B). In some embodiments the triggering of HCR occurs as the result of the formation of the cooperative probe junction and the colocalization of the first and second fractional initiators via the proximity probe and thus indicates that the first and second targets are proximal to each other in a sample.

HCR with Reporter-Labeled Signal Probes

Some embodiments of reporter-labeled signal probes are depicted in FIGS. 37B, 56A-56N, 57A-57B, 58A-58B, 59A-59F, 60A-60D. In some embodiments, a target is bound directly by a reporter-labeled signal probe (for example, FIGS. 37B, 56A-B, 56E-56J, 56M-56N, 57A-57B, 58A-58B, 59A-59F, 68D, and 68F-68I). In some embodiments, a target is bound indirectly by a reporter-labeled signal probe (for example, FIGS. 56C-56D and 56K-56L). In some embodiments, a reporter-labeled signal probe comprises one or more reporters (for example, FIGS. 56A-56N, 57A-57B, 58A-58B, 59A-59F, 68D, and 68F-68I). In some embodiments, a reporter labeled signal probe comprises multiple reporters (for example, FIGS. 56B, 56D, 56F, 56J, 56N, 57A-57B, 58B). In some embodiments, a target is detected by an anti-target reporter-labeled signal probe (for example, FIGS. 37B, 56A-56N, 57A-57B, 58A-58B, 59A-59F, 60A-60D, 68D, and 68F-68I) (for example, an anti-target reporter-labeled primary antibody; FIGS. 56I-56J, 59C-59D, 60A-60D), which in turn is detected by an anti-reporter initiator-labeled signal probe (for example, FIGS. 58A-58B, 59A-59F, 60A-60D, 68D, and 68F-68I) (for example, an anti-reporter initiator-labeled primary antibody; FIGS. 58A, 59C, and 60A-60D) or by two or more anti-reporter fractional-initiator probes (for example, FIG. 58B) (for example, two or more anti-reporter fractional-initiator primary antibodies).

In some embodiments, using reporter-labeled signal probes avoids the need to conjugate one or more initiators to the anti-target signal probe that contains a target-binding region, eliminating a potential source of interference with probe/target binding. Another strategy for avoiding conjugation of an initiator to an anti-target signal probe would be to use an unmodified anti-target primary antibody signal probe, and then to use an initiator-labeled secondary antibody to detect the primary antibody. However, this approach introduces challenges for multiplex imaging of multiple different targets in the same sample, since each anti-target primary antibody would need to be a different isotype or raised in a different host organism to enable specific detection by different secondary antibodies, or alternatively probes would need to be stripped from the sample after imaging each target and prior to imaging the next target. In some embodiments, using reporter-labeled signal probes avoids these difficulties and enables straightforward multiplexing as the anti-target reporter-labeled signal probe can be detected by an anti-reporter initiator-labeled signal probe (for example, FIG. 58A, 59A-59F, 60A-60D). For example, in some embodiments, the target can be detected by an anti-target reporter-labeled primary antibody (FIGS. 56I-56J, 59C-59D, 60A-60D) which is in turn detected by an anti-reporter initiator-labeled primary antibody (FIGS. 58A, 59C, and 60A-60D). Notably, in some embodiments, two layers of primary antibodies are used and no secondary antibodies are used. In some embodiments, either of the two layers of primary antibodies can instead be a primary nanobody (FIGS. 59B, 59D-59F). For multiplexing using reporter-labeled signal probes, all targets can be detected at the same time by different anti-target primary antibodies (or anti-target primary nanobodies) each of the same isotype or raised in the same host organism, but labeled with different reporters (FIGS. 60A-60D). These reporters can then all be detected at the same time by different anti-reporter initiator-labeled primary antibodies (or anti-reporter initiator-labeled primary nanobodies), where the initiator sequence is different for each target (FIGS. 60A-60D). In some embodiments, reporter-labeled signal probes enhance probe/target binding and/or facilitate straightforward multiplexing.

Figure 37A:
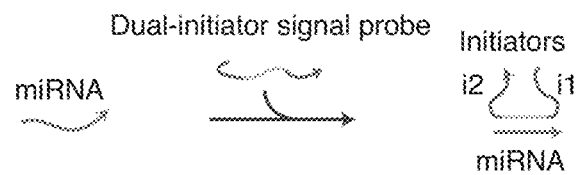
FIG. 37A-37C depict some embodiments of probes for detecting short RNA targets including miRNAs and mRNA splice junctions.
Figure 37B:
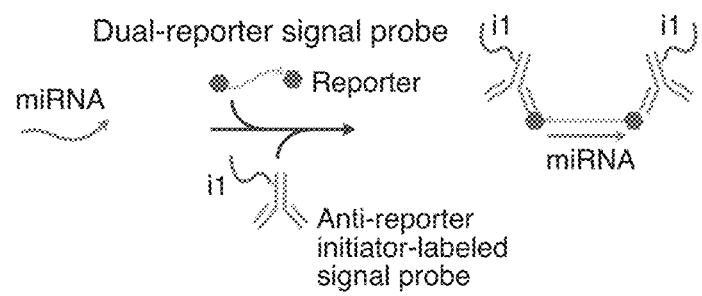
Figure 37C:
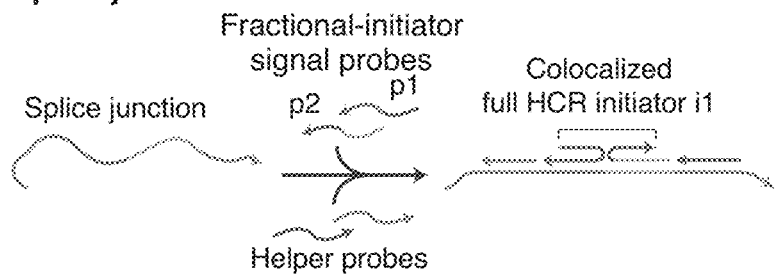

In some embodiments, a target is detected with an anti-target reporter-labeled primary signal probe (for example, FIGS. 58A-58B, 59A-59F, 60A, 60C). In some embodiments, the anti-target reporter-labeled primary signal probe comprises multiple reporters (for example, FIGS. 56B, 56D, 56F, 56J, 56N, 57A-57B, 58B). In some embodiments, the anti-target reporter-labeled primary signal probe is detected with an anti-reporter initiator-labeled secondary signal probe (for example, FIGS. 58A, 59A-59F, 60A, 60C). In some embodiments, the anti-target reporter-labeled primary signal probe is detected with an anti-reporter fractional-initiator secondary signal probe (for example, FIG. 58B). In some contexts, labeling an anti-target signal probe with one or more initiators may inhibit binding of the probe to the target or cause increased background due to non-specific binding mediated by the one or more initiators. In some embodiments, the target comprises a small RNA or another oligonucleotide and the anti-target signal probe is a nucleic acid probe labeled with one or more initiators at one or both ends (for example, FIG. 37A), or alternatively, the anti-target signal probe is a nucleic acid probe labeled with one or more reporters (for example, FIG. 37B), which are in turn detected by an anti-reporter initiator-labeled secondary signal probe. In some embodiments, use of an anti-target reporter-labeled primary signal probe and an anti-reporter initiator-labeled secondary signal probe increases the strength of probe:target binding relative to use of an anti-target initiator-labeled signal probe. In some embodiments, use of an anti-target reporter-labeled primary signal probe and an anti-reporter initiator-labeled secondary signal probe reduces background relative to use of an anti-target initiator-labeled signal probe.

Figures 60A, 60B:
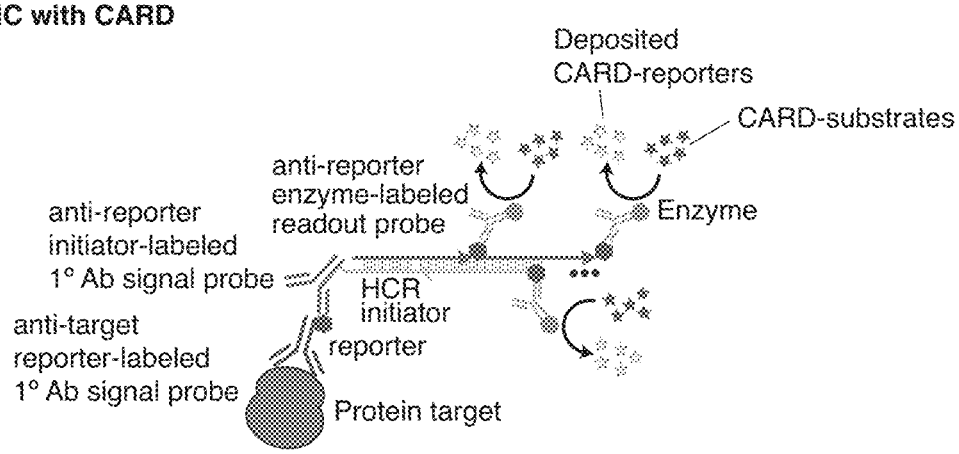
FIGS. 60A-60D depict some embodiments of ultrasensitive multiplex HCR IHC and ultrasensitive multiplex HCR IF using anti-target reporter-labeled signal probes and anti-reporter initiator-labeled signal probes.
Figures 60C, 60D:
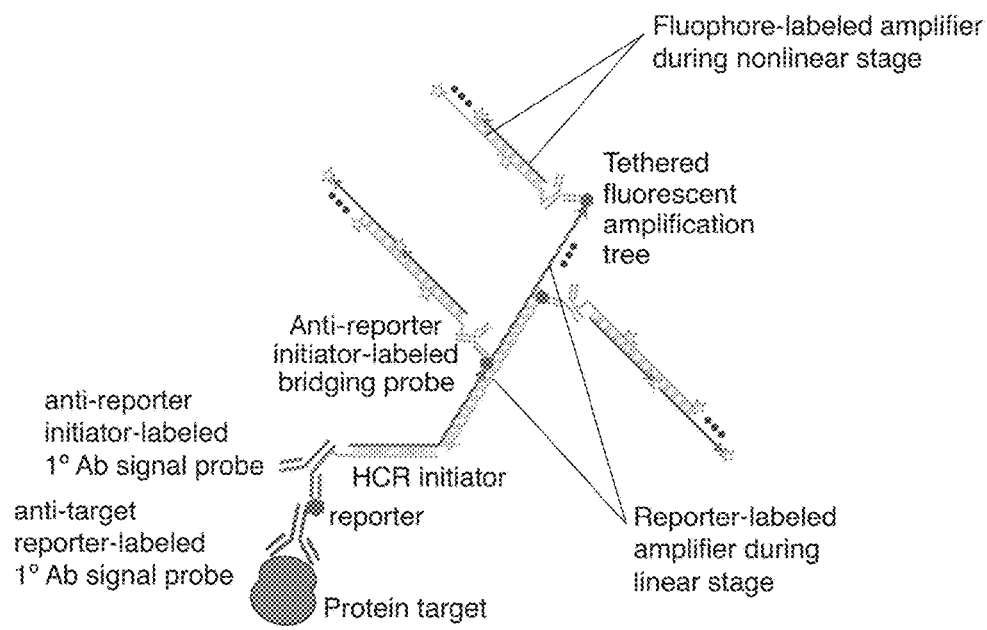
Figure 61A:
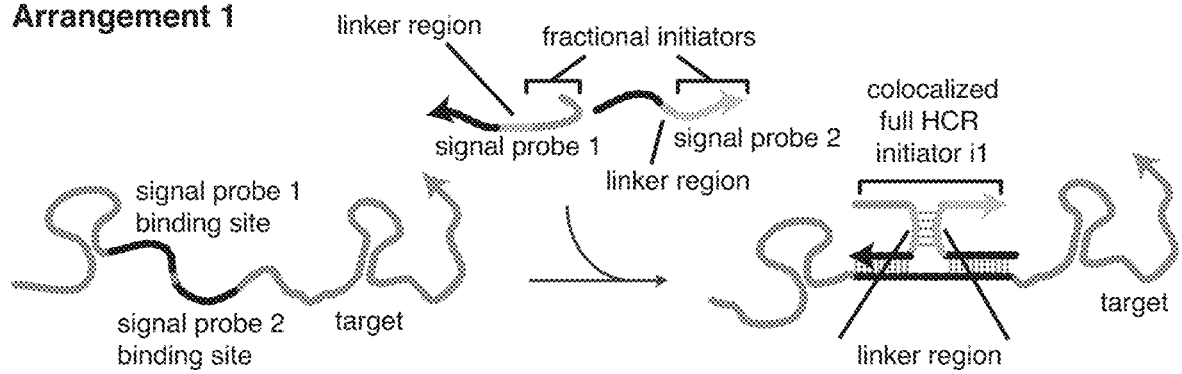
FIGS. 61A-61E depict some embodiments of cooperative probe junctions for fractional-initiator probes.
Figure 61B:
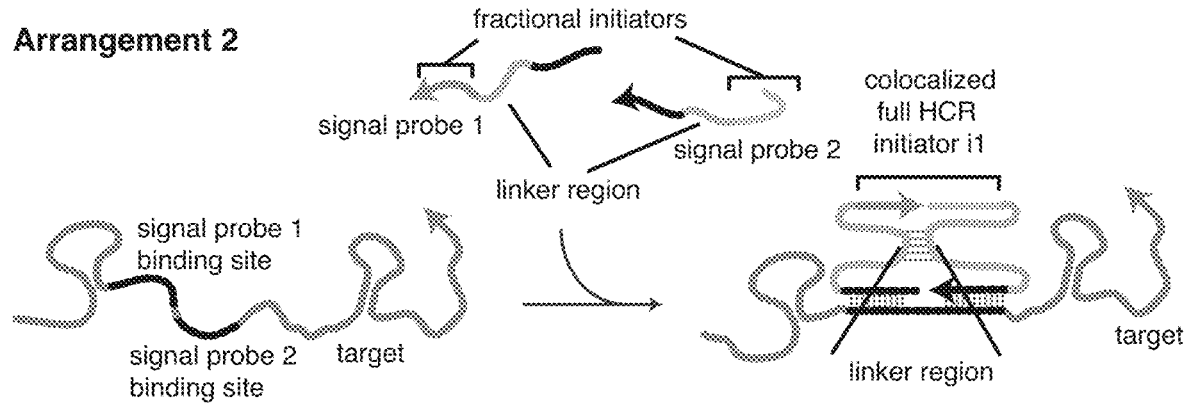
Figure 61C:
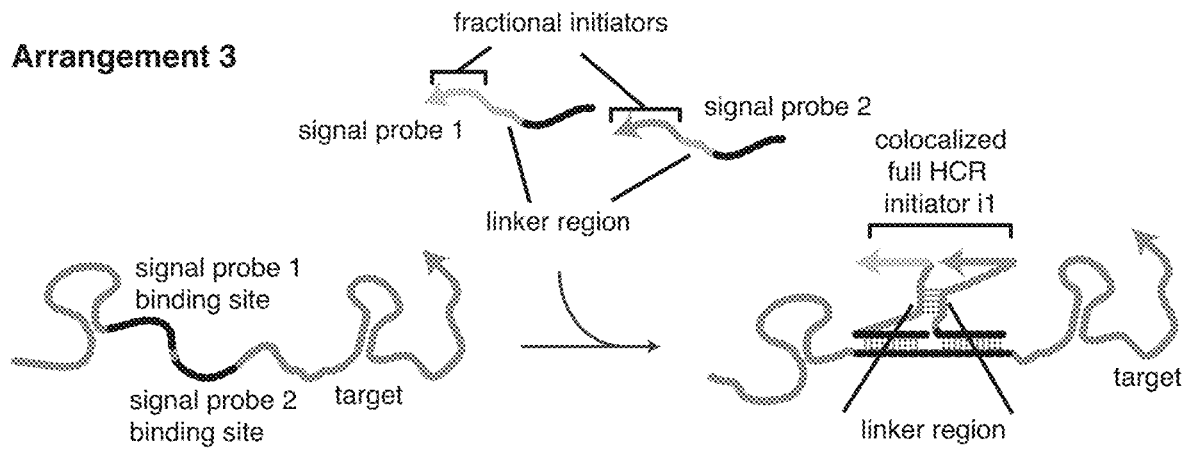
Figure 61D:
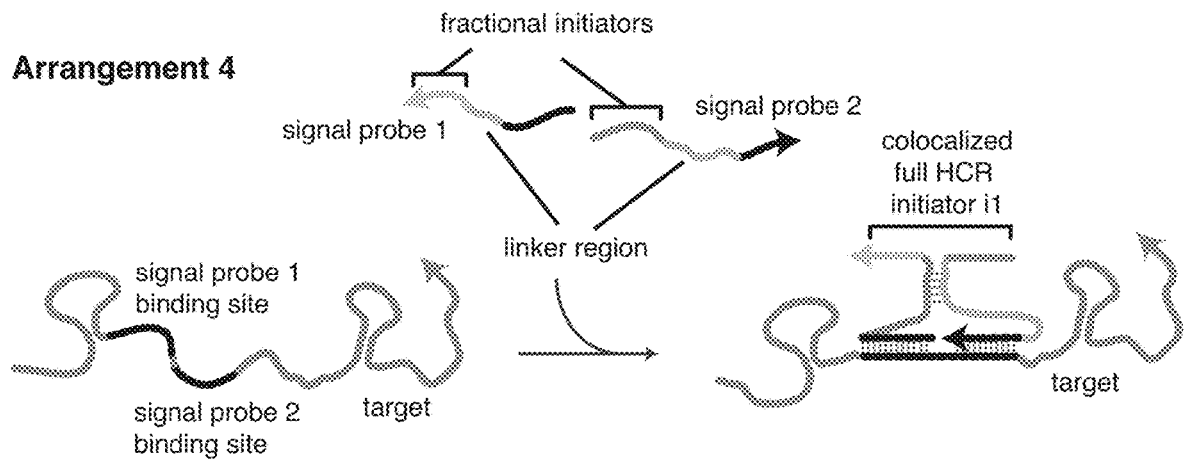
Figure 61E:
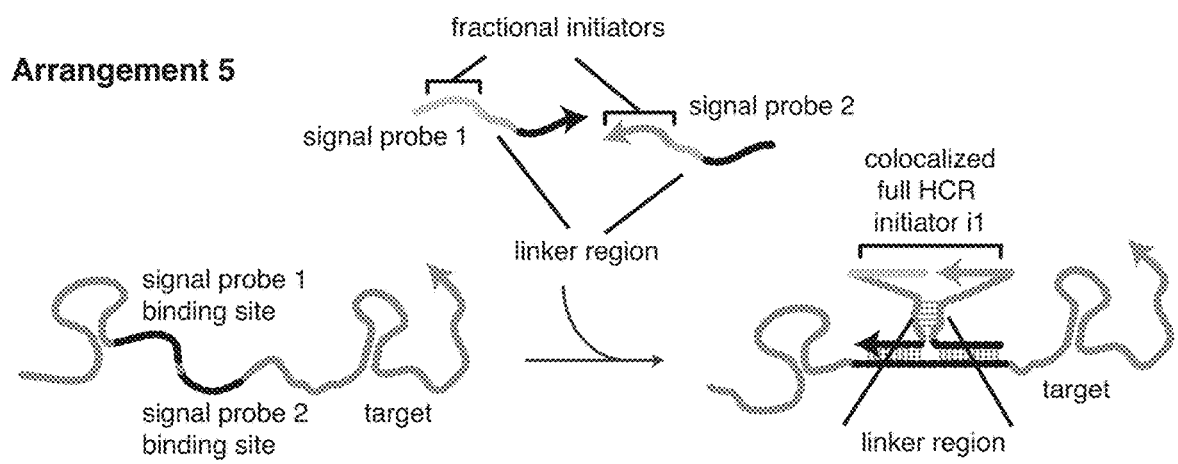
Figure 62B:
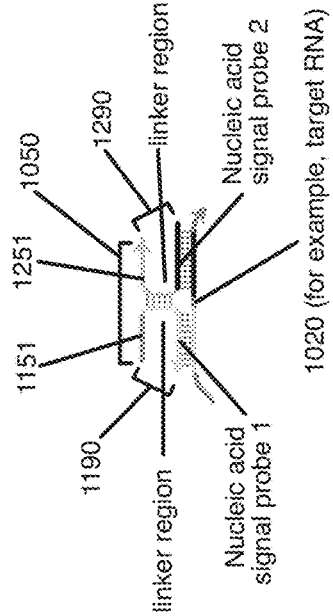
FIGS. 62A-62D depict some embodiments of cooperative probe junctions for fractional-initiator probes.
Figure 62D:
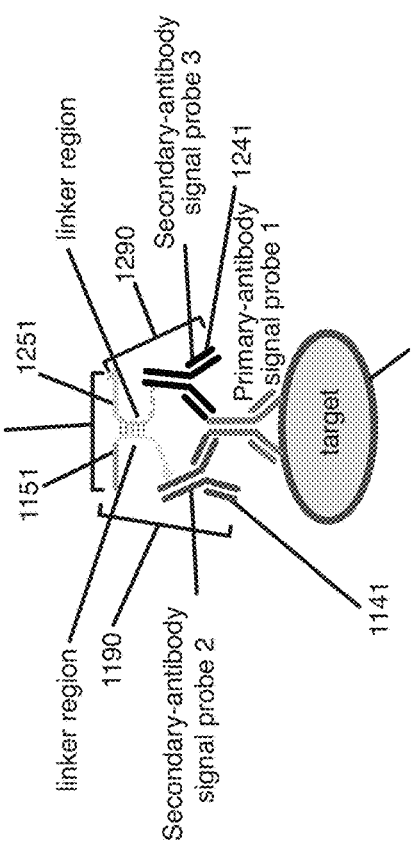
Figure 62A:
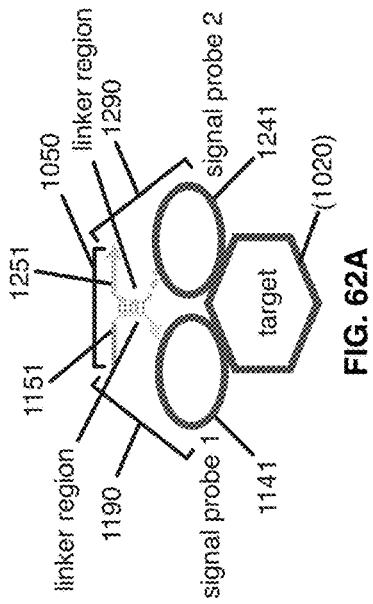
Figure 62C:
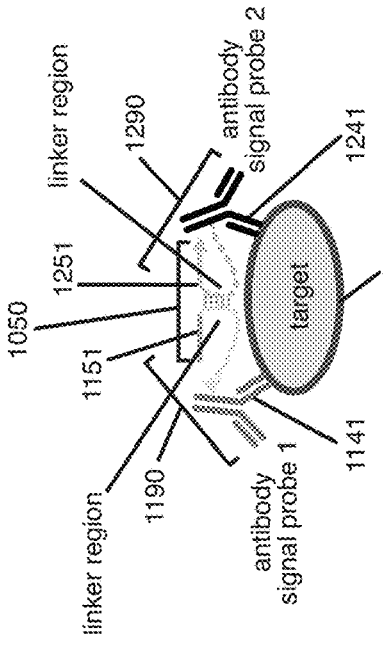

In some embodiments, a reporter-labeled signal probe is used to perform HCR imaging with or without catalytic reporter deposition (CARD) (for example, FIGS. 60A and 60C). In some embodiments, the target is detected with an anti-target reporter-labeled signal probe, which in turn is detected with an anti-reporter initiator-labeled signal probe (for example, FIGS. 60A and 60C). In some embodiments, HCR signal amplification is performed using an auxiliary-reporter-labeled HCR amplifier to generate auxiliary-reporter-decorated HCR amplification polymers tethered to the target. In some embodiments the HCR signal amplification is linear (for example, FIG. 60A) or nonlinear (for example, FIGS. 38A-38B, 60C, and 73). In some embodiments, an anti-auxiliary-reporter enzyme-labeled readout probe is used to bind the auxiliary reporters on the HCR amplification polymer and mediate CARD signal amplification directly or indirectly (for example, FIGS. 38A-38B and 60A). In some embodiments, the readout probe acts on CARD-substrates to catalyze deposition of CARD-reporters in the vicinity of the target. In some embodiments, the reporter that labels the anti-target signal probe is the same as the auxiliary reporter that labels the HCR amplifier. In some embodiments, CARD signal amplification generates a fluorescent signal or a chromogenic signal.

In some embodiments, reporter-labeled signal probes are used to perform HCR imaging with or without catalytic reporter deposition (CARD) for two targets in a complex or in proximity. In some embodiments, two targets (Target1 and Target2) in a complex or in proximity are detected using an anti-Target1 Reporter1-labeled signal probe to bind Target1, and an anti-Target2 Reporter2-labeled signal probe to bind Target2 (for example, FIGS. 58C and 68D). In some embodiments, Reporter1 is then detected using an anti-Reporter1 signal probe comprising fractional initiator1 and proximity domain1, and Reporter2 is detected using an anti-Reporter2 signal probe comprising fractional initiator2 and proximity domain2 (for example, FIGS. 58C and 68D). In some embodiments, if and only if Target1 and Target2 are in a complex or in proximity, proximity domain 1 and proximity domain 2 are close enough to bind simultaneously to a proximity probe to colocalize a full HCR initiator i1 capable of triggering HCR signal amplification (for example, see FIGS. 58C and 68D). In some embodiments, HCR signal amplification is performed using auxiliary-reporter-labeled hairpins to generate tethered fluorescent amplification polymers. In some embodiments the HCR signal amplification is linear (for example, FIG. 60A) or nonlinear (for example, FIGS. 38A-38B and 73). In some embodiments, the auxiliary reporter is a hapten, a fluorophore, a chromophore, or a rare-earth element or compound. In some embodiments, the auxiliary reporter mediates CARD signal amplification. In some embodiments, an anti-auxiliary-reporter enzyme-labeled readout probe is used to bind the auxiliary reporters on the HCR amplification polymer and mediate CARD signal amplification directly or indirectly. In some embodiments, the readout probe acts on CARD-substrates to catalyze deposition of CARD-reporters in the vicinity of the target. In some embodiments, CARD signal amplification generates a fluorescent signal or a chromogenic signal.

In some embodiments, HCR imaging with or without catalytic reporter deposition (CARD) is performed for two or more targets in a complex or in proximity using one or more proximity probes in conjunction with possibly different signal probe compositions for each target that is in a complex or in proximity, wherein at least one target that is in a complex or in proximity is detected using a reporter-labeled signal probe that is in turn detected by an anti-reporter signal probe (for example, FIGS. 68F-68I). In some embodiments, the targets that are in a complex or in proximity can be the same or different types of molecules. For example, for three targets in a complex or in proximity, one target could be a protein, one target could be an RNA, and one target could be a DNA; or for example, all three targets could be proteins; or for example, two targets could be proteins and one target could be an RNA, and so forth. For example, for two targets in a complex or in proximity, one target could be a protein and one target could be an RNA, or one target could be a protein and one target could be a DNA, or one target could be an RNA and one target could be DNA, or both targets could be proteins, or both targets could be RNA targets, or both targets could be DNA targets, or one target could be a protein and one target could be a small-molecule target, or one target could be a protein target and one target could be a non-protein target, and so forth.

In some embodiments, two targets (Target1 and Target2) in a complex or in proximity are detected using an anti-Target1 signal probe to bind Target1, and an anti-Target2 Reporter2-labeled signal probe to bind Target2 (for example, FIG. 68F). In some embodiments, anti-Target1 is then detected using an anti-anti-Target1 signal probe comprising fractional initiator1 and proximity domain1, and Reporter2 is detected using an anti-Reporter2 signal probe comprising fractional initiator2 and proximity domain2 (for example, FIG. 68F). In some embodiments, if and only if Target1 and Target2 are in a complex or in proximity, proximity domain 1 and proximity domain 2 are close enough to bind simultaneously to a proximity probe to colocalize a full HCR initiator i1 capable of triggering HCR signal amplification (for example, see FIG. 68F). In some embodiments, HCR signal amplification is performed using auxiliary-reporter-labeled hairpins to generate tethered fluorescent amplification polymers. In some embodiments the HCR signal amplification is linear (for example, FIG. 60A) or nonlinear (for example, FIGS. 38A-38B and 73). In some embodiments, the auxiliary reporter is a hapten, a fluorophore, a chromophore, or a rare-earth element or compound. In some embodiments, the auxiliary reporter mediates CARD signal amplification. In some embodiments, an anti-auxiliary-reporter enzyme-labeled readout probe is used to bind the auxiliary reporters on the HCR amplification polymer and mediate CARD signal amplification directly or indirectly. In some embodiments, the readout probe acts on CARD-substrates to catalyze deposition of CARD-reporters in the vicinity of the target. In some embodiments, CARD signal amplification generates a fluorescent signal or a chromogenic signal.

In some embodiments, two targets (Target1 and Target2) in a complex or in proximity are detected using an anti-Target1 signal probe to bind Target1, wherein the anti-Target1 signal probe comprises fractional initiator1 and proximity domain1, and an anti-Target2 Reporter2-labeled signal probe to bind Target2 (for example, FIG. 68G). In some embodiments, Reporter2 is detected using an anti-Reporter2 signal probe comprising fractional initiator2 and proximity domain2 (for example, FIG. 68G). In some embodiments, if and only if Target1 and Target2 are in a complex or in proximity, proximity domain 1 and proximity domain 2 are close enough to bind simultaneously to a proximity probe to colocalize a full HCR initiator i1 capable of triggering HCR signal amplification (for example, see FIG. 68G). In some embodiments, HCR signal amplification is performed using auxiliary-reporter-labeled hairpins to generate tethered fluorescent amplification polymers. In some embodiments the HCR signal amplification is linear (for example, FIG. 60A) or nonlinear (for example, FIGS. 38A-38B and 73). In some embodiments, the auxiliary reporter is a hapten, a fluorophore, a chromophore, or a rare-earth element or compound. In some embodiments, the auxiliary reporter mediates CARD signal amplification. In some embodiments, an anti-auxiliary-reporter enzyme-labeled readout probe is used to bind the auxiliary reporters on the HCR amplification polymer and mediate CARD signal amplification directly or indirectly. In some embodiments, the readout probe acts on CARD-substrates to catalyze deposition of CARD-reporters in the vicinity of the target. In some embodiments, CARD signal amplification generates a fluorescent signal or a chromogenic signal.

Figure 68A:
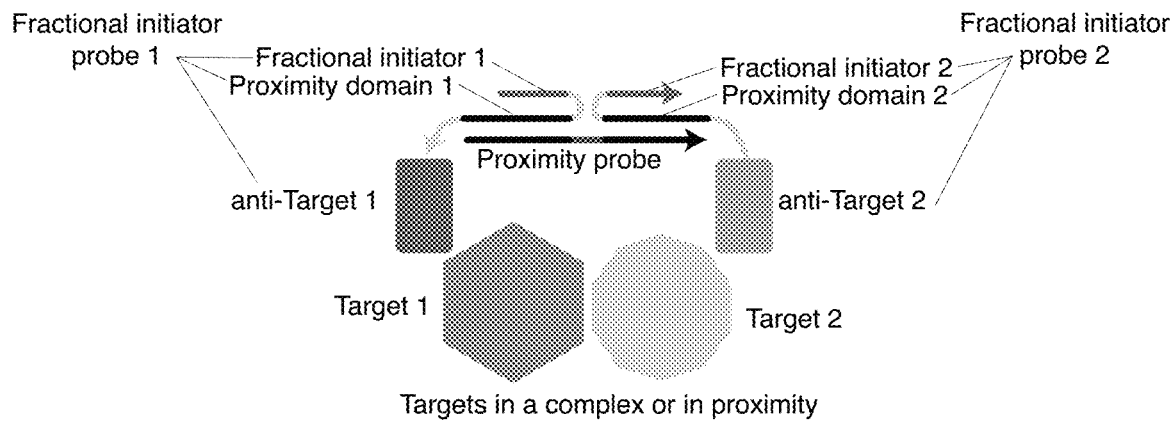
FIG. 68A depicts some embodiments of detection of targets in a complex or in proximity using fractional-initiator probes and a proximity probe, wherein the fractional-initiator probes directly bind the sample.
Figure 68B:
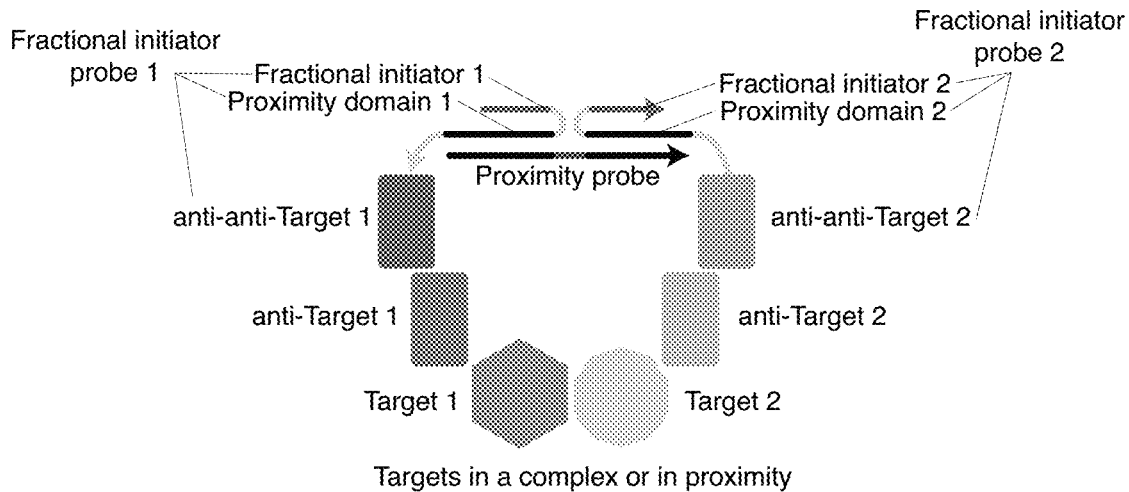
FIG. 68B depicts some embodiments of detection of targets in a complex or in proximity using fractional-initiator probes and a proximity probe, wherein the fractional-initiator probes indirectly bind the sample.
Figure 68C:
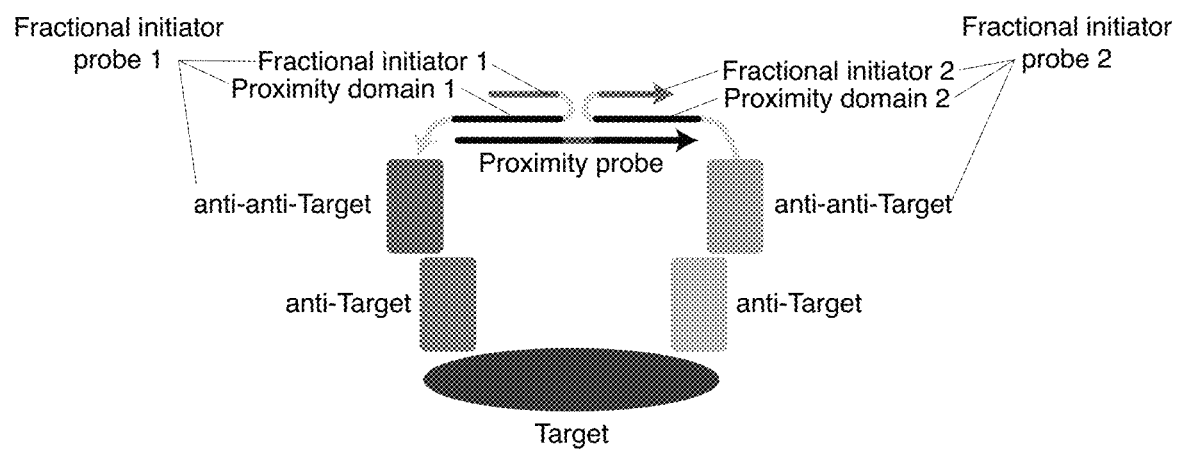
FIG. 68C depicts some embodiments of detection of a target using fractional-initiator probes and a proximity probe.
Figure 68H:
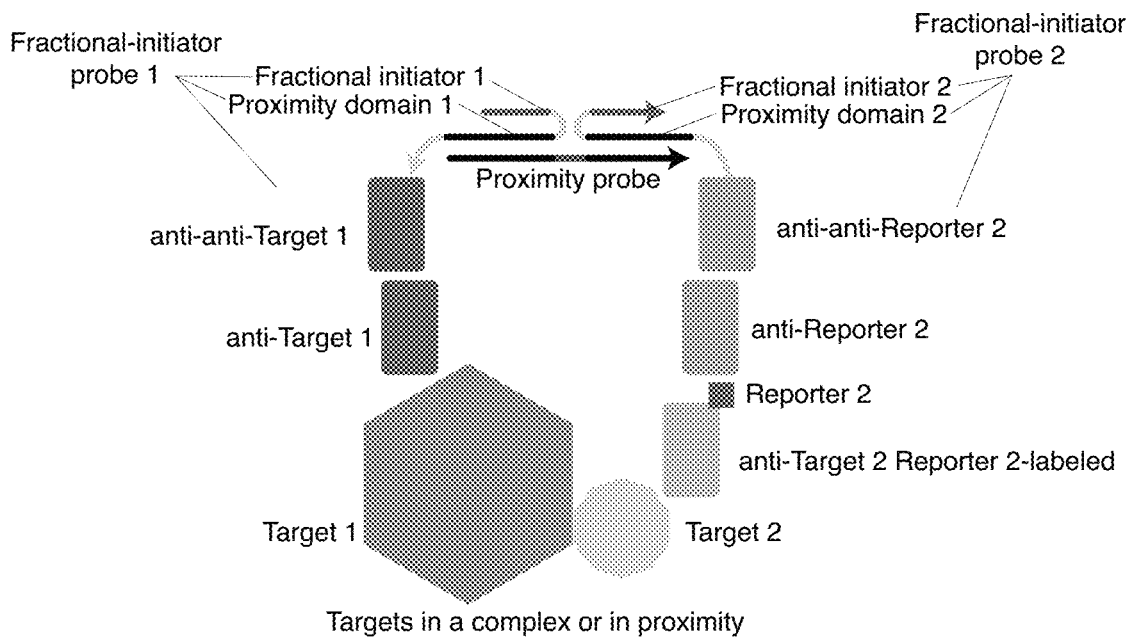

In some embodiments, two targets (Target1 and Target2) in a complex or in proximity are detected using an anti-Target1 signal probe to bind Target1, and an anti-Target2 Reporter2-labeled signal probe to bind Target2 (for example, FIG. 68H). In some embodiments, anti-Target1 is then detected using an anti-anti-Target1 signal probe comprising fractional initiator1 and proximity domain1, and Reporter2 is detected using an anti-Reporter2 signal probe (for example, FIG. 68H). In some embodiments, anti-Reporter2 is detected using an anti-anti-Reporter2 signal probe comprising fractional initiator2 and proximity domain2 (for example, FIG. 68H). In some embodiments, if and only if Target1 and Target2 are in a complex or in proximity, proximity domain 1 and proximity domain 2 are close enough to bind simultaneously to a proximity probe to colocalize a full HCR initiator i1 capable of triggering HCR signal amplification (for example, see FIG. 68H). In some embodiments, HCR signal amplification is performed using auxiliary-reporter-labeled hairpins to generate tethered fluorescent amplification polymers. In some embodiments the HCR signal amplification is linear (for example, FIG. 60A) or nonlinear (for example, FIGS. 38A-38B and 73). In some embodiments, the auxiliary reporter is a hapten, a fluorophore, a chromophore, or a rare-earth element or compound. In some embodiments, the auxiliary reporter mediates CARD signal amplification. In some embodiments, an anti-auxiliary-reporter enzyme-labeled readout probe is used to bind the auxiliary reporters on the HCR amplification polymer and mediate CARD signal amplification directly or indirectly. In some embodiments, the readout probe acts on CARD-substrates to catalyze deposition of CARD-reporters in the vicinity of the target. In some embodiments, CARD signal amplification generates a fluorescent signal or a chromogenic signal.

Figure 68I:
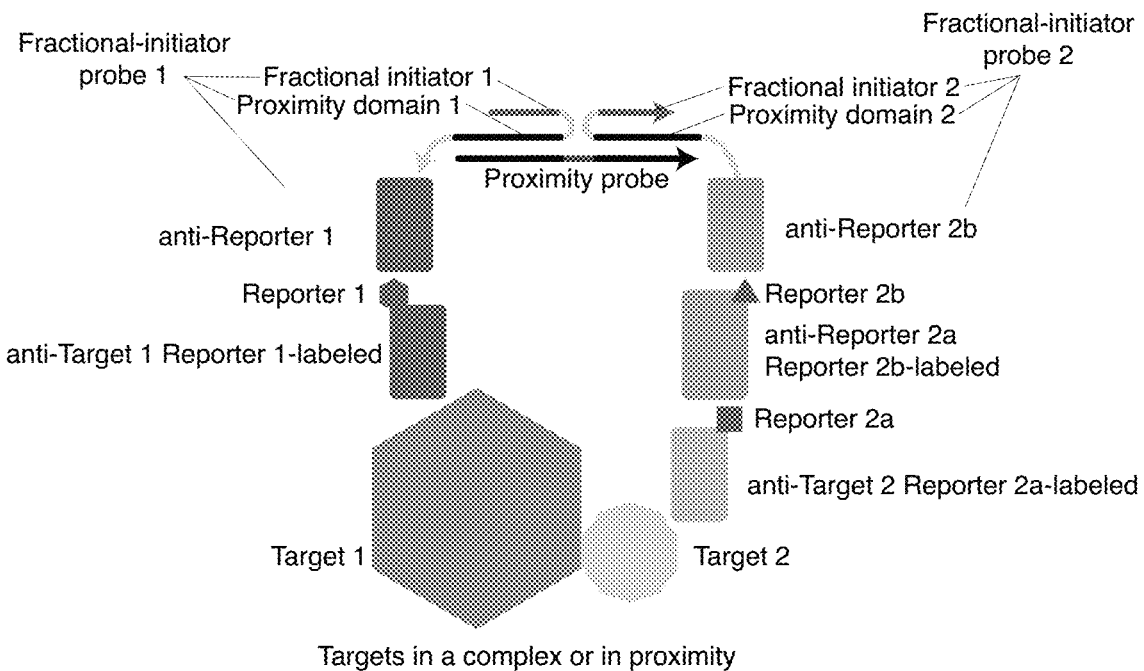

In some embodiments, two targets (Target1 and Target2) in a complex or in proximity are detected using an anti-Target1 Reporter1-labeled signal probe to bind Target1, and an anti-Target2 Reporter2a-labeled signal probe to bind Target2 (for example, FIG. 68I). In some embodiments, Reporter1 is then detected using an anti-Reporter1 signal probe comprising fractional initiator1 and proximity domain1, and Reporter2a is detected using an anti-Reporter2a Reporter2b-labeled signal probe (for example, FIG. 68I). In some embodiments, Reporter2b is detected using an anti-Reporter2b signal probe comprising fractional initiator2 and proximity domain2 (for example, FIG. 68I). In some embodiments, if and only if Target1 and Target2 are in a complex or in proximity, proximity domain 1 and proximity domain 2 are close enough to bind simultaneously to a proximity probe to colocalize a full HCR initiator i1 capable of triggering HCR signal amplification (for example, see FIG. 68I). In some embodiments, HCR signal amplification is performed using auxiliary-reporter-labeled hairpins to generate tethered fluorescent amplification polymers. In some embodiments the HCR signal amplification is linear (for example, FIG. 60A) or nonlinear (for example, FIGS. 38A-38B and 73). In some embodiments, the auxiliary reporter is a hapten, a fluorophore, a chromophore, or a rare-earth element or compound. In some embodiments, the auxiliary reporter mediates CARD signal amplification. In some embodiments, an anti-auxiliary-reporter enzyme-labeled readout probe is used to bind the auxiliary reporters on the HCR amplification polymer and mediate CARD signal amplification directly or indirectly. In some embodiments, the readout probe acts on CARD-substrates to catalyze deposition of CARD-reporters in the vicinity of the target. In some embodiments, CARD signal amplification generates a fluorescent signal or a chromogenic signal.

In some embodiments, reporter-labeled signal probes are used for HCR imaging with CARD for N targets in a sample (where N is a positive integer; for example, see the reagents of FIG. 60B). In some embodiments, the jth target (for j=1, . . . , N where j is a positive integer) is detected with a jth anti-target signal probe comprising a jth reporter (for example, see FIG. 60A). In some embodiments, the jth reporter is in turn detected with a jth anti-reporter signal probe comprising a jth HCR initiator (for example, see FIG. 60A). In some embodiments, signal amplification for the jth target is provided by a jth HCR amplifier labeled with a jth auxiliary reporter (for example, see FIG. 60A). In some embodiments, the HCR signal amplification for the jth target is linear HCR signal amplification (for example, FIG. 60A) or nonlinear HCR signal amplification (for example, FIGS. 38A-38B and 73). In some embodiments, the jth auxiliary reporter is a jth fluorophore. In some embodiments, the jth auxiliary reporter mediates CARD signal amplification for the jth target. In some embodiments, a jth anti-auxiliary-reporter readout probe comprising a jth enzyme is used to bind the jth auxiliary reporters on the jth HCR amplification polymer and mediate CARD signal amplification directly or indirectly for the jth target. In some embodiments, the jth readout probe acts on jth CARD-substrates to catalyze deposition of jth CARD-reporters in the vicinity of the jth target. In some embodiments, the same enzyme is used to mediate CARD for all targets. In some embodiments, CARD signal amplification generates a jth fluorescent signal or a jth chromogenic signal for the jth target.

HCR with Reporter-Labeled Probes and Nonlinear HCR Signal Amplification

In some embodiments, a reporter-labeled signal probe is used to perform HCR imaging with nonlinear HCR signal amplification (for example, FIG. 60C). In some embodiments, the target is detected with an anti-target signal probe comprising a reporter, which in turn is detected with an anti-reporter signal probe comprising a first HCR initiator (for example, FIG. 60C). In some embodiments, during the linear amplification stage, HCR signal amplification is performed using an auxiliary-reporter-labeled first HCR amplifier using the first HCR initiator to trigger growth of auxiliary-reporter-decorated HCR amplification polymers tethered to the target (for example, FIGS. 38A and 60C). In some embodiments, bridging to the nonlinear amplification stage is provided by an anti-auxiliary-reporter bridging probe comprising a second HCR initiator (for example, FIGS. 38A and 60C). In some embodiments, the bridging probe comprises a primary bridging probe comprising an anti-auxiliary reporter domain and a secondary bridging probe comprising a second HCR initiator (for example, FIGS. 38A, 45, and 47A). In some embodiments, the bridging probe bridges between the reporter and the second HCR initiator directly or indirectly. In some embodiments, during the nonlinear amplification stage, HCR signal amplification is performed using a tertiary-reporter-labeled second HCR amplifier using the second HCR initiator to trigger growth of tertiary-reporter-decorated HCR amplification polymers tethered to the HCR amplification polymers from the linear amplification stage (for example, FIGS. 38A and 60C). In some embodiments, the reporter on the signal probe, the auxiliary reporter on the first HCR amplifier, and/or the tertiary reporter on the second HCR amplifier are the same. In some embodiments, the first HCR initiator on the signal probe and the second HCR initiator on the bridging probe are the same. In some embodiments, the first HCR amplifier during the linear stage and the second HCR amplifier during the nonlinear stage are the same. In some embodiments, additional rounds of bridging and nonlinear HCR amplification are performed (for example, one additional round of bridging and HCR signal amplification, two additional rounds of bridging and HCR signal amplification, or M additional rounds of bridging and HCR signal amplification; see for example FIG. 73). In some embodiments, multiple rounds of HCR signal amplification are performed using the same bridging probe and HCR amplifier. In some embodiments, the tertiary reporter is a fluorophore (for example, FIG. 60C). In some embodiments, the tertiary reporter mediates CARD signal amplification (for example, FIG. 38A). In some embodiments, an anti-auxiliary-reporter enzyme-labeled readout probe is used to bind the tertiary reporters on the HCR amplification polymer and mediate CARD signal amplification directly or indirectly (for example, FIGS. 38A-38B). In some embodiments, the readout probe acts on CARD-substrates to catalyze deposition of CARD-reporters in the vicinity of the target. In some embodiments, the anti-target signal probe comprises an antibody, a nanobody, an oligonucleotide, or a molecule comprising a target-binding domain. In some embodiments, the anti-reporter signal probe comprises an antibody, a nanobody, a nucleic acid, or a molecule comprising a reporter-binding domain. In some embodiments, the target is a protein and HCR imaging is used to perform HCR immunohistochemistry (IHC) or immunofluorescence (IF) with or without CARD. In some embodiments, the target is a nucleic acid (for example, FIGS. 37B, 56G-56H, and 59A-59B) and HCR imaging is used to perform HCR in situ hybridization (ISH) with or without CARD. In some embodiments, CARD signal amplification generates a fluorescent signal or a chromogenic signal.

In some embodiments, N reporter-labeled signal probes are used for HCR imaging of N targets in a sample (where N is a positive integer) using nonlinear HCR signal amplification (for example, see the reagents of FIG. 60D). In some embodiments, the jth target (for j=1, . . . , N where j is a positive integer), is detected with a jth anti-target signal probe comprising a jth reporter. In some embodiments, the jth reporter is in turn detected with a jth anti-reporter signal probe comprising a jth first HCR initiator. In some embodiments, during the linear amplification stage, signal amplification for the jth target is provided by a jth first HCR amplifier comprising a jth auxiliary reporter, using the jth first HCR initiator to trigger growth of jth auxiliary-reporter decorated HCR amplification polymers tethered to the jth target. In some embodiments, bridging to the nonlinear amplification stage is provided by a jth anti-auxiliary-reporter bridging probe comprising a jth second HCR initiator. In some embodiments, the jth bridging probe comprises a jth primary bridging probe comprising a jth anti-auxiliary reporter domain and a jth secondary bridging probe comprising a jth second HCR initiator (for example, FIGS. 38A, 45, and 47A). In some embodiments, the jth bridging probe bridges between the jth reporter and the jth second HCR initiator directly or indirectly. In some embodiments, during the nonlinear amplification stage, HCR signal amplification is performed for the jth target using a jth second HCR amplifier comprising a jth tertiary reporter using the jth second HCR initiator to trigger growth of jth tertiary-reporter-decorated HCR amplification polymers tethered to the jth HCR amplification polymers from the linear amplification stage (for example, FIGS. 38A and 60C). In some embodiments, the jth reporter on the jth signal probe, the jth auxiliary reporter on the jth first HCR amplifier, and/or the jth tertiary reporter on the jth second HCR amplifier are the same. In some embodiments, the jth first HCR initiator carried by the jth signal probe and the jth second HCR initiator carried by the jth bridging probe are the same. In some embodiments, the jth first HCR amplifier during the linear stage and the jth second HCR amplifier during the nonlinear stage are the same. In some embodiments, additional rounds of bridging and nonlinear HCR signal amplification are performed (for example, one additional round of bridging and HCR signal amplification, two additional rounds of bridging and HCR signal amplification, or M additional rounds of bridging and HCR signal amplification). In some embodiments, the same jth bridging probe and jth HCR amplifier are used for multiple rounds of HCR signal amplification for the jth target. In some embodiments, the jth tertiary reporter is a jth fluorophore (for example, FIG. 60D). In some embodiments, the jth tertiary reporter mediates CARD signal amplification for the jth target (for example, FIG. 38A). In some embodiments, a jth anti-tertiary-reporter readout probe comprising a jth enzyme is used to bind the jth tertiary reporters on the jth HCR amplification polymer and mediate CARD signal amplification directly or indirectly for the jth target. In some embodiments, the jth readout probe acts on jth CARD-substrates to catalyze deposition of jth CARD-reporters in the vicinity of the jth target. In some embodiments, the same enzyme is used to mediate CARD for all targets. In some embodiments, CARD signal amplification generates a jth fluorescent signal or a jth chromogenic signal for the jth target. In some embodiments, the jth anti-target signal probe comprises a jth antibody, a jth nanobody, a jth nucleic acid, or a jth molecule comprising a jth target-binding domain. In some embodiments, the jth anti-reporter signal probe comprises a jth antibody, a jth nanobody, a jth nucleic acid, or a jth molecule comprising a jth reporter-binding domain. In some embodiments, the jth target is a protein and HCR imaging is used to perform HCR immunohistochemistry (IHC) or immunofluorescence (IF) with or without CARD. In some embodiments, the jth target is a nucleic acid (for example, FIGS. 37B, 56G-56H, and 59A-59B) and HCR imaging is used to perform HCR in situ hybridization (ISH) with or without CARD.

Nonlinear HCR Signal Amplification

Figure 38A:
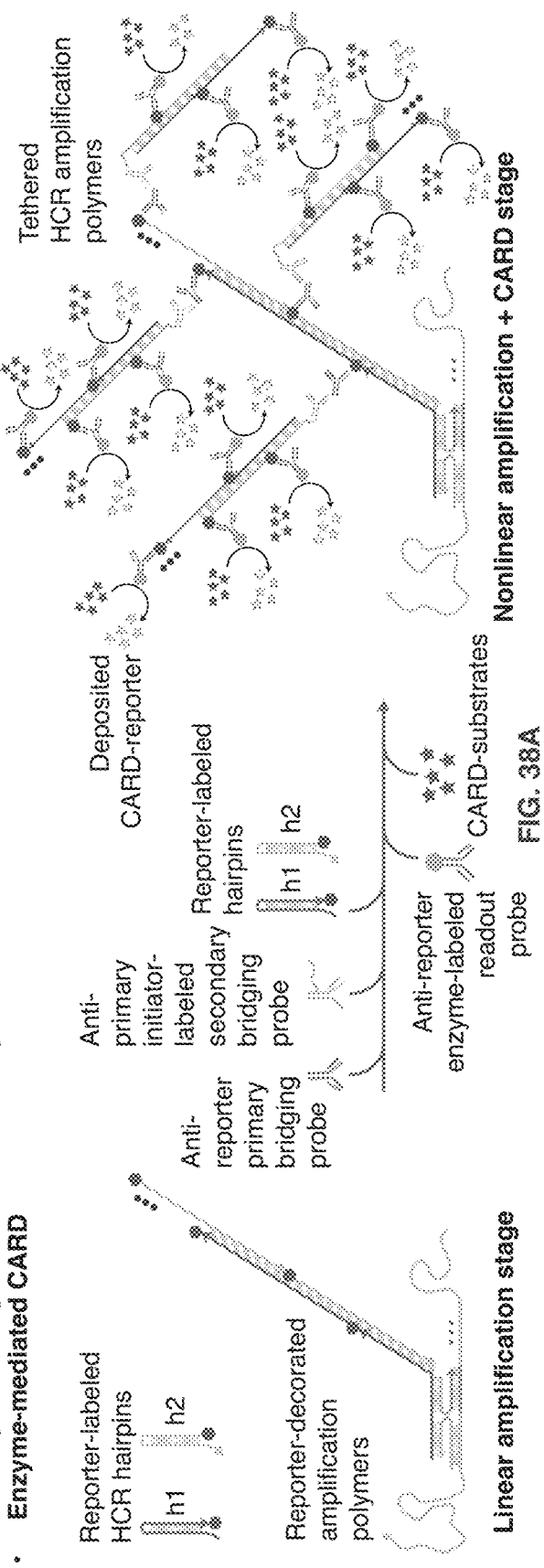
FIG. 38A-38B depict some embodiments of nonlinear HCR signal amplification used to mediate CARD signal amplification for ultrasensitive HCR RNA-CISH.
Figure 38B:
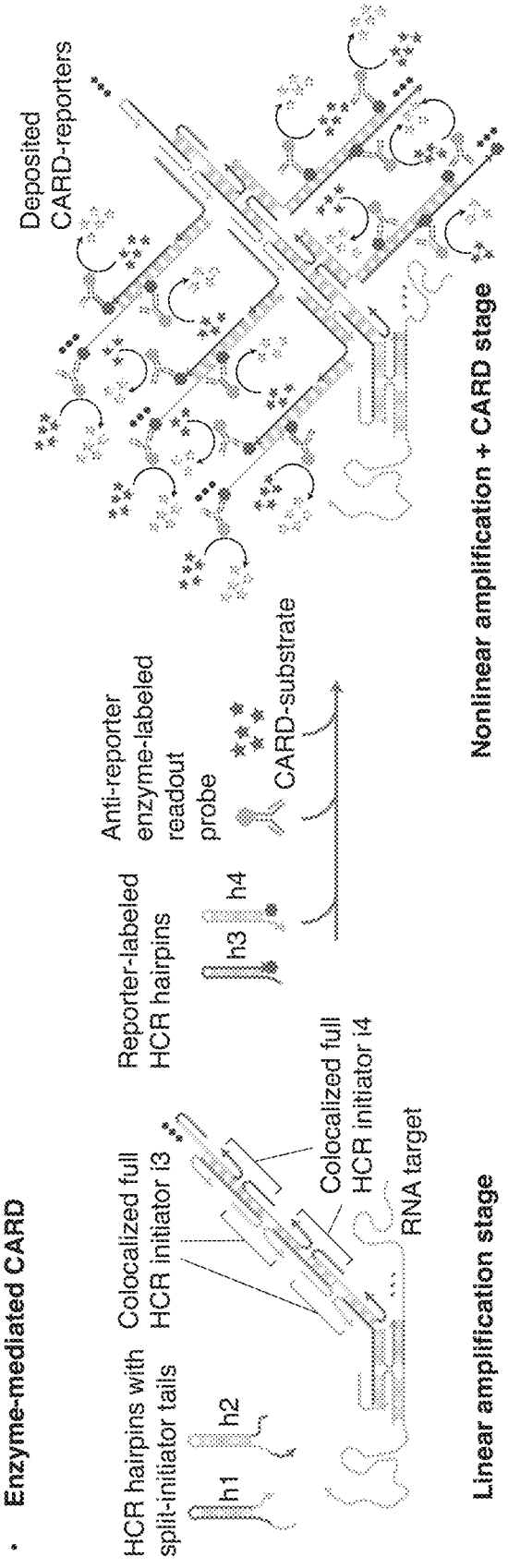

Some embodiments of nonlinear HCR signal amplification are depicted for HCR RNA-ISH with CARD in FIG. 38AB. Some embodiments of enzyme-free nonlinear HCR signal amplification are depicted for HCR RNA-FISH in FIGS. 45, 47A-47B, and 49A-49B. Some embodiments of nonlinear HCR signal amplification are depicted for HCR IF in FIGS. 51A, 52A-52B, and 54. In some embodiments, ultrasensitive detection is achieved using branched HCR amplification polymers (FIGS. 38A, 45, 47A-47B, 49A-49B, 51A, 52A-52B, and 54), wherein probes trigger self-assembly of reporter-labeled HCR hairpins to form tethered reporter-decorated HCR amplification polymers during a linear amplification stage, wherein anti-reporter initiator-labeled bridging probes bind to the reporters on the linear amplification polymers, and wherein the bridging probes trigger self-assembly of auxiliary-reporter-labeled HCR hairpins to form tethered auxiliary-reporter-decorated branched amplification polymers during a nonlinear amplification stage. In some embodiments, ultrasensitive detection is achieved using branched HCR amplification polymers (FIGS. 38B, 71, and 73), wherein initiator-labeled probes that comprise a first HCR initiator (or fractional-initiator probes that colocalize a full first HCR initiator upon specific binding to the target) trigger self-assembly of self-bridging split-initiator-tailed HCR hairpins to form tethered HCR amplification polymers that colocalize a full second HCR initiator during a linear amplification stage, and wherein the colocalized full second HCR initiator triggers self-assembly of reporter-labeled HCR hairpins to form tethered reporter-decorated branched amplification polymers during a nonlinear amplification stage. In some embodiments, a split-initiator tail on an HCR hairpin comprises a fractional initiator. In some embodiments, polymerization of the reporter-decorated HCR amplification polymer tethered to the target colocalizes a full initiator from the split-initiator-tailed HCR hairpins that allows for amplification of a second set of hairpins in a different direction, starting from each of the colocalized fractional initiators. In some embodiments, the auxiliary reporters on the branched amplification polymers directly or indirectly mediate catalytic reporter deposition (CARD) (FIGS. 38A-38B).

Nonlinear HCR Signal Amplification Using Bridging Probes

In some embodiments, a target is detected in a sample using nonlinear HCR signal amplification. In some embodiments, the target is detected with an initiator-labeled signal probe (for example FIGS. 52A and 71) comprising a first HCR initiator. In some embodiments, the target is detected with fractional-initiator signal probes that colocalize a full first HCR initiator if they bind specifically to their cognate binding sites on the target (for example, FIGS. 38A-38B, 47A, 49A, 71). In some embodiments, the target is a target complex (or a set of target molecules in proximity) that is detected using two or more fractional-initiator probes and one or more proximity probes to colocalize a full first HCR initiator (for example, FIGS. 58C, 68AB, 68D-68I, and 69AB). In some embodiments, the target is detected with an anti-target signal probe comprising a reporter, which in turn is detected with an anti-reporter signal probe comprising a first HCR initiator (for example, FIG. 60C). In some embodiments, during the linear amplification stage, HCR signal amplification is performed using an auxiliary-reporter-labeled first HCR amplifier using the first HCR initiator (or colocalized full first HCR initiator) to trigger growth of auxiliary-reporter-decorated HCR amplification polymers tethered to the target (for example, FIGS. 38A, 47A, 49A, 52A, and 60C). In some embodiments, bridging to the nonlinear amplification stage is provided by an anti-auxiliary-reporter bridging probe comprising a second HCR initiator (for example, FIGS. 38A, 49A, 52A, and 60C). In some embodiments, the bridging probe comprises a primary bridging probe comprising an anti-auxiliary reporter domain and a secondary bridging probe comprising a second HCR initiator (for example, FIGS. 38A, 45, and 47A). In some embodiments, the bridging probe bridges between the reporter and the second HCR initiator directly or indirectly. In some embodiments, during the nonlinear amplification stage, HCR signal amplification is performed using a tertiary-reporter-labeled second HCR amplifier, using the second HCR initiator to trigger growth of tertiary-reporter-decorated HCR amplification polymers tethered to the HCR amplification polymers from the linear amplification stage (for example, FIGS. 38A, 47A, 49A, 52A, and 60C). In some embodiments, any of the optional reporter on the signal probe, the auxiliary reporter on the first HCR amplifier, and/or the tertiary reporter on the second HCR amplifier are the same. In some embodiments, the first HCR initiator carried by the signal probe and the second HCR initiator carried by the bridging probe are the same. In some embodiments, the sequence of the first HCR amplifier during the linear stage and the sequence of the second HCR amplifier during the nonlinear stage are the same. In some embodiments, additional rounds of bridging and HCR signal amplification are performed (for example, one additional round of bridging and HCR signal amplification, two additional rounds of bridging and HCR signal amplification, or M additional rounds of bridging and HCR signal amplification; see for example FIG. 73). In some embodiments, multiple rounds of HCR signal amplification are performed using the same bridging probe and HCR amplifier (for example, FIG. 73). In some embodiments, the tertiary reporter is a fluorophore, a chromophore, or a rare-earth element or compound (for example, FIGS. 47A, 49A, 52A, 60C). In some embodiments, the tertiary reporter mediates CARD signal amplification (for example, FIG. 38A). In some embodiments, an anti-auxiliary-reporter enzyme-labeled readout probe is used to bind the tertiary reporters on the HCR amplification polymer and mediate CARD signal amplification directly or indirectly (for example, FIG. 38A). In some embodiments, the readout probe acts on CARD-substrates to catalyze deposition of CARD-reporters in the vicinity of the target. In some embodiments, a signal probe comprises an antibody, a nanobody, a nucleic acid, a molecule comprising a target-binding domain, and/or a molecule comprising a reporter-binding domain. In some embodiments, the target is a protein and HCR imaging is used to perform HCR immunohistochemistry (IHC) or immunofluorescence (IF) with or without CARD. In some embodiments, the target is a nucleic acid and HCR imaging is used to perform HCR in situ hybridization (ISH) with or without CARD. In some embodiments, CARD signal amplification generates a fluorescent signal or a chromogenic signal.

Nonlinear HCR Signal Amplification Via Multiple Rounds of Bridging and HCR Signal Amplification In some embodiments, the target is detected using an anti-target signal probe comprising a first HCR initiator (or using fractional-initiator signal probes that colocalize a full first HCR initiator when they bind specifically to their cognate binding sites on the target). In some embodiments, a first round of HCR signal amplification (also known as the linear amplification stage) is performed using a first-reporter-labeled HCR amplifier using the first HCR initiator to trigger growth of a first-reporter-decorated HCR amplification polymer tethered to the target (for example, see FIG. 73). In some embodiments, bridging to a second round of HCR amplification is provided by an anti-first-reporter bridging probe comprising a second HCR initiator. In some embodiments, a second round of HCR signal amplification (also known as the first nonlinear amplification stage or the quadratic amplification stage) is performed using a second-reporter-labeled HCR amplifier using the second HCR initiator to trigger growth of a second-reporter-decorated HCR amplification polymer tethered to the first-reporter-decorated HCR amplification polymer tethered to the target (for example, see FIG. 73). In some embodiments, bridging to a third round of HCR amplification is provided by an anti-second-reporter bridging probe comprising a third HCR initiator. In some embodiments, a third round of HCR signal amplification (also known as the second nonlinear amplification stage or the cubic amplification stage) is performed using a third-reporter-labeled HCR amplifier using the third HCR initiator to trigger growth of a third-reporter-decorated HCR amplification polymer tethered to the second-reporter-decorated HCR amplification polymer tethered to the first-reporter-decorated HCR amplification polymer tethered to the target (for example, see FIG. 73). In some embodiments, additional rounds of bridging (using an anti-reporter initiator-labeled bridging probe) and HCR signal amplification (using a reporter-labeled HCR amplifier) can be performed to increase the strength of the signal tethered to the target. For example, a total of M rounds of HCR signal amplification can be performed, where M=2, 3, 4, 5, 10, 20, 50, or 100 rounds, or any number of rounds intermediate to those numbers. In some embodiments, some or all of the first reporter, the second reporter, the third reporter, . . . , and the Mth reporter are the same reporter. In some embodiments, some or all of the bridging probes used to bridge between rounds of HCR signal amplification are the same. In some embodiments, some or all of the first HCR initiator, the second HCR initiator, the third HCR initiator, . . . , and the Mth HCR initiator have the same sequence. In some embodiments, some or all of the first HCR amplifier, the second HCR amplifier, the third HCR amplifier, . . . , and the Mth HCR amplifier have the same sequence. In some embodiments, the reporter carried by the HCR amplifier used for the final round of HCR signal amplification is a fluorophore. In some embodiments, the reporter carried by the HCR amplifier used for the final round of HCR signal amplification is a chromophore. In some embodiments, the reporter carried by the HCR amplifier used for the final round of HCR signal amplification directly or indirectly mediates CARD signal amplification.

Nonlinear HCR Signal Amplification for N Targets Using Bridging Probes

Figure 47A:
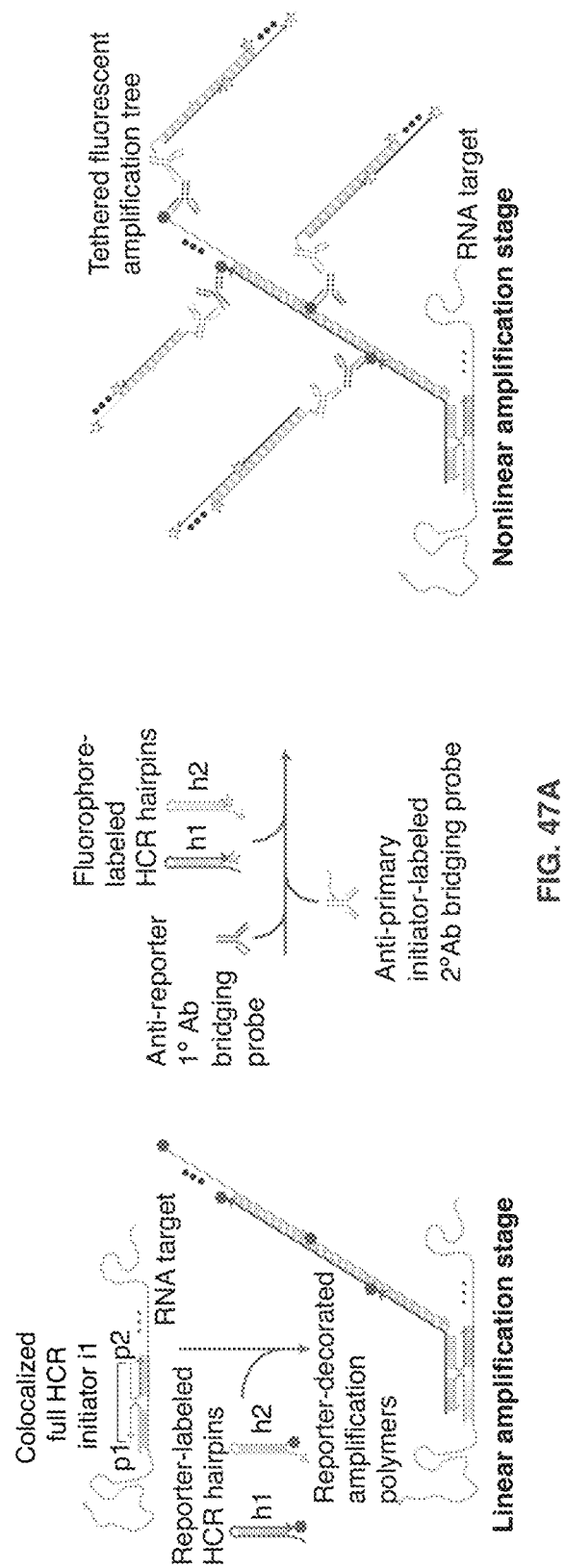
FIGS. 47A-47B depict some embodiments of ultrasensitive multiplex HCR RNA-FISH using nonlinear enzyme-free HCR signal amplification.
Figure 47B:
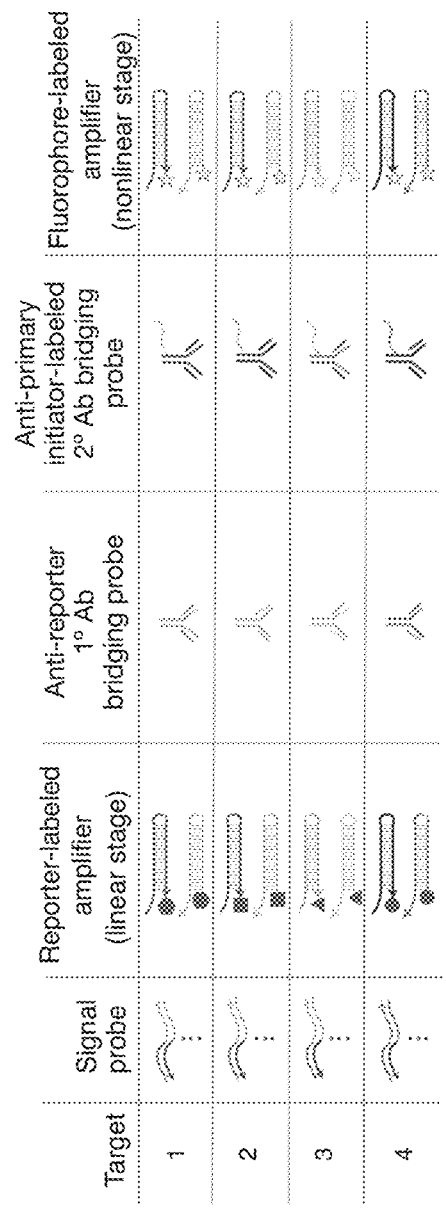
Figure 52B:
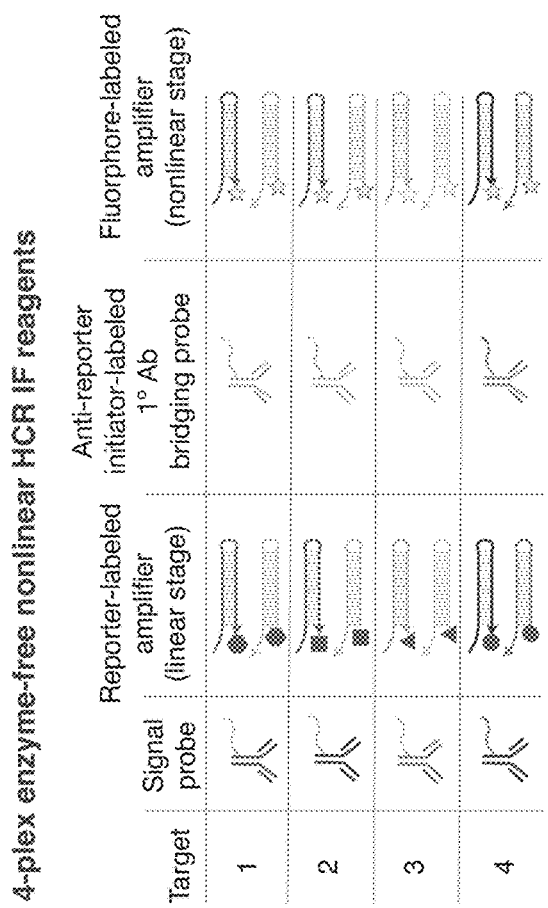
FIGS. 52A-52B depict some embodiments of ultrasensitive multiplex HCR IF using nonlinear enzyme-free HCR signal amplification.

In some embodiments, N signal probes are used to detect N targets in a sample (where N is a positive integer) using nonlinear HCR signal amplification (for example, see the reagents of FIGS. 47B, 52B, and 60D). In some embodiments, the jth target (for j=1, . . . , N where j is a positive integer) is detected with a jth initiator-labeled signal probe (for example FIGS. 52A and 71) comprising a jth first HCR initiator. In some embodiments, the jth target is detected with a jth fractional-initiator signal probe set that colocalizes a jth full first HCR initiator when the probes within a probe unit bind specifically to their cognate binding sites on the jth target (for example, FIGS. 38A-38B, 47A, 49A, 71). In some embodiments, the jth target is a target complex (or a set of target molecules in proximity) that is detected using a jth fractional-initiator probe set and a jth proximity probe to colocalize a jth full first HCR initiator (for example, FIGS. 58C, 68AB, 68D-68I, and 69AB). In some embodiments, the jth target is detected with a jth anti-target signal probe comprising a jth reporter (for example, FIG. 60C). In some embodiments, the jth reporter is in turn detected with a jth anti-reporter signal probe comprising a jth first HCR initiator. In some embodiments, during the linear amplification stage, signal amplification for the jth target is provided by a jth first HCR amplifier comprising a jth auxiliary reporter, using the jth first HCR initiator to trigger growth of jth auxiliary-reporter decorated HCR amplification polymers tethered to the jth target. In some embodiments, bridging to the nonlinear amplification stage is provided by a jth anti-auxiliary-reporter bridging probe comprising a jth second HCR initiator. In some embodiments, the jth bridging probe comprises a jth primary bridging probe comprising a jth anti-auxiliary reporter domain and a jth secondary bridging probe comprising a jth second HCR initiator (for example, FIGS. 38A, 45, and 47A). In some embodiments, the jth bridging probe bridges between the jth reporter and the jth second HCR initiator directly or indirectly. In some embodiments, during the nonlinear amplification stage, HCR signal amplification is performed for the jth target using a jth second HCR amplifier comprising a jth tertiary reporter using the jth second HCR initiator to trigger growth of jth tertiary-reporter-decorated HCR amplification polymers tethered to the jth HCR amplification polymers from the linear amplification stage (for example, FIGS. 38A and 60C). In some embodiments, any of the jth reporter on the jth signal probe, the jth auxiliary reporter on the jth first HCR amplifier, and/or the jth tertiary reporter on the jth second HCR amplifier are the same. In some embodiments, the jth first HCR initiator carried by the jth signal probe and the jth second HCR initiator carried by the jth bridging probe are the same. In some embodiments, the jth first HCR amplifier during the linear stage and the jth second HCR amplifier during the nonlinear stage have the same sequence. In some embodiments, additional rounds of bridging and HCR signal amplification are performed (for example, one additional round of bridging and HCR signal amplification, two additional rounds of bridging and HCR signal amplification, or M additional rounds of bridging and HCR signal amplification; see for example FIG. 73). In some embodiments, the same jth bridging probe and jth HCR amplifier are used for multiple rounds of HCR signal amplification for the jth target (for example, FIG. 73). In some embodiments, the jth tertiary reporter is a jth fluorophore or jth chromomore or a jth rare-earth element or compound (for example, FIGS. 47A-47B, 52A-52B, 60C-60D). In some embodiments, the jth tertiary reporter mediates CARD signal amplification for the jth target (for example, FIG. 38A). In some embodiments, a jth anti-tertiary-reporter readout probe comprising a jth enzyme is used to bind the jth tertiary reporters on the jth HCR amplification polymer and mediate CARD signal amplification directly or indirectly for the jth target. In some embodiments, the jth readout probe acts on jth CARD-substrates to catalyze deposition of jth CARD-reporters in the vicinity of the jth target. In some embodiments, the same enzyme is used to mediate CARD for all targets. In some embodiments, CARD signal amplification generates a jth fluorescent signal or a jth chromogenic signal for the jth target. In some embodiments, the jth signal probe comprises a jth antibody, a jth nanobody, a jth nucleic acid, a jth molecule comprising a jth target-binding domain, or a jth molecule comprising a jth reporter-binding domain. In some embodiments, the jth target is a protein and HCR imaging is used to perform HCR immunohistochemistry (IHC) or immunofluorescence (IF) with or without CARD. In some embodiments, the jth target is a nucleic acid and HCR imaging is used to perform HCR in situ hybridization (ISH) with or without CARD.

In some embodiments, HCR RNA-FISH/IF is performed with enzyme-free nonlinear HCR signal amplification using a 4 stage protocol (for example, FIG. 54) comprising: 1) Protein Detection Stage: incubate all anti-target initiator-labeled signal probes; optional wash; 2) RNA Detection Stage: incubate all fractional-initiator signal probe sets; optional wash; 3) Linear Amplification Stage for all RNA and protein targets: incubate all reporter-labeled HCR amplifiers; optional wash; 4) Nonlinear Amplification Stage for all RNA and protein targets: incubate all anti-reporter initiator-labeled bridging probes; optional wash; incubate all auxiliary-reporter-labeled HCR amplifiers; optional wash.

In some embodiments, HCR imaging of protein targets, protein:protein target complexes, and RNA targets is performed with enzyme-free nonlinear HCR signal amplification using a 5 stage protocol (for example, FIG. 70) comprising: 1) Protein Detection Stage: incubate all anti-target primary signal probes; optional wash; incubate all anti-primary initiator-labeled signal probes; optional wash; (alternatively, incubate all anti-target initiator-labeled signal probes; optional wash); 2) Proximity stage: incubate all proximity probes; optional wash; 3) RNA Detection Stage: incubate all fractional-initiator signal probe sets; optional wash; 4) Linear Amplification Stage for all targets: incubate all reporter-labeled HCR amplifiers; optional wash; 5) Nonlinear Amplification Stage for all RNA and protein targets: incubate all anti-reporter initiator-labeled bridging probes; optional wash; incubate all auxiliary-reporter-labeled HCR amplifiers; optional wash.

Nonlinear HCR Signal Amplification Using Self-Bridging Hairpins

In some embodiments, a target is detected in a sample using nonlinear HCR signal amplification. In some embodiments, the target is detected with an initiator-labeled signal probe (for example FIGS. 52A and 71) comprising a first HCR initiator. In some embodiments, the target is detected with two or more fractional-initiator signal probes that colocalize a full first HCR initiator if they bind specifically to their cognate binding sites on the target (for example, FIGS. 38A-38B, 47A, 49A, 71). In some embodiments, the target is a target complex (or a set of target molecules in proximity) that is detected using two or more fractional-initiator probes and one or more proximity probes to colocalize a full first HCR initiator (for example, FIGS. 58C, 68AB, 68D-68I, and 69AB). In some embodiments, the target is a target complex (or a set of target molecules in proximity) that is detected using two or more fractional-initiator probes, wherein the interaction between linking regions on the fractional initiator probes colocalizes a full first HCR initiator. In some embodiments, the target is detected with an anti-target signal probe comprising a reporter, which in turn is detected with an anti-reporter signal probe comprising a first HCR initiator (for example, FIG. 60C). In some embodiments, during the linear amplification stage, HCR signal amplification is performed using a self-bridging first HCR amplifier comprising two or more hairpins each comprising split-initiator tails, using the first HCR initiator (or colocalized full first HCR initiator) to trigger growth of HCR amplification polymers tethered to the target that colocalize a full second HCR initiator within the amplification polymers (for example, FIGS. 38B and 71). In some embodiments, the self-bridging first HCR amplifier comprises two HCR hairpins (for example, FIG. 38) wherein each hairpin comprises zero, one or two split-initiator tails. In some embodiments, the self-bridging first HCR amplifier comprises 4 HCR hairpins (for example, FIGS. 16C-16D and 71) wherein each hairpin comprises zero, one, or two split-initiator tails. In some embodiments, the self-bridging first HCR amplifier comprises 4 HCR hairpins h1, h2, h3, and h4 (see for example, FIG. 71), wherein h1 and h3 each comprise a single split-initiator HCR tail and colocalize full second HCR initiator i5 when the 4 hairpins polymerize, and wherein h2 and h4 each comprise a single split-initiator HCR tail and colocalize full second HCR initiator i6 when the 4 hairpins polymerize, wherein polymerization of the 4 hairpins occurs upon exposure to first initiator i1. In some embodiments, h1 and h3 both each comprise a single split-initiator tail or h2 and h4 both each comprise a single split-initiator-tail, such that h1 and h3 colocalize a full HCR initiator i5, or h2 and h4 colocalize a full HCR initiator i6, when the 4 hairpins polymerize upon exposure to first initiator i1. In some embodiments, the colocalized full second HCR initiator bridges between the linear amplification stage and the nonlinear amplification stage without use of a bridging probe. In some embodiments, during the nonlinear amplification stage, HCR signal amplification is performed using a tertiary-reporter-labeled second HCR amplifier, using the colocalized full second HCR initiator to trigger growth of tertiary-reporter-decorated HCR amplification polymers tethered to the HCR amplification polymers from the linear amplification stage (for example, FIGS. 38A, 47A, 49A, 52A, and 60C). In some embodiments, the optional reporter on the signal probe and the tertiary reporter on the second HCR amplifier are the same. In some embodiments, additional rounds of HCR signal amplification are performed (for example, one additional round of HCR signal amplification, two additional rounds of HCR signal amplification, or M additional rounds of HCR signal amplification). In some embodiments, the same self-bridging HCR amplifier is used for multiple rounds of HCR signal amplification. In some embodiments, the tertiary reporter is a fluorophore or a chromophore or a rare-earth element or compound (for example, FIG. 71). In some embodiments, the tertiary reporter mediates CARD signal amplification (for example, FIG. 38B). In some embodiments, an anti-auxiliary-reporter enzyme-labeled readout probe is used to bind the tertiary reporters on the HCR amplification polymer and mediate CARD signal amplification directly or indirectly (for example, FIG. 38B). In some embodiments, the readout probe acts on CARD-substrates to catalyze deposition of CARD-reporters in the vicinity of the target. In some embodiments, a signal probe comprises an antibody, a nanobody, a nucleic acid, a molecule comprising a target-binding domain, and/or a molecule comprising a reporter-binding domain. In some embodiments, the target is a protein and HCR imaging is used to perform HCR immunohistochemistry (IHC) or immunofluorescence (IF) with or without CARD. In some embodiments, the target is a nucleic acid and HCR imaging is used to perform HCR in situ hybridization (ISH) with or without CARD. In some embodiments, CARD signal amplification generates a fluorescent signal or a chromogenic signal.

Nonlinear HCR Signal Amplification for N Targets Using Self-Bridging Hairpins

In some embodiments, N signal probes are used to detect N targets in a sample (where N is a positive integer) using nonlinear HCR signal amplification (for example, see the reagents of FIGS. 47B, 52B, and 60D). In some embodiments, the jth target (for j=1, . . . , N where j is a positive integer) is detected with a jth initiator-labeled signal probe (for example FIGS. 52A and 71) comprising a jth first HCR initiator. In some embodiments, the jth target is detected with a jth fractional-initiator signal probe set that colocalizes a jth full first HCR initiator when the probes within a probe unit bind specifically to their cognate binding sites on the jth target (for example, FIGS. 38A-38B, 47A, 49A, 71). In some embodiments, the jth target is a target complex (or a set of target molecules in proximity) that is detected using a jth fractional-initiator probe set and a jth proximity probe to colocalize a jth full first HCR initiator (for example, FIGS. 58C, 68AB, 68D-68I, and 69AB). In some embodiments, the jth target is detected with a jth anti-target signal probe comprising a jth reporter (for example, FIG. 60C). In some embodiments, the jth reporter is in turn detected with a jth anti-reporter signal probe comprising a jth first HCR initiator. In some embodiments, during the linear amplification stage, signal amplification for the jth target is provided by a jth self-bridging first HCR amplifier comprising split-initiator tails, using the jth first HCR initiator to trigger growth of jth HCR amplification polymers that colocalize a jth full second HCR initiator within the polymer tethered to the jth target. In some embodiments, the colocalized jth full second HCR initiator bridges between the linear amplification stage and the nonlinear amplification stage without use of a bridging probe. In some embodiments, during the nonlinear amplification stage, HCR signal amplification is performed for the jth target using a jth second HCR amplifier comprising a jth tertiary reporter using the colocalized jth full second HCR initiator to trigger growth of jth tertiary-reporter-decorated HCR amplification polymers from the linear amplification stage (for example, FIGS. 38B and 71). In some embodiments, the optional jth reporter on the jth signal probe and the jth tertiary reporter on the jth second HCR amplifier are the same. In some embodiments, additional rounds of HCR signal amplification are performed (for example, one additional round of HCR signal amplification, two additional rounds of HCR signal amplification, or M additional rounds of HCR signal amplification). In some embodiments, the same jth self-bridging HCR amplifier is used for multiple rounds of HCR signal amplification for the jth target. In some embodiments, the jth tertiary reporter is a jth fluorophore or a jth chromophore or a jth rare-earth element or compound (for example, FIG. 71). In some embodiments, the jth tertiary reporter mediates CARD signal amplification for the jth target (for example, FIG. 38B). In some embodiments, a jth anti-tertiary-reporter readout probe comprising a jth enzyme is used to bind the jth tertiary reporters on the jth HCR amplification polymer and mediate CARD signal amplification directly or indirectly for the jth target. In some embodiments, the jth readout probe acts on jth CARD-substrates to catalyze deposition of jth CARD-reporters in the vicinity of the jth target. In some embodiments, the same enzyme is used to mediate CARD for all targets. In some embodiments, CARD signal amplification generates a jth fluorescent signal or a jth chromogenic signal for the jth target. In some embodiments, the jth anti-target signal probe comprises a jth antibody, a jth nanobody, a jth nucleic acid, a jth molecule comprising a jth target-binding domain, or a jth molecule comprising a jth reporter-binding domain. In some embodiments, the jth target is a protein and HCR imaging is used to perform HCR immunohistochemistry (IHC) or immunofluorescence (IF) with or without CARD. In some embodiments, the jth target is a nucleic acid and HCR imaging is used to perform HCR in situ hybridization (ISH) with or without CARD.

Figure 64A:
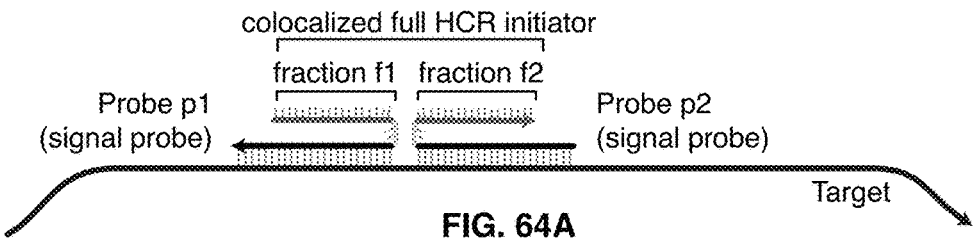
FIGS. 64A-64D depict some embodiments of probe sets comprising one or more probe units and optionally comprising one or more helper probes.
Figure 64B:
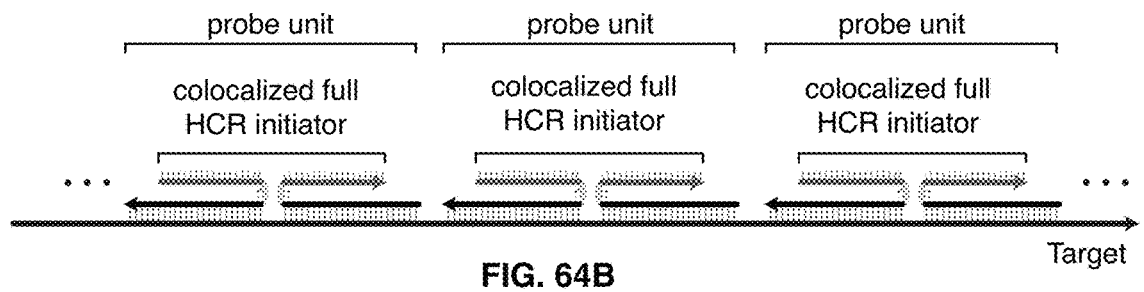
Figure 64C:
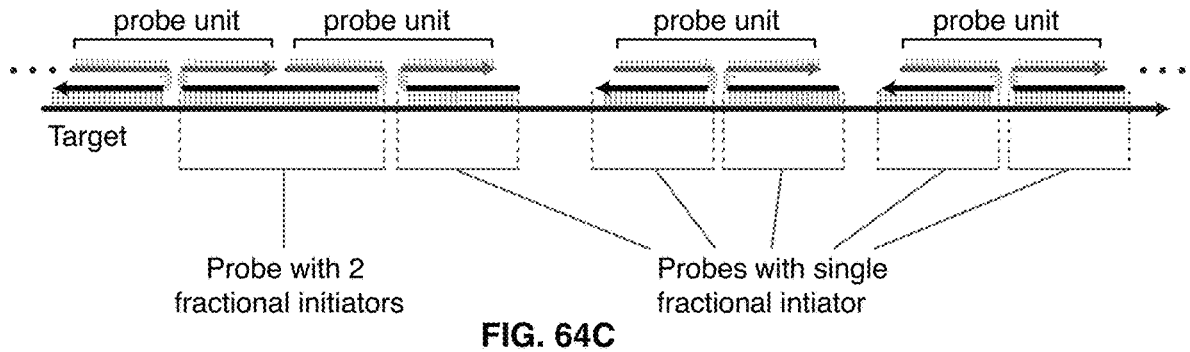
Figure 64D:
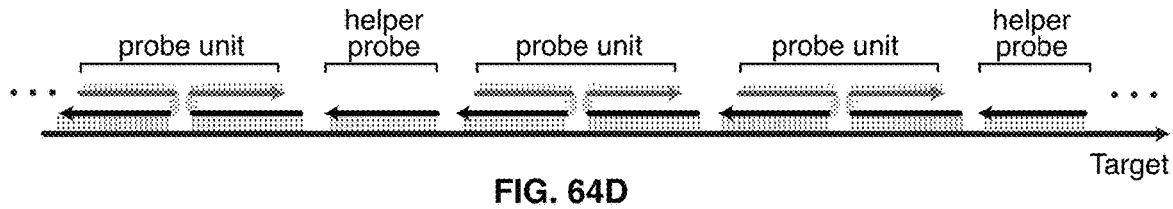
Figure 65A:
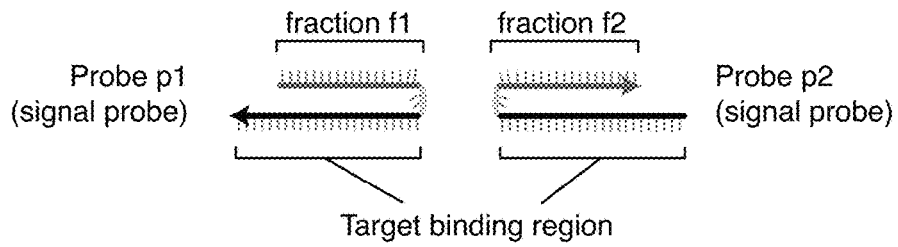
FIGS. 65A-65C depict some embodiments of probe units comprising fractional-initiator probes.
Figure 65B:
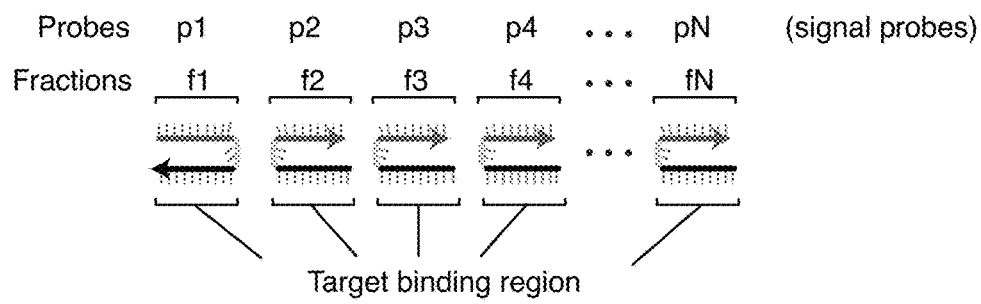
Figure 65C:
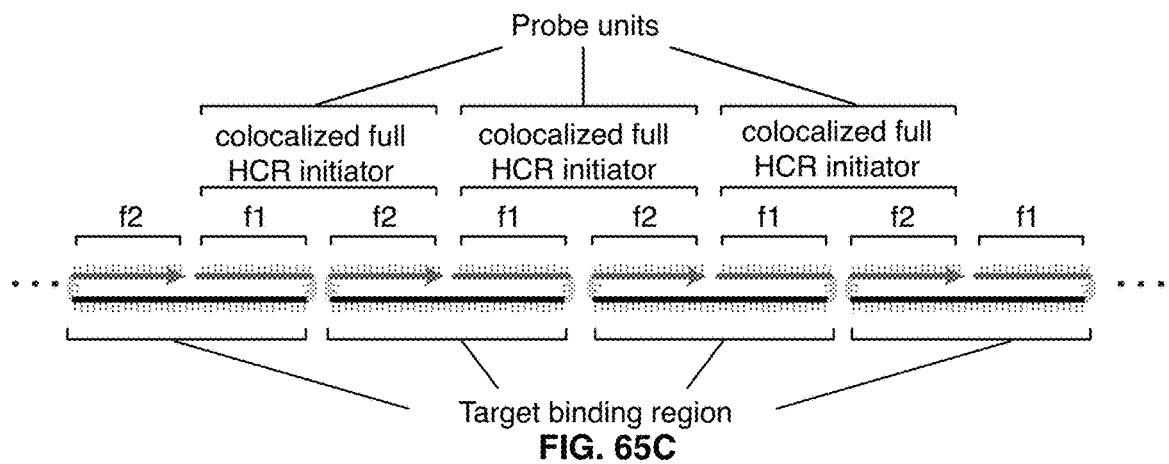

Full HCR Initiator Formed by Colocalization of 2 or More Fractional-Initiator Probes We refer to each set of fractional-initiator probes that generate a full HCR initiator (also known as a colocalized full HCR initiator or a full initiator or a colocalized full initiator) as a probe unit (for example, see FIGS. 64 and 65). In some embodiments, a colocalized full HCR initiator is generated by a pair of fractional-initiator probes that each carry a fraction of the full HCR initiator such that together they comprise the full HCR initiator (fraction f1 for probe p1 and fraction f2 for probe p2 such that f1+f2=1); in this case, a probe unit consists of two fractional-initiator probes (for example, see FIG. 65A). In some embodiments, the fractions f1 and f2 are sufficiently small compared to the full HCR initiator (for example, f1=0.5 with f2=0.5; or f1=0.45 with f2=0.55; or f1=0.4 with f2=0.6; or f1=0.3 with f2=0.7) such that HCR signal amplification is suppressed if the full HCR initiator is not colocalized by the target.

In some embodiments, an HCR initiator (i1 or i2) is split between three fractional-initiator probes (fraction f1 for probe P1, fraction f2 for probe P2, fraction f3 for probe 3 such that f1+f2+f3=1); in this case, a probe unit consists of three fractional-initiator probes. In some embodiments, an HCR initiator (i1 or i2) is split between N fractional-initiator probes (fraction f1 for probe P1, fraction f2 for probe P2, . . . , fraction fN for probe PN such that f1+f2+ . . . fN=1; for example, see FIG. 51B) with N=2, 3, 4, or more; in this case, a probe unit consists of N fractional-initiator probes. In some embodiments, for any of these values of N, HCR signal amplification is suppressed if the full HCR initiator is not colocalized by the target.

In some embodiments, a full HCR initiator is generated by colocalization of a pair (or set) of probes that each carry a fraction of an HCR initiator such that the sum of the fraction f1 for probe p1 and the fraction f2 for probe p2 (f1+f2) is sufficiently close to 1 (for example, f1=0.47, f2=0.47, f1+f2=0.94; or f1=0.44, f2=0.42, f1+f2=0.86) such that HCR signal amplification is triggered by the colocalized full initiator that results from binding of the pair of probes to their cognate binding sites on the target. In some embodiments, the fractional-initiator probes within a probe unit generate a full HCR initiator corresponding to 100% of an HCR initiator. In some embodiments, the fractional-initiator probes within a probe unit generate a sufficient fraction of an HCR initiator to provide efficient HCR signal amplification relative to the rate of signal amplification when no fractional-initiator probes are present or when individual fractional-initiator probes are present but are not colocalized by the target. In some embodiments, the fraction of a full HCR initiator generated by colocalized probes within a probe unit is 99%, 95%, 90%, 80%, or 60%, including any range above any one of the preceding values or defined between any two of the preceding values of a full HCR initiator. In some embodiments, a probe unit comprises 2, 3, 4, 5 or more fractional-initiator probes. In some embodiments, the fractional-initiators in the probe unit are sufficient to be functional as an HCR initiator when the probes within the probe unit are colocalized by binding to their adjacent or proximal cognate binding sites on the target. In some embodiments, while an HCR initiator may have a sequence of a particular length (e.g., 15 nucleotides), the fractional initiators within a probe unit need not be the exact same length. For example, in some embodiments, their combined length could be 14 or 13 nucleotides, if, when colocalized, they still function as an HCR initiator. In some embodiments, any two or more fractional initiators can be used, as long as, together, they provide the function of an HCR initiator.

In some embodiments, a full HCR initiator is generated by colocalization of a pair of probes that each carry a fraction of an HCR initiator further comprising one or a few or several sequence modifications such that the sum of the fraction f1 for probe p1 and the fraction f2 for probe p2 (f1+f2) is sufficiently close to 1 (for example, f1=0.45, f2=0.47, f1+f2=0.92) such that HCR signal amplification is triggered by the colocalized full initiator that results from binding of the pair of probes to their adjacent or proximal cognate binding sites on the target. In some embodiments, the fractional-initiator probes within a probe unit generate a colocalized full HCR initiator (also known as a full HCR initiator or a colocalized full initiator or a full initiator) that has 100% sequence identity with an HCR initiator. In some embodiments, the fractional-initiator probes within a probe unit generate sufficient sequence identity to an HCR initiator to allow efficient HCR signal amplification relative to the rate of signal amplification when no fractional-initiator probes are present or when individual fractional-initiator probes are present but are not colocalized by the target. In some embodiments, the full HCR initiator generated by colocalized probes within a probe unit has 99%, 95%, 90%, 80%, or 60% sequence identity with an HCR initiator, including any range above any one of the preceding values or defined between any two of the preceding values.

Increasing Signal Strength Using Helper Probes

In order to maintain selectivity for the target, the probe set size is sometimes constrained to be no more than 1 probe or 1 probe unit, or no more than 2 probes or 2 probe units, or no more than N probes or N probe units, where N is less than the number of probes or probe units, N+M, that would be preferentially used to maximize signal strength. In this scenario where the probe set size is constrained by selectivity considerations, the amount of signal generated can be less relative to detection of the same target using N+M probe units both because the probe set has the potential for generating M fewer full initiators for triggering HCR signal amplification and because the absence of the M additional probe units can reduce the binding yield of the N remaining probe units due to cooperative effects.

In some embodiments, signal probes carry one or more initiators or fractional-initiators (for example, see FIG. 64A). In some embodiments, helper probes do not carry initiators or fractional-initiators. In some embodiments, a helper probe does not comprise a proximity domain. In some embodiments, binding of one or more helper probes to the target increases target accessibility to facilitate the binding of one or more fractional-initiator probes to the target. In some embodiments, in order to increase signal without decreasing selectivity, a signal probe set comprising N probe units can be augmented with M helper probes (for example, see FIG. 64D).

HCR Amplifiers with 2 Hairpins

In some embodiments, an HCR amplifier comprises two hairpins (h1 and h2; for example, see FIGS. 2A-2B and 17A-17F). In some embodiments, each hairpin comprises an input domain with a single-stranded toehold and a stem section, and an output domain with a single-stranded loop and a complement to the stem section. In some embodiments, in the absence of an HCR initiator (i1 or i2), hairpins h1 and h2 coexist metastably, that is, they are kinetically trapped and do not polymerize.

Initiation with Initiator i1

In some embodiments, an initiator i1 comprises a domain complementary to the toehold of hairpin h1 and a domain complementary to the stem section of h1. In some embodiments, if an h1 hairpin encounters initiator i1, the initiator i1 hybridizes to the input domain of hairpin h1 via toehold-mediated strand displacement, opening hairpin h1 to expose the output domain of hairpin h1 and form complex i1-h1. In some embodiments, the output domain of hairpin h1 comprises a domain complementary to the toehold of hairpin h2 and a domain complementary to the stem section of h2. In some embodiments, if an h2 hairpin encounters an i1-h1 complex, the exposed output domain of h1 hybridizes to the input domain of hairpin h2 via toehold-mediated strand displacement, opening hairpin h2 to expose the output domain of hairpin h2 and form complex i1-h1-h2. In some embodiments, the output domain of hairpin h2 comprises a domain complementary to the toehold of hairpin h1 and a domain complementary to the stem section of h1. In some embodiments, if an h1 hairpin encounters an i1-h1-h2 complex, the exposed output domain of h2 hybridizes to the input domain of hairpin h1 via toehold-mediated strand displacement, opening hairpin h1 to expose the output domain of hairpin h1 and form complex i1-h1-h2-h1. In some embodiments, this polymerization process can repeat with alternating h1 and h2 polymerization steps to generate polymers of the form i1-h1-h2-h1-h2-h1-h2- . . . , which we may denote i1-(h1-h2)$_N$ for a polymer that incorporates N alternating copies of hairpins h1 and h2. For example, a polymer might incorporate several h1 and h2 molecules, or dozens of h1 and h2 molecules, or hundreds of h1 and h2 molecules, or thousands of h1 and h2 molecules, or tens of thousands of h1 and h2 molecules, or more. In some embodiments, it is possible for a polymer to end with either h1 or h2, so i1-(h1-h2)$_N$-h1 and i1-(h1-h2)$_N$-h1-h2 are both possible, the latter being equivalent to i1-(h1-h2)$_{N+1}$.

Initiation with Initiator i2

In some embodiments, an initiator i2 comprises a domain complementary to the toehold of hairpin h2 and a domain complementary to the stem section of h2. In some embodiments, if an h2 hairpin encounters initiator i2, the initiator i2 hybridizes to the input domain of hairpin h2 via toehold-mediated strand displacement, opening hairpin h2 to expose the output domain of hairpin h2 and form complex i2-h2. In some embodiments, if an h1 hairpin encounters an i2-h2 complex, the exposed output domain of h2 hybridizes to the input domain of hairpin h1 via toehold-mediated strand displacement, opening hairpin h1 to expose the output domain of hairpin h1 and form complex i2-h2-h1. In some embodiments, if an h2 hairpin encounters an i2-h2-h1 complex, the exposed output domain of h1 hybridizes to the input domain of hairpin h2 via toehold-mediated strand displacement, opening hairpin h2 to expose the output domain of hairpin h2 and form complex i2-h2-h1-h2. In some embodiments, this polymerization process can repeat with alternating h2 and h1 polymerization steps to generate polymers of the form i2-h2-h1-h2-h1-h2-h1 . . . , which can be denoted i2-(h2-h1)$_N$ for a polymer that incorporates N alternating copies of h2 and h1. For example, a polymer might incorporate several h1 and h2 molecules, or dozens of h1 and h2 molecules, or hundreds of h1 and h2 molecules, or thousands of h1 and h2 molecules, or tens of thousands of h1 and h2 molecules, or more. In some embodiments, it is possible for a polymer to end with either h1 or h2, so i2-(h2-h1)$_N$-h2 and i2-(h2-h1)$_N$-h2-h1 are both possible, the latter being equivalent to i2-(h2-h1)$_{N+1}$.

Self-Bridging HCR Amplifiers with Split-Initiator Tails

In some embodiments, an HCR amplifier comprises two or more HCR hairpins, two or more of which comprise split-initiator tails such that initiation to trigger growth of an HCR amplification polymer leads to colocalization of two split-initiator tails at a junction between hairpins within the amplification polymer, yielding a colocalized full HCR initiator tethered to the resulting HCR amplification polymer (for example, see FIGS. 16C-16D, 38B, 71). In some embodiments, HCR amplifiers comprising 2 or more HCR hairpins with split-initiator tails are self-bridging between successive rounds of HCR signal amplification because polymerization of the HCR amplifier colocalizes a full HCR initiator that can be used to initiate a new round of HCR signal amplification. In some embodiments, a self-bridging HCR amplifier bridges between one round of HCR signal amplification that generates one or more colocalized full HCR initiators tethered to the resulting HCR amplification polymer and another round of HCR signal amplification that generates a new HCR amplification polymer tethered to each full HCR initiator colocalized by the previous HCR amplification polymer. In some embodiments, a self-bridging HCR amplifier comprising two HCR hairpins, one or both of which comprise two split-initiator tails (for example, FIG. 38B). In some embodiments, HCR hairpins with two split-initiator tails can cause leakage of an HCR amplifier out of the kinetically trapped metastable state in the absence of an HCR initiator or a colocalized full HCR initiator. In some embodiments, a self-bridging HCR amplifier comprises 4 HCR hairpins, at least two of which comprise exactly one split-initiator tail such that growth of an HCR amplification polymer leads to colocalization of a full HCR initiator tethered to the resulting amplification polymer (for example, see hairpins h1 and h3 that colocalize full HCR initiator i5 and hairpins h2 and h4 that colocalize full HCR initiator i6 in FIGS. 16C and 71) without the need to use any HCR hairpins comprising two split-initiator tails. In some embodiments, a self-bridging HCR amplifier comprises 4 HCR hairpins, comprising two versions of a first hairpin (each version comprising a different split-initiator tail), and two versions of a second hairpin (each version comprising a different split-initiator tail) such that growth of an HCR amplification polymer leads to random colocalization of a full HCR initiator tethered to the resulting amplification polymer depending on which versions of the hairpins are incorporated as neighbors at each junction in the polymer (for example, see FIG. 16D).

HCR Amplifiers with 4 Hairpins

Figure 16A:
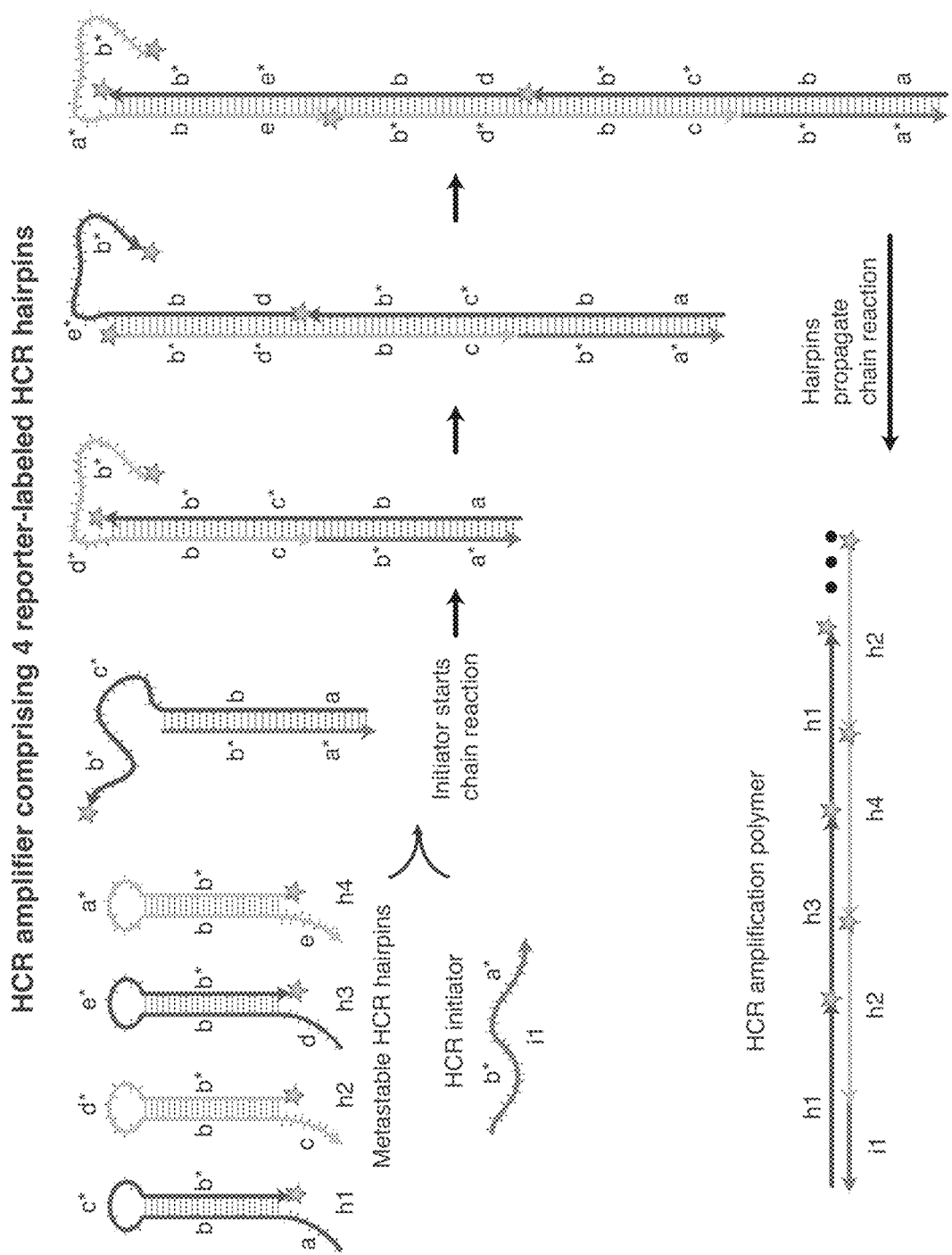
FIGS. 16A-16D depict some embodiments of HCR amplification using four HCR hairpins.
Figure 16B:
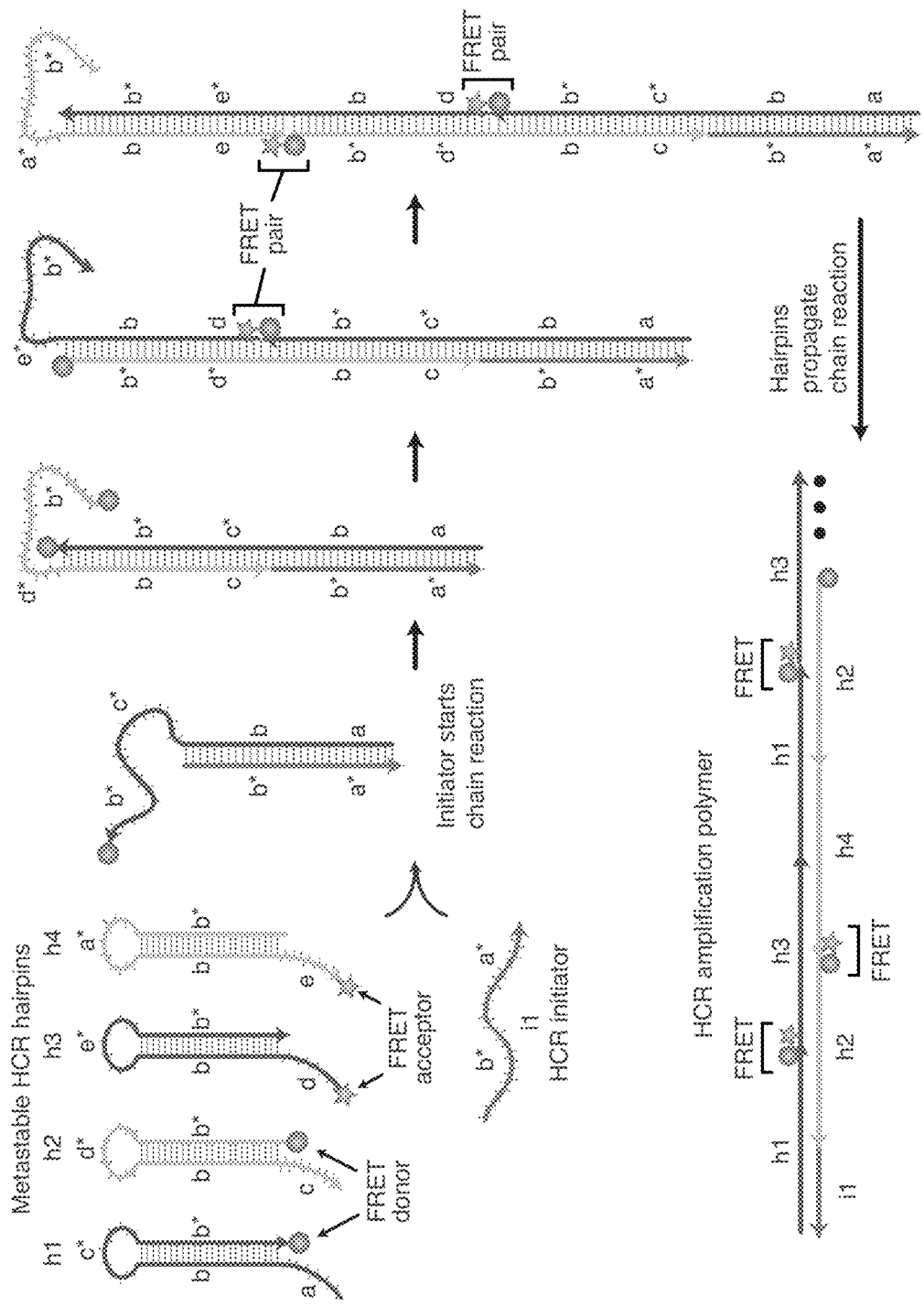

In some embodiments, an HCR amplifier can comprise more than 2 hairpins. For example, an HCR amplifier might comprise 4 hairpins h1, h2, h3, h4 (for example, see FIGS. 16A-16C). In some embodiments, just as for 2-hairpin HCR, each hairpin comprises an input domain comprising a single-stranded toehold and a stem section, and an output domain comprising a single-stranded loop and a complement to the stem section. In some embodiments, two or more hairpins comprise a single split-initiator tail (for example, see FIGS. 16C and 71) such that they colocalize a full second HCR initiator (for example, i5 or i6 in FIGS. 16C and 71) when they polymerize, and are thus self-bridging to a new round of HCR signal amplification. In some embodiments, the new round of HCR signal amplification is performed using an HCR amplifier (for example, the HCR amplifier comprising hairpins h5 and h6 in FIGS. 16C and 71) that is configured to be initiated by the colocalized full second HCR initiator. In some embodiments, in the absence of an HCR initiator (i1, i2, i3, or i4), hairpins h1, h2, h3, h4 coexist metastably, that is, they are kinetically trapped and do not polymerize. In some embodiments, the output domain of hairpin h1 comprises a domain complementary to the toehold of hairpin h2 and a domain complementary to the stem section of h2; the output domain of hairpin h2 comprises a domain complementary to the toehold of hairpin h3 and a domain complementary to the stem section of h3; the output domain of hairpin h3 comprises a domain complementary to the toehold of hairpin h4 and a domain complementary to the stem section of h4; the output domain of hairpin h4 comprises a domain complementary to the toehold of hairpin h1 and a domain complementary to the stem section of h1. In some embodiments, initiator i1 comprises a domain complementary to the toehold of hairpin h1 and a domain complementary to the stem section of h1; initiator i2 comprises a domain complementary to the toehold of hairpin h2 and a domain complementary to the stem section of h2; initiator i3 comprises a domain complementary to the toehold of hairpin h3 and a domain complementary to the stem section of h3; initiator i4 comprises a domain complementary to the toehold of hairpin h4 and a domain complementary to the stem section of h4. In some embodiments, analogous to the case of 2-hairpin HCR, if a hairpin h1 encounters an initiator i1, the initiator i1 opens hairpin h1 to form complex i1-h1 with an exposed h1 output domain, which in turn opens hairpin h2 to form complex i1-h1-h2 with an exposed h2 output domain, which in turn opens hairpin h3 with an exposed output domain to form complex i1-h1-h2-h3 with an exposed h3 output domain, which in turn opens hairpin h4 to form complex i1-h1-h2-h3-h4 with an exposed h4 output domain, which in turn opens hairpin h1 to form complex i1-h1-h2-h3-h4-h1 with an exposed h1 output domain, and so on and so forth, leading to polymerization via alternating h1, h2, h3, and h4 polymerization steps to generate polymers of the form i1-h1-h2-h3-h4-h1-h2-h3-h4-h1-h2-h3-h4 . . . , which can be denoted i1-(h1-h2-h3-h4)$_N$ for a polymer that incorporates N alternating copies of h1, h2, h3, and h4. In some embodiments, it is possible for a polymer to end with h1, h2, h3, or h4, so i1-(h1-h2-h3-h4)$_N$-h1, i1-(h1-h2-h3-h4)$_N$-h1-h2, i1-(h1-h2-h3-h4)$_N$-h1-h2-h3, and i1-(h1-h2-h3-h4)$_N$-h1-h2-h3-h4 are all possible, the latter being equivalent to i1-(h1-h2-h3-h4)$_{N+1}$. In some embodiments, it is possible for HCR polymerization to be triggered by any of the cognate initiators (i1, i2, i3, or i4). For example, initiation by initiator i3 could generate polymers of the form i3-(h3-h4-h1-h2)$_N$. In some embodiments, HCR amplifiers with 4 hairpins are convenient for generating a signal that is absent in the unpolymerized state and present in the polymer state (for example, FIG. 16B illustrates FRET pairs that are colocalized to generate a FRET signal only when hairpins are colocalized within an amplification polymer, providing a basis for wash-free methods since unused hairpins that are not washed from the sample will not participate in FRET, and hence will avoid generating background).

Self-Bridging HCR Amplifier Comprising 4 Hairpins with at Most One Split-Initiator Tail Per Hairpin In some embodiments, an HCR amplifier comprises 4 HCR hairpins (for example, see FIGS. 16C and 71): 1) a first HCR hairpin (h1) comprising a first input domain (sequence domains "a-b") comprising a first toehold (sequence domain "a") and a first stem section (sequence domain "b"), a first output domain (sequence domains "c*-b*") comprising a first loop (sequence domain "c*") and a partner to the first stem section (sequence domain "b*") that is configured to bind the first stem section, and a first split-initiator tail (sequence domain "f"), and 2) a second HCR hairpin (h2) comprising a second input domain (sequence domains "b-c") comprising a second toehold (sequence domain "c") and a second stem section (sequence domain "b"), a second output domain (sequence domains "b-d*") comprising a second loop (sequence domain "d*") and a partner to the second stem section (sequence domain "b*") that is configured to bind the second stem section, and a second split-initiator tail (sequence domain "h"); 3) a third HCR hairpin (h3) comprising a third split-initiator tail (sequence domain "g"), a third input domain (sequence domains "d-b") comprising a third toehold (sequence domain "d") and a third stem section (sequence domain "b"), and a third output domain (sequence domains "e*-b*") comprising a third loop (sequence domain "e*") and a partner to the third stem section (sequence domain "b*") that is configured to bind the first stem section, and 4) a fourth HCR hairpin (h4) comprising fourth split-initiator tail (sequence domain "i"), a fourth input domain (sequence domains "b-e") comprising a fourth toehold (sequence domain "e") and a fourth stem section (sequence domain "b"), and a fourth output domain (sequence domains "b*-a*") comprising a fourth loop (sequence domain "a*") and a partner to the fourth stem section (sequence domain "b*") that is configured to bind the fourth stem section. In some embodiments, a first initiator (i1; sequence domains "b*-a*") comprises a partner to the first toehold (sequence domain "a*") and a partner to the first stem section (sequence domain "b*"). In some embodiments, the first initiator is configured to bind the first input domain. In some embodiments, binding of the first initiator to the first input domain opens the first HCR hairpin to expose the first output domain. In some embodiments, the exposed first output domain is configured to bind the second input domain. In some embodiments, binding of the exposed first output domain to the second input domain opens the second HCR hairpin to expose the second output domain. In some embodiments, the exposed second output domain is configured to bind the third input domain. In some embodiments, binding of the exposed second output domain to the third input domain opens the third HCR hairpin to expose the third output domain. In some embodiments, the exposed third output domain is configured to bind the fourth input domain. In some embodiments, binding of the exposed third output domain to the fourth input domain opens the fourth HCR hairpin to expose the fourth output domain. In some embodiments, the exposed fourth output domain is configured to bind the first input domain. In some embodiments, binding of the exposed fourth output domain to the first input domain leads to HCR polymerization in which first, second, third, and fourth HCR hairpins are successively opened and added to the growing polymer in periodic fashion. In some embodiments, when initiator i1 initiates growth of an HCR amplification polymer comprising successive addition and opening of h1, h2, h3, and h4 hairpins, the split-initiator tails of h1 and h3 colocalize a full fifth HCR initiator i5 (sequence domains "g-f") tethered to the HCR amplification polymer and the split-initiator tails of h2 and h4 colocalize a full sixth HCR initiator i6 (sequence domains "h-i") tethered to the HCR amplification polymer. In some embodiments, the colocalized full fifth HCR initiator i5 and the colocalized full sixth HCR initiator i6 provide the basis for bridging to a new round of HCR signal amplification by triggering growth of a new HCR amplification polymer tethered to the original HCR amplification polymer.

In some embodiments, the 4-hairpin amplifier comprising hairpins h1, h2, h3, and h4 can also be initiated by a second initiator i2 (sequence domains "c*-b*") comprising a partner to the second toehold (sequence domain "c*") and a partner to the second stem section (sequence domain "b*"), by a third initiator i3 (sequence domains "b*-d*") comprising a partner to the third toehold (sequence domain "d*") and a partner to the third stem section (sequence domain "b*"), and/or by a fourth initiator i4 (sequence domains "e*-b*") comprising a partner to the fourth toehold (sequence domain "e*") and a partner to the fourth stem section (sequence domain "b*").

In some embodiments, the colocalized full fifth HCR initiator i5 and/or the colocalized full sixth HCR initiator i6 are configured to trigger polymerization of an HCR amplification polymer comprising two HCR hairpins (for example, see FIGS. 16C and 71): 1) a fifth HCR hairpin (h5) comprising a fifth input domain (sequence domains "j-k") comprising a fifth toehold (sequence domain "j") and a fifth stem section (sequence domain "k"), and a fifth output domain (sequence domains "l-k*") comprising a fifth loop (sequence domain "l*") and a partner to the fifth stem section (sequence domain "k*") that is configured to bind the fifth stem section, and 2) a sixth HCR hairpin (h6) comprising a sixth input domain (sequence domains "k-l") comprising a sixth toehold (sequence domain "l") and a sixth stem section (sequence domain "k"), and a sixth output domain (sequence domains "k*-j*") comprising sixth loop (sequence domain "j*") and a partner to the sixth stem section (sequence domain "k*") that is configured to bind the sixth stem section.

Figure 16C:
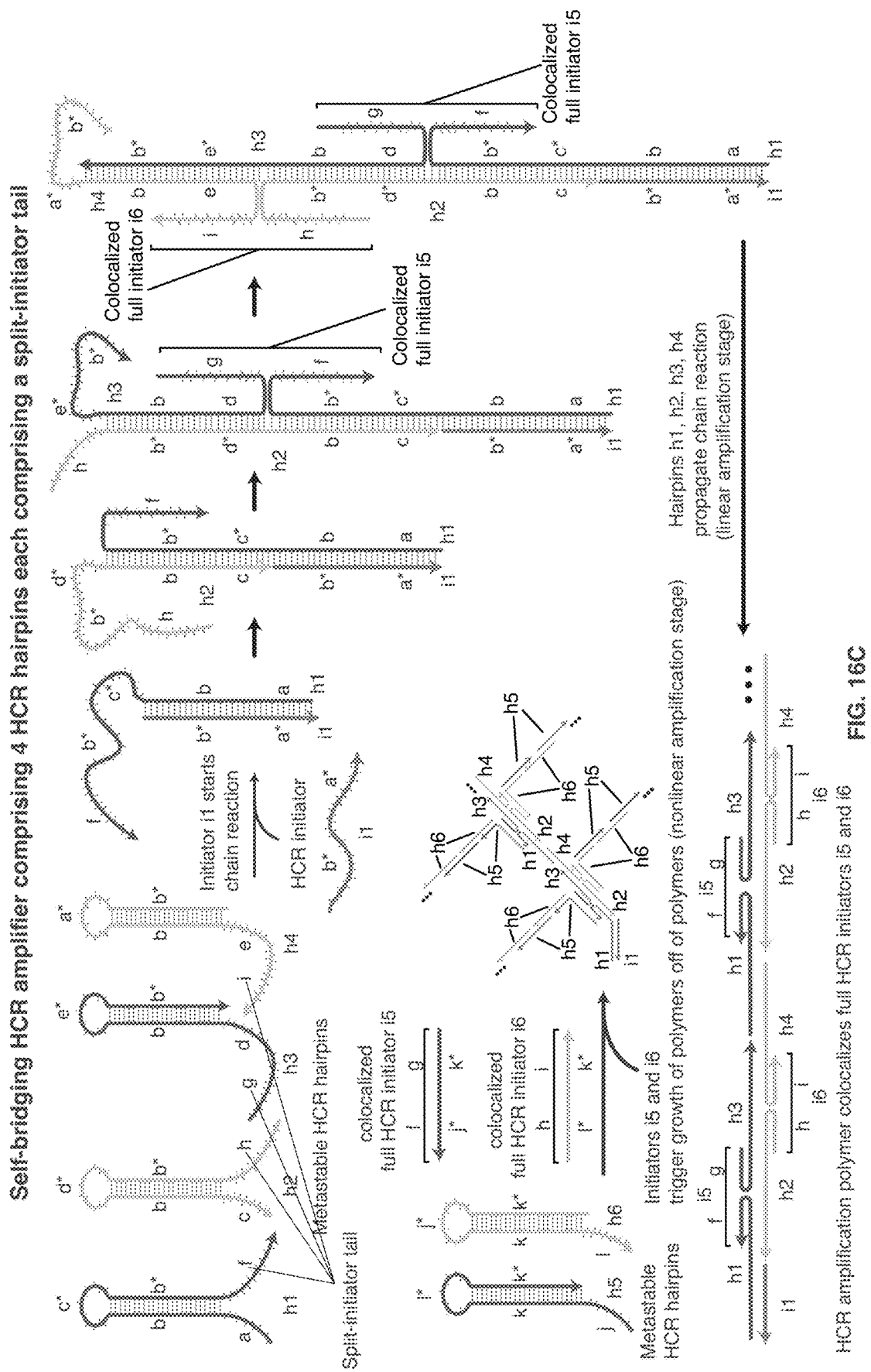
Figure 16D:
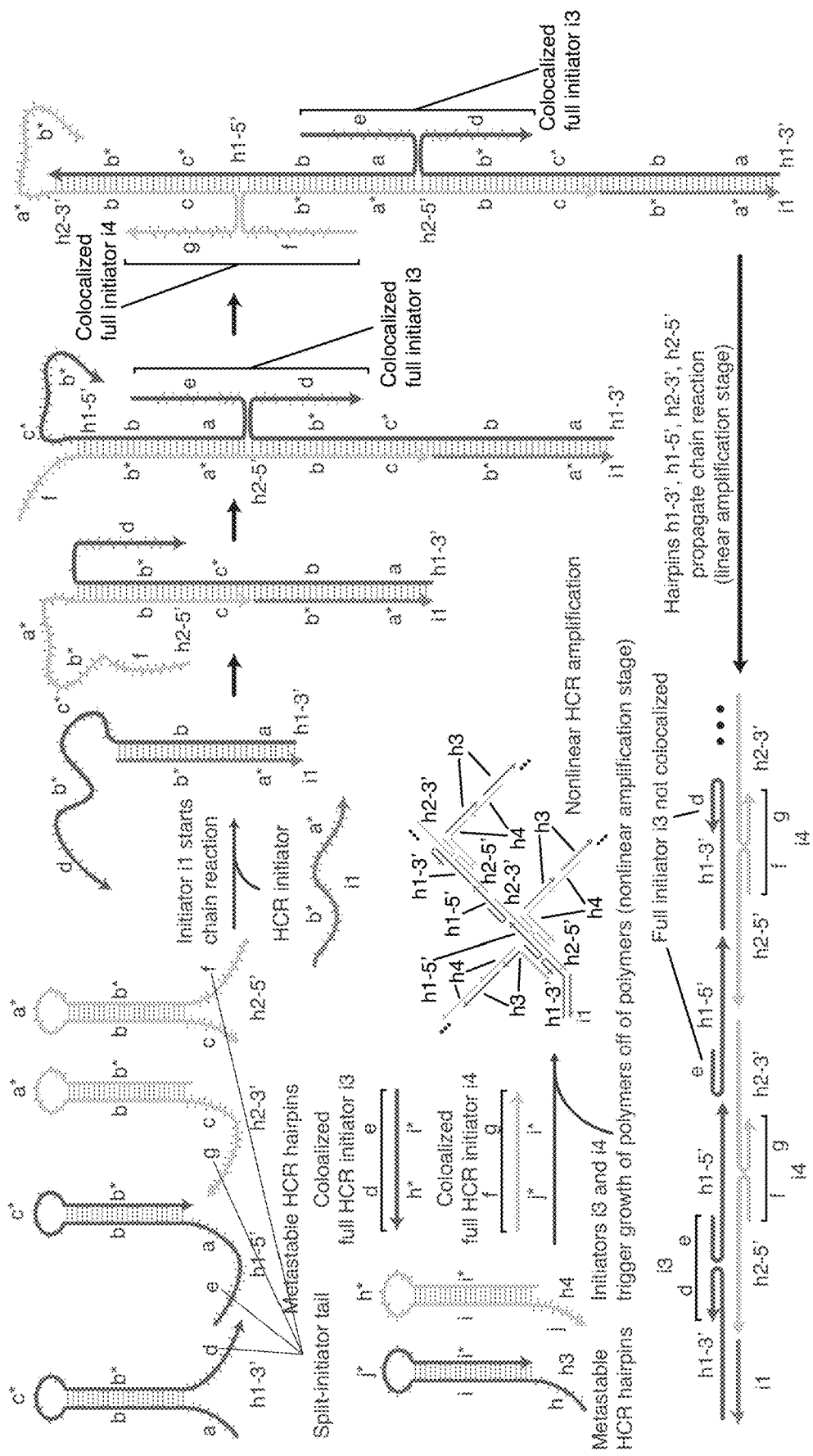
Figure 17A:
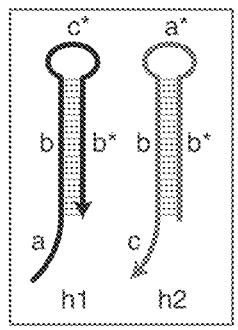
FIGS. 17A-17F depict some embodiments of HCR amplifiers.
Figure 17B:
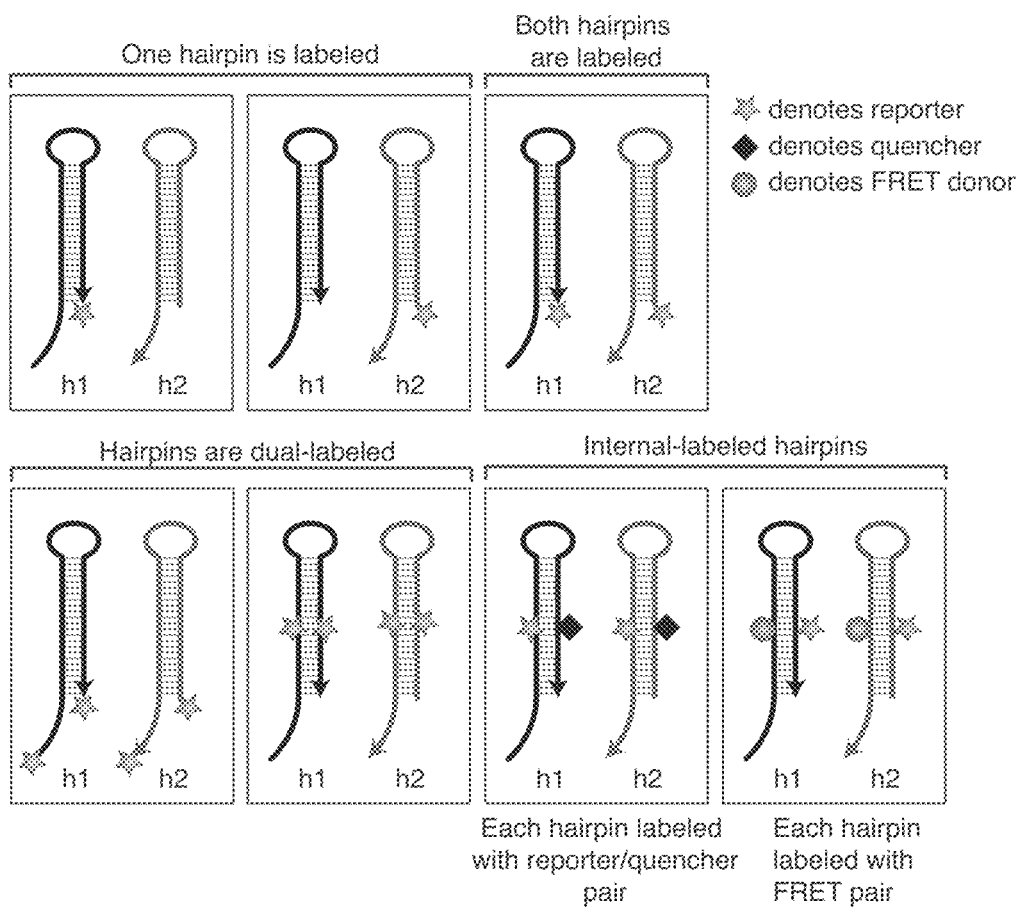
Figure 17C:
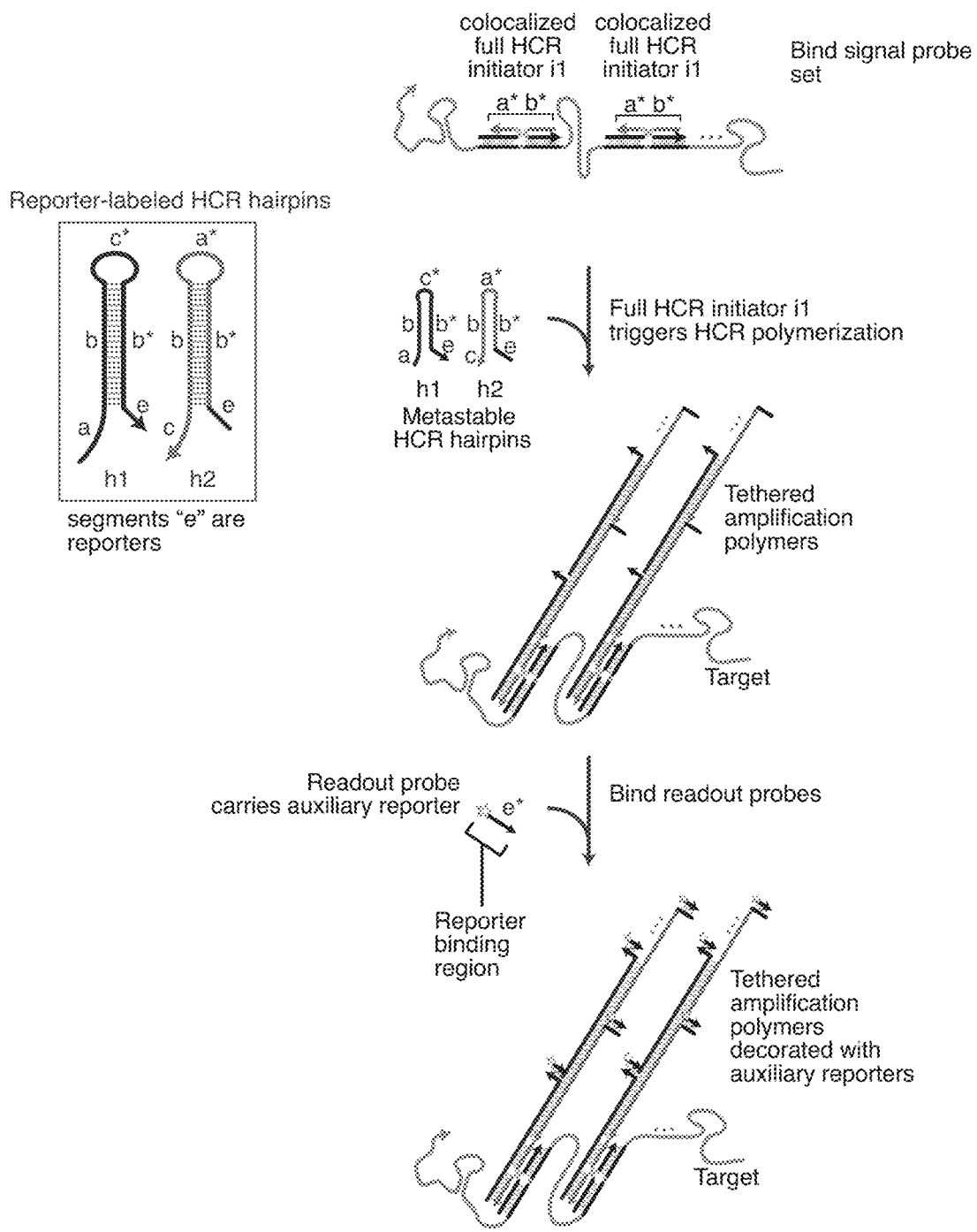
Figure 17D:
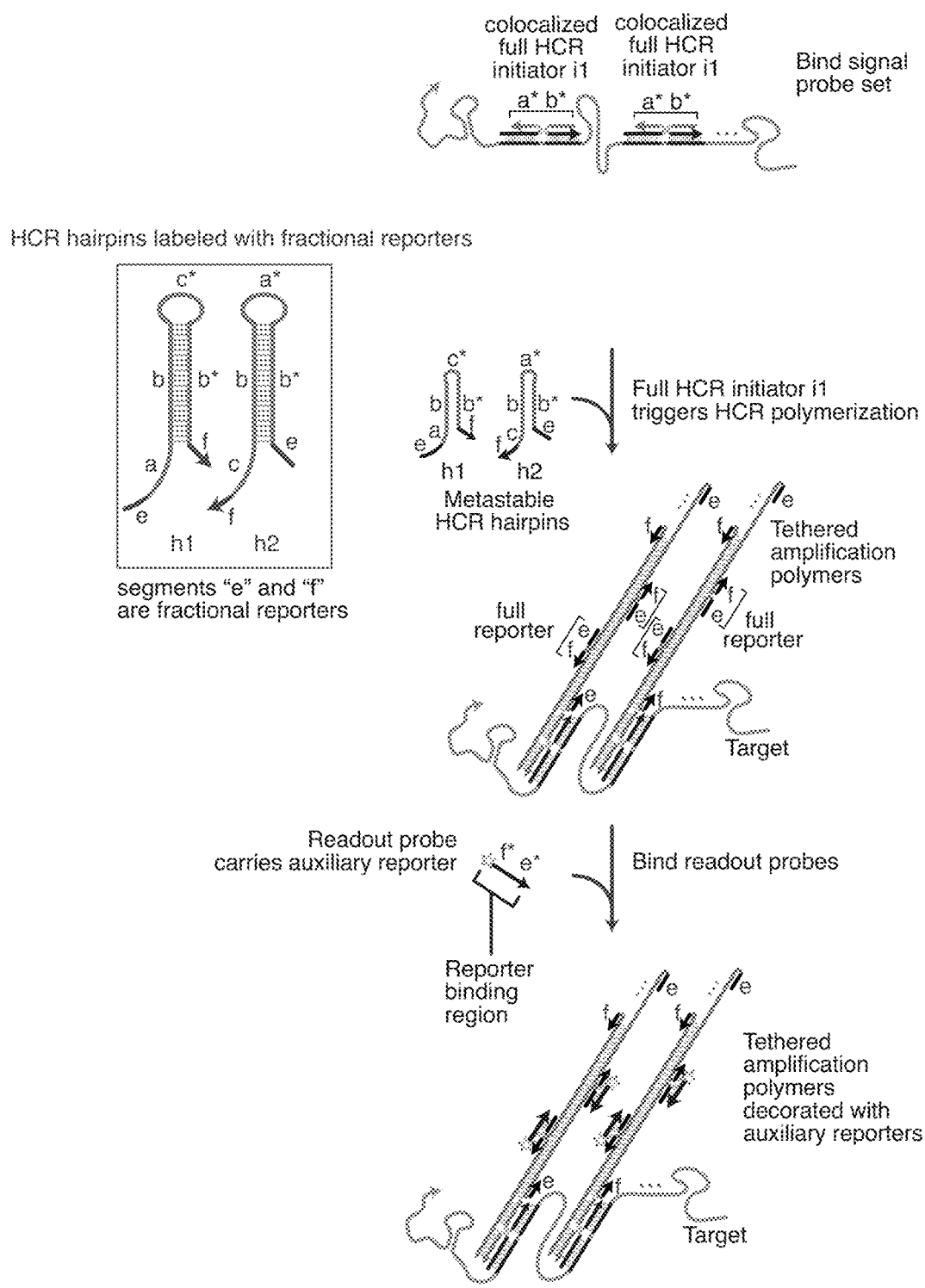
Figure 17E:
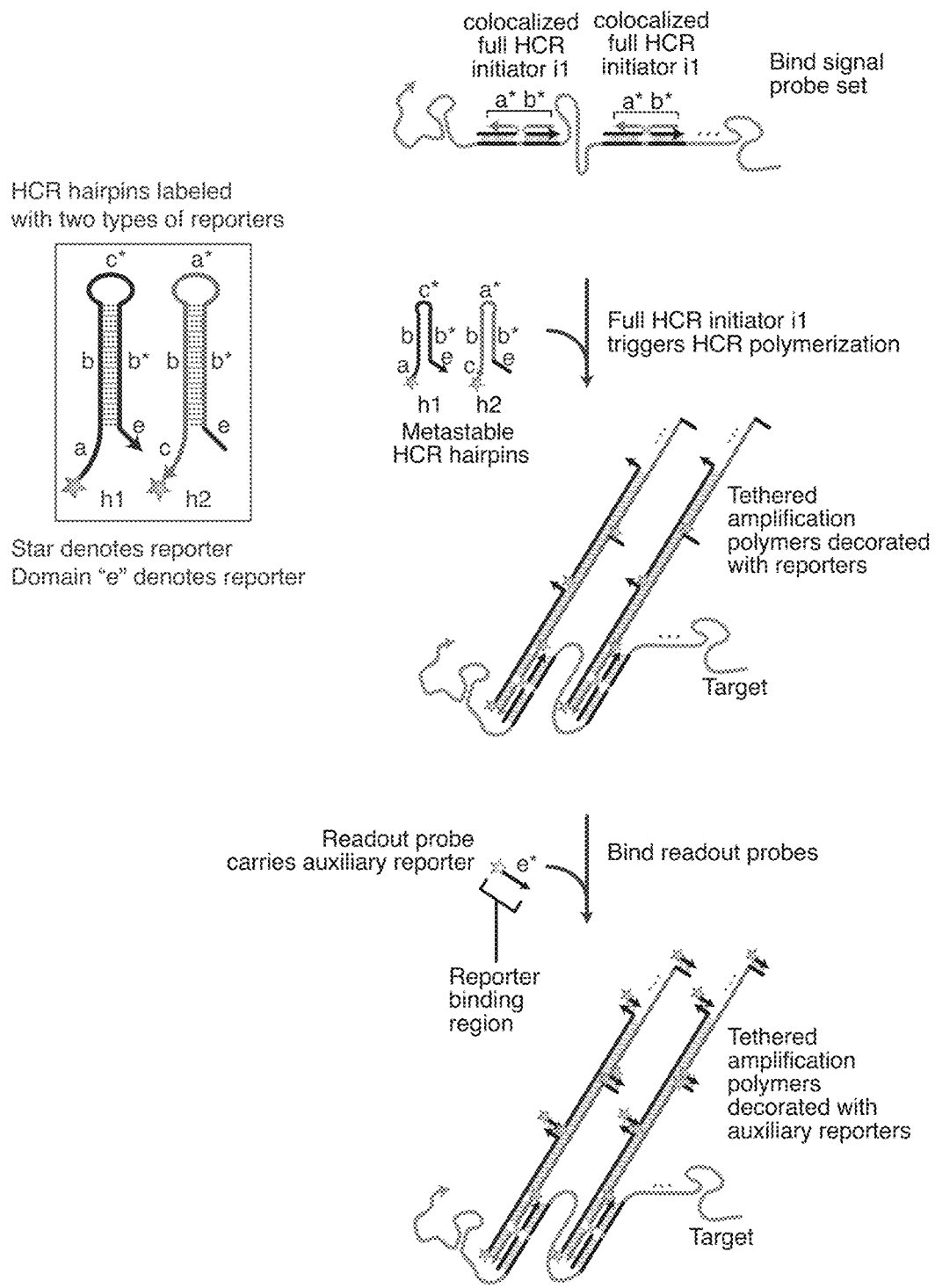
Figure 17F:
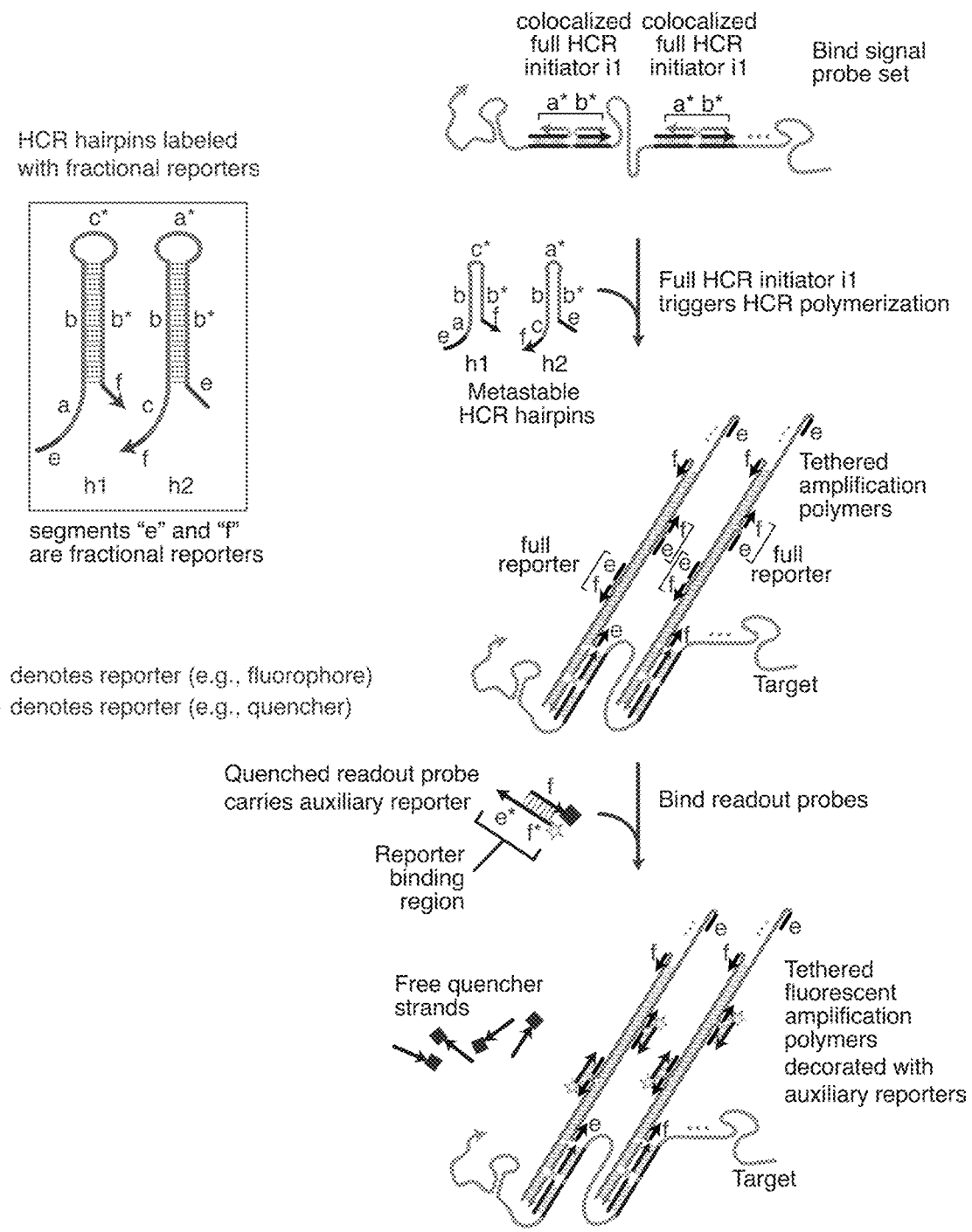
Figure 18G:
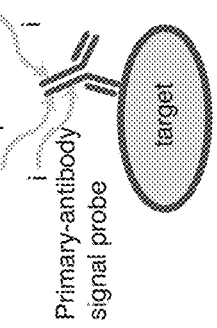
FIGS. 18A-18N depict some embodiments of initiator-labeled probes.
Figure 18H:
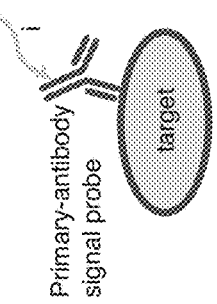
Figure 18I:
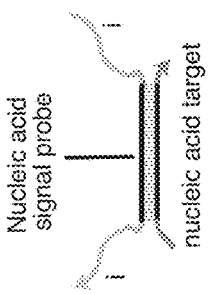
Figure 18J:
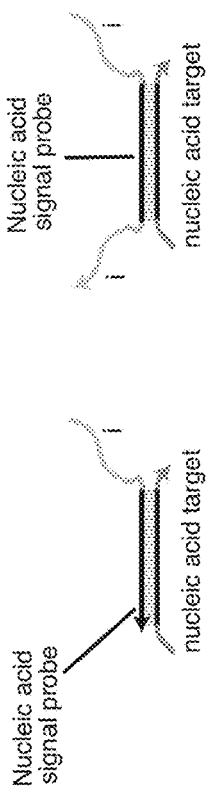
Figure 18K:
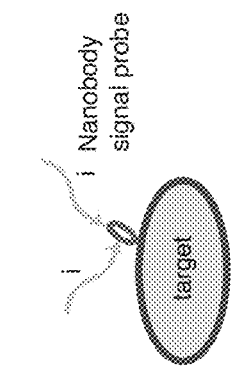
Figure 18L:
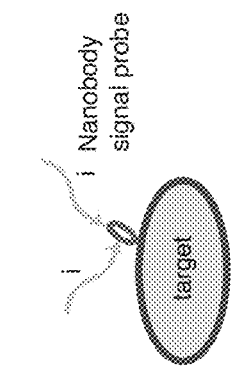
Figure 18M:
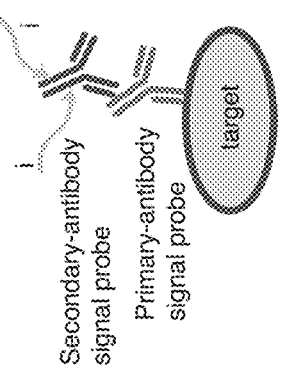
Figure 18N:
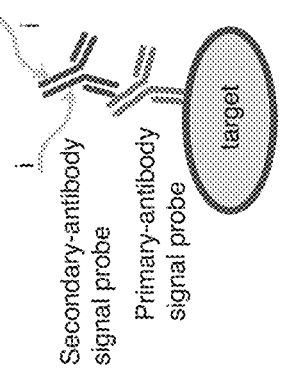
Figure 19D:
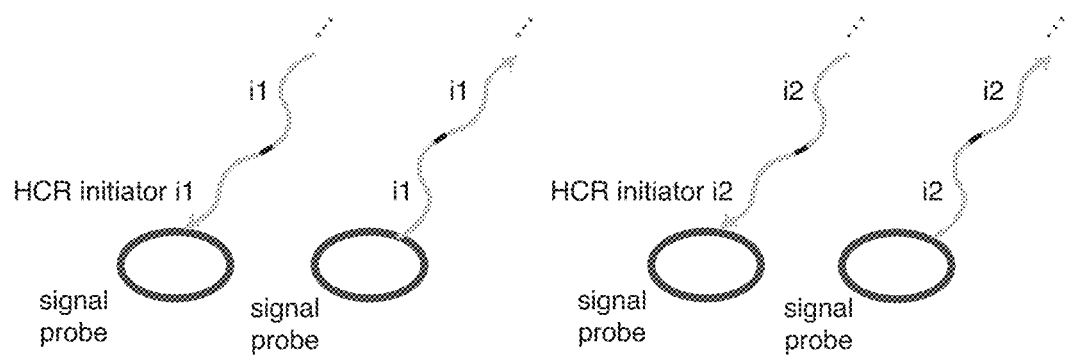
Figure 20A:
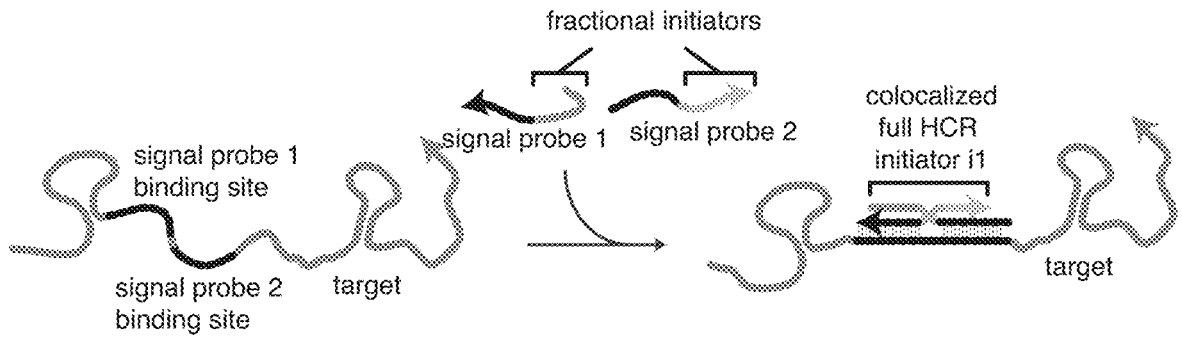
FIGS. 20A-20E depict some embodiments of fractional-initiator probes colocalized by a target.
Figure 20B:
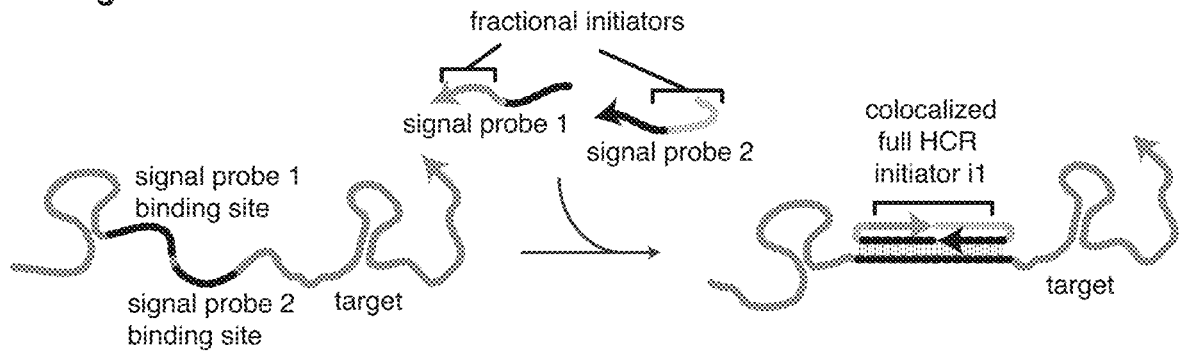
Figure 20C:
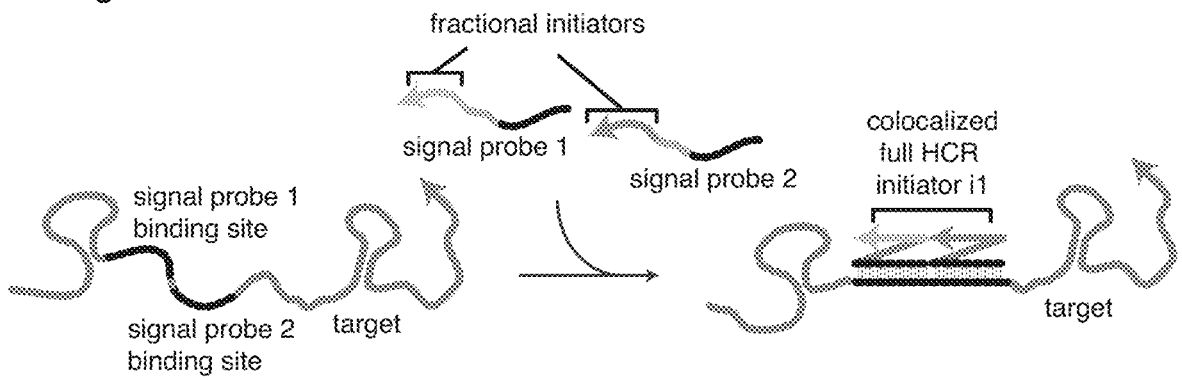
Figure 20D:
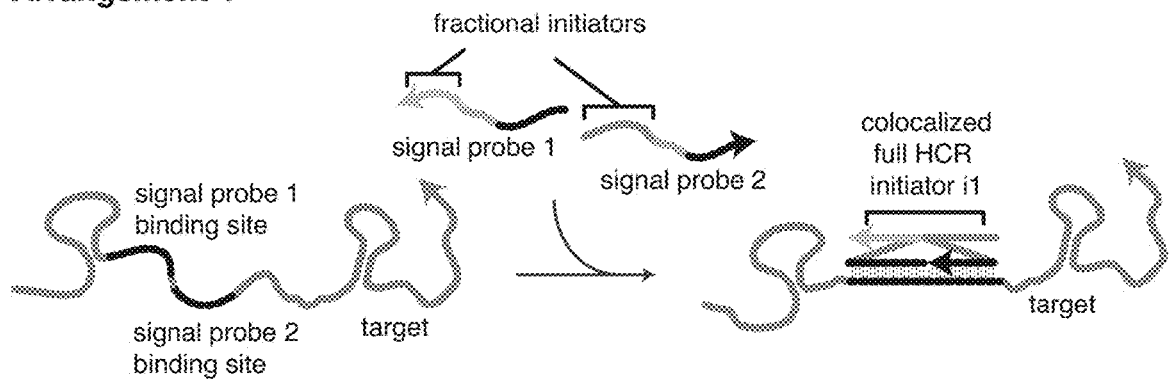
Figure 20E:
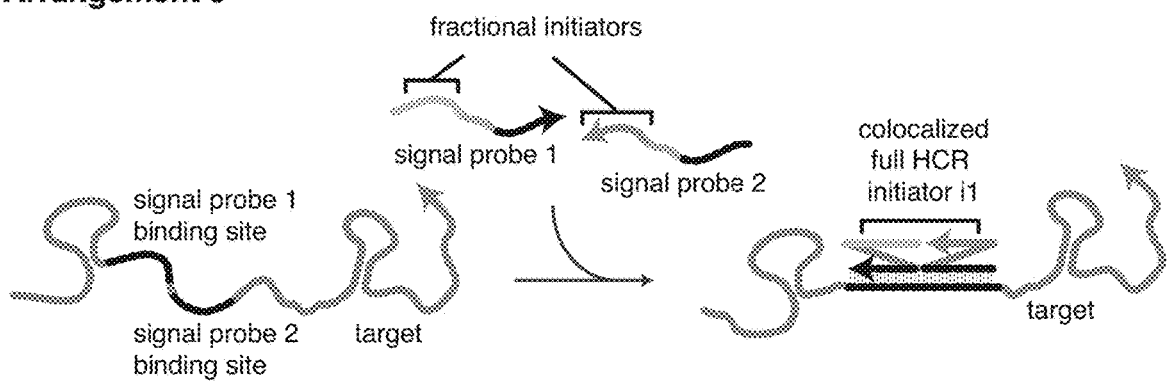
Figure 23:
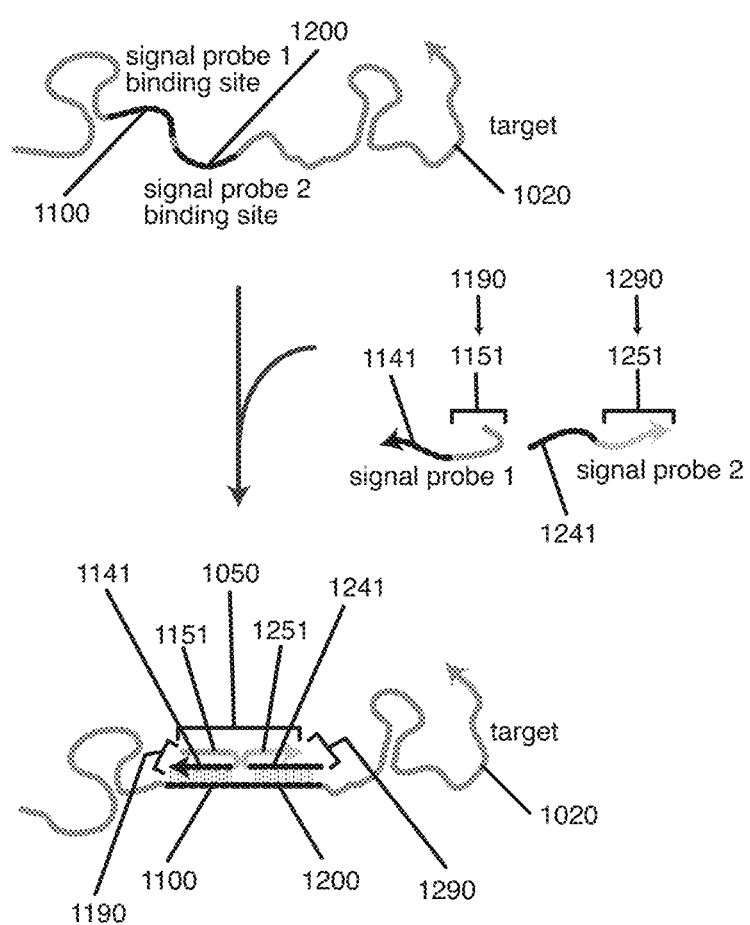
FIG. 23 depicts some embodiments of fractional-initiator probes colocalized by a target.
Figure 24A:
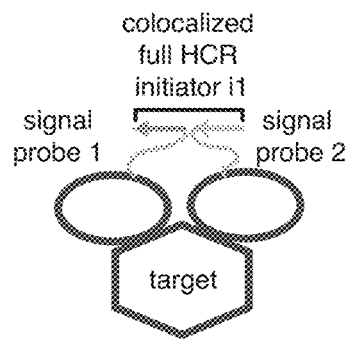
FIGS. 24A-24R depicts some embodiments of fractional-initiator probes colocalized by a target either directly or indirectly.
Figure 24B:
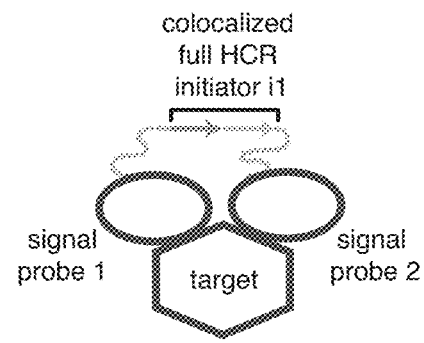
Figure 24C:
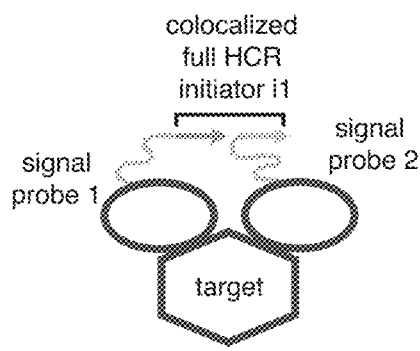
Figure 24D:
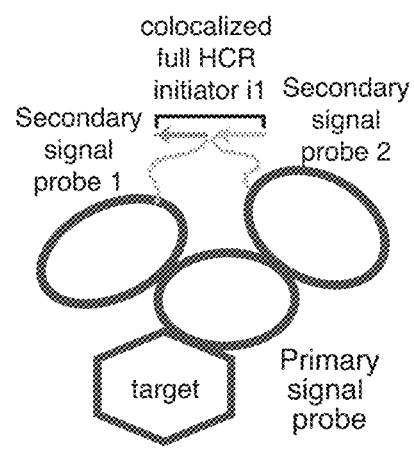
Figure 24E:
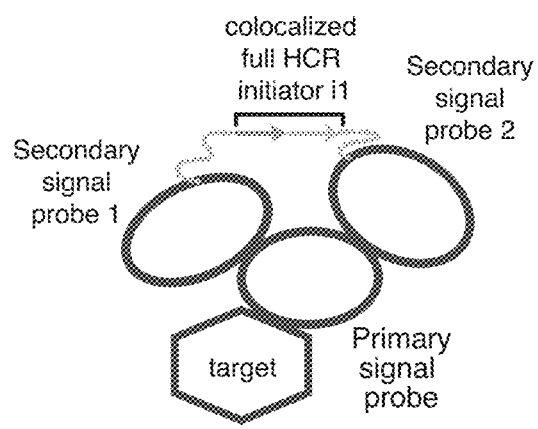
Figure 24F:
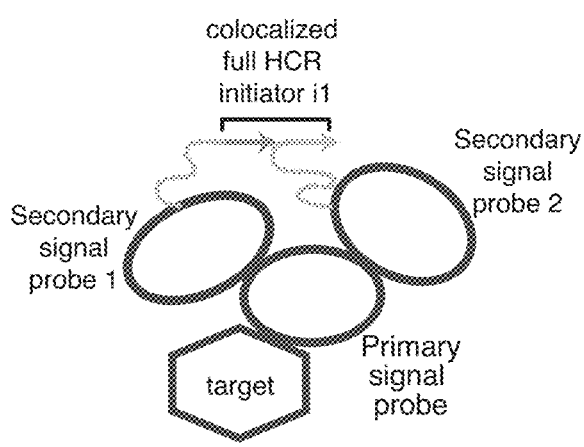
Figures 24G, 24H:
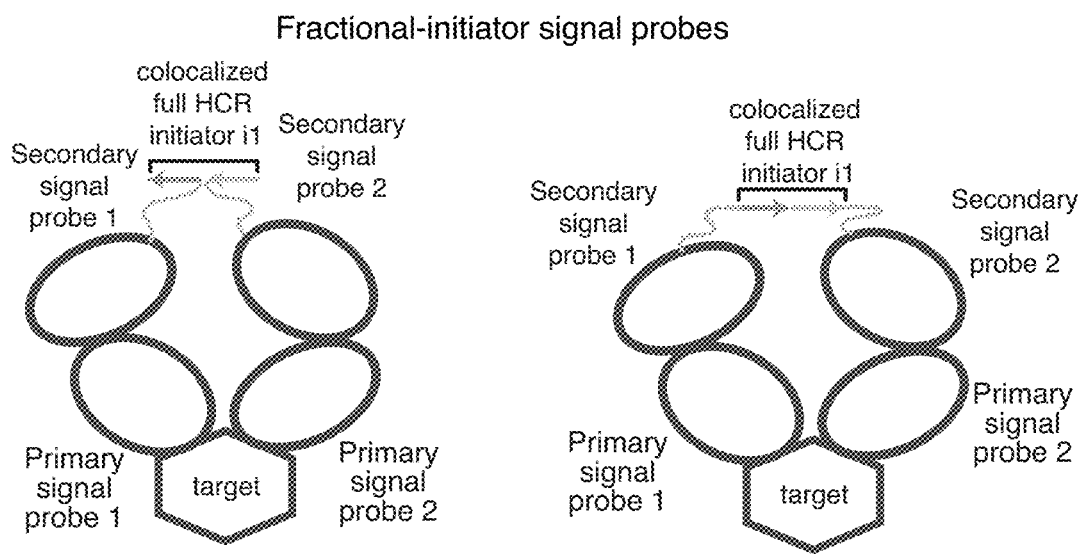
Figures 24I, 24J:
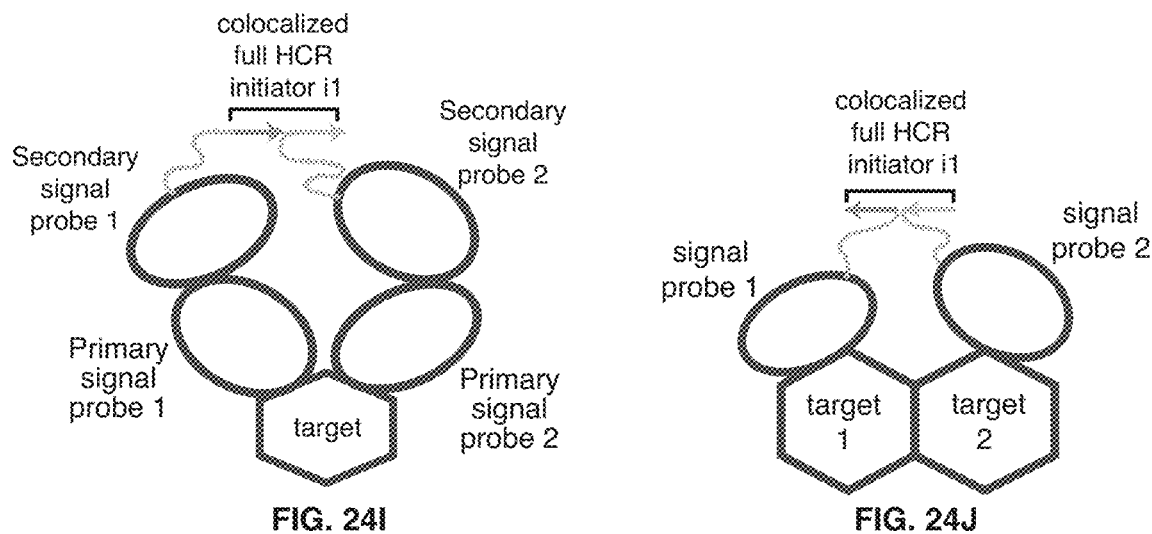
Figures 24K, 24L:
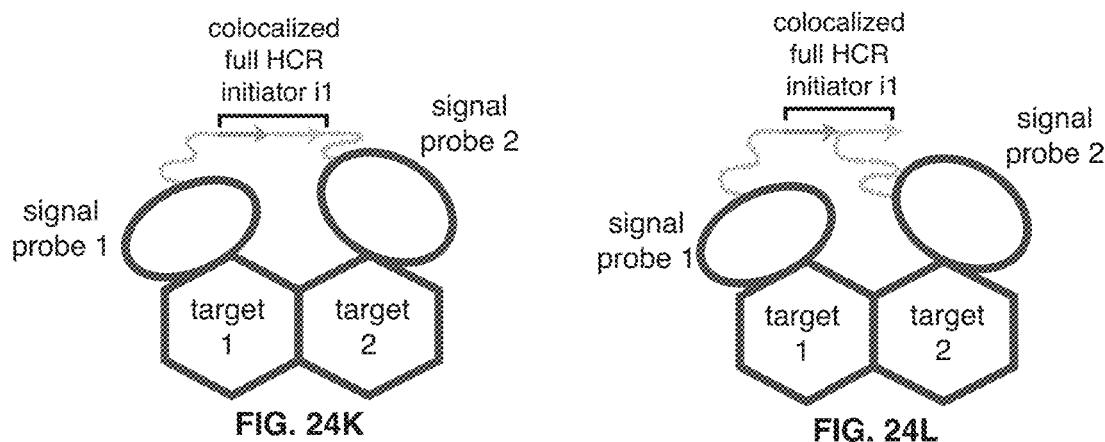
Figure 24M:
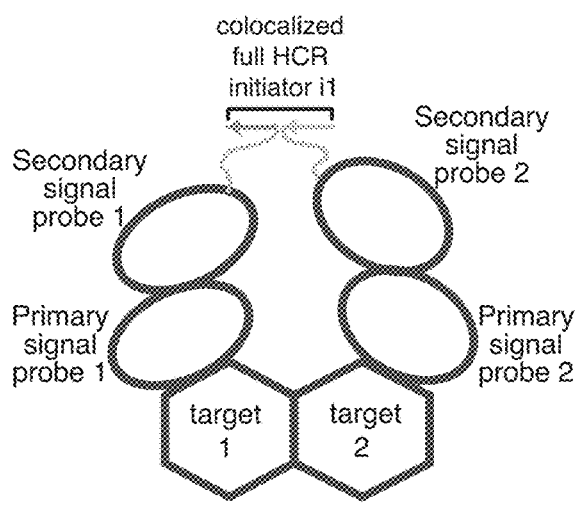
Figure 24N:
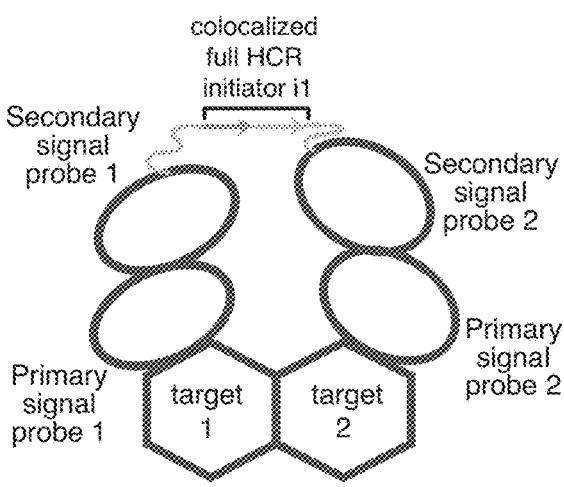
Figure 24O:
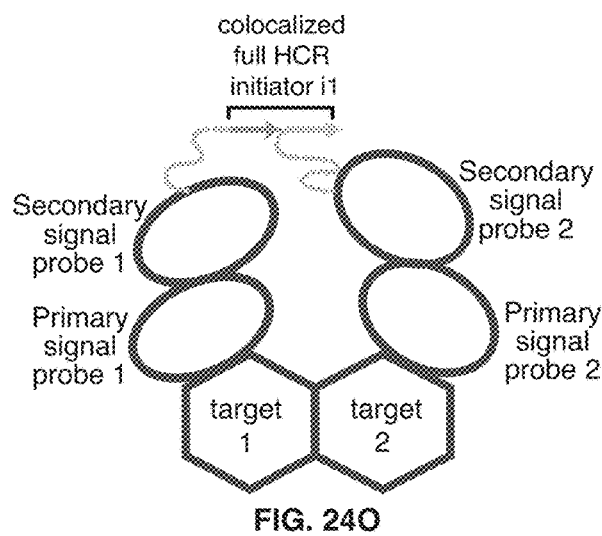
Figure 24P:
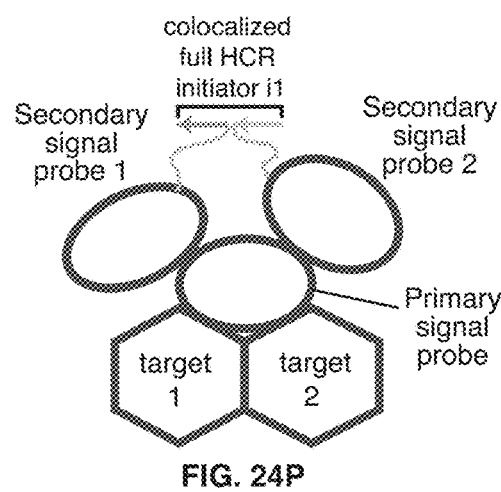
Figure 24Q:
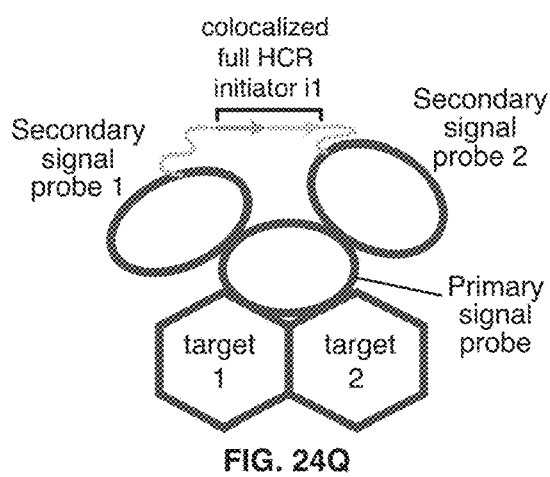
Figure 24R:
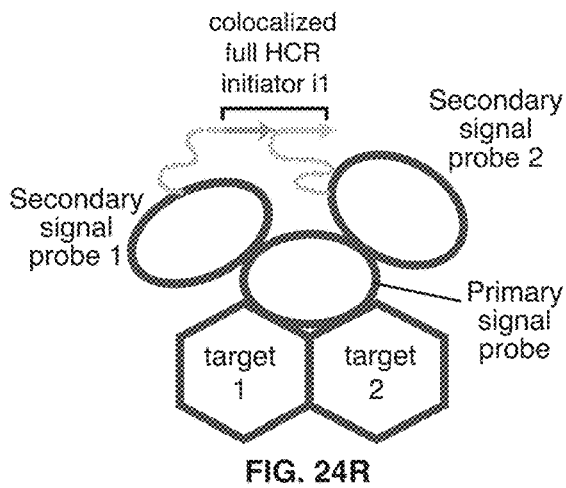
Figure 25A:
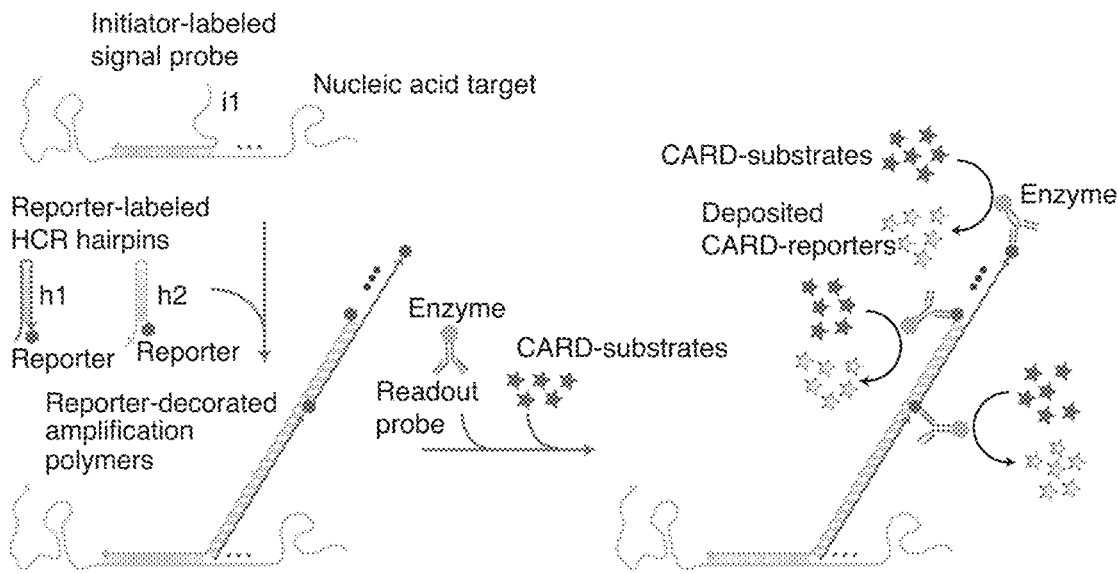
FIGS. 25A-25E depict some embodiments for using HCR amplification to mediate CARD signal amplification for different targets and signal probes.
Figure 25B:
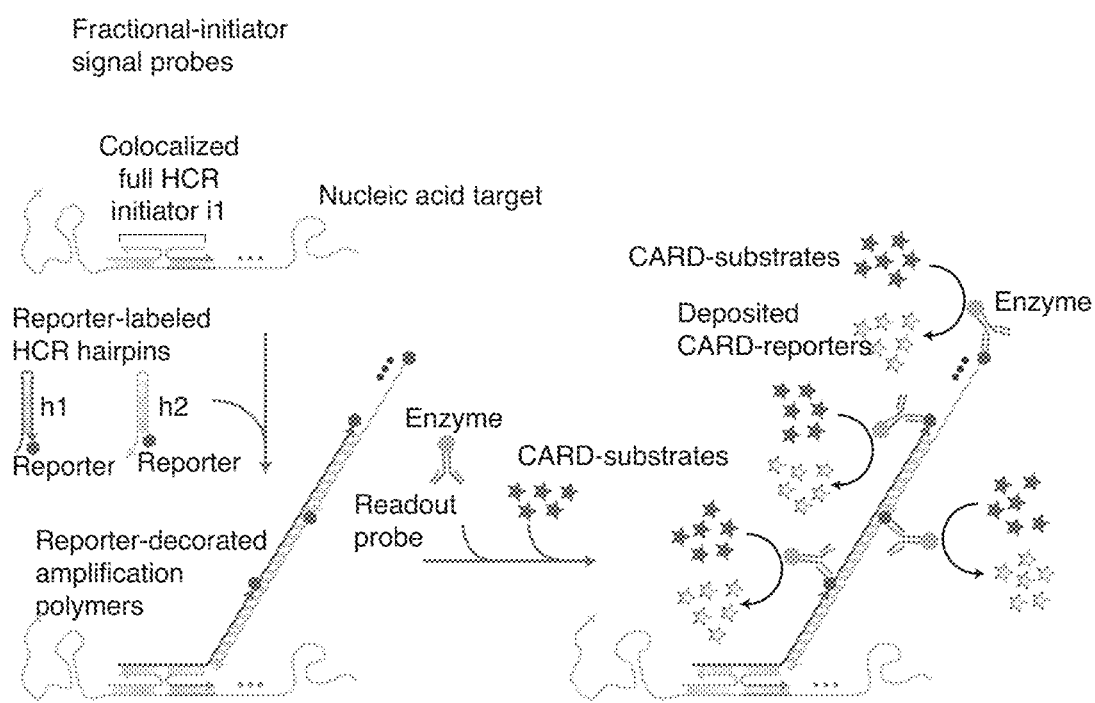
Figure 25C:
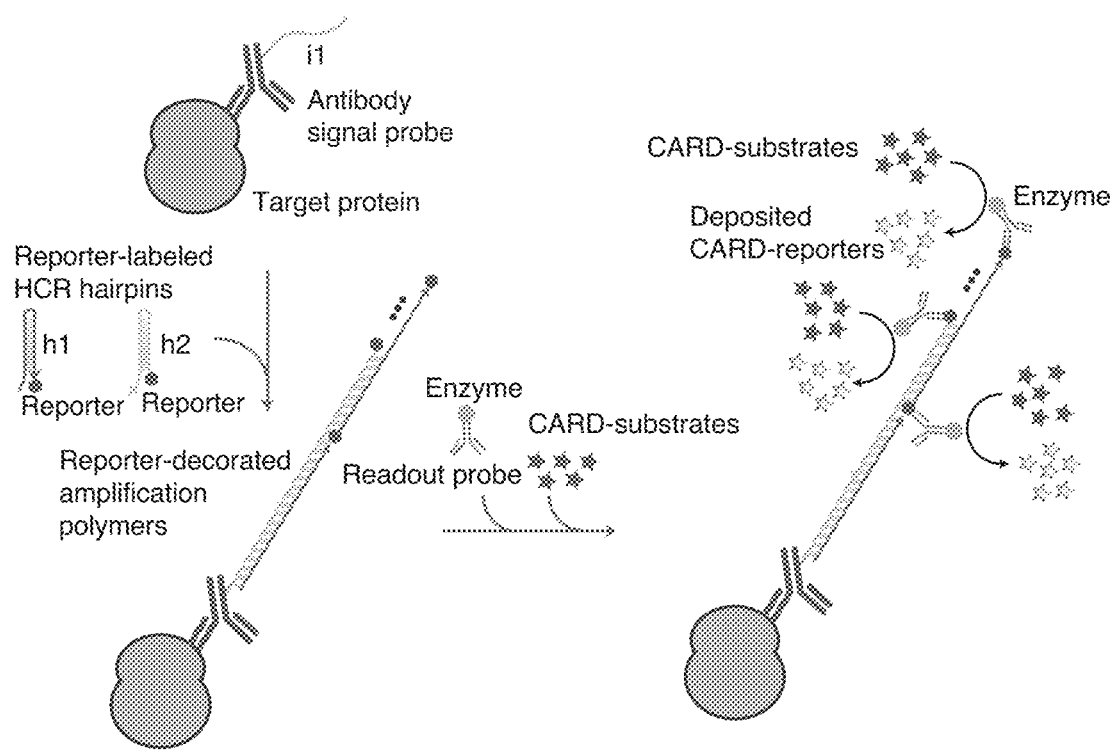
Figure 25D:
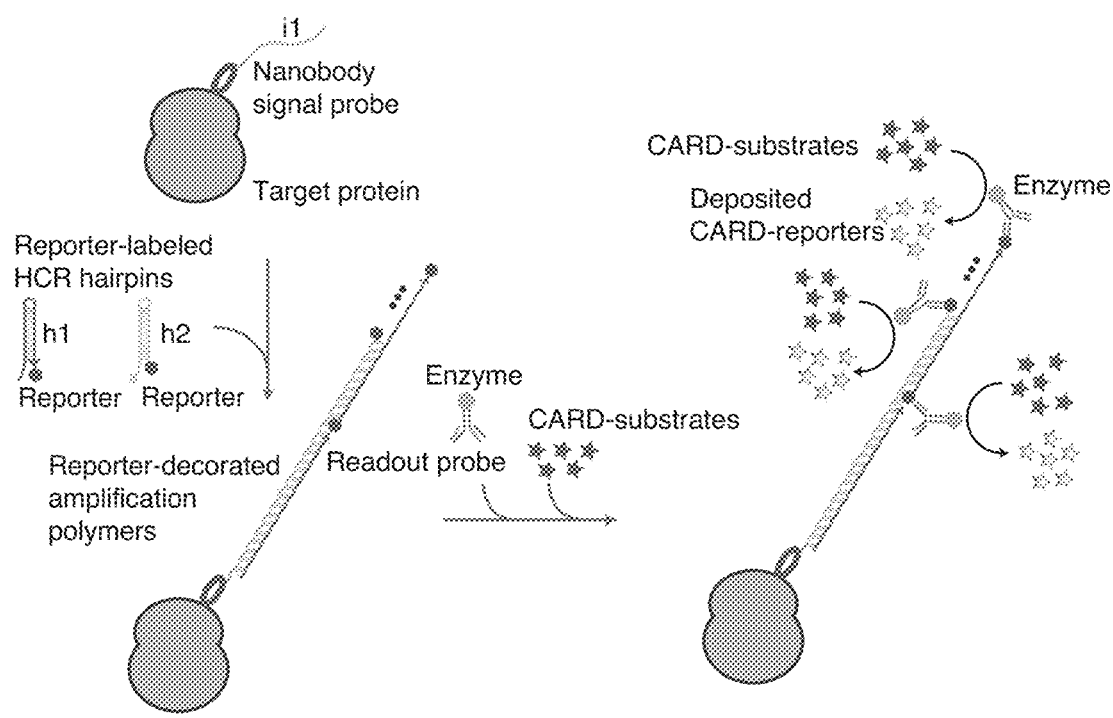
Figure 25E:
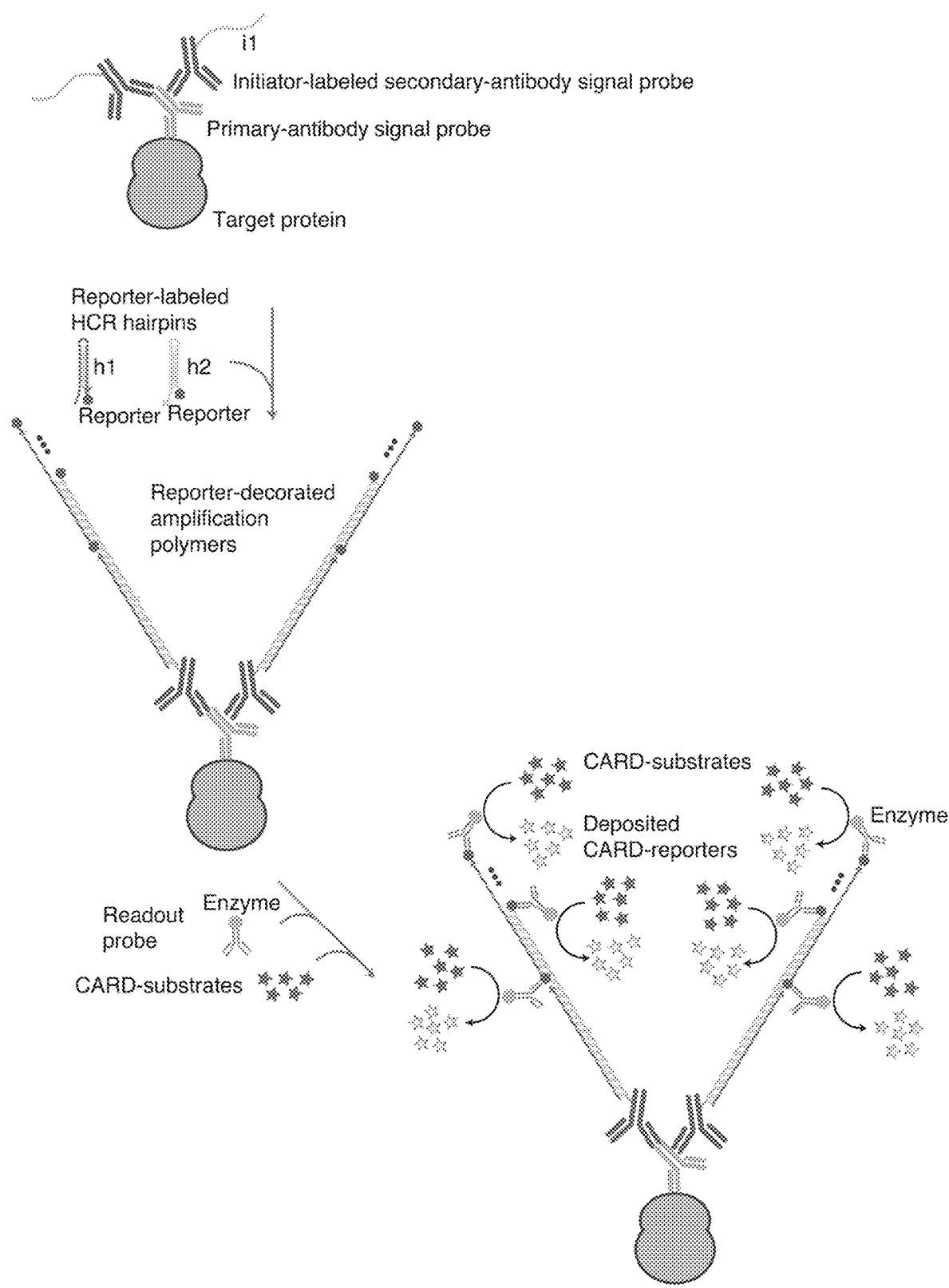
Figure 26A:
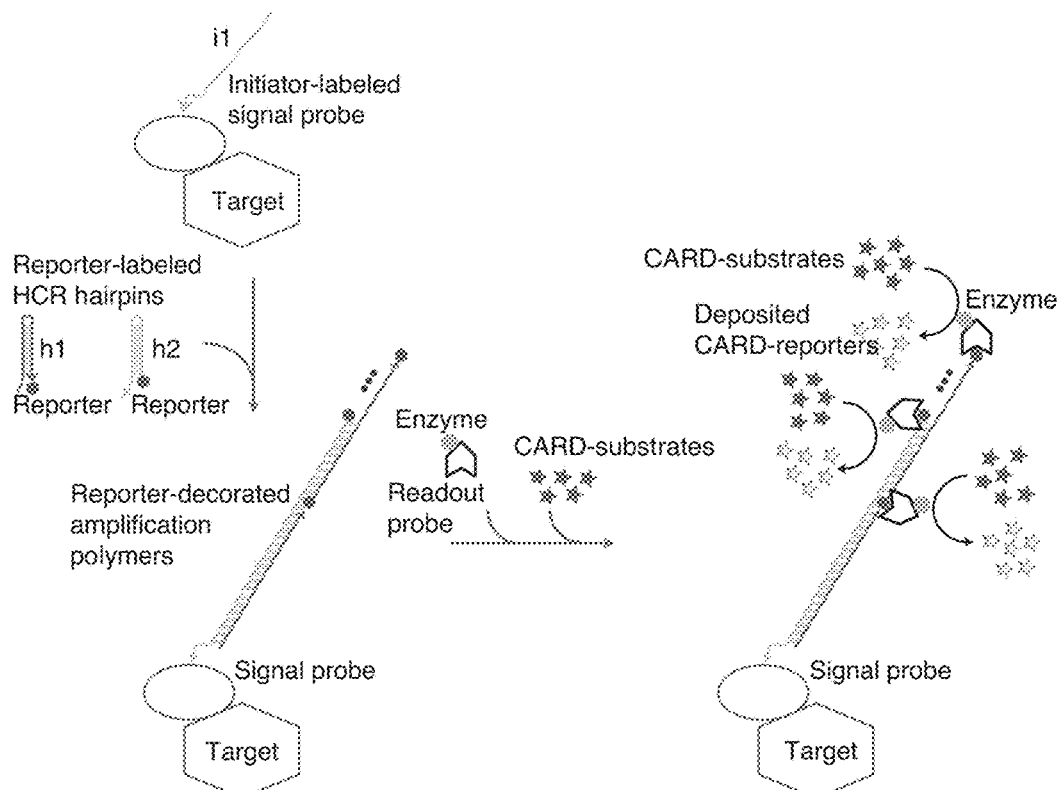
FIGS. 26A-26C depict some embodiments using HCR signal amplification to mediate CARD signal amplification for generic targets and signal probes.
Figure 26B:
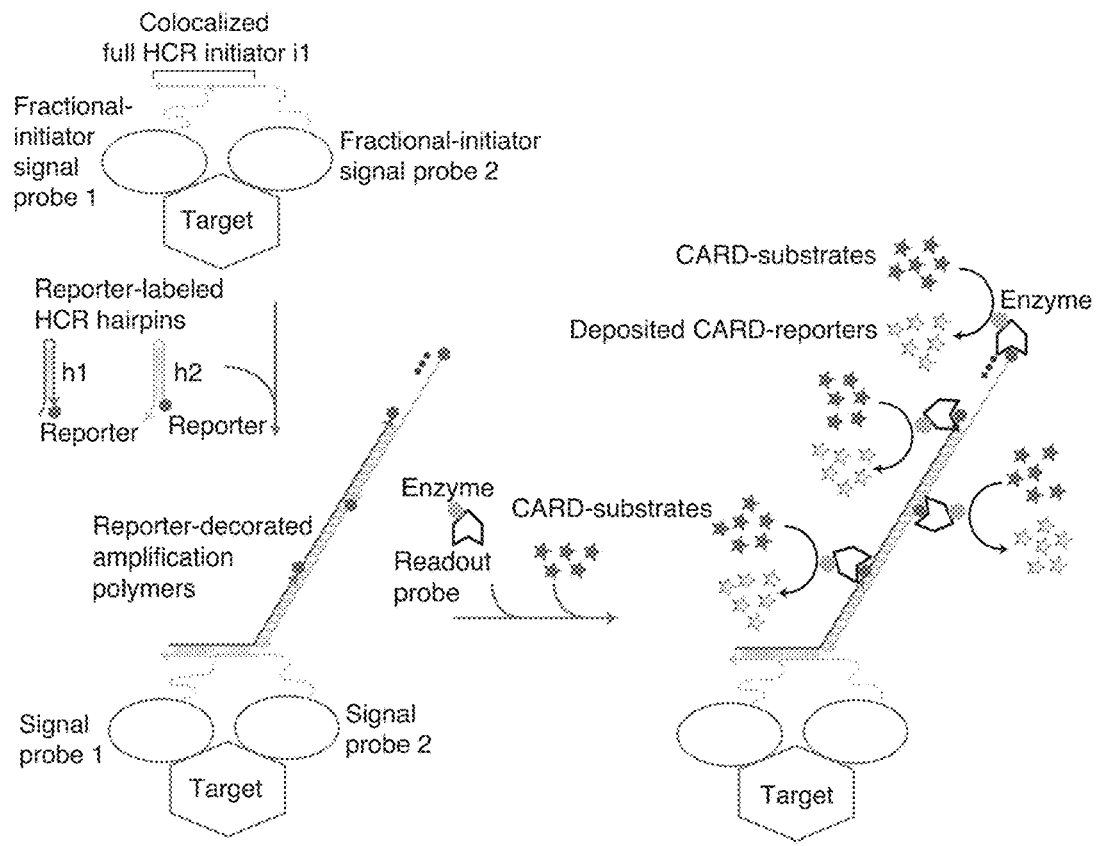
Figure 26C:
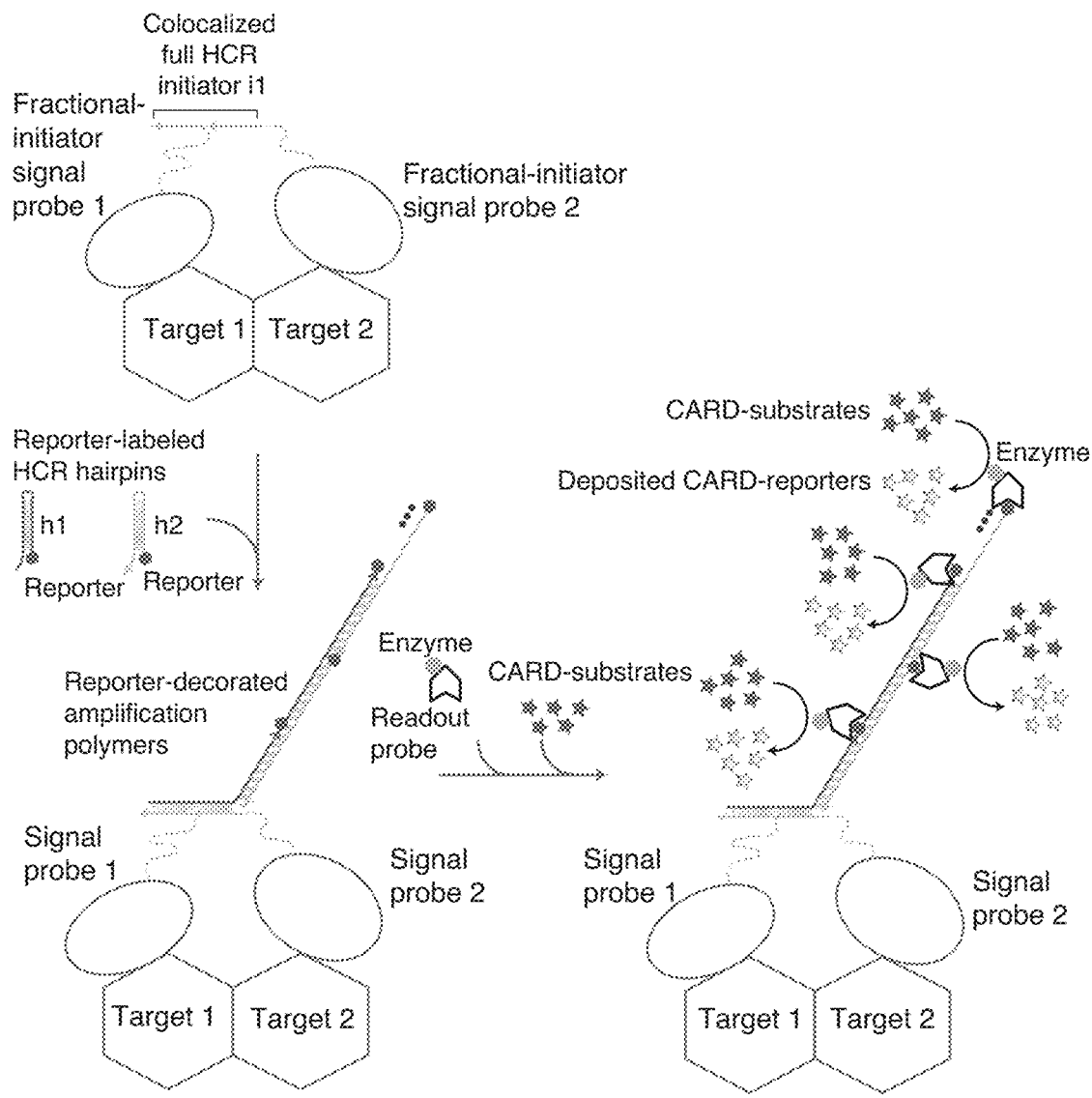

In some embodiments, the fifth initiator (i5; sequence domains "k*-j*") comprises a partner to the fifth toehold (sequence domain "j*") and a partner to the fifth stem section (sequence domain "k*"). In some embodiments, the fifth initiator is configured to bind the fifth input domain. In some embodiments, the sequence of the fifth HCR initiator i5 can be expressed either as "k*-j*" (where the "j*" sequence domain is the partner to the fifth toehold and the "k*" sequence domain is the partner to the fifth stem section) or as "g-f" (where the "g" sequence domain is the third split-initiator tail and the "f" sequence domain is the first split-initiator tail). In some embodiments, the concatenated sequence "k*-j*" is the same as the concatenated sequence "g-f" but with the boundary between sequence domains is at a different point within the concatenated sequence. In some embodiments, binding of the fifth initiator to the fifth input domain opens the fifth HCR hairpin to expose the fifth output domain. In some embodiments, the exposed fifth output domain is configured to bind the sixth input domain. In some embodiments, binding of the exposed fifth output domain to the sixth input domain opens the sixth HCR hairpin to expose the sixth output domain. In some embodiments, the exposed sixth output domain is configured to bind the fifth input domain. In some embodiments, binding of the exposed sixth output domain to the fifth input domain leads to HCR polymerization in which fifth and sixth HCR hairpins are successively opened and added to the growing polymer in alternating fashion, wherein the new polymer comprising alternating h5 and h6 hairpins is tethered to the original polymer comprising periodic h1, h2, h3, and h4 hairpins. In some embodiments, the first and third split-initiator tails are optional (for example, domains "f" and "g" in FIG. 16C are optional).

In some embodiments, the sixth initiator (i6; sequence domains "l*-k*") comprises a partner to the sixth toehold (sequence domain "l*") and a partner to the sixth stem section (sequence domain "k*"). In some embodiments, the sixth initiator is configured to bind the sixth input domain. In some embodiments, the sequence of the sixth HCR initiator i6 can be expressed either as "l*-k*" (where the "l*" sequence domain is the partner to the sixth toehold and the "k*" sequence domain is the partner to the sixth stem section) or as "h-i" (where the "h" sequence domain is the second split-initiator tail and the "i" sequence domain is the fourth split-initiator tail). In some embodiments, the concatenated sequence "l*-k*" is the same as the concatenated sequence "h-i" but with the boundary between sequence domains at a different point within the concatenated sequence. In some embodiments, binding of the sixth initiator to the sixth input domain opens the sixth HCR hairpin to expose the sixth output domain. In some embodiments, the exposed sixth output domain is configured to bind the fifth input domain. In some embodiments, binding of the exposed sixth output domain to the fifth input domain opens the fifth HCR hairpin to expose the fifth output domain. In some embodiments, the exposed fifth output domain is configured to bind the sixth input domain. In some embodiments, binding of the exposed fifth output domain to the sixth input domain leads to HCR polymerization in which sixth and fifth HCR hairpins are successively opened and added to the growing polymer in alternating fashion, wherein the new polymer comprising alternating h6 and h5 hairpins is tethered to the original polymer comprising periodic h1, h2, h3, and h4 hairpins. In some embodiments, the second and fourth split-initiator tails are optional. (for example, domains "h" and "i" in FIG. 16C are optional).

In some embodiments, a self-bridging HCR amplifier comprises 4 HCR hairpins (for example, see FIG. 16D), comprising two versions of a first hairpin h1 (one version, h1-3', with a 3' split-initiator tail and one version, h1-5', with a 5' split-initiator tail) and two versions of a second hairpin h2 (one version, h2-3', with a 3' split-initiator tail and one version, h2-5', with a 5' split-initiator tail). In some embodiments, when an i1 initiator triggers polymerization of an HCR amplification polymer from hairpins h1-3', h1-5', h2-3', and h2-5', either version of the h1 hairpin is randomly incorporated during the h1 polymerization steps and either version of the h2 hairpin is randomly incorporated during the h2 polymerization steps (for example, see FIG. 16D), such that at any junction where the 5'-tail of h1-5' and the 3'-tail of h1-3' are colocalized at a junction within the polymer, a colocalized full third HCR initiator i3 is produced tethered to the amplification polymer, and at any junction where the 5'-tail of h2-5' and the 3'-tail of h2-3' are colocalized, a colocalized full fourth HCR initiator i4 is produced tethered to the amplification polymer. In some embodiments, one or more colocalized full HCR initiators i3 and/or i4 can then trigger a second HCR amplifier comprising h3 and h4 hairpins to grow an HCR amplification polymer comprising alternating h3 and h4 hairpins tethered to each colocalized full HCR initiator i3 or i4 tethered to the previous HCR amplification polymer comprising alternating h1 and h2 hairpins (where each h1 hairpin is randomly either an h1-3' or an h1-5' hairpin and each h2 hairpin is randomly either an h2-3' or an h3-5' hairpin). In some embodiments, a self-bridging HCR amplifier requires only two hairpin sequences (h1 and h2) without the need to use any HCR hairpins comprising two split-initiator tails (for example, see FIG. 16D).

HCR Amplifiers with 2 or More Hairpins

More generally, in some embodiments, an HCR amplifier may comprise M HCR hairpins (h1, h2, . . . , hM) with M an integer of 2 or more. In the absence of an HCR initiator (i1, i2, . . . , iM), hairpins h1, h2, . . . , hM coexist metastably, that is, they are kinetically trapped and do not polymerize. In the presence of a cognate HCR initiator, polymerization occurs via alternating polymerization steps analogous to 2-hairpin or 4-hairpin HCR. For example, initiator i1 would lead to growth of polymers of the form i1-(h1-h2-. . . -hM)$_N$ for a polymer that incorporates N alternating copies of h1, h2, . . . , hM. It is possible for a polymer to end with any of h1, h2, . . . , hM, so i1-(h1-h2- . . . -hM)$_N$-h1, i1-(h1-h2- . . . -hM)$_N$-h1-h2, . . . , and i1-(h1-h2- . . . -hM)$_N$-h1-h2- . . . -hM are all possible, the latter being equivalent to i1-(h1-h2- . . . -hM)$_{N+1}$. It is possible for HCR polymerization to be triggered by any of the cognate initiators (i1, i2, . . . , iM). For example, initiator by initiator i3 could generate polymers of the form i3-(h3- . . . -hM-h1-h2)$_N$.

Reporter-Labeled HCR Hairpins

For a given HCR amplifier, each HCR hairpin comprises zero, one, or more reporters. Reporters on different hairpins within an amplifier may be the same or different. For example, an amplifier comprising hairpins h1 and h2 might have: 1) the same reporter on h1 and h2, 2) different reporters on h1 and h2, 3) a reporter on h1 but no reporter on h2, 4) a reporter on h2 but no reporter on h1, 5) no reporter on h1 or h2, 6) zero, one, or more reporters on h1 of which zero, one, or more of them are the same or different as zero, one, or more reporters on h2. Similarly, for an HCR amplifier comprising hairpins h1, h2, h3, h4, each hairpin may comprise zero, one, or more reporters (for example 3, 5, or 10 reporters) of which zero, one, or more of them may be the same as zero, one, or more reporters on each of the other hairpins. In some embodiments, one or more of the reporters for a given hairpin can be unique within a mixture of hairpins and/or hairpin reporters. In some embodiments, there are 1, 10, 100, 1000, 10,000, 100,000 or more unique reporters within a mixture (including any range defined between any two of the previous numbers).

In some embodiments, the one or more reporters on a reporter-labeled HCR hairpin directly or indirectly contributes to the generation, alteration, or elimination of a signal. For example, a reporter could be a fluorophore, a chromophore, a luminophore, a phosphor, a FRET pair, a member of a FRET pair, a quencher, a fluorophore/quencher pair, a rare-earth element or compound, a radioactive molecule, a magnetic molecule, an enzyme, or any other molecule that facilitates measurement of a signal.

In some embodiments, a reporter decorating a tethered HCR amplification polymer may bind to the reporter-binding domain of a readout probe to directly or indirectly mediate localization of auxiliary reporters in the vicinity of the reporter, which in turn directly or indirectly mediates generation of an amplified signal.

In some embodiments, the reporter can comprise digoxigenin (DIG) that recruits anti-DIG antibody as the readout probe, where the anti-DIG is directly labeled with one or more auxiliary reporters, or with one or more reporters that serve to directly or indirectly mediate localization of auxiliary reporters in the vicinity of the reporter.

In some embodiments, the reporter can comprise a nucleic acid domain that serves as a substrate with full or partial sequence complementarity to a reporter-binding domain within a readout probe that carries one or more auxiliary reporters (for example, see FIG. 17C), In some embodiments, the reporter can comprise a nucleic acid domain that serves as a substrate with full or partial sequence complementarity to a reporter-binding domain within a readout probe that carries one or more substrates that serve to mediate localization of auxiliary reporters in the vicinity of the reporter.

In some embodiments, the reporter can comprise a nucleic acid domain that serves as a substrate for a readout probe that directly or indirectly mediates localization of auxiliary reporters in the vicinity of the reporter.

In some embodiments, the reporter can comprise a substrate that serves to recruit a readout probe that indirectly mediates localization of auxiliary reporters in the vicinity of the reporter.

Figure 27A:
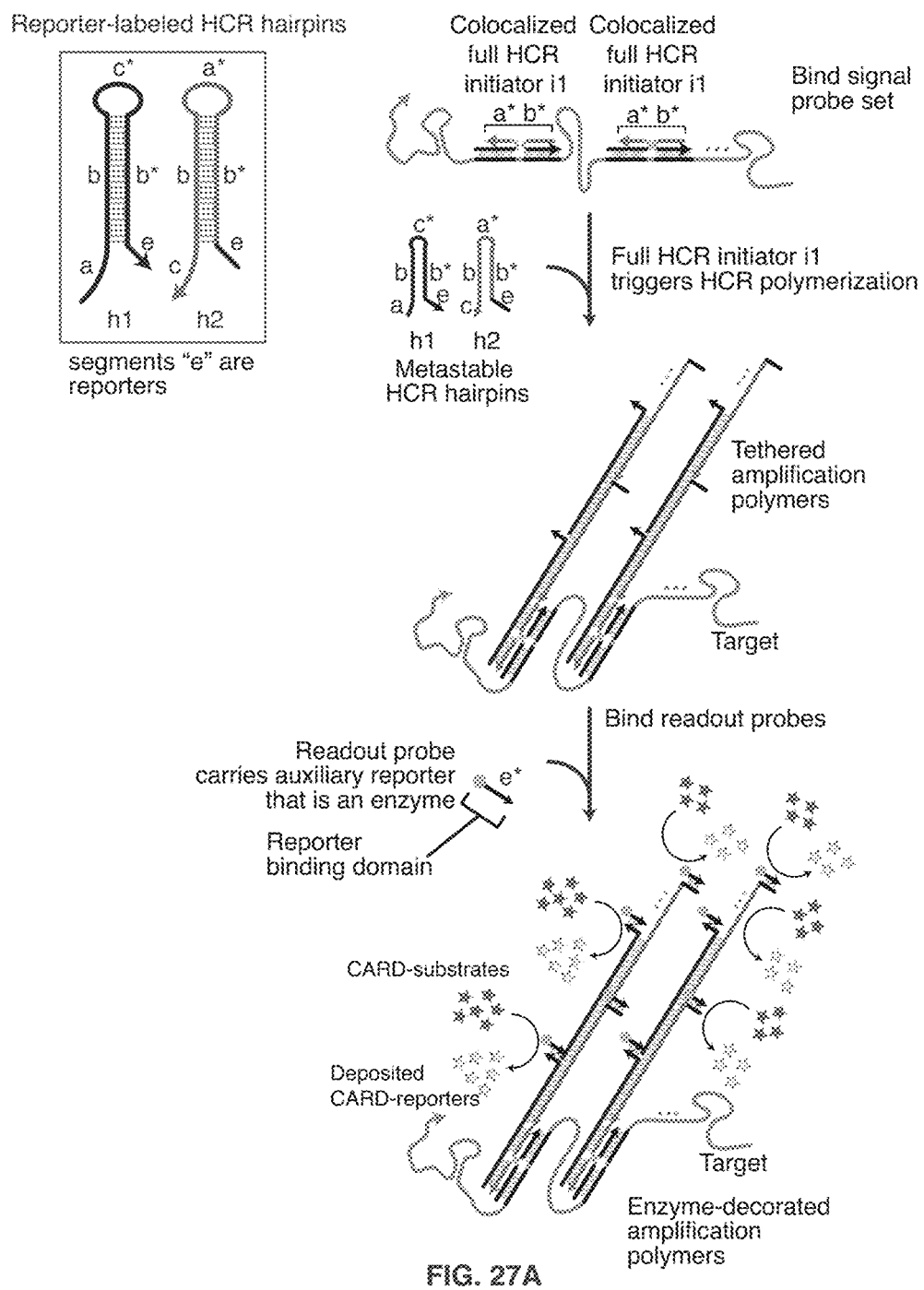
FIGS. 27A-27B depict some embodiments using HCR signal amplification with reporter-labeled or fractional-reporter-labeled HCR hairpins to mediate CARD signal amplification.
Figure 27B:
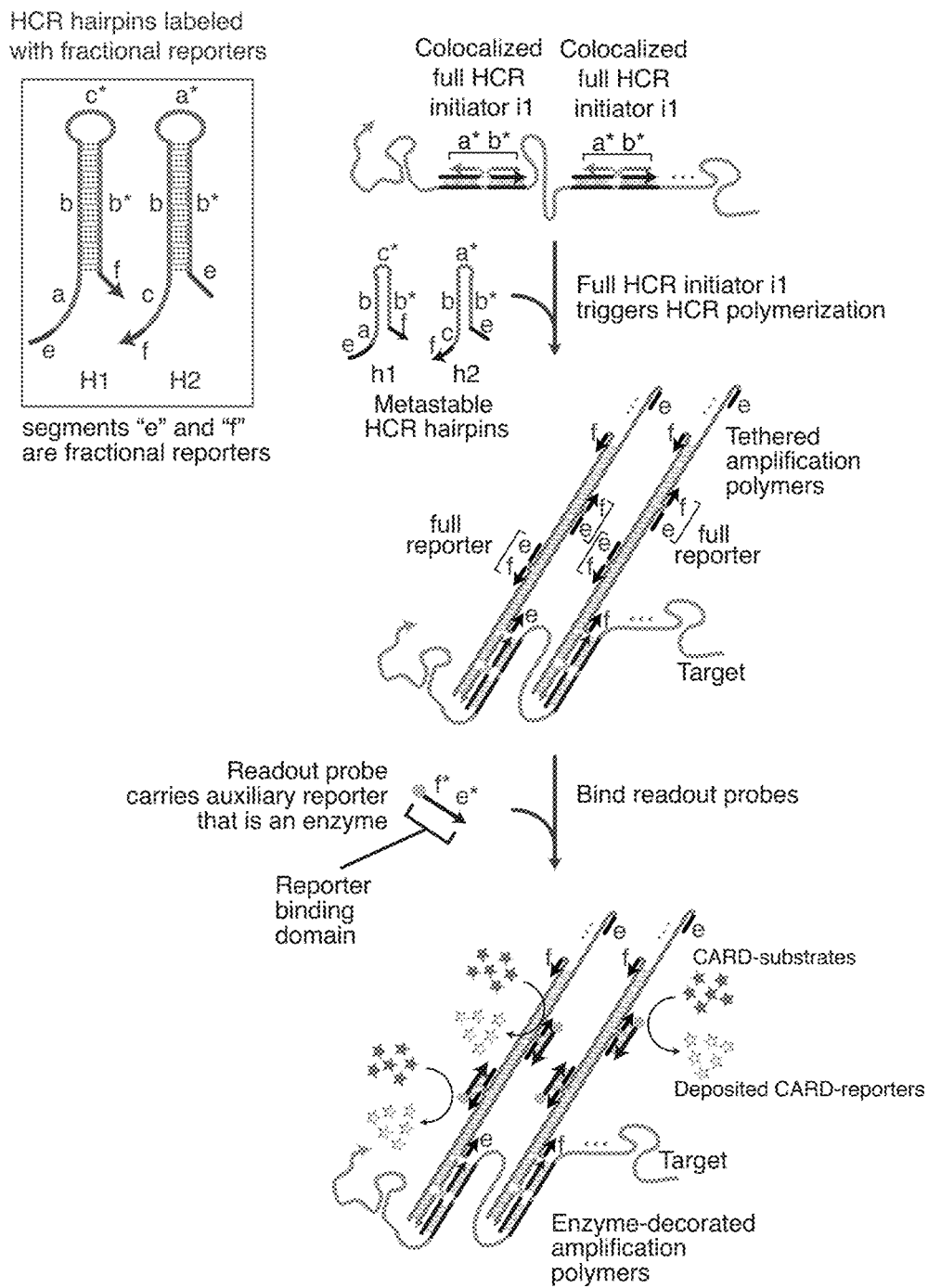
Figure 28A:
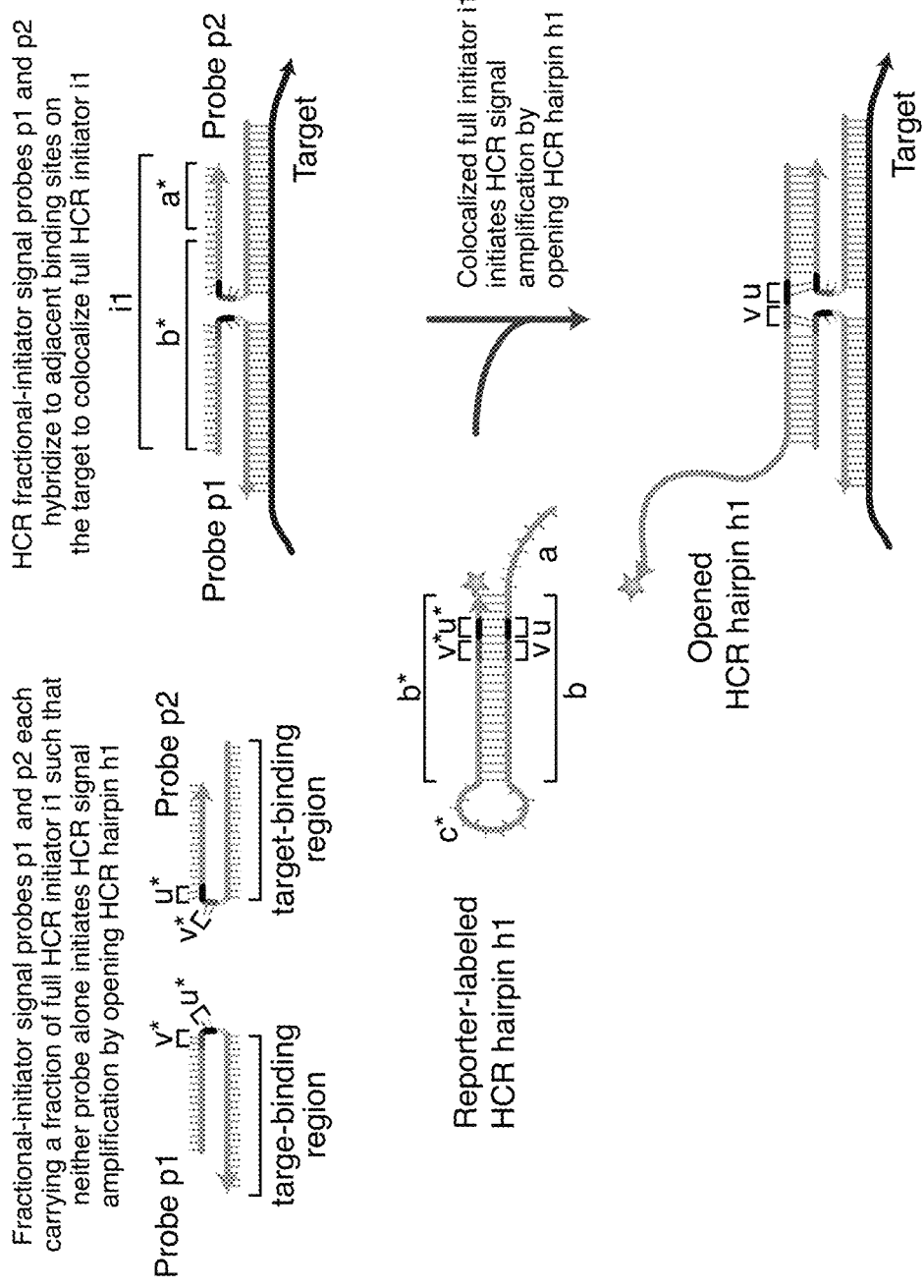
FIGS. 28A-28B depict some embodiments of fractional-initiator probes designed to be complementary to overlapping regions of an HCR hairpin.
Figure 28B:
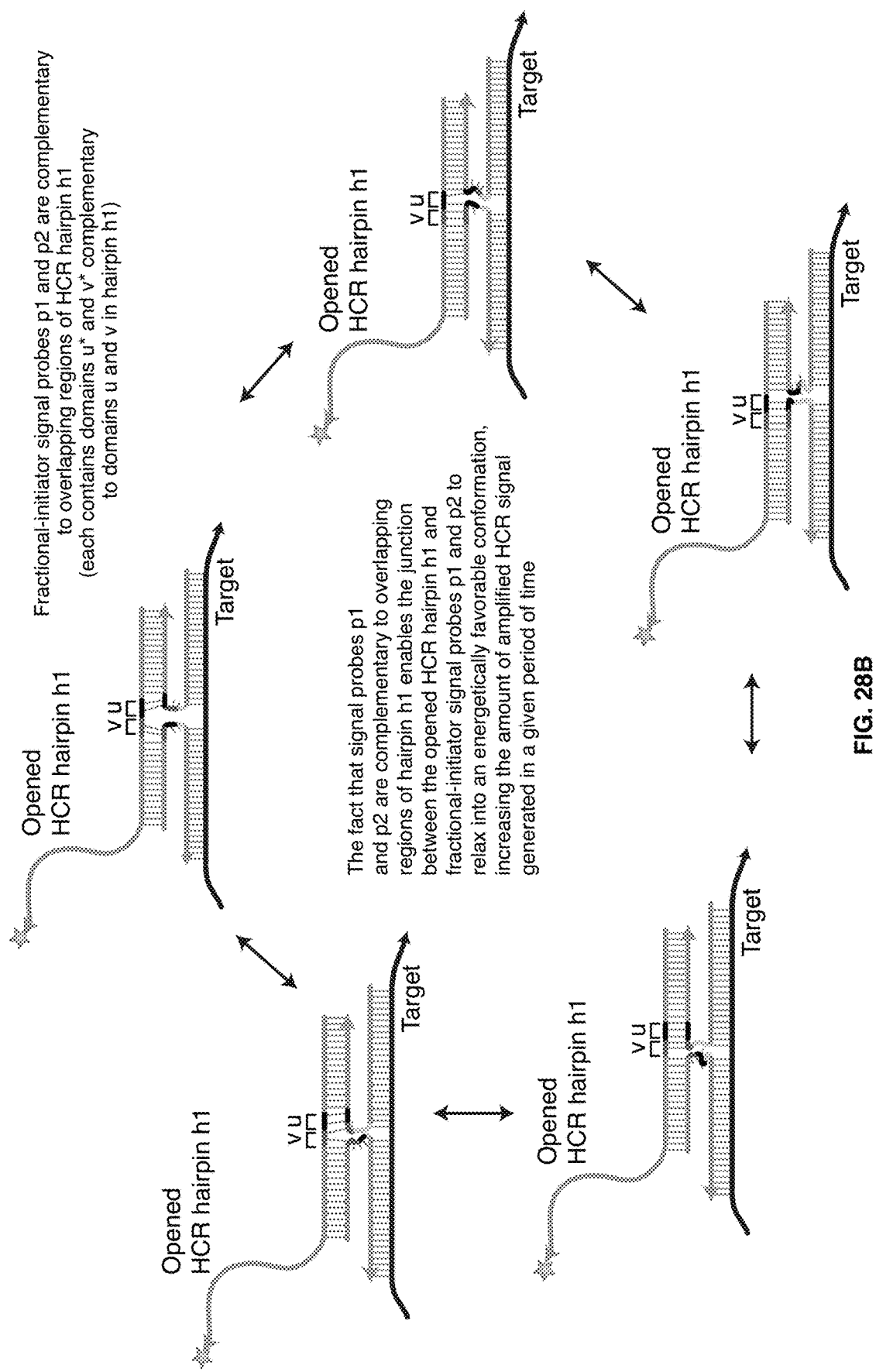
Figure 29:
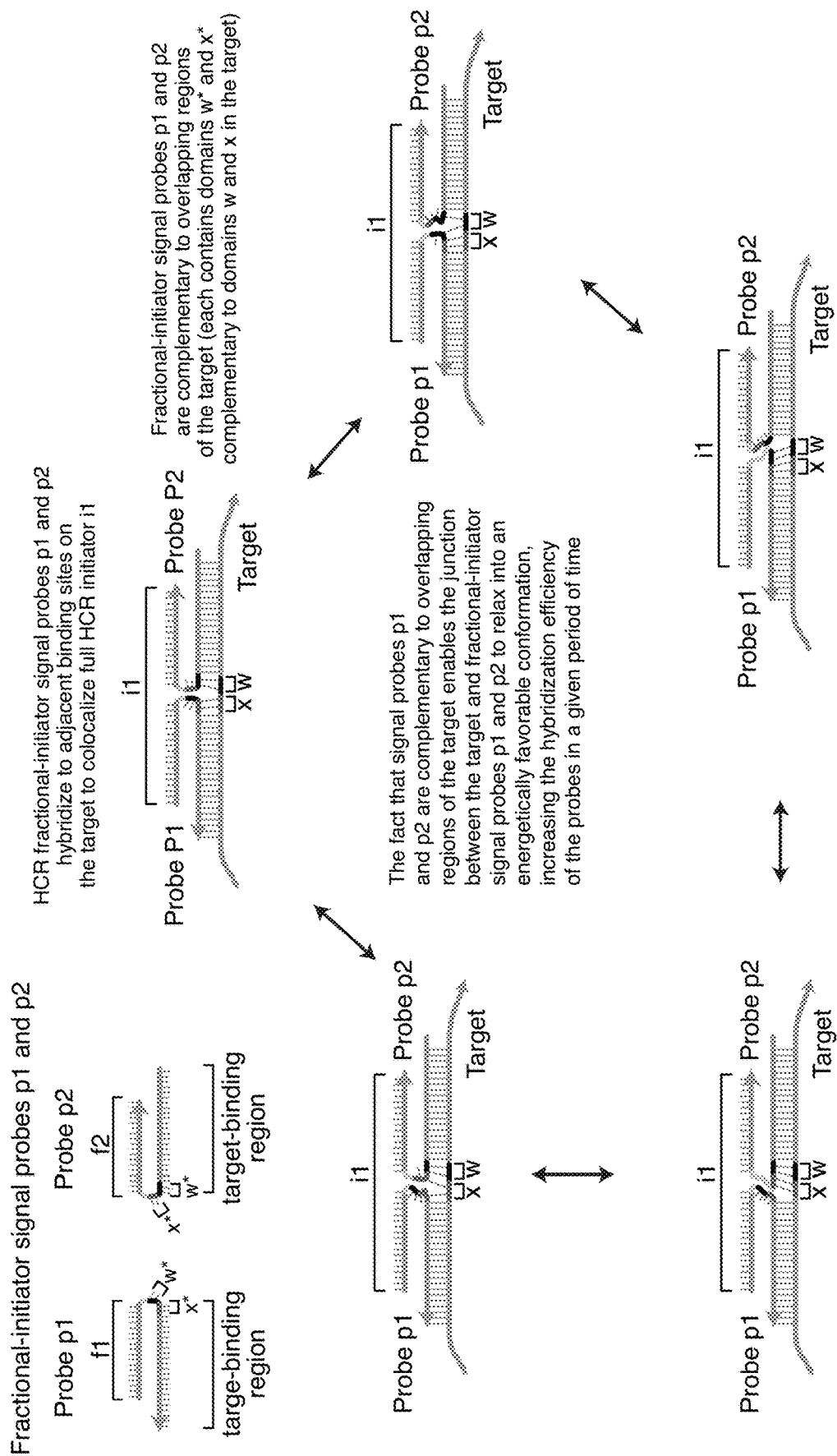
FIG. 29 depicts some embodiments of fractional-initiator probes designed to be complementary to overlapping regions of a target.
Figure 30:
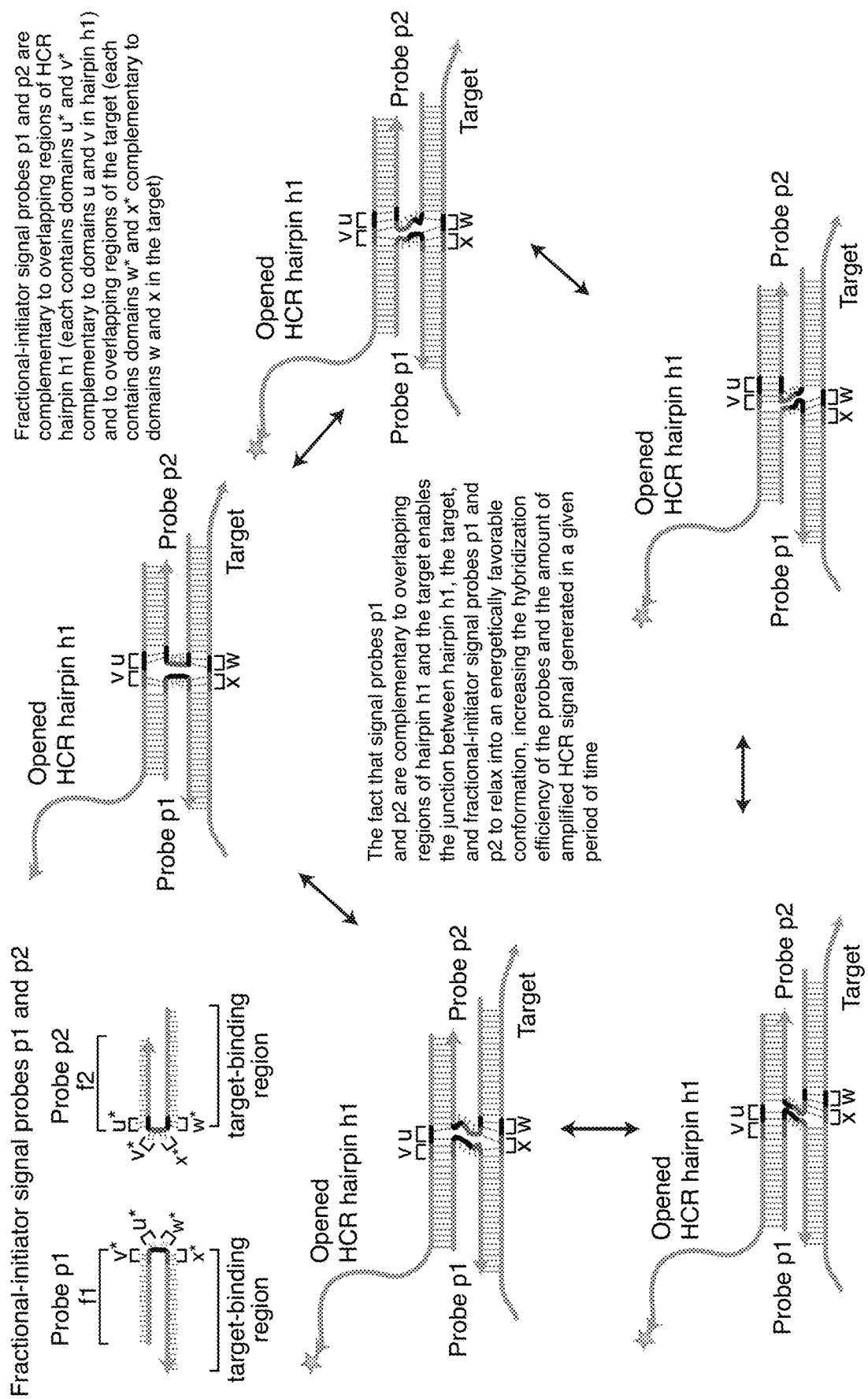
FIG. 30 depicts some embodiments of fractional-initiator probes designed to be complementary to overlapping regions of an HCR hairpin and designed to be complementary to overlapping regions of a target.

In some embodiments, the reporter can comprise a substrate that serves to recruit a readout probe that comprises an enzyme that mediates catalytic reporter deposition (CARD) in the vicinity of the reporter (for example, see FIG. 27A).

In some embodiments, the reporter can comprise biotin that recruits streptavidin (or another biotin-binding molecule) as the readout probe, where the streptavidin is directly labeled with one or more auxiliary reporters, or with one or more substrates that serve to directly or indirectly mediate localization of auxiliary reporters in the vicinity of the reporter.

In some embodiments, the reporter can comprise a hapten that recruits an anti-hapten antibody readout probe or an anti-hapten nanobody readout probe that directly or indirectly mediates localization of reporters in the vicinity of the reporter via CARD signal amplification. For example, the anti-hapten antibody or nanobody readout probe may comprise an enzyme that mediates CARD (for example, see FIGS. 25A-25E).

In some embodiments, the reporter can comprise a hapten that recruits an anti-hapten that directly or indirectly mediates localization of auxiliary reporters in the vicinity of the hairpin reporter. For example, the anti-hapten readout probe may comprise an enzyme that mediates CARD (for example, see FIGS. 26A-26C).

In some embodiments, the reporter can comprise an enzyme that mediates CARD signal amplification to deposit CARD-reporter molecules in the vicinity of the hairpin.

In some embodiments, the hairpin reporter can comprise zero, one, or more haptens (for example, see FIGS. 17A-17B) that mediate, directly or indirectly, localization of auxiliary reporters in the vicinity of the haptens.

In some embodiments, a reporter decorating a tethered HCR amplification polymer binds to the reporter-binding domain of a bridging probe to directly or indirectly mediate localization of one or more HCR initiators in the vicinity of the reporter, which in turn triggers growth of a new HCR amplification polymer tethered to the original HCR amplification polymer.

In some embodiments, a reporter can comprise a hapten that recruits an anti-hapten (for example, an antibody, a nanobody, streptavidin, or another molecule) that is labeled with auxiliary reporters.

In some embodiments provided herein, HCR signal amplification is used to mediate catalytic reporter deposition (CARD), leading to even higher signal gain. In some embodiments, the even higher single gain is about 5, 10, 15, 20, 25, 30, 40, 50, 75, 100, 500, 1000, 2000, 5000, 10,000, 20,000, 50,000, or 100,000-fold, or a value with a range defined by any two of the aforementioned values.

Haptens and Anti-Haptens

In some embodiments, hairpin labels that are substrates comprising a hapten could for example be digoxygenin (DIG), dinitrophenyl (DNP), a fluorophore, biotin, or any small molecule, biological molecule, or non-biological molecule that can recruit an anti-hapten. Examples of anti-haptens can include antibodies, nanobodies, streptavidin, aptamers, or any other molecule or complex of molecules that selectively binds a hapten.

Enzymes for HCR-Mediated Catalytic Reporter Deposition (CARD)

In some embodiments, reporter-decorated HCR amplification polymers mediate signal amplification via catalytic reporter deposition (CARD) by an enzyme that catalyzes a CARD-substrate leading to deposition of CARD-reporters in the vicinity of the HCR amplification polymer (for example, see FIGS. 25A-25E, 26A-26C, 27A-27B).

In some embodiments, the enzyme can be horseradish peroxidase (HRP) (or polymer HRP comprising multiple HRP enzymes) that acts on a CARD-substrate to catalyze deposition a chromogenic CARD-reporter such as AEC, DAB, TMB, or StayYellow, or that catalyzes a CARD-substrate to catalyze deposition of a fluorescent CARD-reporter such as fluorophore-labeled tyramide, or that catalyzes deposition of a hapten-labeled CARD-substrate such as biotin-labeled tyramide, where the hapten serves to mediate localization of CARD-reporters in the vicinity of the reporter-decorated HCR amplification polymer.

In some embodiments, the enzyme can be alkaline phosphatase (AP) (or polymer AP comprising multiple AP enzymes) that acts on a CARD-substrate to catalyze deposition of CARD-reporters, for example a chromogenic CARD-reporter such as but not limited to BCIP/NBT, BCIP/TNBT, Napthol AS-MX phosphate+FastBlue BB, Napthol AS-MX phosphate+FastRed TR, StayGreen.

In some embodiments, the enzyme can be glucose oxidase that acts on a CARD-substrate to catalyze deposition of CARD-reporters, for example NBT.

In some embodiments, the enzyme can be any molecule or complex that directly or indirectly mediates localization of CARD-reporters in the vicinity of a reporter-decorated HCR amplification polymer.

In some embodiments, CARD-reporters deposited in the vicinity of tethered HCR amplification polymers are visible to the human eye. In some embodiments, CARD-reporters deposited in the vicinity of tethered HCR amplification polymers are scanned with an instrument to read a signal.

In some embodiments, the enzyme that mediates CARD is deactivated (aka inactivated) after CARD-reporter deposition (for example, using chemical or heat denaturation). For example, the enzyme that mediates CARD can be deactivated using any combination of:

1. Heat (for example, 65° C. or above);
2. Fixative (for example, 4% PFA);
3. Acid (for example, 0.1 M glycine-HCl with 1% Tween 20 at pH 2.2, 0.2N HCl, 10% acetic acid, 10 mM HCl); and
4. Other chemicals (for example, hydrogen peroxide ($H_2O_2$), hydrogen peroxide+phenol, sodium azide, DEPC, MAB with 10 mM EDTA).

In some embodiments, HRP is inactivated using $H_2O_2$. In some embodiments, AP is inactivated using a combination of heat and acid. In some embodiments, AP is inactivated with fixative. In some embodiments, deactivation of the enzyme that mediates CARD allows repeated CARD using the same enzyme in combination with different substrates for different targets to allow multiplex target analysis using HCR-mediated CARD. In some embodiments, deactivation of the enzyme that mediates CARD allows repeated CARD using different enzymes in combination with different CARD-substrates for different targets to allow multiplex target analysis using HCR-mediated CARD.

In some embodiments, CARD allows storage of stained samples for 10 or more years to allow reanalysis in compliance with regulatory requirements. In some embodiments, the CARD-stained sample is adequately stable for 1, 2, 3, 4, 5, 6, 7, 8, 9, 10, 11, 12, 13, 14, 15 or more years, and still in compliance with regulatory requirements. In some embodiments, CARD staining provides for long-term storage of archival samples. In some embodiments, CARD provides for storage of formalin fixed paraffin embedded (FFPE) samples for decades. In some embodiments, CARD provides for storage of pathology samples for decades to provide for retrospective scientific and medical studies. In some embodiments, CARD staining provides for long-term storage of archival samples.

Target Types

In some embodiments, an initiator-labeled probe comprises a target-binding domain and further comprises one or more HCR initiators. In some embodiments, an initiator-labeled probe can detect a target comprising: any molecule including but not limited to an RNA molecule (for example, mRNA, rRNA, lncRNA, siRNA, shRNA, microRNA, non-coding RNA, synthetic RNA, or modified RNA), a DNA molecule, a non-natural nucleic acid molecule, a protein molecule, a small molecule, a biological molecule, a chemically modified biological molecule, a non-biological molecule, any complex of molecules comprising any combination of RNA, DNA, protein, small molecules, biological molecules, and/or non-biological molecules (for example, an RNA/RNA complex, an RNA/protein complex, a DNA/protein complex, an RNA/DNA/protein complex, a protein/protein complex), a prokaryotic cell, a eukaryotic cell, a virus, or any combination of the above.

In some embodiments, a fractional-initiator probe comprises a target-binding domain and further comprises one or more fractional-initiators. In some embodiments, a probe unit comprises two or more fractional-initiator probes such that the fractional-initiator probes in the probe unit combine to create a full HCR initiator. In some embodiments, a probe unit can detect a target comprising: any molecule including but not limited to an RNA molecule (for example, mRNA, rRNA, lncRNA, siRNA, shRNA, microRNA, non-coding RNA, synthetic RNA, or modified RNA), a DNA molecule, a non-natural nucleic acid molecule, a protein molecule, a small molecule, a biological molecule, a chemically modified biological molecule, a non-biological molecule, any complex of molecules comprising any combination of RNA, DNA, protein, small molecules, biological molecules, and/or non-biological molecules (for example, an RNA/RNA complex, an RNA/protein complex, a DNA/protein complex, an RNA/DNA/protein complex, a protein/protein complex), any collection of proximal molecules or complexes such that the fractional-initiators in the probe unit can colocalize to form a full HCR initiator when the fractional-initiator probes comprising the probe unit are bound to their respective targets within the collection of proximal molecules or complexes, a prokaryotic cell, a eukaryotic cell, a virus, any combination of the above.

In any of the embodiments provided herein, the fractional-initiators within a probe unit are designed to be (or are) complementary to non-overlapping regions of an HCR hairpin (for example, regions separated by 0, 1, 2, or more nucleotides), or are designed to be (or are) complementary to overlapping regions of an HCR hairpin (for example, regions that overlap by 1, 2 or more nucleotides), or are designed to be (or are) substantially complementary to an HCR hairpin (for example, complementary except for 0, 1, 2, a few, or several mismatches), or are configured to bind an HCR hairpin.

In any of the embodiments provided herein, the target-binding regions within a probe unit are configured to bind to non-overlapping regions of the target (for example, regions separated by 0, 1, 2, or more nucleotides or regions separated by 0, 1, 2, or more nanometers), or are configured to bind to overlapping regions of the target (for example, regions that overlap by 1, 2 or more nucleotides, or regions that overlap by 1, 2, or more nanometers).

Signal Probe Sets for Multiplexing

In some embodiments, signal probe sets are designed for multiplex experiments in which 2, 3, 4, 5, 10, 20, or 100 or more signal probe sets are used to bind to different targets in the same sample, where 1, 2, 3, 4, 5, 10, 20, or 100 or more of the signal probe sets comprise one or more initiator-labeled probes, or one or more probe units each comprising two or more fractional-initiator probes. In some embodiments, signal probe sets are designed for multiplex experiments in which 2, 3, 4, 5, 10, 20, or 100 or more signal probe sets are used in the same sample, where more than 1%, more than 2%, more than 5%, more than 10%, more than 30%, more than 50%, or 100% of the signal probe sets comprise one or more initiator-labeled probes, or one or more probe units each comprising two or more fractional-initiator probes.

Signal Probes Configured to Bind to Overlapping or Non-Overlapping Regions of the Target and/or Designed to have Fractional Initiators that Hybridize to Overlapping or Non-Overlapping Regions of an HCR Hairpin In some embodiments, a probe unit comprises two or more fractional-initiator probes each comprising a target-binding region and a fractional-initiator.

In some embodiments, the fractional-initiators within a probe unit are designed to be complementary to adjacent regions of an HCR hairpin.

In some embodiments, the fractional-initiators within a probe unit are designed to be complementary to non-overlapping regions of an HCR hairpin (for example, regions separated by 0, 1, 2, or more nucleotides).

In some embodiments, the fractional-initiators within a probe unit are designed to be complementary to overlapping regions of an HCR hairpin (for example, regions that overlap by 1, 2 or more nucleotides).

In some embodiments, the fractional-initiators within a probe unit are designed to be substantially complementary to an HCR hairpin (for example, complementary except for 0, 1, 2, a few, or several mismatches).

In some embodiments, the fractional-initiators within a probe unit are designed to hybridize to adjacent regions of an HCR hairpin.

In some embodiments, the fractional-initiators within a probe unit are designed to hybridize to non-overlapping regions of an HCR hairpin.

In some embodiments, the fractional-initiators within a probe unit are designed to hybridize to overlapping regions of an HCR hairpin.

In some embodiments, the fractional-initiators within a probe unit are designed to have sequences that are complementary to adjacent regions of an HCR hairpin.

In some embodiments, the fractional-initiators within a probe unit are designed to have sequences that are complementary to non-overlapping regions of an HCR hairpin.

In some embodiments, the fractional-initiators within a probe unit are designed to have sequences that are complementary to overlapping regions of an HCR hairpin.

In some embodiments, the fractional-initiators within a probe unit are designed to have sequences that are substantially complementary to adjacent regions of an HCR hairpin.

In some embodiments, the fractional-initiators within a probe unit are designed to have sequences that are substantially complementary to non-overlapping regions of an HCR hairpin, In some embodiments, the fractional-initiators within a probe unit are designed to have sequences that are substantially complementary to overlapping regions of an HCR hairpin.

In some embodiments, the target-binding regions within a probe unit are configured to bind to adjacent regions of the target. In some embodiments, the target-binding regions within a probe unit are configured to bind to non-overlapping regions of the target (for example, regions separated by 0, 1, 2, or more nucleotides, or regions separated by 0, 1, 2, or more nm). In some embodiments, the target-binding regions within a probe unit are configured to bind to overlapping regions of the target (for example, regions overlapping by 1, 2, or more nucleotides, or regions overlapping by 1, 2, or more nm). In some embodiments, the target-binding regions within a probe unit are designed to bind to adjacent regions of the target. In some embodiments, the target-binding regions within a probe unit are designed to bind to non-overlapping regions of the target. In some embodiments, the target-binding regions within a probe unit are designed to bind to overlapping regions of the target, or are designed to have sequences that hybridize to adjacent regions of the target. In some embodiments, the target-binding regions within a probe unit are designed to have sequences that hybridize to non-overlapping regions of the target. In some embodiments, the target-binding regions within a probe unit are designed to have sequences that hybridize to overlapping regions of the target.

In some embodiments, a probe unit comprises two fractional-initiator probes. In some embodiments, the two fractional-initiator probes bind to the cognate target to colocalize a full HCR initiator. In some embodiments, the colocalized full HCR initiator then binds to the cognate HCR hairpin to initiate HCR polymerization, with one fractional-initiator hybridizing to the hairpin to form a first duplex and the other fractional-initiator hybridizing to the hairpin to form a second duplex. In some embodiments, there is an energetically unfavorable junction between the two duplexes that leads to a kinetic barrier during the branch migration process that opens the first HCR hairpin to initiate polymerization. In some embodiments, by configuring the fractional initiators to bind to overlapping regions of the hairpin, the junction can relax into an energetically more favorable conformation to reduce the height of the kinetic barrier, increasing the efficiency of HCR initiation and/or increasing the affinity between the colocalized full HCR initiator and the first HCR hairpin so as to increase the amount of amplified HCR signal generated in a given period of time (for example, FIGS. 28 and 31). In some embodiments the affinity between the two probes and the cognate target can be increased by configuring the target-binding regions of the two probes to bind to overlapping regions of the target so as to permit the junction between the molecules to relax to an energetically favorable conformation.

In some embodiments, probe sets are designed for multiplex experiments in which 2, 3, 4, 5, 10, 20, or 100 or more probe sets are used to bind to different targets in the same sample, where 1, 2, 3, 4, 5, 10, 20, or 100 or more of the probe sets comprise one or more initiator-labeled probes. In some embodiments, probe sets are designed for multiplex experiments in which 2, 3, 4, 5, 10, 20, or 100 or more probe sets are used in the same sample, where more than 1%, more than 2%, more than 5%, more than 10%, more than 30%, more than 50%, or 100% of the probe sets comprise one or more initiator-labeled probes.

In some embodiments, probe sets are designed for multiplex experiments in which 2, 3, 4, 5, 10, 20, or 100 or more probe sets are used to bind to different targets in the same sample, where 1, 2, 3, 4, 5, 10, 20, or 100 or more of the probe sets comprise one or more probe units comprising fractional-initiators that are designed to hybridize to overlapping regions of an HCR hairpin. In some embodiments, probe sets are designed for multiplex experiments in which 2, 3, 4, 5, 10, 20, or 100 or more probe sets are used in the same sample, where more than 1%, more than 2%, more than 5%, more than 10%, more than 30%, more than 50%, or 100% of the probe sets comprise one or more probe units comprising fractional-initiators with sequences that are designed to be complementary to overlapping regions of an HCR hairpin.

In some embodiments, probe sets are designed for multiplex experiments in which 2, 3, 4, 5, 10, 20, or 100 or more probe sets are used to bind to different targets in the same sample, where 1, 2, 3, 4, 5, 10, 20, or 100 or more of the probe sets comprise one or more probe units comprising target-binding regions that are designed to bind to overlapping regions of a target. In some embodiments, probe sets are designed for multiplex experiments in which, 3, 4, 5, 10, 20, or 100 or more probe sets are used in the same sample, where more than 1%, more than 2%, more than 5%, more than 10%, more than 30%, more than 50%, or 100% of the probe sets comprise one or more probe units comprising target-binding regions that are designed to bind to overlapping regions of a target.

In some embodiments, probe sets are designed for multiplex experiments in which 2, 3, 4, 5, 10, 20, or 100 or more probe sets are used to bind to different targets in the same sample, where 1 or more of the probe sets comprise one or more initiator-labeled probes and 1 or more of the probe sets comprise one or more probe units each comprising two or more fractional-initiator probes. In some embodiments, probe sets are designed for multiplex experiments in which 2, 3, 4, 5, 10, 20, or 100 or more probe sets are used in the same sample, where more than 0.1%, more than 1%, more than 2%, more than 5%, more than 10%, more than 30%, or more than 50% of the probe sets comprise one or more initiator-labeled probes, and where more than 0.1%, more than 1%, more than 2%, more than 5%, more than 10%, more than 30%, or more than 50% of the probe sets comprise one or more probe units each comprising two or more fractional-initiator probes.

In some embodiments, a probe unit comprises fractional-initiators that are designed to bind to overlapping regions of an HCR hairpin, where the overlapping regions overlap by 1 base, or 2 bases, or 3 bases, or 4 bases, or 5 bases, or more bases.

In some embodiments, a probe unit comprises target-binding regions that are designed to bind to overlapping regions of the target, where the overlapping regions overlap by at least 0.1 nm, or at least 0.2 nm, or at least 0.3 nm, or at least 0.5 nm, or at least 1 nm, or at least 2 nm, or at least 3 nm, or at least 5 nm. In some embodiments, a probe unit comprises target-binding regions comprising sequences that are designed to bind to overlapping regions of the target, where the overlapping regions overlap by at least 1 base, or 2 bases, or 3 bases, or 4 bases, or 5 bases, or more bases.

Materials and Compositions of Initiator-Labeled Probes

In some embodiments, an initiator-labeled probe comprises one or more target-binding domains and one or more HCR initiators (for example, see FIGS. 18A-18N and 19A-19F). In some embodiments, each domain may comprise one or more materials including DNA, RNA, 2'OMe-RNA, PNA, XNA, chemically modified nucleic acids, synthetic nucleic acid analogs, amino acids, chemical linkers, synthetic amino acid analogs, and/or any other molecule suited for the purpose of the domain.

In some embodiments, an initiator-labeled probe may comprise one or more initiators made of DNA and a target-binding domain made of DNA.

In some embodiments, an initiator-labeled probe may comprise one or more initiators made of DNA, a chemical linker, and a target-binding domain made of amino acids (for example, an antibody or a nanobody or an antibody fragment).

In some embodiments, an initiator-labeled probe may comprise an initiator made of a synthetic nucleic acid analog and a target-binding domain made of a combination of DNA and 2'OMe-RNA.

In some embodiments, an initiator-labeled probe may comprise an initiator made of 2'OMe-RNA and a target-binding domain made of a combination of RNA and protein.

In some embodiments, an initiator-labeled probe may comprise an initiator made of DNA and a target-binding domain made of PNA.

In some embodiments, an initiator-labeled probe may comprise one or more initiators made of any nucleic acid or nucleic acid analog and one or more target-binding domains made of any combination of materials suitable for binding the target molecule.

In some embodiments, an initiator-labeled probe may comprise a single covalently linked molecule or may comprise two or more molecules (each covalently linked) that interact non-covalently to form a complex.

In some embodiments, an initiator-labeled probe may comprise an initiator made of DNA that is covalently linked to a target-binding domain made of DNA.

In some embodiments, an initiator-labeled probe may comprise one or more initiators made of DNA that are covalently linked to dCas9 (or another Cas) which is non-covalently bound to a guide RNA (gRNA) such that the target-binding domain comprises the gRNA:dCas9 complex (or gRNA:Cas complex using another Cas).

In some embodiments, an initiator-labeled probe may comprise one or more initiators made of DNA that are covalently linked to a gRNA that is non-covalently bound to dCas9 (or another Cas) such that the target-binding domain comprises the gRNA:dCas9 complex (or gRNA:Cas complex using another Cas).

In some embodiments, an initiator-labeled probe may comprise an initiator made of a nucleic acid or nucleic acid analog that is covalently linked or non-covalently bound to a target-binding domain comprising one or more molecules.

Materials and Composition of Fractional-Initiator Probes

In some embodiments, a fractional-initiator probe comprises one or more target-binding domains and one or more fractional-initiators (for example, see FIGS. 20A-20E, 21A-21D, 22A-22E, and 24A-24R). In some embodiments, a fractional-initiator probe may further comprise one or more proximity domains. In some embodiments, each domain may comprise one or more materials including DNA, RNA, 2'OMe-RNA, PNA, XNA, chemically modified nucleic acids, synthetic nucleic acid analogs, chemical linkers, amino acids, synthetic amino acid analogs, and/or any other molecule suited for the purpose of the domain.

In some embodiments, a fractional-initiator probe may comprise one or more fractional-initiators made of DNA and a target-binding domain made of DNA.

In some embodiments, a fractional-initiator probe may comprise one or more fractional-initiators made of DNA, a chemical linker, and a target-binding domain made of amino acids (for example, an antibody or a nanobody or an antibody fragment).

In some embodiments, a fractional-initiator probe may comprise a fractional-initiator made of a synthetic nucleic acid analog and a target-binding domain made of a combination of DNA and 2'OMe-RNA.

In some embodiments, a fractional-initiator probe may comprise a fractional-initiator made of 2'OMe-RNA and a target-binding domain made of a combination of RNA and protein.

In some embodiments, a fractional-initiator probe may comprise a fractional-initiator made of DNA and a target-binding domain made of PNA.

In some embodiments, a fractional-initiator probe may comprise one or more fractional-initiators made of any nucleic acid or nucleic acid analog and one or more target-binding domains made of any combination of materials suitable for binding the target molecule.

In some embodiments, a proximity domain may comprise a nucleic acid or a nucleic acid analog.

In some embodiments, a fractional-initiator probe may comprise a single covalently linked molecule or may comprise two or more molecules (each covalently linked) that interact non-covalently to form a complex.

In some embodiments, a fractional-initiator probe may comprise a fractional-initiator made of DNA that is covalently linked to a target-binding domain made of DNA.

In some embodiments, a fractional-initiator probe may comprise one or more fractional-initiators made of DNA that are covalently linked to dCas9 (or another Cas) which is non-covalently bound to a guide RNA (gRNA) such that the target-binding domain comprises the gRNA:dCas9 complex (or gRNA:Cas complex using another Cas).

In some embodiments, a fractional-initiator probe may comprise one or more fractional-initiators made of DNA that are covalently linked to a gRNA that is non-covalently bound to dCas9 (or another Cas) such that the target-binding domain comprises the gRNA:dCas9 complex (or gRNA:Cas complex using another Cas).

In some embodiments, a fractional-initiator probe may comprise a fractional-initiator made of a nucleic acid or nucleic acid analog that is covalently linked or non-covalently bound to a target-binding domain comprising one or more molecules. Each fractional-initiator probe within a probe unit may have the same or different material compositions from the other fractional-initiator probes in the probe unit. Each fractional-initiator probe within a probe unit may have target-binding regions that bind to different detection sites on the same target molecule, or to different detection sites within a target molecular complex, or to different detection sites within a target collection of proximal molecules or complexes.

Materials and Compositions for Reporter-Labeled Probes

In some embodiments, a reporter-labeled probe comprises one or more reporters. In some embodiments, a reporter comprises a hapten, a tag, a small molecule, a fluorophore, a chromophore, a luminophore, a phosphor, a FRET pair, a member of a FRET pair, a quencher, a fluorophore/quencher pair, a rare-earth element or compound, a radioactive molecule, a magnetic molecule, an enzyme, a nucleic acid, biotin, DIG, or another molecule that directly or indirectly mediates generation of a signal. In some embodiments, a reporter-labeled probe is detected using an anti-reporter initiator-labeled probe capable of triggering HCR signal amplification. In some embodiments, an anti-target reporter-labeled probe comprises a reporter and an antibody, a nanobody, a nucleic acid, or any molecule or complex comprising a target-binding domain. In some embodiments, an anti-reporter initiator-labeled probe comprises an HCR initiator and an antibody, a nanobody, a nucleic acid, or any molecule or complex comprising a reporter-binding domain.

Materials and Compositions for Bridging Probes

In some embodiments, a bridging probe bridges between two rounds of HCR signal amplification. In some embodiments, a bridging probe bridges from a reporter-decorated HCR amplification polymer generated during a previous round of HCR signal amplification to an initiator capable of triggering a new round of HCR signal amplification. In some embodiments, an anti-reporter initiator-labeled bridging probe comprises a reporter-binding domain and one or more HCR initiators. In some embodiments, an anti-reporter initiator-labeled bridging probe comprises: a) an antibody, a nanobody, a nucleic acid, or any molecule or complex comprising a reporter-binding domain, and b) one or more HCR initiators. In some embodiments, an anti-reporter initiator-labeled bridging probe comprises an anti-reporter primary bridging probe comprising a reporter-binding domain and an anti-primary secondary bridging probe comprising one or more HCR initiators. In some embodiments, the primary bridging probe comprises an antibody, a nanobody, and/or a nucleic acid. In some embodiments, the secondary bridging probe comprises an antibody, a nanobody, and/or a nucleic acid. In some embodiments, a bridging probe directly or indirectly bridges between a reporter decorating an HCR amplifier from a previous round of HCR signal amplification and an HCR initiator that will be used to trigger a new round of HCR signal amplification.

Removal of Signal from the Sample

In some embodiments, HCR signal is removed from the sample after detecting the signal. In some embodiments, signal can be removed from the sample by any method that reduces the number of signal-generating reporters and/or auxiliary reporters and/or tertiary reporters and/or first reporters and/or second reporters and/or third reporters, for example: photobleaching fluorescent reporter molecules using light and/or chemical reagents, chemically cleaving reporters from HCR hairpins and flowing them from the sample (e.g., TCEP), chemically cleaving reporters from readout probes and flowing them from the sample, chemically cleaving hairpins to fragment HCR amplification polymers and flowing the fragments from the sample, chemically cleaving probes to untether HCR amplification polymers from the target and flowing the untethered amplification polymers from the sample, using an auxiliary strand to dehybridize hairpins from HCR amplification polymers and flowing the hairpins from the sample, using an auxiliary strand to dehybridize readout probes from HCR amplification polymers and flowing the readout probes from the sample, using chemical denaturants and/or elevated temperature to destabilize HCR amplification polymers and then flowing the hairpins from the sample, using chemical denaturants and/or elevated temperature to destabilize the interaction between probes and their targets and then flowing the untethered amplification polymers from the sample, using chemical denaturants and/or elevated temperature to destabilize the interaction between readout probes and their substrates and then flowing the readout probes from the sample, using enzymes to degrade amplification polymers and/or probes and flowing the degraded molecules from the sample, using DNases to degrade DNA amplification polymers and/or DNA probes and/or DNA targets and flowing the resulting molecules from the sample, using RNases to degrade RNA targets and then flowing the untethered amplification polymers from the sample, using proteases to degrade protein targets and then flowing the untethered amplification polymers from the sample, using a combination of RNases to degrade RNA targets and DNases to degrade DNA amplification polymers and/or DNA probes and flowing the resulting molecules from the sample, using a combination of proteases to degrade protein targets and DNases to degrade DNA amplification polymers and/or DNA probes and/or DNA targets and flowing the resulting molecules from the sample, using two or more of the above methods, or any other method for removing signal from the sample, at the same time or at different times.

Assay Formats

In some embodiments, an HCR signal can be measured in different assay formats including but not limited to: blots, northern blots, western blots, Southern blots, spot blots, paper assays, flow cytometry assays, lateral flow assays, fluorescent flow cytometry assays, cell sorting assays, fluorescence-activated cell sorting assays, magnetic-activated cell sorting assays, microscopy assays, light microscopy assays, epifluorescence microscopy assays, confocal microscopy assays, light sheet microscopy assays, microarray assays, bead-based assays, mass spectrometry assays, fluorescent microscopy assays, mass spectrometry microscopy assays, mass spectrometry flow cytometry assays, fluorescence assays, chemiluminescence assays, bioluminescence assays, colorimetric assays, electrochemical impedance assays, electrochemical chemiluminescence assays, energy dissipation assays, assays using the human eye, assays using a cell phone camera, gel electrophoresis assays, in situ hybridization (ISH) assays, RNA-ISH assays, DNA-ISH assays, immunohistochemistry (IHC) assays, autoradiography assays, or any assay capable of detecting a signal generated by an HCR amplification polymer.

Sample Types

In some embodiments, initiator-labeled probes and/or fractional-initiator probes can be used with HCR amplification hairpins to detect a target in a sample, the target comprising a molecule, a complex, or a collection of proximal molecules or complexes. The target molecule may be contained within a sample, including for example: a bacterium, a zebrafish embryo, a chicken embryo, a mouse embryo, a human biopsy specimen, a human tissue section, an FFPE tissue section, a urine sample, a blood sample, a stool sample, a mouse tissue section, a brain slice, a sea urchin embryo, a nematode larva, a fruit fly embryo, a model organism, a non-model organism, a multi-species mixture of organisms, an environmental sample containing unknown organisms, a consortium of organisms (for example, a mixture of protists and bacteria within the gut of another organism), a termite, a microbiome, a clinical specimen, a diagnostic sample, a sputum sample, a tumor biopsy sample, a research sample, a sample comprising material from a human, a sample comprising material from a pet (for example, a dog, cat, rabbit, lizard, snake, or fish), material from a wild animal (for example, a cheetah, elephant, rhinoceros, or chimpanzee), material from an extinct animal (for example, a woolly mammoth, a dodo, a giant auk, a triceratops, or a passenger pigeon), living cells (for example, bacteria or cultured mammalian cells), or a living organism (for example a living mouse or a living human).

In some embodiments, the target may be free in solution within the sample. For example, the target may be free in solution within: a test tube, a cell, an embryo, an organism, a tissue section, a biological specimen, or other sample.

In some embodiments, the target may be covalently crosslinked or non-covalently bound to one or more capture probes covalently or non-covalently attached to a solid support. For example, bound directly or indirectly to a capture probe covalently linked to a microarray or bead.

In some embodiments, the target may be fixed, covalently crosslinked, or non-covalently bound directly or indirectly to a solid support. For example, the target may be bound, fixed, or covalently cross-linked to a slide, a blot, a membrane, a paper substrate, or any other substrate. The target may be fixed or covalently crosslinked to a cell, embryo, organism, tissue section, biological specimen, or any other sample. The target may be covalently linked within a sample that is fixed and permeabilized, fixed but not permeabilized, or not fixed but permeabilized.

In some embodiments, the target may be free within a living cell, living embryo, living organism, living ecosystem, or consortium of organisms (for example, the microbiome within the gut of a mammal). The target may be associated with but exterior to a cell or organism, or it may be contained within a cell or organism. The target may be covalently crosslinked within a living cell, living embryo, living organism, living ecosystem, or living consortium of organisms. The target may be present within or absent from one or more cell types within the sample. The target may be present within or absent from one or more species of organism within the sample. The target may be present in a sample that contains one or more off-targets that have different degrees of similarity to the target molecule. The target may be present within an expanded sample. The target may be present within a compressed sample. The sample may be expanded prior to detecting the target so as to increase the spatial separation between molecules. The sample may be compressed prior to detecting the target so as to decrease the spatial separation between molecules. The target and/or other molecules may be crosslinked to an expanded sample so as to maintain the relative position between molecules in the sample as the sample expands. The target and/or other molecules may be crosslinked to a gel, matrix, or other reagents introduced to the sample so as to expand the sample while maintaining the relative position and/or orientation of molecules in the sample as the sample expands. The sample may be differentially expanded and/or compressed with different expansion and/or compression factors in different tissues and/or organs within the sample.

Fixing the Sample

In some embodiments, target molecules can be crosslinked to the sample so that they are retained during subsequent steps in an experiment. For example, target molecules can be crosslinked to the sample using chemical reagents (for example, formaldehyde, paraformaldehyde, EDC (1-ethyl-3-(3-dimethylaminopropyl) carbodiimide)).

Permeabilizing the Sample

In some embodiments, the sample can be treated to enhance the accessibility of target molecules to HCR probes and amplifiers. For example, the sample (for example, cells, tissue sections, or whole-mount embryos) can be permeabilized using chemical reagents (for example, methanol, ethanol, detergent) or enzymes (for example, proteinase K). Target accessibility can also be enhanced via sample homogenization, microdissection, electroporation, sectioning, heat treatment (for example, 1, Gunasekera T S, Barardi C R, Veal D, Vesey G (2004) J Appl Microbiol 96(2):409-417), and/or microwave treatment (for example, Lan H Y, Mu W, NG Y Y, Nikolic-Paterson D H, & Atkins R C (1996) J Histochem Cytochem 44(3):281-287). Another option is to deliver HCR probes and amplifiers across the cell membrane using chemical transfection reagents.

Washes to Remove Unbound Reagents from the Sample

In some embodiments, background can be reduced by washing unused imaging reagents from the sample. For example, washes can be used to remove probes, initiator-labeled probes, fractional-initiator probes, HCR amplification hairpins, amplification reagents, proximity probes, bridging probes, label probes, antibodies, and/or other imaging reagents from the sample. Washes can be performed at a temperature using chemical reagents such that imaging reagents that are bound specifically are predominantly not removed (retaining signal) and imaging reagents that are bound non-specifically are predominantly removed (reducing background). For example, wash buffers could include denaturing agents (e.g., formamide, urea), salt buffer (e.g., sodium chloride sodium citrate (SSC), phosphate buffered saline (PBS)), acids (e.g., citric acid), surfactants (e.g., Tween 20, Triton-X, SDS), or blocking agents (e.g., tRNA, salmon sperm DNA, BSA, ficoll, polyvinilypyrolidone, heparin). Wash buffer can be combined with wash temperature (e.g., 25-80° C.) to optimize wash stringency.

Accurate and Precise Target Quantitation

In some embodiments, HCR probes and HCR amplifiers provide quantitative analysis of target molecules in an anatomical context, generating a signal that scales approximately linearly with the number of target molecules per imaging voxel. In some embodiments, this quantitative property follows from summation of signal that occurs at three levels during imaging: 1) summation over one or more initiator-labeled probes per target molecule or over one or more probe units (each comprising two or more fractional-initiator probes) per target molecule. 2) Summation over multiple HCR amplification hairpins per amplification polymer tethered to an initiator-labeled probe or to a probe unit of fractional-initiator probes that colocalize a full initiator. 3) Summation over zero, one, or more target molecules in an imaging pixel. In some embodiments, quantitative precision can be increased while still maintaining subcellular resolution by defining imaging voxels that average the intensities of neighboring pixels (for example, accurate and precise quantitative imaging with subcellular resolution is demonstrated for mRNA targets in FIGS. 6A-6B and for protein targets in FIGS. 11A-11C). In some embodiments, the quantitative nature of HCR signal follows from the binding properties of HCR probes, the polymerization properties of HCR amplification hairpins, and the central limit theorem, which collectively leverage summation and averaging during and after image acquisition to generate signals that scale approximately linearly with target abundance. In some embodiments, the same quantitative properties apply to other assay formats, with summation and/or averaging occurring during and/or after data acquisition (for example, by a flow cytometer, a blot scanner, or a lateral flow assay viewed with the human eye).

Multiplexing Using Initiator-Labeled Probes

In some embodiments, HCR probe sets comprising initiator-labeled probes and HCR amplifiers comprising HCR hairpins can be used for multiplex target analysis (for example, target analysis via imaging, blotting, flow cytometry, mass cytometry, gel analysis, or any other analysis mode) in which multiple targets are analyzed in the same sample at the same time. Consider a sample containing some or all of N target types of interest as well as zero, one, or more additional off-target species that are not of interest. Each target can be detected using a probe set comprising one or more initiator-labeled probes (each comprising one or more HCR initiators) that selectively bind the cognate target. In some embodiments, the probe set for each of N target types is labeled with HCR initiators for a different HCR amplifier. For example, Target 1 can be detected with Probe Set 1 labeled with HCR initiators for HCR Amplifier 1, Target 2 can be detected with Probe Set 2 labeled with HCR initiators for HCR Amplifier 2, and so on, with Probe Set N labeled with HCR initiators for HCR Amplifier N.

In some embodiments, the N probe sets operate orthogonally such that each probe set selectively binds its cognate target independent of whether the other probe sets and/or targets are present in the sample. In some embodiments, the N amplifiers operate orthogonally such that; 1) the hairpins for each amplifier coexist metastably in the absence of a cognate HCR initiator, 2) each amplifier is selectively triggered to polymerize if its cognate initiator is present independent of whether the other amplifiers are present in the sample. In some embodiments, the reporters carried by each HCR amplifier are orthogonal such that the analysis method is able to measure the signal generated by each HCR amplifier whether or not the other reporters are present in the sample (for example, fluorescent reporters that can be distinguished using fluorescence microscopy, or rare earth reporters that can be distinguished using mass cytometry). For example, multiplex imaging using initiator-labeled probes and simultaneous HCR signal amplification for all targets are shown in FIGS. 9, 10, 11, and 50.

In some embodiments, multiplex target analysis for N target types (types j=1, . . . , N) can be achieved using N orthogonal HCR initiator-labeled probe sets to detect all targets simultaneously (with initiator-labeled probes from probe set j binding to target j for target types j=1, . . . , N).

In some embodiments, multiplex target analysis for N target types (types j=1, . . . , N) can be achieved sing N orthogonal HCR amplifiers to amplify the signal for all target types simultaneously (with hairpins from amplifier j polymerizing in response to initiator j to form an amplification polymer j tethered to target type j for j=1, . . . , N).

In some embodiments, multiplex target analysis for N target types (types j=1, . . . , N) can be achieved by analyzing the sample using a measurement device to detect reporter j either directly carried by one or more of the hairpins in amplifier j or indirectly bound to one or more of the hairpins in amplifier j, for target types j=1, . . . , N.

Multiplexing Using Fractional-Initiator Probes

In some embodiments, HCR probe sets comprising fractional-initiator probes and HCR amplifiers comprising HCR hairpins can be used for multiplex target analysis (for example, target analysis via imaging, blotting, flow cytometry, mass cytometry, gel analysis, or any other analysis mode) in which multiple targets are analyzed in the same sample at the same time. Consider a sample containing some or all of N target types of interest as well as zero, one, or more additional off-target species that are not of interest. Each target can be detected using a probe set comprising one or more probe units (each comprising two or more fractional-initiator probes) that selectively bind the cognate target so that each bound probe unit colocalizes a full HCR initiator. In some embodiments, the probe set for each of N target types colocalizes full HCR initiators for a different HCR amplifier. For example, Target 1 can be detected with Probe Set 1 that colocalizes one or more full HCR initiators for HCR Amplifier 1, Target 2 can be detected with Probe Set 2 that colocalizes one or more full HCR initiators for HCR Amplifier 2, and so on, with Probe Set N colocalizing one or more full HCR initiators for HCR Amplifier N.

In some embodiments, the N probe sets operate orthogonally such that each probe set selectively binds its cognate target independent of whether the other probe sets and/or targets are present in the sample. In some embodiments, the N amplifiers operate orthogonally such that; 1) the hairpins for each amplifier coexist metastably in the absence of a cognate full initiator colocalized by the cognate target, 2) each amplifier is selectively triggered to polymerize if its cognate full initiator is colocalized by its cognate target independent of whether the other amplifiers are present in the sample. In some embodiments, the reporters carried by each HCR amplifier are orthogonal such that the analysis method is able to measure the signal generated by each HCR amplifier whether or not the other reporters are present in the sample (for example, fluorescent reporters that can be distinguished using fluorescence microscopy, or rare earth reporters that can be distinguished using mass cytometry). For example, multiplex imaging using fractional-initiator probes and simultaneous HCR signal amplification for all targets are shown in FIGS. 4 and 5.

In some embodiments, multiplex target analysis for N target types (types j=1, . . . , N) can be achieved using N orthogonal HCR fractional-initiator probe sets to detect all targets simultaneously (with fractional-initiator probes from probe set j binding to target j so as to colocalize a full HCR initiator j for each probe unit in probe set j for target types j=1, . . . , N).

In some embodiments, multiplex target analysis for N target types (types j=1, . . . , N) can be achieved using N orthogonal HCR amplifiers to amplify the signal for all target types simultaneously (with hairpins from amplifier j polymerizing in response to full HCR initiator j to form an amplification polymer j tethered to target type j for j=1, . . . , N).

In some embodiments, multiplex target analysis for N target types (types j=1, . . . , N) can be achieved by analyzing the sample using a measurement device to detect reporter j either directly carried by one or more of the hairpins in amplifier j or indirectly bound to one or more of the hairpins in amplifier j, for target types j=1, . . . , N.

Multiplexing Using a Combination of Initiator-Labeled Probes and Fractional-Initiator Probes In some embodiments, multiplex analysis is performed in a sample using initiator-labeled probes to detect one or more targets (of possibly different types) and fractional-initiator probes to detect one or more other targets (of possibly different types). For example, in the same sample, one or more protein targets and one or more small RNA targets could be detected with orthogonal initiator-labeled probes, one or more mRNA targets and/or DNA targets could be detected with orthogonal fractional-initiator probes, and one or more complex targets (comprising a complex of two or more non-covalently linked molecules) could be detected with fractional-initiator probes. In some embodiments, the probe set for each target (comprising one or more initiator-labeled probes or one or more probe units each comprising two or more fractional-initiator probes and optionally one or more proximity probes) would trigger an orthogonal HCR amplifier that generates (directly or indirectly) an orthogonal signal. In some embodiments, HCR signal amplification is performed for all target types simultaneously. For example, multiplex imaging using initiator-labeled probes for one or more targets and fractional-initiator probes for one or more targets with simultaneous HCR signal amplification for all targets are shown in FIGS. 8E-8F, 12A-12B and 13A-13B.

Multiplexing Using Spectral Imaging

In some embodiments, the number of labels that can be distinguished from each other can be increased using spectral analysis. For example, if two fluorophores have overlapping emissions spectra such that measurement of emissions intensity using a bandpass filter would not be able to distinguish between the two labels, they can be distinguished using spectral imaging in which multiple emissions measurements at different wavelengths are used to distinguish between the signal coming from the two labels even though the emissions spectra of the labels are substantially overlapping. Using spectral imaging, in some embodiments, 10 fluorescent dyes can be spectrally distinguished, or 20 fluorescent dyes can be spectrally distinguished, or 30 or more fluorescent dyes can be spectrally distinguished.

Multiplexing Using Hybrid Spectra Using Multi-Reporter Polymers

In some embodiments, HCR polymerization proceeds via alternating h1 and h2 polymerization steps so the resulting HCR amplification polymer contains either: 1) the same number of h1 and h2 hairpins, 2) one more h1 hairpin, 3) or one more h2 hairpin. In some embodiments, as the length of the polymer increases, the fraction of h1 hairpins in the polymer approaches 0.5 and the fraction of h2 hairpins in the polymer also approaches 0.5. In some embodiments, hairpin h1 is labeled with reporter r1 and hairpin h2 is labeled with reporter r2. In some embodiments, the signal produced by the HCR amplification polymer is a 1:1 blend of the signal produced by reporter r1 and reporter r2 with a new hybrid spectrum. Consider a set of N reporters with distinct spectra. In some embodiments, the N reporters can be used to create N*(N−1)/2 hybrid spectra corresponding to the number of distinct pairs of reporters that can be selected from the set of N reporters. For example: 1) with 6 reporters it is possible to create 6*5/2=15 hybrid reporter spectra, 2) with 8 reporters it is possible to create 8*7/2=28 hybrid reporter spectra, 3) with 15 reporters it is possible to create 15*14/2=105 hybrid reporter spectra, 4) with 50 reporters it is possible to create 50*49/2=1225 hybrid reporter spectra, 5) with 100 reporters it is possible to create 100*99/2=4950 hybrid reporter spectra.

Computational Sequence Design of Orthogonal HCR Amplifiers Using NUPACK

In some embodiments, a set of orthogonal HCR amplifiers (with or without substrates and/or auxiliary strands) is designed using the reaction pathway designer within the NUPACK software suite.[13,14] In some embodiments, sequence design is formulated as a multistate optimization problem using a set of target test tubes to represent elementary steps in the reaction pathway as well as to model global crosstalk.[14] In some embodiments, each elementary step tube contains a set of desired on-target complexes (each with a target secondary structure and target concentration), corresponding to the on-pathway hybridization products for a given step, and a set of undesired off-target complexes (each with vanishing target concentration), corresponding to on-pathway reactants and off-pathway hybridization crosstalk for a given step.[56] In this scenario, these elementary step tubes promote full conversion of cognate reactants into cognate products and against local hybridization crosstalk between these same reactants. In some embodiments, to simultaneously design N orthogonal systems, elementary step tubes are specified for each orthogonal system. In some embodiments, to design against off-pathway interactions between systems, a single global crosstalk tube is also specified.[56] In some embodiments, in the global crosstalk tube, the on-target complexes correspond to all reactive species generated during all elementary steps for all systems (for example, the single-stranded output domains of HCR hairpins that have been opened via polymerization). In some embodiments, in the global crosstalk tube, the off-target complexes correspond to noncognate interactions between these reactive species. In some embodiments, the global crosstalk tube ensemble omits the cognate products that the reactive species are intended to form (they appear as neither on-targets nor off-targets). In this scenario, all reactive species in the global crosstalk tube can be forced to either perform no reaction (remaining as desired on-targets) or to undergo a crosstalk reaction (forming undesired off-targets), providing the basis for minimization of global crosstalk during sequence optimization. In some embodiments, sequence design is performed subject to complementarity constraints inherent to the reaction pathway (for example in FIG. 1A, domain "a" complementary to domain "a*", domain "b" complementary to domain "b*").[14] In some embodiments, sequences are optimized by reducing the ensemble defect quantifying the average fraction of incorrectly paired nucleotides over the multi-tube ensemble.[14] In some embodiments, defect weights are applied within the ensemble defect to prioritize design effort.[14] Optimization of the ensemble defect implements both a positive design paradigm, explicitly design for on-pathway elementary steps, and a negative design paradigm, explicitly design against off-pathway crosstalk.[14]

Multiplexing Using Repeated Reporter Detection

In some embodiments, the number of targets that can be analyzed in a sample can be increased using the same N labels to detect multiple targets in successive rounds of analysis. For example, N targets can be imaged using N labels and then the signal can be removed from the sample and another set of N targets detected using the same N labels. In some embodiments, this repeated imaging approach is applicable for imaging multiple target types in the same sample: 1) regardless of whether the expression levels of the different target types are high, low, variable within each target type, and/or variable across different target types, 2) regardless of whether the expression patterns of the different target types are spatially overlapping or non-overlapping within the sample. In some embodiments, the choice of probe type can be different for different targets and can, optionally, be mixed within any process. In some embodiments: 1) all targets may be detected with initiator-labeled probes, or 2) all targets may be detected with fractional-initiator probes, or 3) one or more targets may be detected with initiator-labeled probes and other targets may be detected with fractional-initiator probes. Thus, the disclosure of one option herein provides the options for the other and for their combination. For example the statement "Providing N probe sets each comprising either: a) one or more HCR initiator-labeled probes, or b) one or more probe units each comprising two or more HCR fractional-initiator probes" implies that any one of the N probe sets can be of either type (a or b), including the possibility that all probe sets are of the same type (all of type a or all of type b) and the possibility that some probe sets are of one type and some probe sets are of the other type (some of type a and some of type b). It is also appreciated that in the disclosures in the specification, the types can be mixed for any of the embodiments where the "either . . . or" is denoted in this context (unless explicitly noted otherwise). In some embodiments, methods for repeated imaging can be combined with CARD, enzyme deactivation, and/or repeated CARD.

In some embodiments, any one or more of the optional steps of any one or more of the methods herein can be combined with any one or more of the other optional steps of any one or more of the methods herein. In some embodiments, any one or more of the steps that are different for any one or more of the methods herein can be combined with any one or more of the other steps that are different for any one or more of the methods herein. In some embodiments, any one or more of the optional steps that are different for any one or more of the methods herein can be combined with any one or more of the other optional steps that are different for any one or more of the methods herein.

Multiplexing Using Single-Molecule Barcoding

In some embodiments, the number of targets that can be analyzed in a sample can be increased by analyzing each target molecule in multiple analysis rounds such that the labels used for different target types in different analysis rounds are varied so as to create a distinct barcode for each species of target molecule. The barcode for a given target molecule is then read out as a barcode of signal measurements. For example, using single-molecule imaging to read out the signal of each target molecule as a diffraction-limited dot, consider 3 rounds of imaging. For each given target type, consider assigning a probe set comprising one or more probe units such that each probe unit in a probe set colocalizes a full HCR initiator corresponding to an HCR amplifier comprising HCR hairpins labeled with either red or green reporters depending on the target type and the round of imaging. Then, for example, a target molecule of type 1 can be read out with barcode (red, red, green; denoting a red dot for round 1 using an HCR amplifier labeled with red reporters, a red dot for round 2 using an HCR amplifier labeled with red reporters, and a green dot for round 3 using an HCR amplifier labeled with green reporters), a target molecule of type 2 can have barcode (red, green, red), a target molecule of type 3 can have barcode (red, red, red), a target molecule of type 4 can have barcode (green, red, green), and so on.

In some embodiments, the number of targets that can be analyzed in a sample can be increased by detecting each target molecule in only a fraction of the barcoding rounds. For example, in an experiment with 4 rounds, a target molecule of type 1 can be read out with barcode (red, ---, ---, red; denoting a red dot for round 1, no dot for round 2, no dot for round 3, a red dot for round 4), a target molecule of type 2 can be read out with barcode (green, red, ---, ---), and so on.

EXAMPLES

The following examples are non-limiting and other variants within the scope of the skill in the art are also contemplated.

Example 1—Cooperative Initiation of HCR Using Fractional-Initiator Probes

FIGS. 3A-3C demonstrate cooperative initiation of HCR using fractional-initiator probes. FIG. 3A displays target-mediated colocalization of fractional-initiator probes. Fractional-initiator probes p1 and p2 each carry a fraction of HCR initiator i1. Selective binding of p1 and p2 to the target mRNA colocalizes the full HCR initiator i1, allowing cooperative initiation of the HCR amplification cascade. FIG. 3B displays in vitro validation of cooperative initiation of HCR using fractional-initiator probes p1 and p2. Reaction conditions: hairpins h1 and h2 at 0.5 μM each (Lanes 1-7); oligos i1, p1, p2, and/or Target at 5 nM each (Lanes as noted on the gel); 5×SSCT buffer; overnight reaction at room temperature. Hairpins h1 and h2 labeled with Alexa 647 fluorophore. dsDNA 1 kb ladder pre-stained with SYBR Gold. Lane 1: Metastable hairpins h1 and h2 exhibit minimal leakage out of their kinetically trapped states in the absence of HCR initiator i1. Lane 2: Full conversion of HCR hairpin monomers h1 and h2 into amplification polymer in the presence of HCR initiator i1 (i1 as an oligo). Lane 3: Strong conversion of hairpins h1 and h2 to polymer in the presence of Target and both fractional-initiator (aka split-initiator) probes p1 and p2, demonstrating cooperative initiation of HCR. Lanes 4-6: Minimal conversion of HCR hairpin monomers h1 and h2 into polymer in the presence of probe p1, probe p2, or both probes p1 and p2, demonstrating active background suppression. Lane 7: Minimal conversion of HCR hairpin monomers h1 and h2 into polymer in the presence of Target alone. FIG. 3C displays quantification of the polymer bands in FIG. 3B. Multi Gauge software (Fuji Photo Film) was used to calculate the Alexa 647 intensity profile surrounding the polymer band for Lanes 1-7. Each intensity profile is displayed for ±3 mm of gel migration distance with the peak value centered at 0. The quantification percentages were calculated using Multi Gauge with auto-detection of signal and background; the calculated values were normalized to the measured value for Lane 2.

The gel study of FIG. 3B demonstrates cooperative initiation of HCR using fractional-initiator probes. Lane 1 shows that there is minimal leakage of hairpins h1 and h2 out of their kinetically trapped states in the absence of HCR initiator i1. As a positive control, Lane 2 demonstrates conversion of metastable HCR hairpin monomers h1 and h2 into polymer in the presence of HCR initiator i1 (where i1 is a single oligo).

Using fractional-initiator (alternatively known as split-initiator) probes, strong conversion of metastable HCR hairpin monomers h1 and h2 into polymer were observed if the target was present together with fractional-initiator probes p1 and p2. However, minimal conversion to polymer was observed if p1 or p2 is present alone (Lanes 4 and 5), or if p1 and p2 were present together but in the absence of the Target (Lane 6).

These results demonstrated the active background suppression properties of fractional-initiator probes: probes that are not colocalized via selective hybridization to the target predominantly do not trigger HCR amplification. The fact that in the absence of the target, p1 and p2 do not trigger HCR even when they are both present in solution (Lane 6), indicates that fractional-initiator probes provide automatic background suppression even in the absence of washes.

Example 2—Comparison of Performance of Initiator-Labeled Probes and Fractional-Initiator Probes for HCR RNA-FISH FIGS. 4A-4D compare the performance of initiator-labeled probes (alternatively known as standard probes) and fractional-initiator probes as the size of the probe set is increased for imaging of a mRNA target in whole-mount chicken embryos. For tests with initiator-labeled probes, an optimized probe set of 5 probes was used, and then these probes were augmented with additional unoptimized probes to form probe sets of 10 probes and 20 probes. For tests with fractional-initiator probes, probe sets were used with 5, 10, and 20 probe pairs, where each probe pair targets approximately the same binding site as the corresponding initiator-labeled probe. Using initiator-labeled probes, increasing the probe set size resulted in a substantial increase in background (FIG. 4A) and a corresponding decrease in the signal-to-background ratio as a result of some subset of the additional probes binding non-specifically within the sample.

These data illustrate the importance of probe set optimization using initiator-labeled probes that do not provide active background suppression: if there are any bad probes in the probe set, they will undermine performance by generating amplified background. In contrast, using fractional-initiator probes, as the number of probe pairs increases from 5 to 10 to 20, the background remains approximately constant (FIG. 4A) and the signal-to-background ratio increases monotonically (FIG. 4B).

These data illustrate the significant benefit of automatic background suppression using fractional-initiator probes: even if there are bad probes in the fractional-initiator probe set, they do not generate amplified background, making it straightforward to increase signal-to-background by increasing the number of probes without performing probe set optimization. Representative images using the probe sets with 20 probes (initiator-labeled probes) or 20 probe pairs (fractional-initiatory probes) are shown in FIG. 4C. Representative pixel intensity distributions for these images are shown in FIG. 4D. With fractional-initiator probes, the pixel intensity distributions for background and signal plus background are predominantly non-overlapping.

Figure 4A:
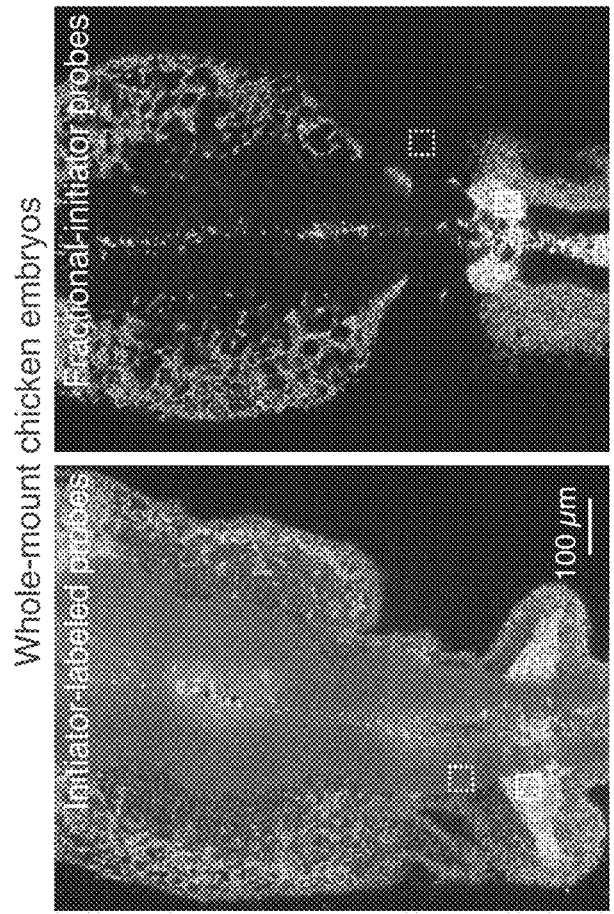
FIGS. 4A-4D depict background and the signal-to-background ratio using initiator-labeled probes and fractional-initiator probes.
Figure 4B:
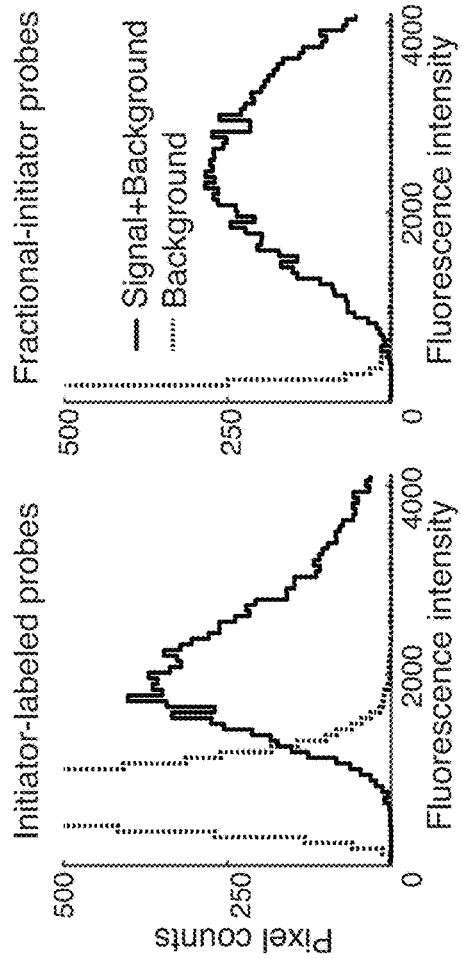
Figure 4C:
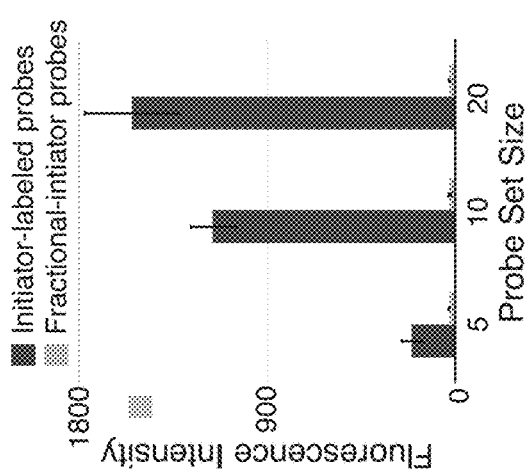
Figure 4D:
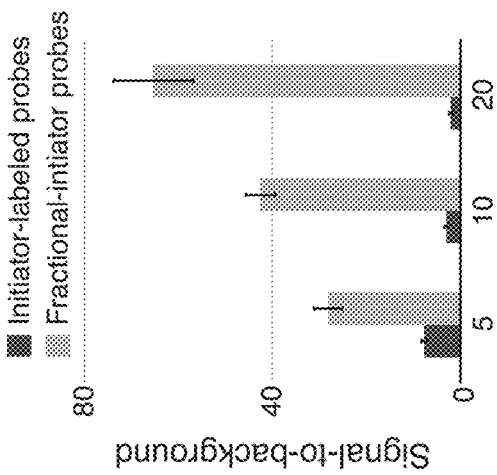

The following is provided for slightly more detail for FIGS. 4A-4D, which present background and signal-to-background using initiator-labeled probes and fractional-initiator probes. FIG. 4A displays the fluorescent background using probe sets with 5, 10, or 20 probes (initiator-labeled probes) vs 5, 10, or 20 probe pairs (fractional-initiator probes). Unoptimized initiator-labeled probes resulted in non-specific probe binding, leading to generation of amplified background. Unoptimized fractional-initiator probes that bind non-specifically in the sample did not co-localize a full HCR initiator, and thus did not trigger HCR signal amplification, avoiding generation of amplified background. FIG. 4B displays the signal-to-background ratio for the probe sets of FIG. 4A. Fractional-initiator probes with automatic background suppression outperformed unoptimized standard probes in signal-to-background measurements. FIG. 4C displays confocal micrographs in the neural crest of fixed whole-mount chicken embryos. Probe sets: 20 probes for initiator-labeled probes, 20 probe pairs for fractional-initiator probes. FIG. 4D displays pixel intensity histograms for Signal+Background (pixels within solid boundary in FIG. 4C) and Background (pixels within dashed boundary in FIG. 4C). For each image, the total number of pixels within solid and dashed boundaries is the same. Embryos fixed: stage HH10. Target: Sox10.

Example 3—Imaging Four Target mRNAs in Whole-Mount Chicken Embryos with High Signal-to-Background Using Unoptimized Fractional-Initiator Probes FIGS. 5A-5D demonstrate imaging for four target mRNAs in whole-mount chicken embryos with high signal-to-background using unoptimized fractional-initiator probes. Due to the automatic background suppression property of fractional-initiator probes, the signal-to-background ranges from approximately 25 to 60 for the four target mRNAs without performing any probe set optimization. FIG. 5A displays expression schematics for four target mRNAs: FoxD3, EphA4, Sox10, Dmbx1. FIG. 5B displays four-channel confocal micrographs in the head and neural crest. FIG. 5C displays zoom of depicted region of FIG. 4B. FIG. 5D displays four individual channels from FIG. 5C with signal-to-background measurements. Probe sets: 12-20 pairs of unoptimized fractional-initiator probes per target. Amplifiers: four orthogonal HCR amplifiers carrying spectrally distinct fluorophores (one HCR amplifier per target). Embryo fixed: stage HH10.

Figure 6B:
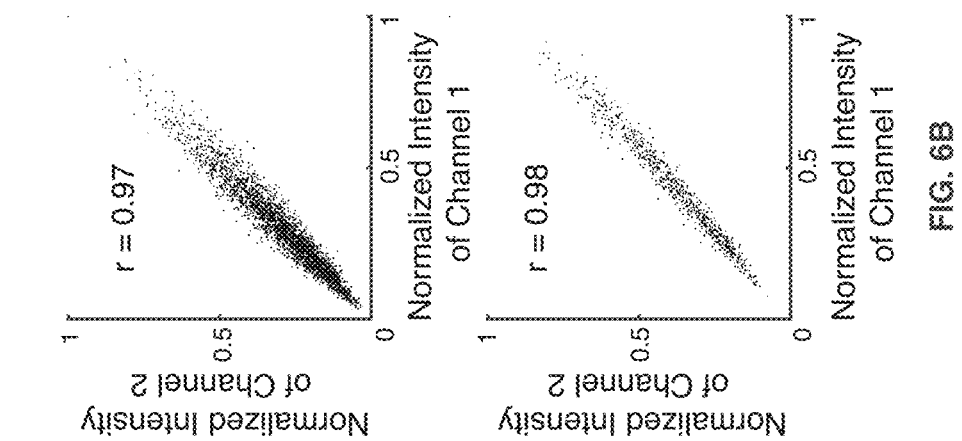
FIGS. 6A-6B depict quantitative imaging of mRNA expression with subcellular resolution in fixed whole-mount chicken embryos using fractional-initiator probes.
Figure 6A:
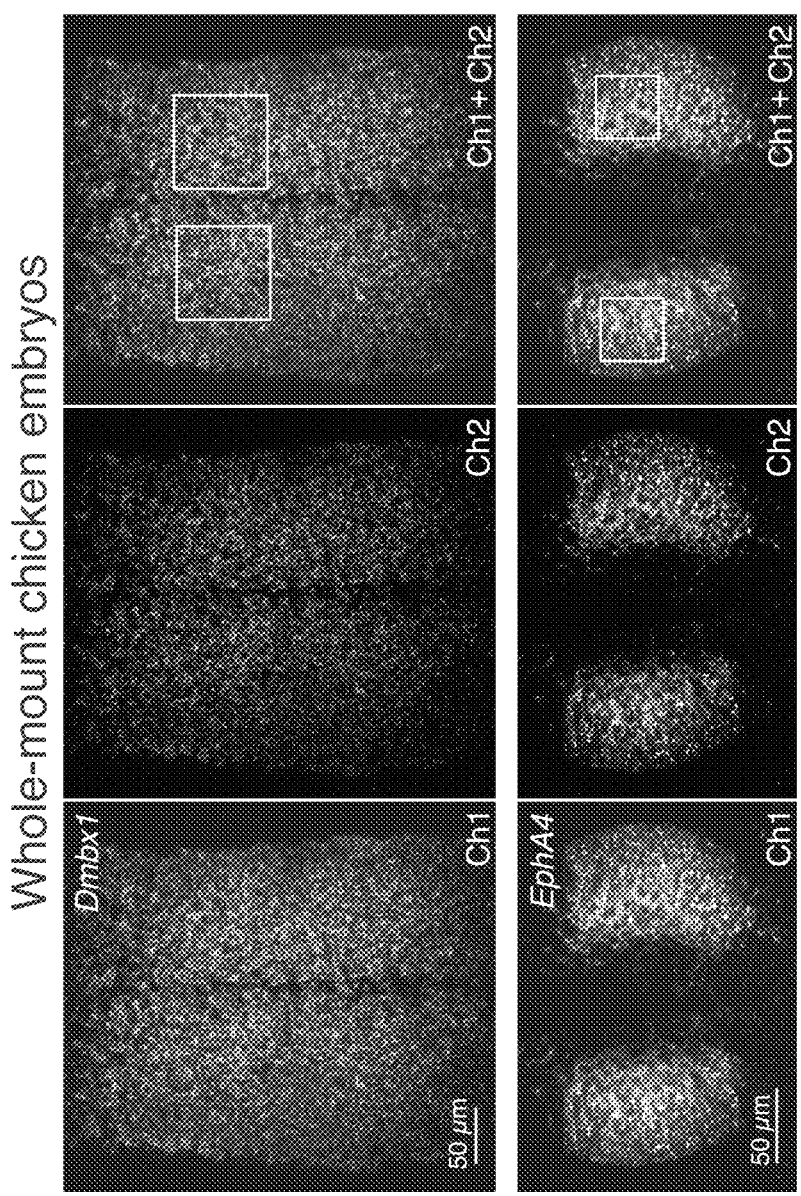

Example 4—HCR RNA-FISH Using Fractional-Initiator Probes for Quantitative Analysis of mRNA Expression with Subcellular Resolution FIGS. 6A-6B demonstrate that HCR RNA-FISH using fractional-initiator probes allows for quantitative analysis of mRNA expression with subcellular resolution within whole-mount chicken embryos. Each target mRNA was redundantly detected using two fractional-initiator probe sets that each triggered a different spectrally-distinct HCR amplifier. Plotting a 2-channel scatter plot of normalized voxel intensities resulted in a tight linear relationship with approximately zero intercept, indicating that HCR signal scales linearly with the number of target mRNAs per imaging voxel. Accuracy improves as the distribution becomes linear and the intercept vanishes; precision improves as the scatter becomes tighter. The 2×2 µm voxels provided subcellular resolution. These results demonstrate that HCR RNA-FISH with fractional-initiator probes allows accurate and precise relative quantitation of mRNA expression with subcellular resolution in an anatomical context without the need for probe set optimization. FIG. 6A displays two-channel redundant detection of target mRNAs. Targets: Dmbx1 and EphA4. Confocal microscopy: 0.2×0.2 µm pixels. Probe sets: 20 pairs of fractional-initiator probes per channel for each target. Amplifiers: two orthogonal HCR amplifiers carrying spectrally distinct fluorophores for each target. Embryos fixed: stage HH10. FIG. 6B displays highly correlated normalized signal (Pearson correlation coefficient, r) for 2×2 µm voxels in the selected regions of FIG. 6A.

Figure 7:
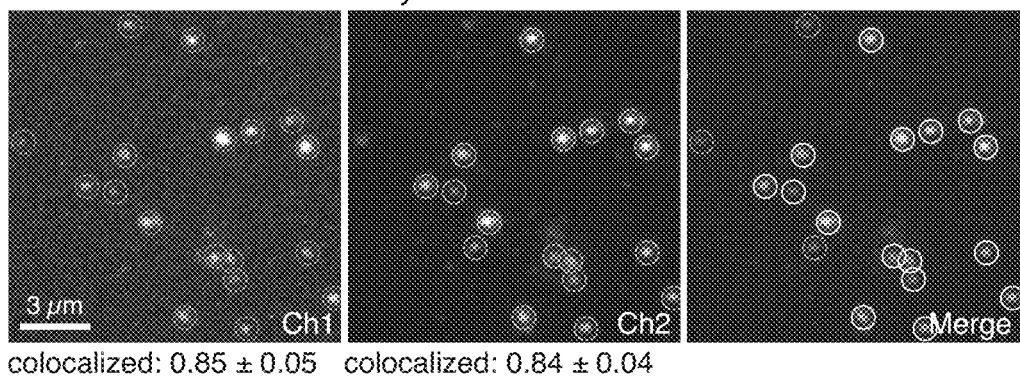
FIG. 7 depicts single-molecule mRNA imaging in a fixed whole-mount chicken embryo using fractional-initiator probes.

Example 5—Single-Molecule mRNA Imaging Using HCR RNA-FISH in Whole-Mount Chicken Embryos FIG. 7 demonstrates single-molecule mRNA imaging using HCR RNA-FISH in whole-mount chicken embryos. Redundant detection of target mRNA Dmbx1 in whole-mount chicken embryos. Probe sets: 25 fractional-initiator probe pairs per channel; no probe set optimization. Pixel size: 0.1×0.1 µm. Embryos fixed at stage HH8. Each target mRNA is detected using two probe sets, each initiating an orthogonal spectrally distinct HCR amplifier (Ch1, Alexa 647; Ch2, Alexa 594). Representative field of view from confocal micrographs. Left panel gray circles: dots detected in Ch1. Middle panel gray circles: dots detected in Ch2. White circles in right panel: dots detected in both channels. Colocalization represents the fraction of dots in one channel that are detected in both channels (mean±SEM, N=3 embryos).

Example 6—Multiplex Imaging of Protein Targets in FFPE Mouse Brain Sections

FIGS. 9A-9B and 10A-10B demonstrate multiplex HCR immunofluorescence (IF) for imaging protein targets in formalin-fixed paraffin-embedded (FFPE) mouse brain sections.

FIGS. 9A-9B employ initiator-labeled primary antibody probes as depicted in FIG. 8A. FIG. 8A displays the 2-stage HCR IF protocol consisting of a protein detection stage (initiator-labeled primary antibody probes bind to protein targets; wash) and an amplification stage (initiators trigger self-assembly of fluorophore-labeled HCR hairpins into tethered fluorescent amplification polymers; wash). FIG. 8B displays the multiplexing timeline in which the same 2-stage protocol is used independent of the number of target proteins. FIG. 9A displays a four-channel epifluorescence micrograph of an FFPE mouse brain section (four target proteins: TH, GFAP, MBP, MAP2) and FIG. 9B displays zooms for the depicted regions of FIG. 9A. The approach of FIG. 9A-9B has the advantage that high levels of multiplexing can be achieved using initiator-labeled primary antibodies where the antibody probes for different protein targets carry orthogonal HCR initiators that operate independently in the sample at the same time. There is no requirement for the primary antibodies to be raised in different organisms, providing flexibility in establishing a large library of primary antibodies for different targets.

FIGS. 10A-10B employ unmodified primary antibody probes and initiator-labeled secondary antibody probes as depicted in FIG. 8C. FIG. 8C displays the 2-stage HCR IF protocol consisting of a protein detection stage (primary antibody probes bind to protein targets; wash; initiator-labeled secondary antibody probes bind to primary antibody probes; wash) and an amplification stage (initiators trigger self-assembly of fluorophore-labeled HCR hairpins into tethered fluorescent amplification polymers; wash). FIG. 8D displays the multiplexing timeline in which the same 2-stage protocol is used independent of the number of target proteins. FIG. 10 demonstrates 4-plex HCR IF in FFPE mouse brain sections. FIG. 10A displays a four-channel epifluorescence micrograph of an FFPE mouse brain section (four target proteins: TH, GFAP, PVALB, MBP) and FIG. 10B displays zooms of the depicted regions of FIG. 10A.

The approach of FIG. 10A-10B has the advantage that primary antibodies can be used without modification, enabling use of a validated library of initiator-labeled secondary antibodies, where different secondary antibodies carry orthogonal HCR initiators that operate independently in the sample at the same time. With this approach, the primary antibodies must be of different isotypes or raised in different organisms so that only one type of initiator-labeled secondary antibody detects each primary antibody.

Figure 11A:
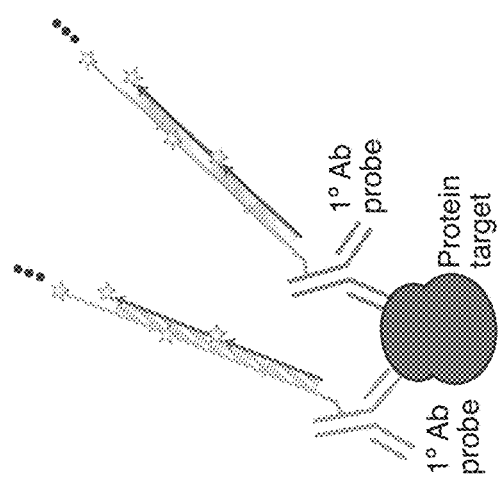
FIGS. 11A-11C depict HCR IF for quantitative imaging of protein expression with subcellular resolution in an FFPE mouse brain tissue section.
Figure 11B:
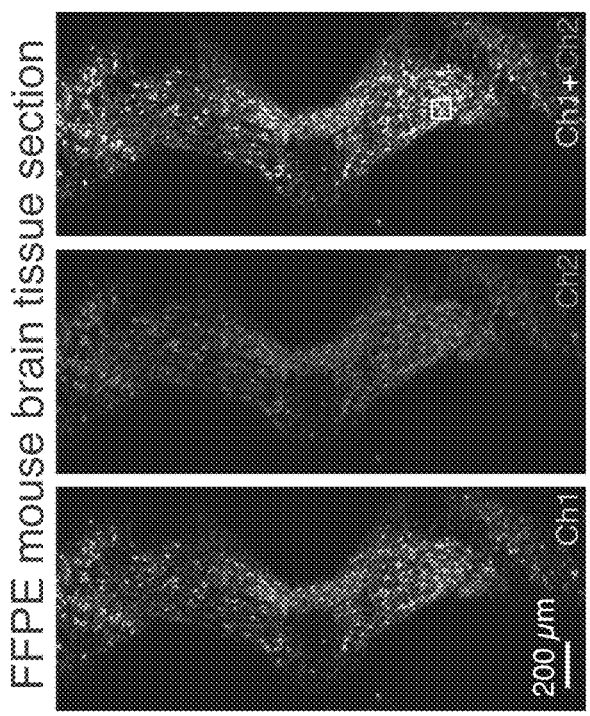
Figure 11C:
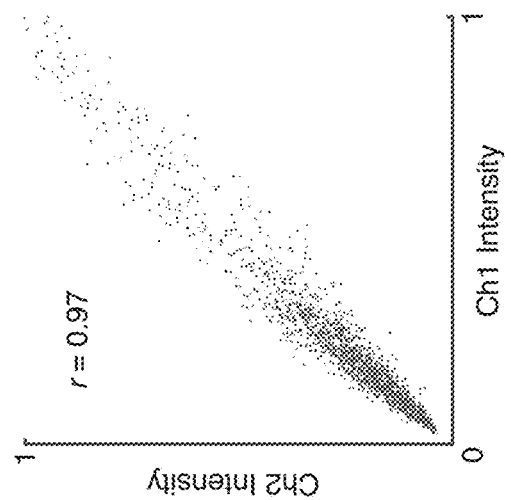

Example 7—Quantitative Analysis of Protein Expression with Subcellular Resolution by HCR IF FIGS. 11A-11C demonstrate that HCR IF allows for quantitative analysis of protein expression with subcellular resolution in an anatomical context. Each target protein was redundantly detected using two initiator-labeled primary antibody probes that each triggered a different spectrally-distinct HCR amplifier. Plotting a 2-channel scatter plot of normalized voxel intensities resulted in a tight linear relationship with approximately zero intercept, indicating that HCR signal scales linearly with the number of target proteins per imaging voxel. FIG. 11A illustrates 2-channel redundant detection of a target protein. The target protein is detected using two initiator-labeled primary antibody probes that bind different epitopes, each initiating an orthogonal spectrally distinct HCR amplifier (Ch1: Alexa 546, Ch2: Alexa 647). FIG. 11B displays epifluorescence micrographs of an FFPE mouse brain section. FIG. 11C displays highly correlated normalized signal (Pearson correlation coefficient, r) for subcellular 2×2 μm voxels in the boxed region of FIG. 11B. In this scatter plot, accuracy corresponds to linearity with zero intercept and precision corresponds to scatter around the line. The 2×2 μm voxels provided subcellular resolution. These results demonstrate that HCR IF allows accurate and precise relative quantitation of protein expression with subcellular resolution in an anatomical context.

Example 8—Multiplex HCR RNA-FISH/IF with HCR Signal Amplification for all mRNA and Protein Targets Simultaneously FIGS. 12A-12B and 13A-13B demonstrate multiplex HCR RNA-FISH/IF with HCR signal amplification performed for all mRNA and protein targets simultaneously.

Figures 12A, 12B:
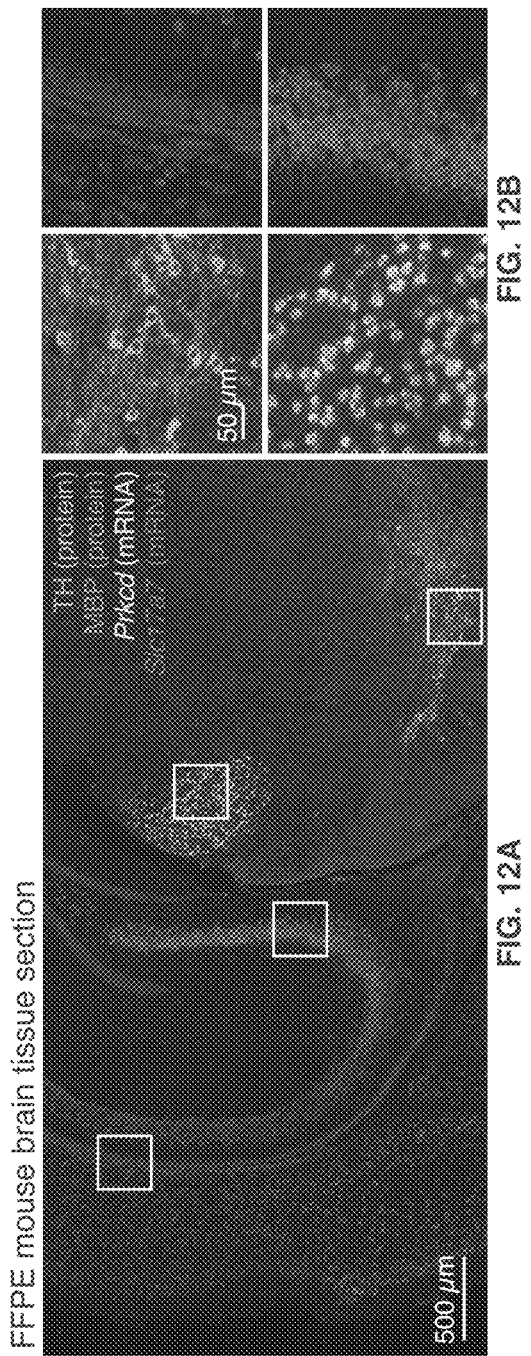
FIGS. 12A-12B depict HCR RNA-FISH/IF for simultaneous multiplex imaging of RNA and protein targets with high signal-to-background in an FFPE mouse brain tissue section using fractional-initiator probes for RNA targets and initiator-labeled primary antibody probes for protein targets, with HCR signal amplification performed for all targets simultaneously.
Figure 14:
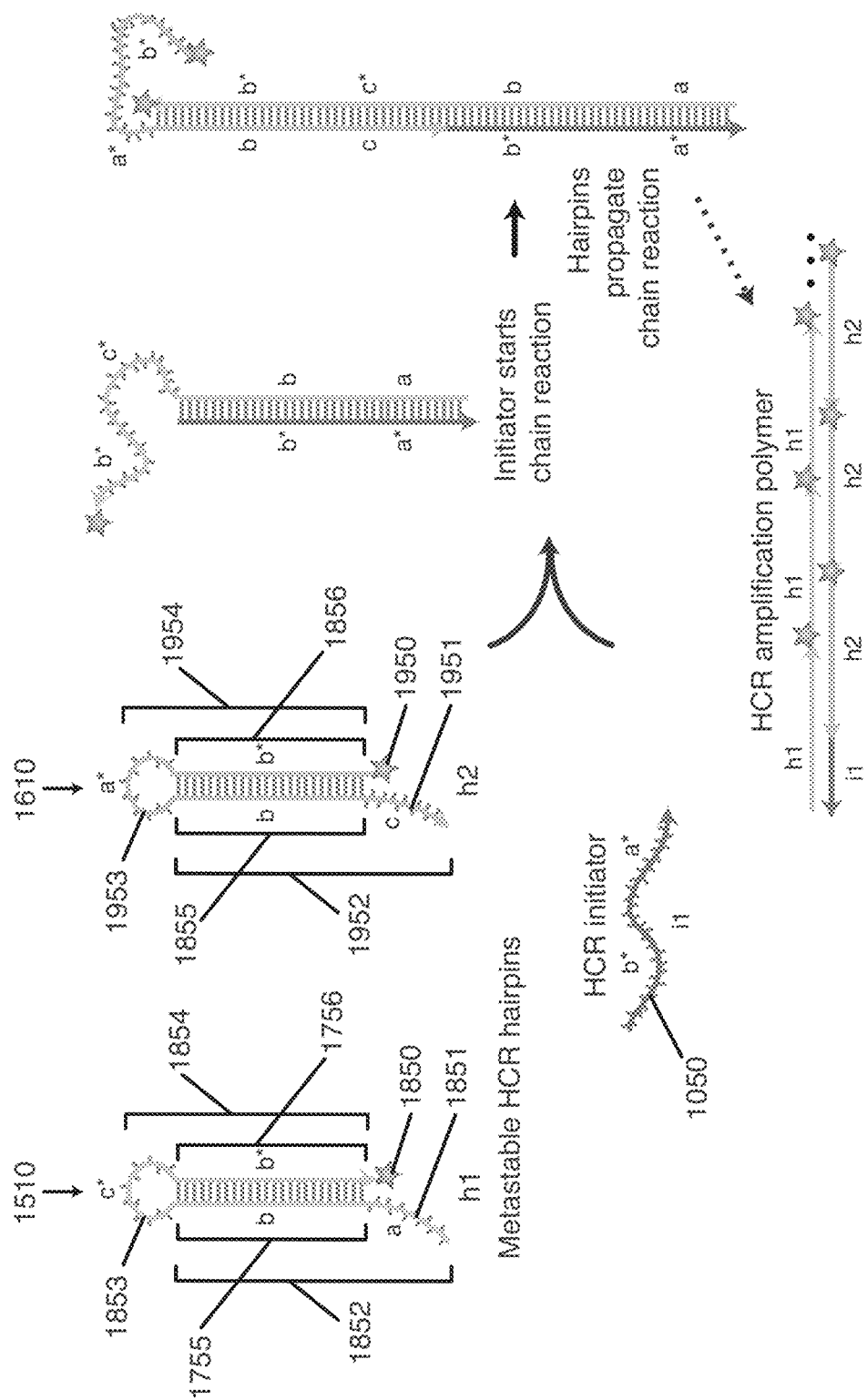
FIG. 14 depicts some embodiments of HCR amplification using two HCR hairpins. 1050 in FIG. 14 depicts colocalized full HCR initiator i1 formed by two fractional-initiator probes colocalized by a target. Only a part of the fractional-initiator probes is depicted.
Figure 15:
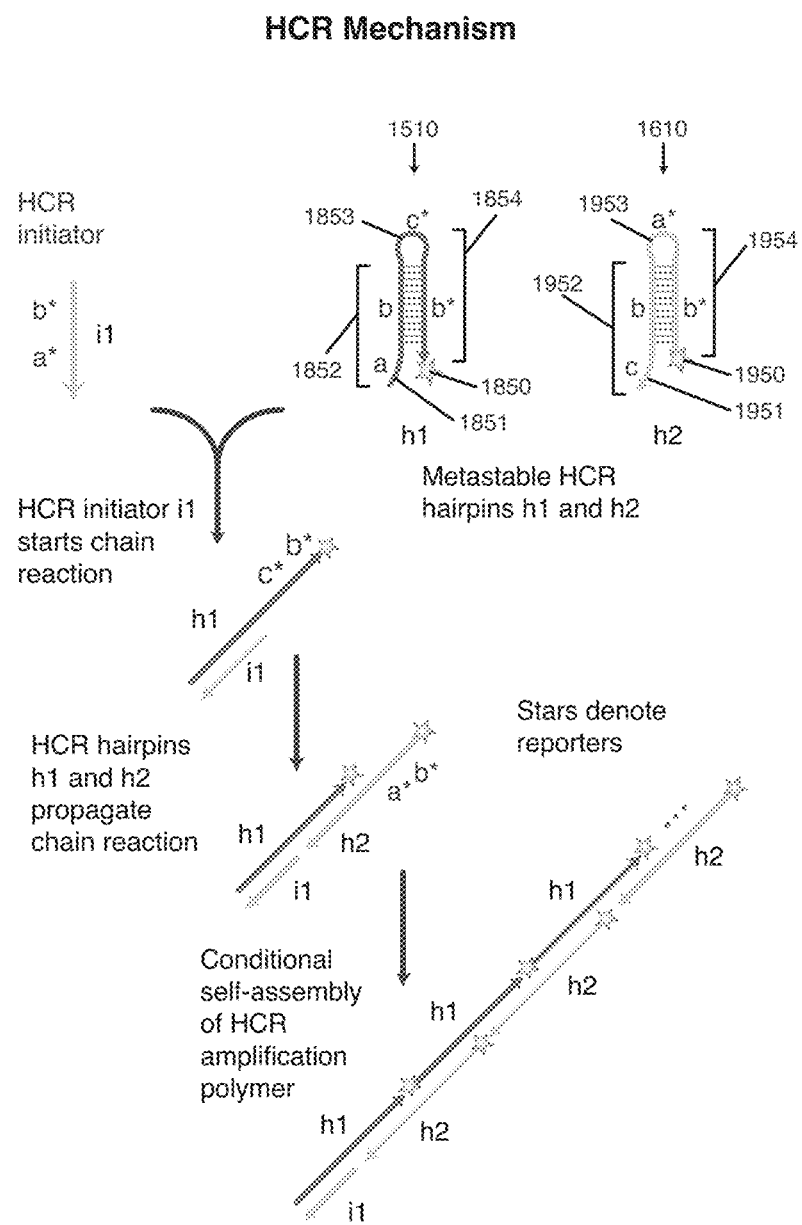
FIG. 15 depicts some embodiments of HCR amplification using two HCR hairpins.

FIGS. 12A-12B demonstrate multiplex HCR RNA-FISH/IF using initiator-labeled primary antibody probes and fractional-initiator DNA probes as displayed in FIG. 8E. FIG. 8E displays a 3-stage HCR RNA-FISH/IF protocol consisting of a protein detection stage (initiator-labeled primary antibody probes bind to protein targets; wash), an RNA detection stage (fractional-initiator DNA probes bind to RNA targets; wash), and an amplification stage (initiators trigger self-assembly of fluorophore-labeled HCR hairpins into tethered fluorescent amplification polymers; wash). The same 3-stage HCR RNA-FISH/IF protocol is used independent of the number of target proteins and target RNAs. FIG. 12A displays a four-channel epifluorescence micrograph of an FFPE mouse brain section (two target proteins (TH, MBP) and two target mRNAs (Prkcd, Slc17a7) and FIG. 12B displays zooms of the depicted regions of FIG. 12A.

FIGS. 13A-13B demonstrate multiplex HCR RNA-FISH/IF using primary antibody probes, initiator-labeled secondary antibody probes, and fractional-initiator DNA probes. FIG. 8F displays a 3-stage HCR RNA-FISH/IF protocol consisting of a protein detection stage (primary antibody probes bind to protein targets; wash; initiator-labeled secondary-antibody probes bind to primary-antibody probes; wash), an RNA detection stage (fractional-initiator DNA probes bind to RNA targets; wash), and an amplification stage (initiators trigger self-assembly of fluorophore-labeled HCR hairpins into tethered fluorescent amplification polymers; wash). The same 3-stage HCR RNA-FISH/IF protocol is used independent of the number of target proteins and target RNAs. FIG. 13A displays a four-channel epifluorescence micrograph of an FFPE mouse brain section (two target proteins (TH, MBP) and two target mRNAs (Prkcd, Slc17a7)) and FIG. 13B displays a zoom of depicted region of FIG. 13A.

Example 9—Optimization of Cooperative Probe Junctions to Enhance Fractional-Initiator HCR Suppression and Conversion FIGS. 31A-31C demonstrate the use of cooperative probe junctions to enhance fractional-initiator HCR suppression (OFF state) and conversion (ON state). In FIG. 31A, fractional-initiator probes p1 and p2 are complementary to overlapping regions of HCR hairpin h1 (each contains domains u* and v* complementary to domains u and v in h1) to enable relaxation of the junction into an energetically favorable conformation that reduces the kinetic barrier to opening the first HCR hairpin to initiate HCR polymerization. In FIG. 31B, leakage (OFF state) is assayed by agarose gel using probes with varying degrees of overlap (u*=0, 1, or 2 nucleotides, v*=0, 1, or 2 nucleotides). The OFF state is characterized by testing HCR initiation by individual probes p1 or p2 (FIG. 31B left), and by quantifying the resulting polymerization bands in the gel (FIG. 31B right). In FIG. 31C, conversion (ON state) is assayed by agarose gel using probes with varying degrees of overlap (u*=0, 1, or 2 nucleotides, v*=0, 1 or 2 nucleotides). The ON state is characterized by testing HCR initiation by probes p1 and p2 plus target (FIG. 31C left) and by quantifying the resulting polymerization bands in the gel (FIG. 31C right). The reaction conditions for FIG. 28 were hairpins h1 and h2 at 500 nM each for OFF state and 60 nM each for ON state (all lanes); initiator i1, probes p1 and p2, and/or DNA target at 0.01× hairpin concentration.

Testing different junction designs, yields probes p1 and p2 with a clean OFF state (fractional-initiator HCR suppression≈0.5% of standard-initiator HCR suppression; boxed FIG. 31B) and a strong ON state (fractional-initiator HCR conversion≈99% of standard-initiator HCR conversion; boxed in FIG. 31C). These results indicate that replacement of a standard probe (v2.0) with a pair of fractional-initiator probes (v3.0) can be engineered to dramatically decrease amplified background (lane 2 vs lanes 4 and 9 in FIG. 31B) without significantly decreasing amplified signal (lane 2 vs lane 6 in FIG. 31C). For this probe junction, the domain dimensions are u*=0 nucleotides and v*=2 nucleotides, corresponding to fractional initiators within a probe unit that hybridize to binding sites in HCR hairpin h1 that overlap by 2 nucleotides.

Figure 32A:
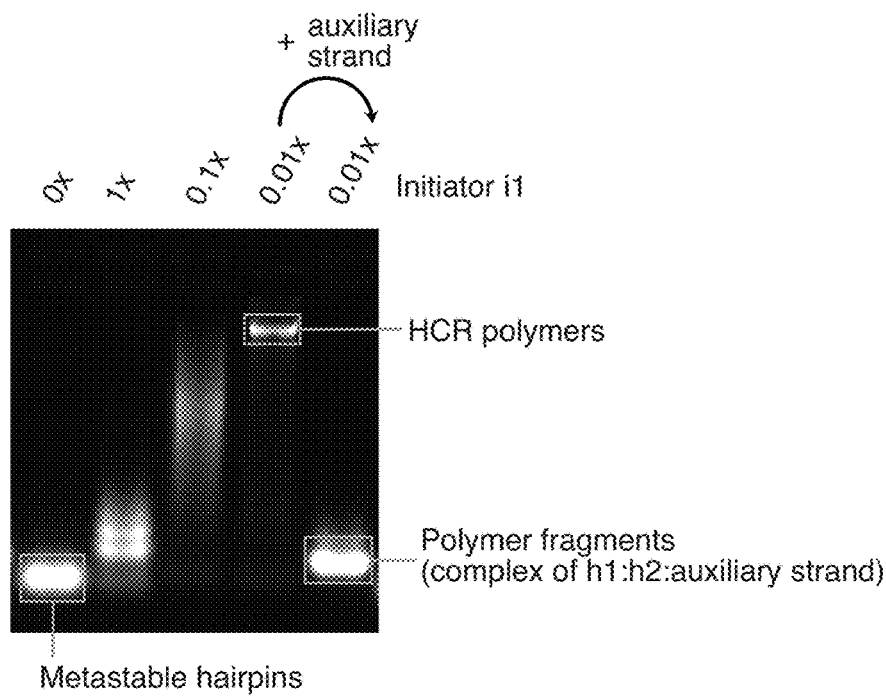
FIGS. 32A-32B depict some embodiments of multiplex in situ hybridization in cultured human cells via repeated reporter detection.

Example 10—Dehybridization of HCR Hairpins from HCR Amplification Polymers Using an Auxiliary Strand FIG. 32A depicts the in vitro validation of dehybridization of HCR hairpins from HCR amplification polymers using an auxiliary strand. Reaction conditions: hairpins h1 and h2 at 0.6 µM each (Lanes 1-5); HCR initiator i1 at 0.6 µM (Lane 2), 60 nM (Lane 3), and 6 nM (Lanes 4 and 5); auxiliary strand at 6 µM (Lane 5); 5×SSCT buffer; overnight HCR amplification at room temperature; 1 hour auxiliary strand incubation at room temperature. Hairpins h1 and h2 labeled with Alexa 647 fluorophore. Lane 1: Metastable hairpins h1 and h2 exhibit minimal leakage in the absence of HCR initiator i1. Lane 2: Formation of short HCR amplification polymers at equimolar HCR initiator i1 concentration. Lanes 3 and 4: Formation of longer HCR amplification polymers at lower HCR initiator concentrations. Lane 5: Dehybridization of hairpins from HCR amplification polymers using an auxiliary strand to yield polymer fragments consisting of h1, h2, and the auxiliary strand.

Some embodiments of sequences used for dehybridization of HCR hairpins from HCR amplification polymers (for example, FIG. 32A) are shown below in TABLE 1. The sequences can be used for any of the embodiments of the methods herein.

TABLE 1

| | |
|---|---|
| Hairpin h1 including toehold for auxiliary strand nucleation | 5'-CGGGTTAAAGTTGAGTGGAGATATAGAGG CAGGGACAAAGTCTAATCCGTCCCTGCCTCTA TATCTCCACTCTATCAT-3' (SEQ ID NO: 1) |
| Hairpin h2 | 5'-GTCCCTGCCTCTATATCTCCACTCAACTT TAACCCGGAGTGGAGATATAGAGGCAGGGACG GATTAGACTTT-3' (SEQ ID NO: 2) |

TABLE 1-continued

| | |
|---|---|
| Initiator i1 | 5'-GTCCCTGCCTCTATATCTCCACTCAACTT TAACCCG-3' (SEQ ID NO: 3) |
| Auxiliary strand | 5'-ATGATAGAGTGGAGATATAGAGGCAGGGA CGGATTAGACTTT-3' (SEQ ID NO: 4) |

Figure 32B:
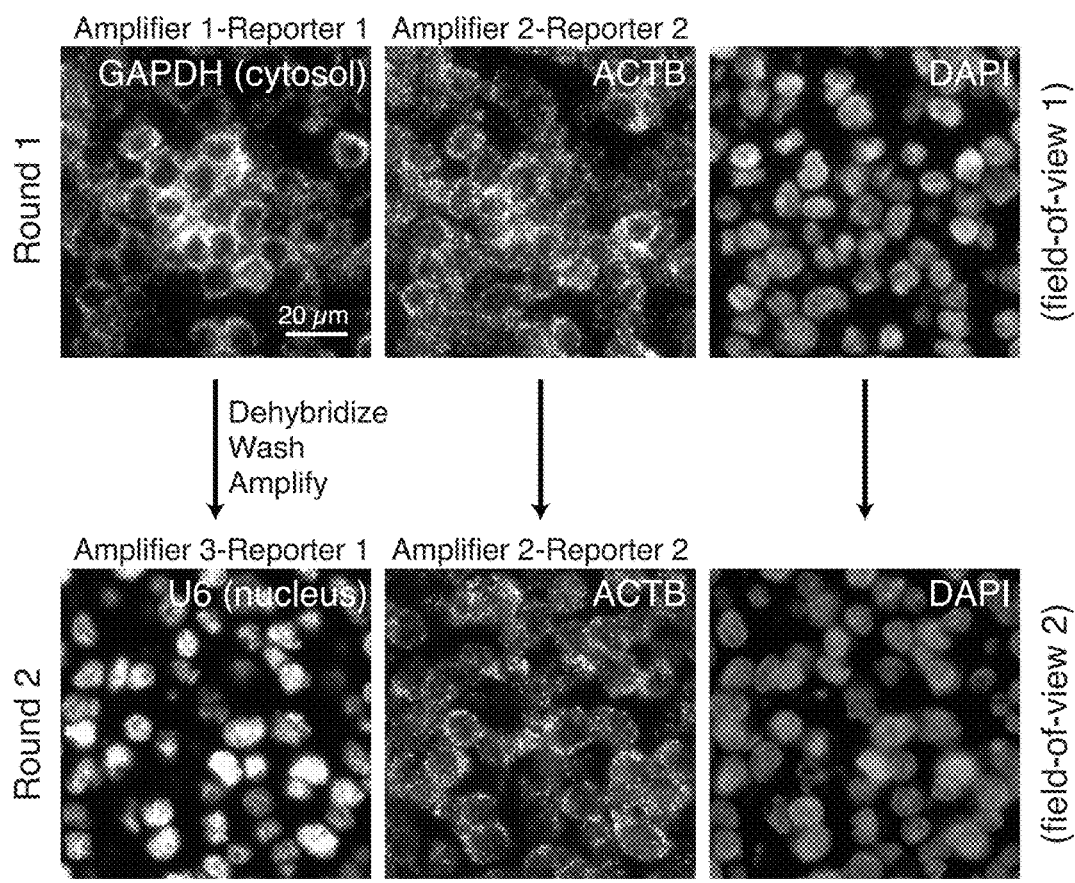

FIG. 32B demonstrates imaging of 3 target mRNAs in FFPE cultured human cell (HEK293) pellets on a slide using repeated reporter detection. Target mRNAs: GAPDH, ACTB, U6. Probe sets for all three targets were introduced simultaneously in the detection stage. In the first round of amplification, only GAPDH and ACTB were detected using amplifiers labeled with spectrally distinct fluorophores (Amplifier 1 labeled with Reporter 1 (Alexa647) for GAPDH, Amplifier 2 labeled with Reporter 2 (Alexa546) for ACTB). Only Amplifier 1 used for GAPDH contained the toehold for auxiliary strand nucleation. After image acquisition, the sample was incubated with Amplifier 1 auxiliary strands for 1 hour at room temperature to dehybridize Alexa647-labeled hairpins from amplification polymers tethered to GAPDH mRNAs; resulting polymer fragments were washed from the sample. In the second round of amplification, a different HCR amplifier labeled with the same reporter as GAPDH (Amplifier 3 labeled with Reporter 1 (Alexa647)) was used for U6 signal amplification.

The images demonstrate the cytoplasmic Reporter 1 (Alexa 647) signal for GAPDH was completely removed by the addition of the Amplifier 1 auxiliary strand followed by washes and was replaced by the nuclear Reporter 1 (Alexa 647) signal of U6 in the second round of imaging. ACTB signal strength (Amplifier 2 labeled with Reporter 2 (Alexa 546)) remains comparable between imaging rounds.

Example 11—Ultrasensitive HCR Signal Amplification with CARD

Figure 33:
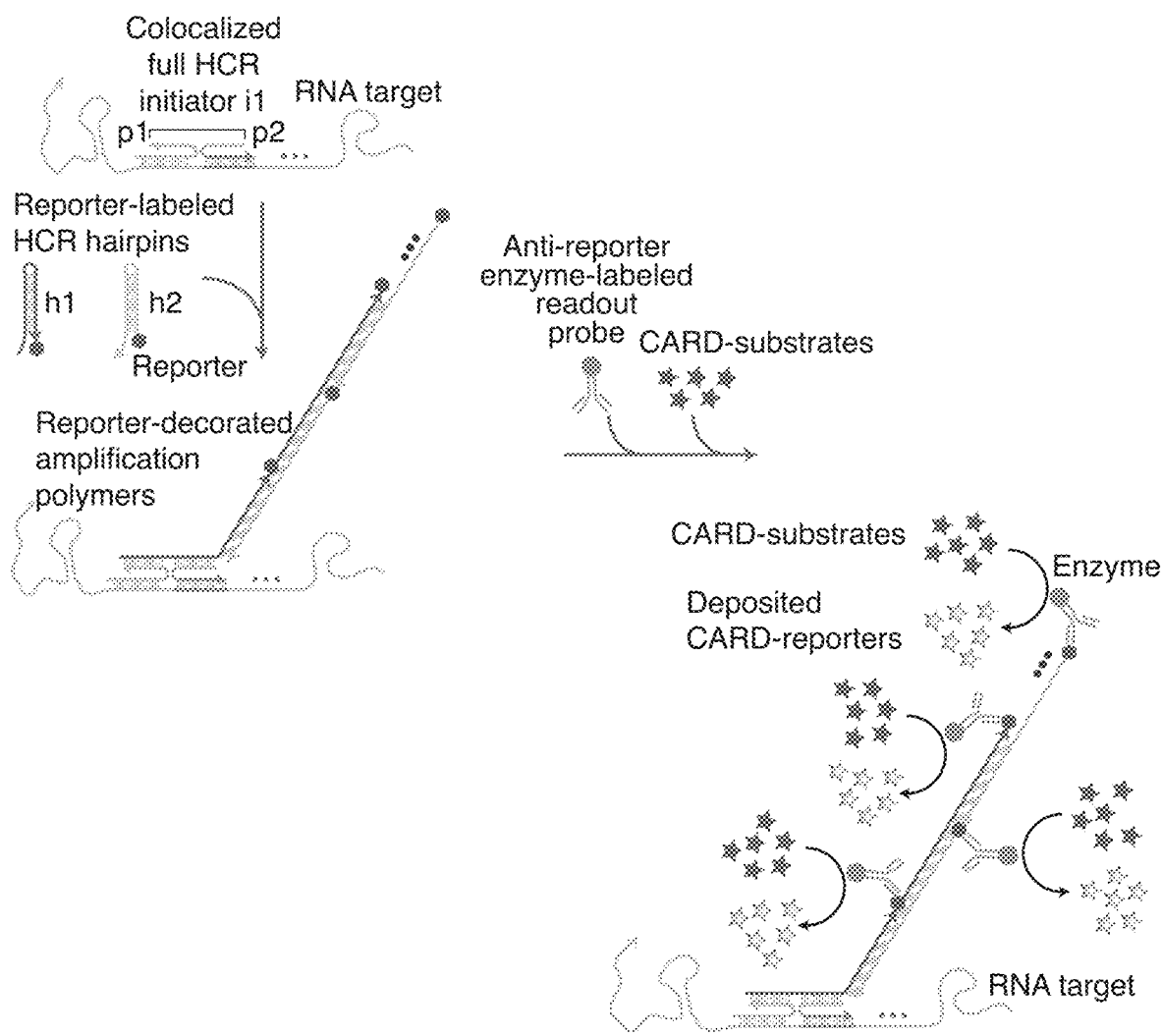
FIG. 33 depicts some embodiments of ultrasensitive HCR RNA-CISH for chromogenic staining of RNA targets using HCR to mediate CARD.
Figures 35A, 35B:
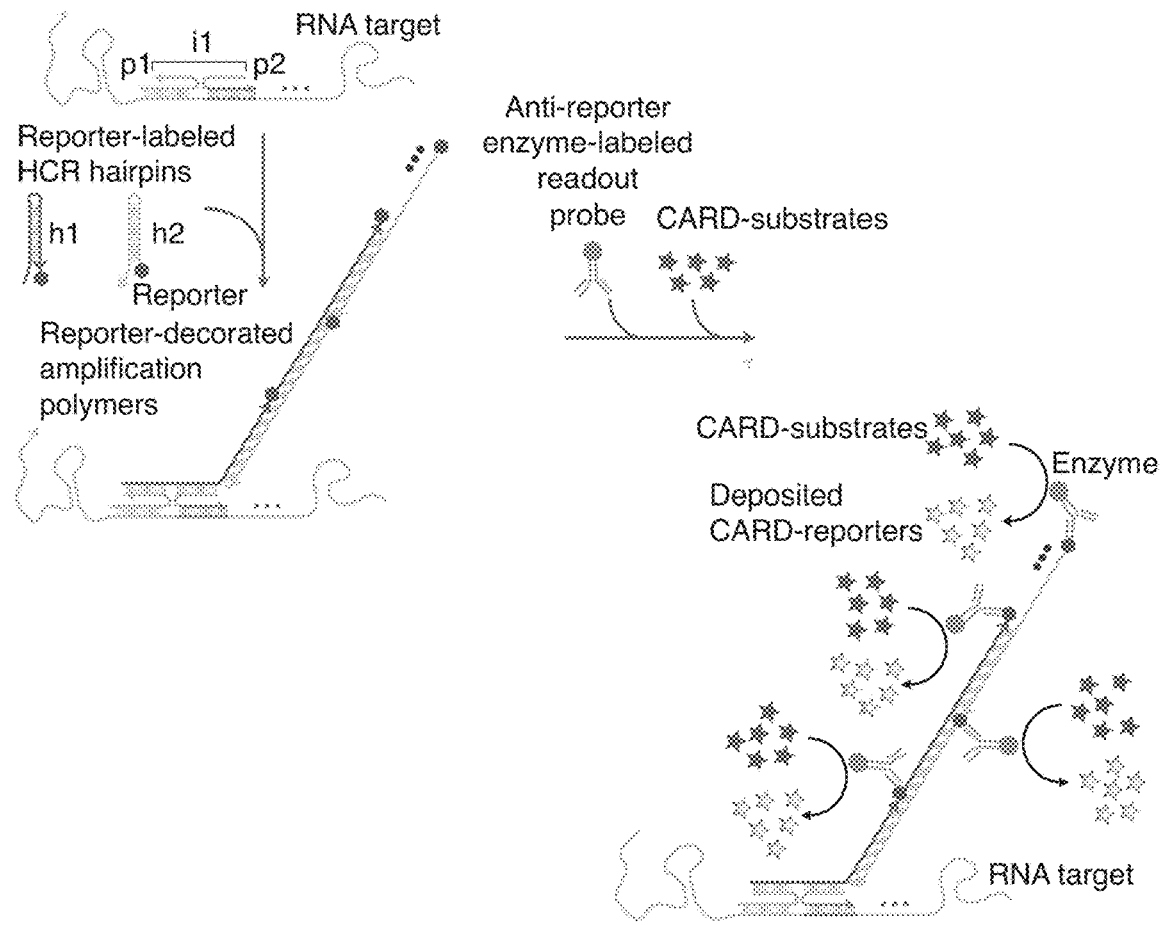
FIG. 35A-35B depict some embodiments of ultrasensitive multiplex HCR RNA-CISH.

FIGS. 33 and 35A depict ultrasensitive HCR RNA-CISH with catalytic reporter deposition (CARD). The RNA target is detected using fractional-initiator probes that colocalize a full HCR initiator i1 upon specific binding to their cognate binding sites on the target. HCR signal amplification is performed using a reporter-labeled HCR amplifier. CARD is mediated by an anti-reporter enzyme-labeled readout probe that acts on a CARD-substrate to catalyze deposition of CARD-reporters in the vicinity of the target.

Figure 34A:
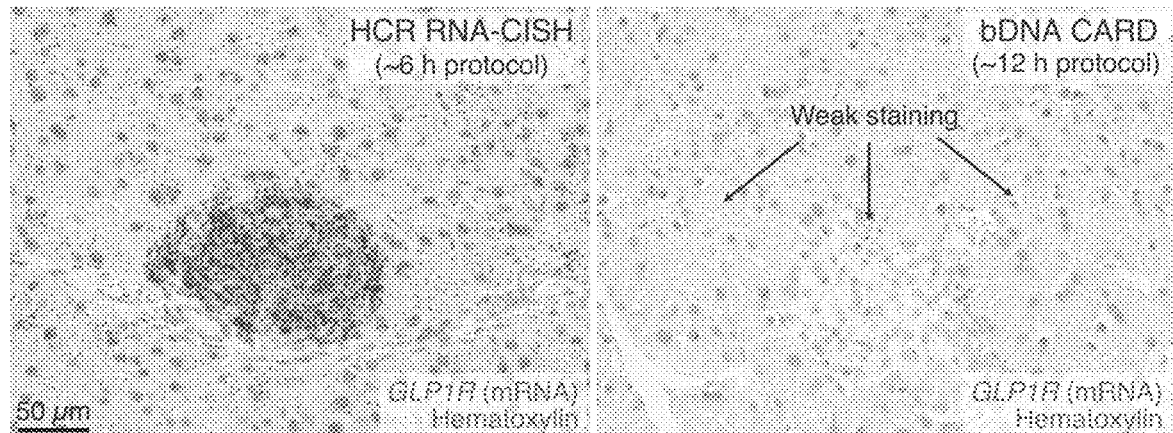
FIG. 34A-34B depict the performance of ultrasensitive HCR RNA-CISH in FFPE tissue sections compared to the weak staining and damaged tissue morphology using bDNA CARD.
Figure 34B:
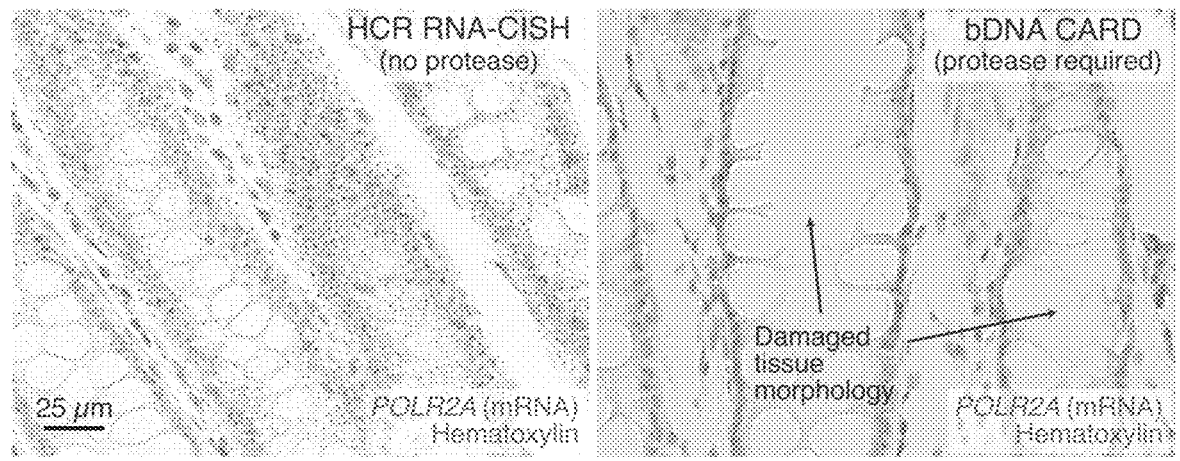

FIGS. 34A-34B demonstrate ultrasensitive HCR RNA-CISH with CARD in 5 µm FFPE tissue sections compared to the weak staining and damaged tissue morphology using branched DNA (bDNA) CARD. HCR RNA-CISH does not require protease pretreatment, preserving sample morphology, in contrast to bDNA CARD, which requires protease pretreatment in order for large bDNA preamplifier and amplifier reagents to penetrate the sample.

FIG. 35B depicts the reagents for 4-plex HCR RNA-CISH using CARD via the approach of FIGS. 33 and 35A. The jth target (for j=1, . . . , 4 where j is a positive integer) is detected using a jth fractional-initiator probe set that colocalizes a jth full initiator when probes binding specifically to their cognate binding sites on the jth target. Signal amplification for the jth target is provided by a jth HCR amplifier labeled with a jth reporter. Readout for the jth target is provided by a jth anti-reporter readout probe labeled with an enzyme that acts on a jth CARD-substrate to mediate deposition of a jth CARD-reporter in the vicinity of the jth target.

Figure 36A:
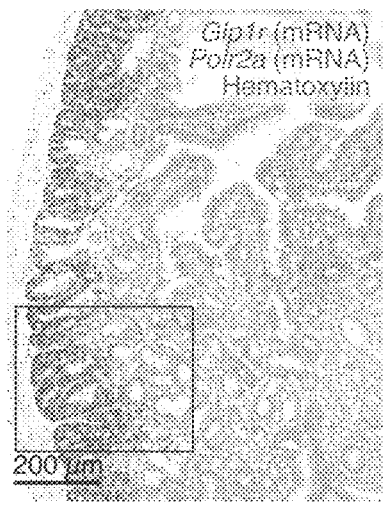
FIG. 36A-36B depict multiplex imaging of RNA targets in an FFPE mouse duodenum tissue section using ultrasensitive HCR RNA-CISH.
Figure 36B:
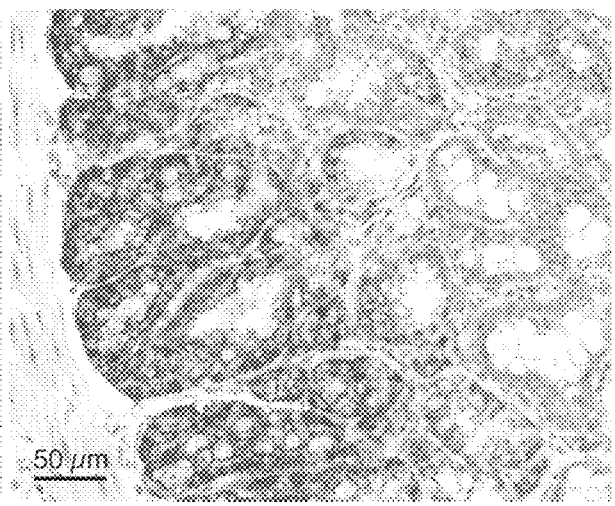

FIGS. 36A and 36B demonstrate 2-plex HCR RNA-CISH with CARD using the approach of FIGS. 33 and 35A and the reagents of FIG. 35B in a 5 μm FFPE mouse duodenum tissue section.

FIG. 38A depicts nonlinear HCR RNA-CISH with CARD (Approach 1). The RNA target is detected using fractional-initiator probes that colocalize a full HCR initiator upon specific binding to their cognate binding sites on the target. During the linear amplification stage, HCR signal amplification is performed using a reporter-labeled first HCR amplifier. Bridging to the nonlinear amplification stage is performed using an anti-reporter primary antibody bridging probe followed by an anti-primary initiator-labeled secondary antibody bridging probe. During the nonlinear amplification stage, HCR signal amplification is performed using a reporter-labeled second HCR amplifier. CARD is mediated by an anti-reporter enzyme-labeled readout probe that acts on a CARD-substrate to catalyze deposition of CARD-reporters in the vicinity of the target.

FIG. 38B depicts nonlinear HCR RNA-CISH with CARD (Approach 2) using fractional-initiator probes to detect the RNA target, a self-bridging HCR amplifier (each hairpin carrying two split-initiator tails) during the linear amplification stage that colocalizes a full HCR initiator i3 and a full HCR initiator i4 upon polymerization, and an anti-reporter enzyme-labeled readout probe to mediate CARD.

Figures 40A, 40B:
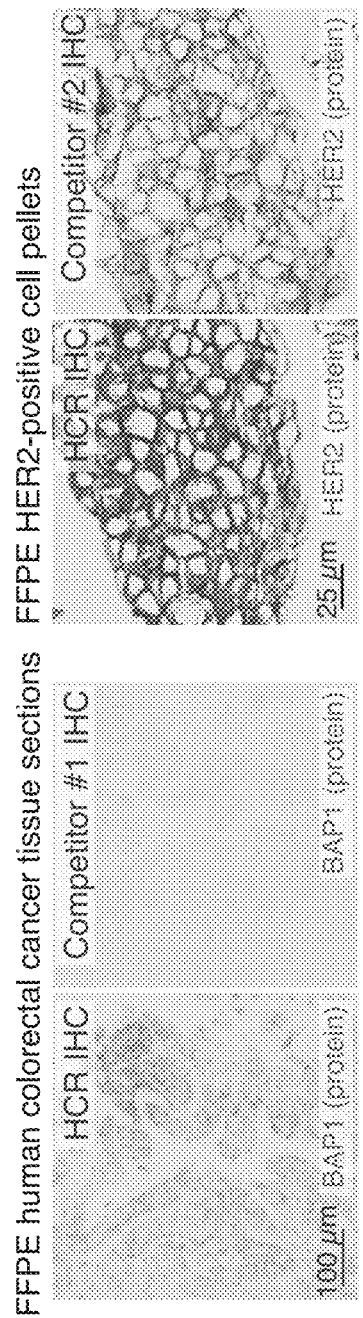
FIG. 40A-40B depict the performance of ultrasensitive HCR IHC for protein imaging in tissue sections and cell pellets relative to the weaker staining using two competing traditional IHC products.

FIGS. 39A-39B depict ultrasensitive HCR IHC with CARD using either direct (FIG. 39A) or indirect (FIG. 39B) detection of the protein target with an initiator-labeled antibody signal probe, HCR signal amplification using a reporter-labeled HCR amplifier, followed by CARD signal amplification mediated by an anti-reporter enzyme-labeled readout probe. FIGS. 40A-40B demonstrate enhanced sensitivity using HCR IHC with CARD compared to two traditional IHC products.

Figures 41A, 41B:
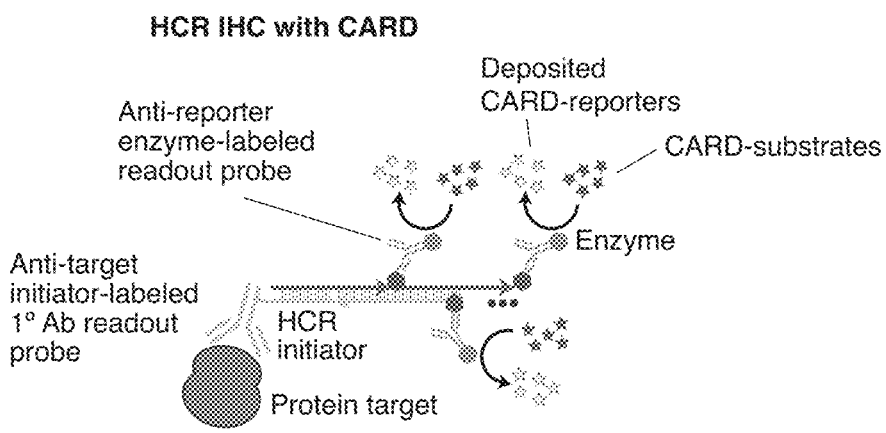
FIG. 41A-41B depict some embodiments of ultrasensitive multiplex HCR IHC using HCR signal amplification to mediate CARD signal amplification.
Figure 42:
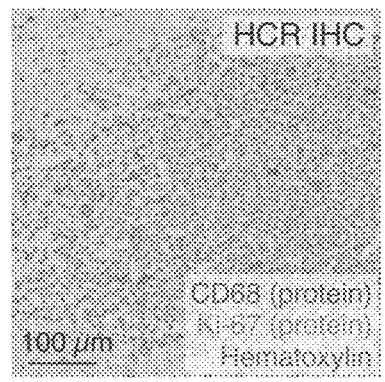
FIG. 42 depicts multiplex imaging of protein targets in an FFPE human tonsil section using HCR to mediate CARD for ultrasensitive HCR IHC.

FIGS. 41A-41B depict reagents for 4-plex HCR IHC with CARD. FIG. 42 demonstrates 2-plex HCR IHC with CARD in 5 μm FFPE human tonsil tissue.

Figure 43:
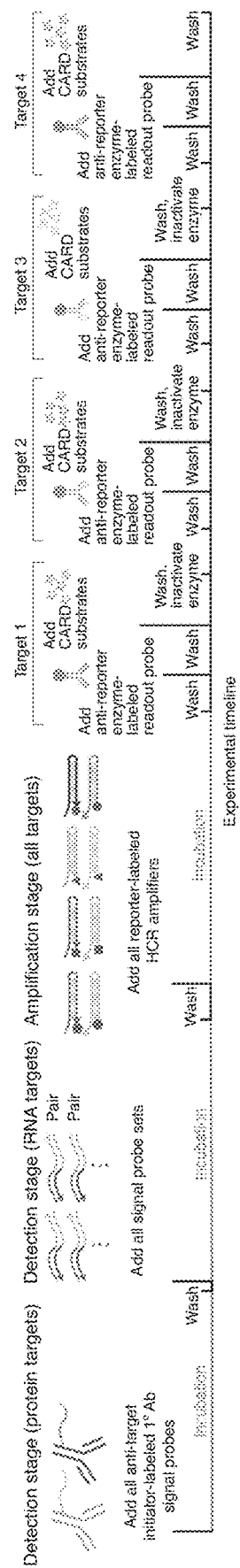
FIG. 43 depicts some embodiments of ultrasensitive multiplex HCR RNA-CISH/IHC using HCR signal amplification to mediate CARD signal amplification for simultaneous RNA/protein imaging with chromogenic staining.

FIG. 43 depicts a protocol summary for multiplex HCR RNA-CISH/IHC with CARD for simultaneous imaging of RNA and protein targets in the same sample.

Figures 44A, 44B:
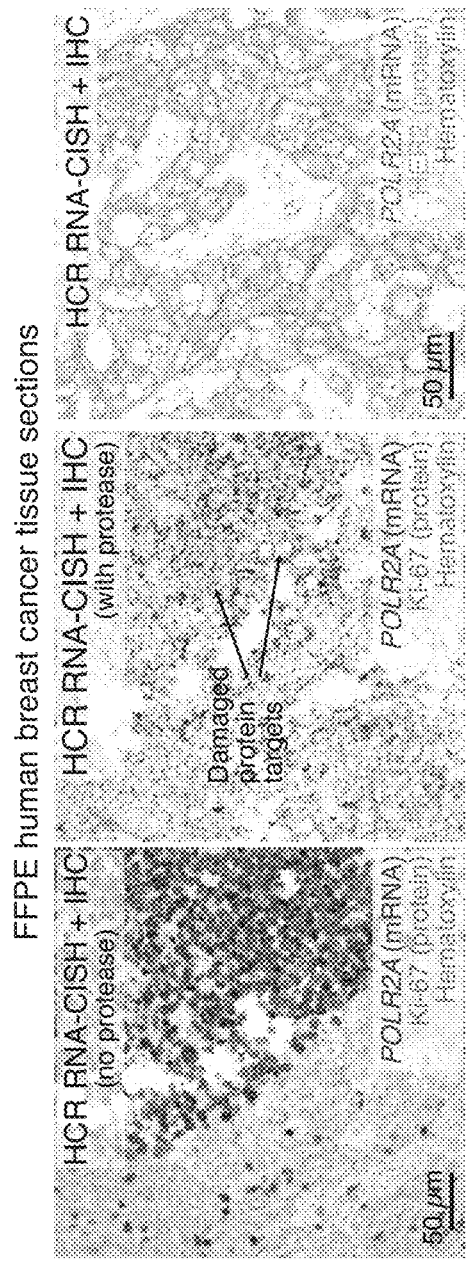
FIG. 44A-44B depict simultaneous imaging of RNA and protein targets in FFPE human breast tissue cancer tissue sections using ultrasensitive HCR RNA-CISH (using HCR to mediate CARD) in combination with traditional IHC, illustrating the benefit that ultrasensitive HCR RNA-CISH does not require a protease pretreatment so protein targets are not damaged and are available for imaging in the same sample as RNA targets.

Protease pretreatment is not required in order for small HCR amplification hairpins to penetrate 5 μm FFPE tissue sections, enabling use of traditional IHC protocols to image protein targets following HCR RNA-CISH, since protein targets are not degraded as part of the RNA imaging workflow. FIG. 44A (left) demonstrates HCR RNA-CISH with CARD followed by traditional IHC without a protease pretreatment step, demonstrating high signal-to-background for both the RNA and protein targets. FIG. 44A (right) demonstrates the reduction in protein signal that occurs when doing the same experiment including the protease pretreatment step from a bDNA RNA-CISH product (resulting in damage to protein targets). FIG. 44B demonstrates HCR RNA-CISH/traditional IHC in a 5 μm FFPE human breast cancer tissue without protease pretreatment.

Example 12—HCR Imaging Using Reporter-Labeled Signal Probes

FIGS. 56A-56N and 57A-57B depict detection of the target using reporter-labeled signal probes that either directly or indirectly bind the target. FIGS. 58A and 59A-59F demonstrate binding of a reporter-labeled signal probe by an anti-reporter initiator-labeled signal probe. FIG. 58B demonstrates binding of a reporter-labeled signal probe by two anti-reporter fractional-initiator signal probes.

FIGS. 58C and 68D depict detection of two targets in a complex or in proximity using a pair of anti-target reporter-labeled signal probes, a pair of anti-reporter fractional-initiator signal probes, and a proximity probe. FIGS. 68F-68I depict detection of two targets in a complex or in proximity using a proximity probe and different signal probe compositions for each of the two targets that are in a complex or in proximity, wherein at least one of the two targets that is in a complex or in proximity is detected using a reporter-labeled signal probe that is in turn detected by an anti-reporter signal probe.

FIG. 60A depicts the use of reporter-labeled probes for HCR IHC with CARD. The target protein is detected with an anti-target reporter-labeled primary antibody signal probe, which in turn is detected with an anti-reporter initiator-labeled primary antibody signal probe. Signal amplification is performed using a reporter-labeled HCR amplifier. These reporters are then bound by an anti-reporter enzyme-labeled readout probe that mediates CARD signal amplification.

FIG. 60B depicts the reagents for 4-plex HCR IHC using CARD via the approach of FIG. 60A. The jth target (for j=1, . . . , 4 where j is a positive integer) is detected using a jth anti-target primary antibody labeled with a jth reporter, which is in turn bound by a jth anti-reporter primary antibody labeled with a jth initiator. Signal amplification for the jth target is provided by a jth HCR amplifier labeled with a jth reporter. Readout for the jth target is provided by a jth anti-reporter readout probe labeled with an enzyme that acts on a jth CARD-substrate to mediate deposition of a jth CARD-reporter in the vicinity of the jth target.

FIG. 60C demonstrates the use of reporter-labeled probes for enzyme-free nonlinear HCR IF. The target protein is detected with an anti-target reporter-labeled primary antibody signal probe, which in turn is detected with an anti-reporter initiator-labeled primary antibody signal probe. During the linear amplification stage, signal amplification is performed using a reporter-labeled first HCR amplifier. Bridging to the nonlinear amplification stage is provided by an anti-reporter initiator-labeled primary antibody bridging probe. During the nonlinear amplification stage, signal amplification is performed using a fluorophore-labeled second HCR amplifier.

FIG. 60D depicts the reagents for 4-plex enzyme-free nonlinear HCR IF using the approach of FIG. 60C. The jth target (for j=1, . . . , 4 where j is a positive integer) is detected using a jth anti-target primary antibody labeled with a jth reporter, which is in turn detected with a jth anti-reporter primary antibody labeled with a jth initiator. During the linear amplification stage, signal amplification for the jth target is provided by a jth first HCR amplifier labeled with a jth reporter. Bridging to the nonlinear amplification stage is provided for the jth target by a jth anti-reporter primary antibody bridging probe labeled with a jth initiator. During the nonlinear amplification stage, signal amplification for the jth target is provided by a jth second HCR amplifier labeled with a jth fluorophore.

Figure 66:
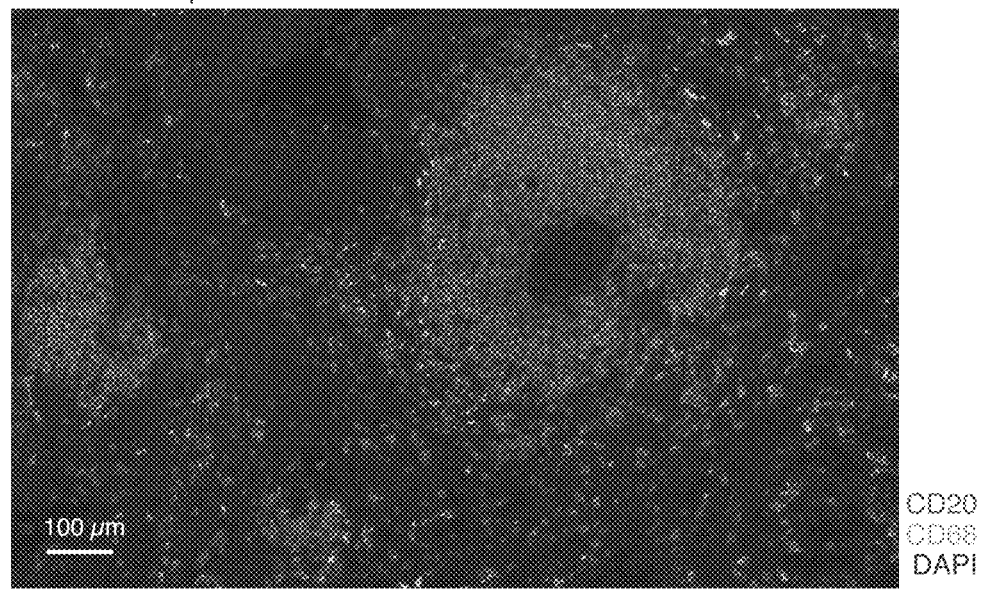
FIG. 66 depicts multiplex HCR IF in an FFPE human spleen tissue section using anti-target reporter-labeled primary-antibody signal probes in combination with anti-reporter, initiator-labeled primary-antibody signal probes to trigger HCR signal amplification.

FIG. 66 demonstrates multiplex HCR IF using reporter labeled probes following the approach of FIGS. 58A and 59C. The jth target (for j=1, 2) is detected using a jth anti-target primary antibody signal probe labeled with a jth reporter, which is in turn detected with a jth anti-reporter primary antibody signal probe labeled with a jth initiator. Signal amplification for the jth target is provided by a jth HCR amplifier labeled with a jth fluorophore.

Example 13—Ultrasensitive Enzyme-Free Nonlinear HCR Signal Amplification

Figure 45:
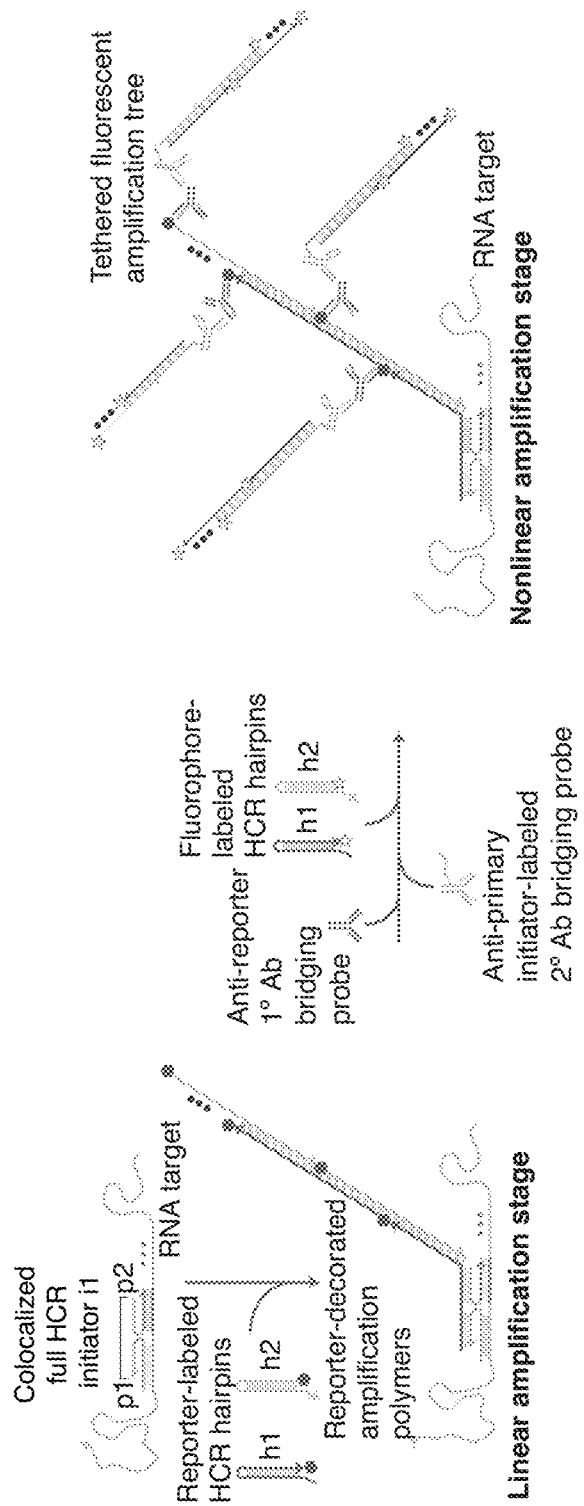
FIG. 45 depicts some embodiments of ultrasensitive HCR RNA-FISH for fluorescent staining of RNA targets using nonlinear enzyme-free HCR signal amplification.

FIGS. 45 and 47A depict enzyme-free HCR RNA-FISH (Approach 1) using fractional-initiator probes to detect the RNA target, a reporter-labeled HCR amplifier during the linear stage, an anti-reporter primary antibody bridging probe followed by an anti-primary initiator-labeled secondary antibody bridging probe, followed by a fluorophore-labeled amplifier during the nonlinear amplification stage.

Figure 46:
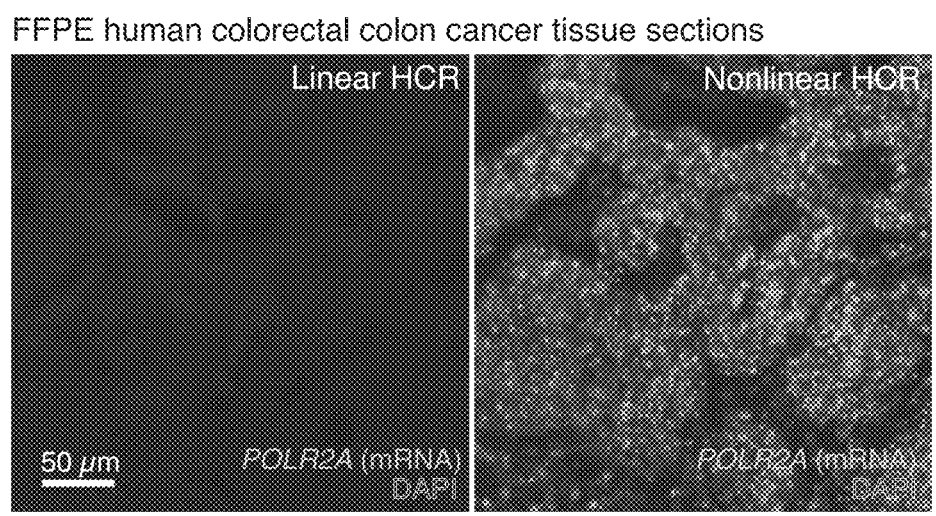
FIG. 46 depicts enhanced sensitivity for HCR RNA-FISH using ultrasensitive nonlinear HCR signal amplification (using anti-reporter 1° Ab bridging probes and anti-primary initiator-labeled 2° Ab bridging probes—see FIG. 45) relative to linear HCR signal amplification.

FIG. 46 demonstrates the enhanced sensitivity (right) achieved using nonlinear HCR signal amplification (following Approach 1 of FIGS. 45 and 47A) compared to linear HCR signal amplification (left) in FFPE human colorectal colon cancer sections.

FIG. 47B depicts the reagents for 4-plex enzyme-free nonlinear HCR RNA-FISH using Approach 1 for FIGS. 45 and 47A. The jth target (for j=1, . . . , 4 where j is a positive integer) is detected using a jth fractional-initiator probe set that colocalizes a jth full HCR initiator when bound specifically to cognate binding sites on the target. During the linear amplification stage, signal amplification for the jth target is provided by a jth first HCR amplifier labeled with a jth reporter. Bridging to the nonlinear amplification stage is provided for the jth target by a jth anti-reporter primary antibody bridging probe followed by a jth anti-primary secondary antibody bridging probe labeled with a jth initiator. During the nonlinear amplification stage, signal amplification for the jth target is provided by a jth second HCR amplifier labeled with a jth fluorophore.

Figure 48:
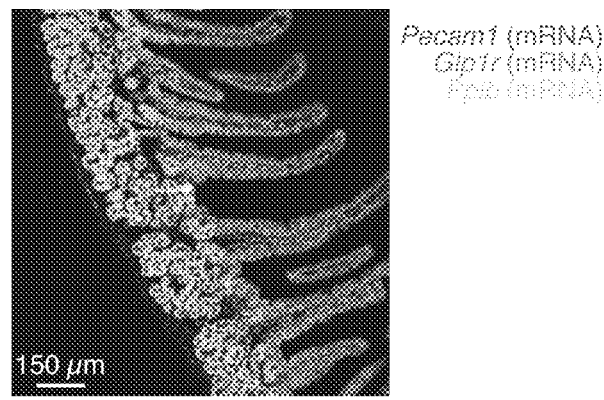
FIG. 48 depicts multiplex imaging of RNA targets in an FFPE mouse duodenum section using ultrasensitive HCR RNA-FISH with nonlinear enzyme-free HCR signal amplification.

FIG. 48 demonstrates 3-plex imaging of target mRNAs in an FFPE mouse duodenum section using enzyme-free nonlinear HCR signal amplification following Approach 1 of FIGS. 45 and 47A using the multiplexing reagents of FIG. 47B.

Figure 49A:
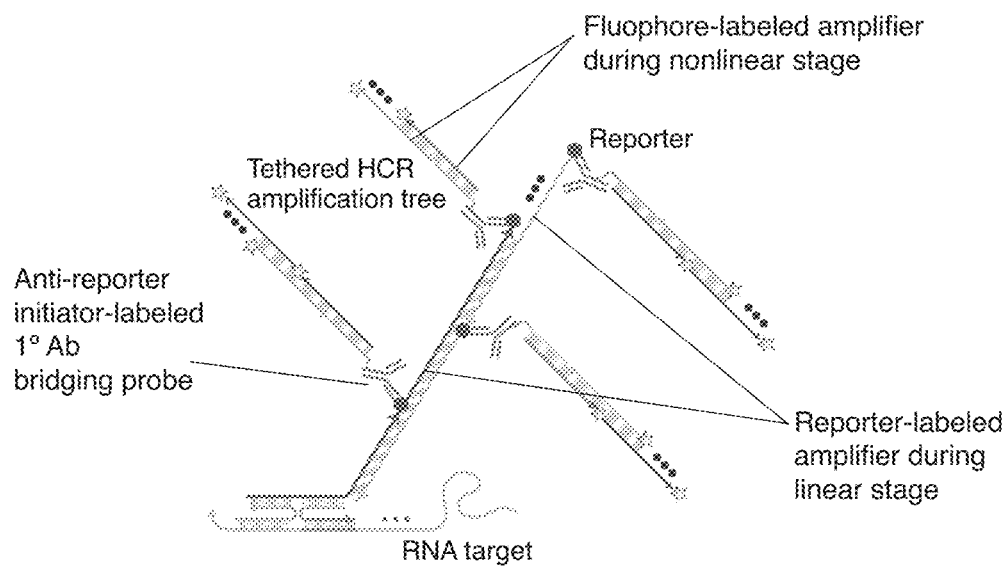
FIG. 49A-49B depict some embodiments of nonlinear enzyme-free HCR signal amplification for ultrasensitive HCR RNA-FISH.

FIG. 49A depicts enzyme-free HCR RNA-FISH (Approach 2) using fractional-initiator probes to detect the RNA target, a reporter-labeled HCR amplifier during the linear amplification stage, an anti-reporter initiator-labeled primary antibody bridging probe, followed by a fluorophore-labeled HCR amplifier during the nonlinear amplification stage.

Figure 67:
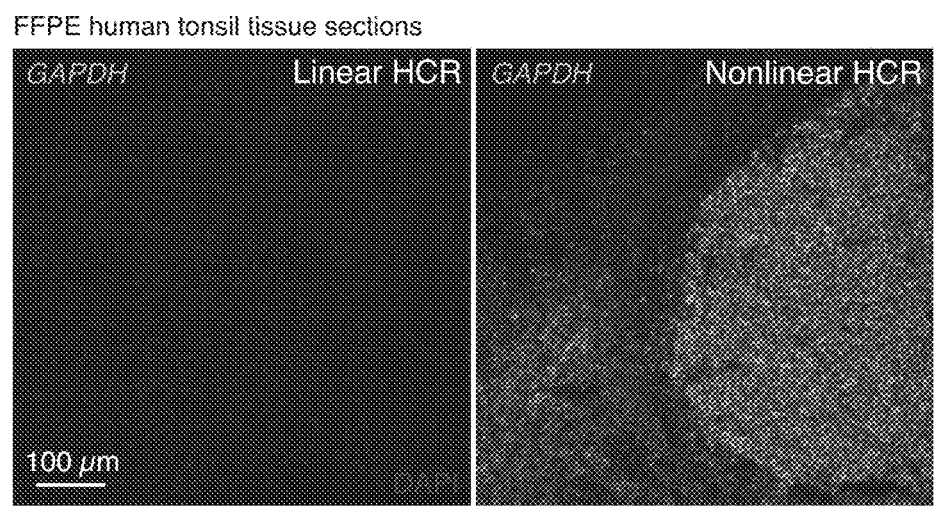
FIG. 67 depicts enhanced sensitivity for HCR RNA-FISH using ultrasensitive nonlinear HCR signal amplification (using anti-reporter initiator-labeled 1° Ab bridging probes—see FIG. 49A) relative to linear HCR signal amplification.

FIG. 67 demonstrates the enhanced sensitivity (right) achieved using nonlinear HCR signal amplification (following Approach 2 of FIG. 49A) compared to linear HCR signal amplification (left) in FFPE human tonsil tissue sections.

Figure 49B:
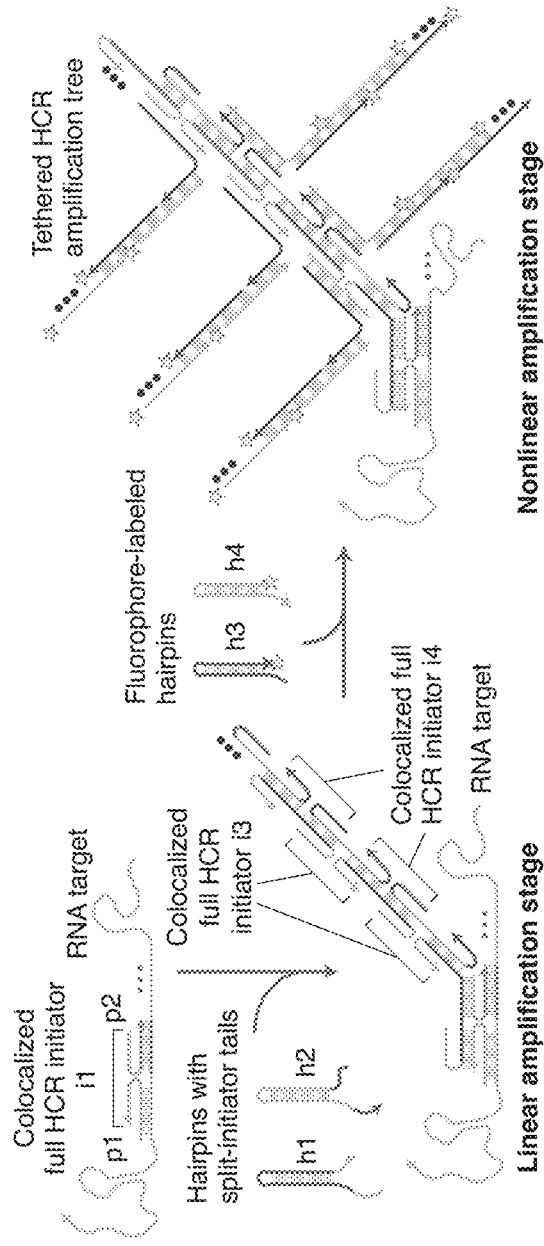
Figure 50A:
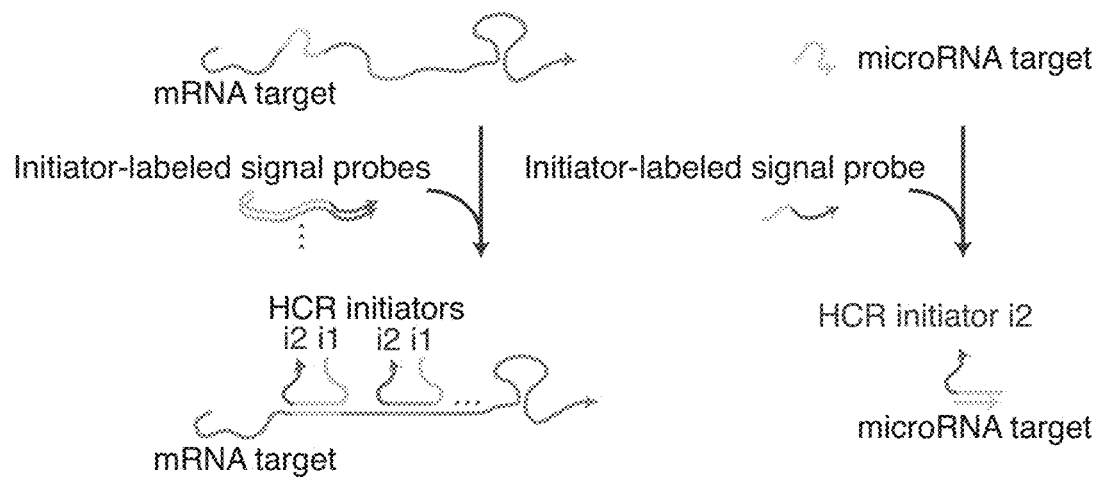
FIG. 50A-50C depicts some embodiments of imaging target microRNAs and mRNAs in whole-mount zebrafish embryos using initiator-labeled probes.
Figures 50B, 50C:
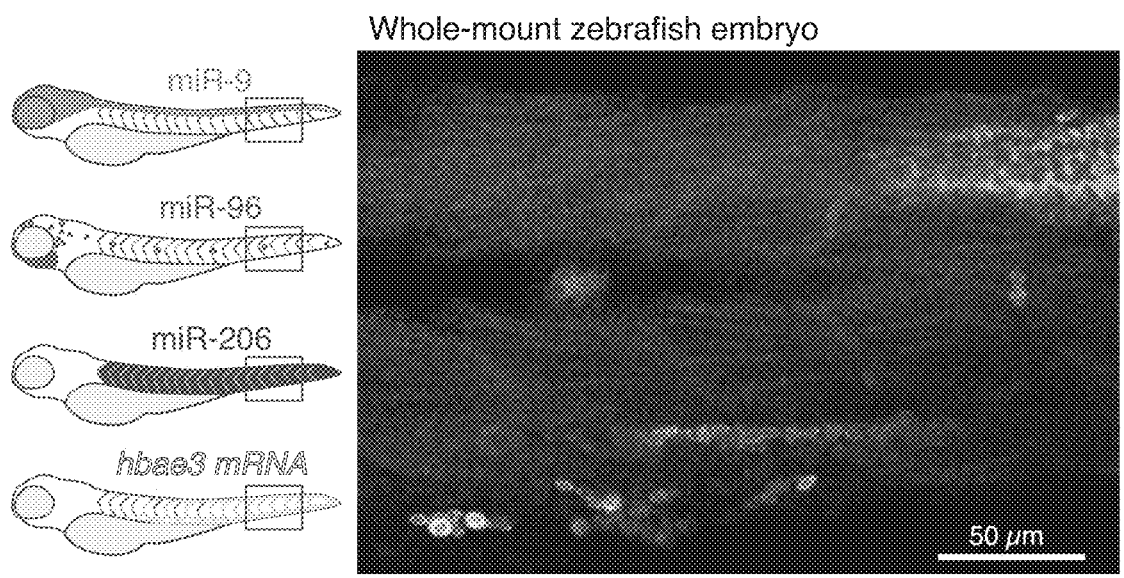

FIG. 49B depicts enzyme-free HCR RNA-FISH (Approach 3) using fractional-initiator probes to detect the RNA target, a self-bridging HCR amplifier (with each hairpin comprising two split-initiator tails) during the linear amplification stage that colocalizes a full HCR initiator i3 and a full HCR initiator i4 upon polymerization, and a fluorophore-labeled HCR amplifier during the nonlinear amplification stage.

Figure 51A:
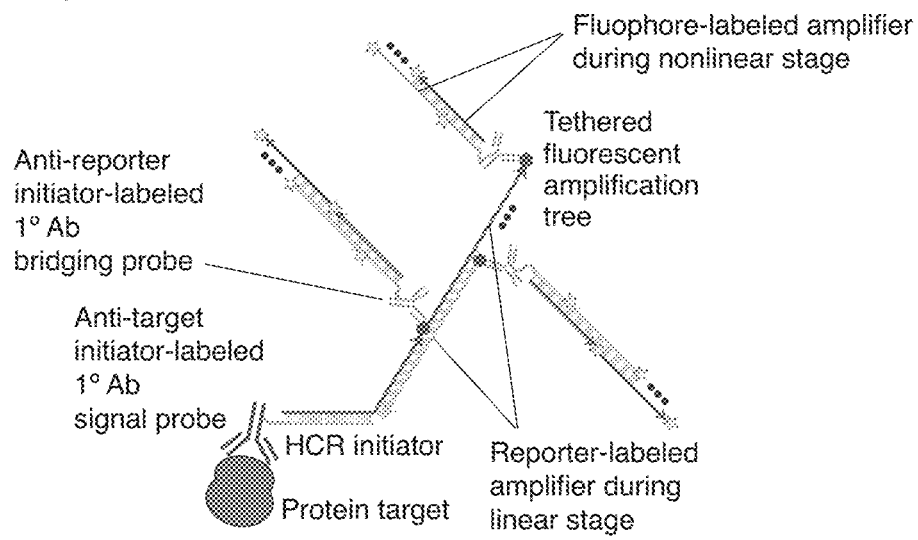
FIG. 51A-51B depict some embodiments of ultrasensitive HCR IF for fluorescent staining of protein targets using nonlinear or linear enzyme-free HCR signal amplification.
Figure 51B:
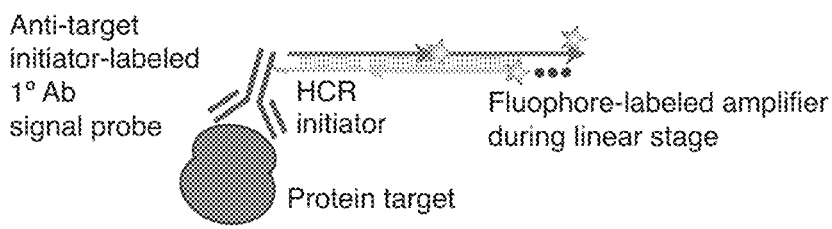
Figure 52A:
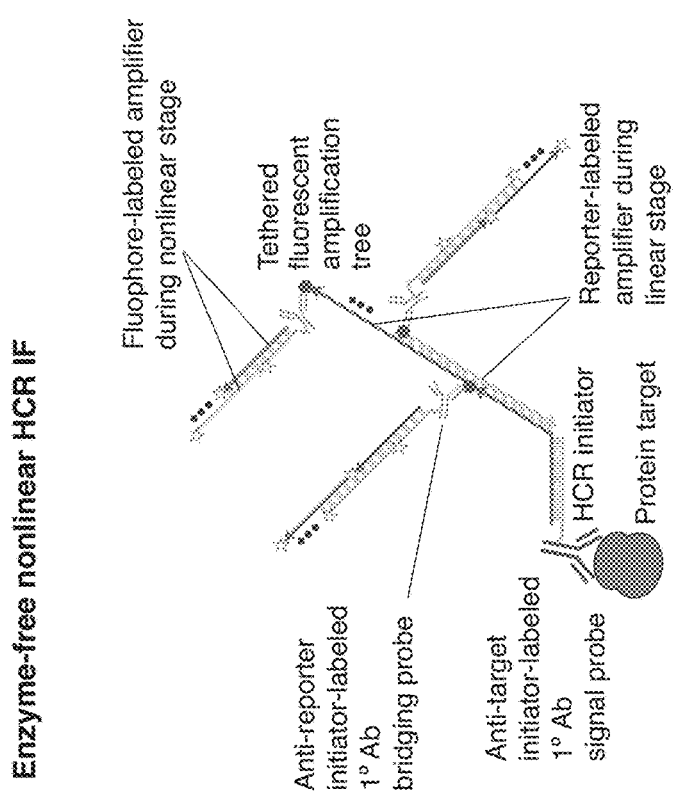

FIGS. 51A and 52A depict enzyme-free HCR IF using an anti-target initiator-labeled primary antibody signal probe to detect the target protein, a reporter labeled HCR amplifier during the linear amplification stage, an anti-reporter initiator-labeled primary antibody bridging probe, followed by a fluorophore-labeled HCR amplifier during the nonlinear amplification stage.

FIG. 52B depicts the reagents for 4-plex enzyme-free nonlinear HCR IF using the approach of FIGS. 51A and 52A. The jth target (for j=1, . . . , 4 where j is a positive integer) is detected using a jth anti-target primary antibody probe labeled with a jth initiator. During the linear amplification stage, signal amplification for the jth target is provided by a jth first HCR amplifier labeled with a jth reporter. Bridging to the nonlinear amplification stage is provided for the jth target by a jth anti-reporter primary antibody bridging probe comprising a jth initiator. During the nonlinear amplification stage, signal amplification for the jth target is provided by a jth second HCR amplifier labeled with a jth fluorophore.

Figure 53:
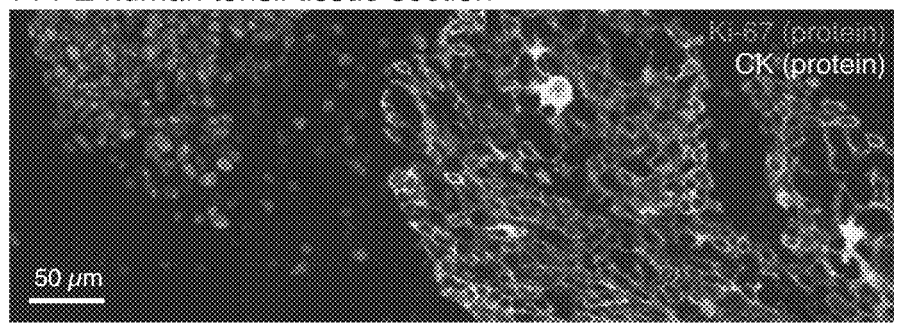
FIG. 53 depicts multiplex protein imaging in FFPE human tonsil tissue using HCR IF with enzyme-free HCR signal amplification.

FIG. 53 demonstrates 2-plex enzyme-free HCR IF in an FFPE human tonsil tissue section.

Figure 54:
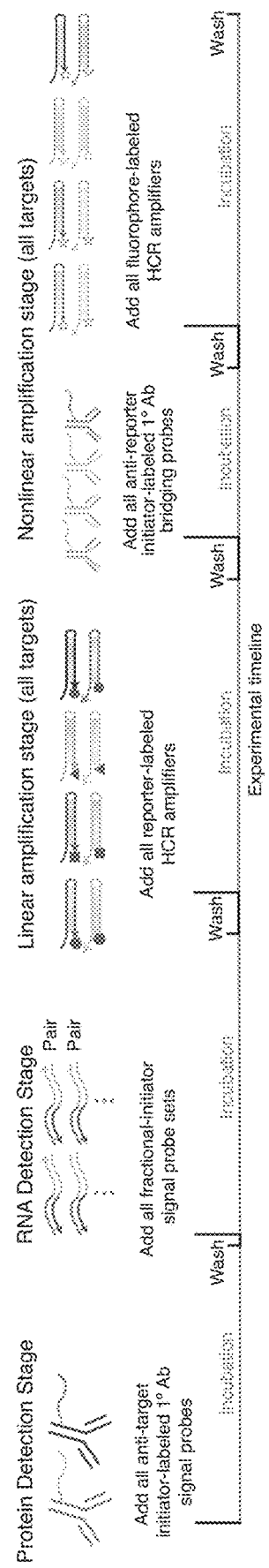
FIG. 54 depicts some embodiments of ultrasensitive multiplex HCR RNA-FISH/IF using nonlinear enzyme-free HCR signal amplification for simultaneous RNA/protein imaging with fluorescent staining.

FIG. 54 depicts a protocol summary for enzyme-free nonlinear HCR RNA-FISH/IF. During the Protein Detection Stage, the jth protein target is detected with a jth anti-target primary antibody signal probe labeled with a jth initiator. During the RNA Detection Stage, the jth RNA target is detected with a jth fractional-initiator probe set that colocalizes a jth initiator when hybridized specifically to the cognate binding sites on the jth RNA target. During the Linear Amplification Stage, signal amplification for the jth target (where j is a positive integer) is provided by a jth first HCR amplifier labeled with a jth reporter. Bridging between the linear and nonlinear amplification stages for the jth target is provided by a jth anti-reporter primary antibody bridging probe labeled with a jth initiator. During the Nonlinear Amplification Stage, signal amplification for the jth target is provided by a jth second HCR amplifier labeled with a jth fluorophore.

Figure 55:
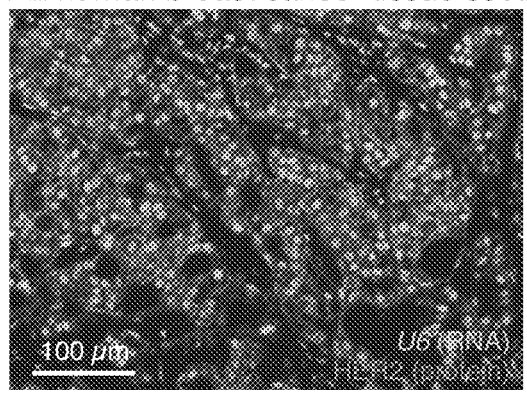
FIG. 55 depicts imaging of a small RNA target and a protein target in FFPE human breast cancer tissue using HCR RNA-FISH/IF with enzyme-free HCR signal amplification.
Figure 57A:
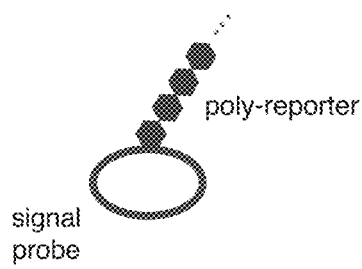
FIG. 57A-57B depict some embodiments of poly-reporter-labeled signal probes.
Figure 57B:
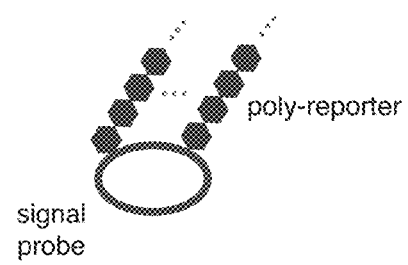

FIG. 55 demonstrates enzyme-free HCR RNA-FISH/IF in an FFPE human breast cancer tissue section.

Figure 70:
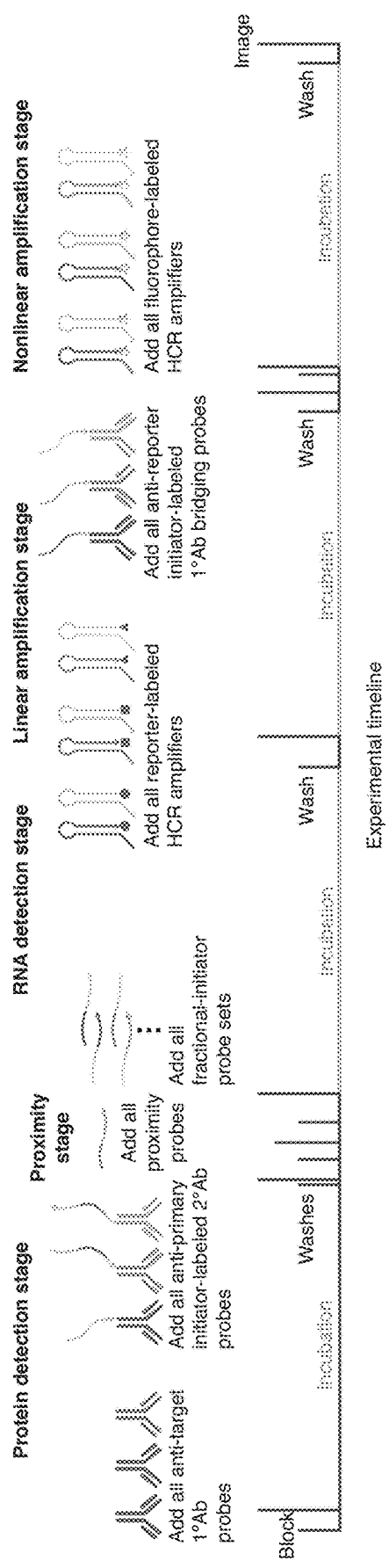
FIG. 70 depicts some embodiments of a protocol for simultaneous HCR imaging of protein targets, protein:protein target complexes, and RNA targets in a sample using enzyme-free nonlinear HCR signal amplification for all target classes simultaneously.

FIG. 70 depicts a protocol summary for HCR imaging of protein targets, protein:protein target complexes, and RNA targets using enzyme-free nonlinear HCR signal amplification for all target classes simultaneously. During the Protein Detection Stage, if a protein target is to be imaged individually, the jth protein target is detected with a jth anti-target primary antibody signal probe, which in turn is detected with a jth anti-primary secondary antibody signal probe labeled with a jth initiator (where j is a positive integer). Alternatively, if a protein target is to be imaged as part of the jth protein:protein target complex, the protein is detected with an anti-target primary antibody signal probe, which in turn is detected with a jth anti-primary secondary antibody signal probe labeled with a jth fractional initiator. During the Proximity Stage, the jth full HCR initiator is colocalized by hybridizing the jth proximity probe to the jth fractional initiator signal probes indirectly bound to the target proteins within the jth target complex. During the RNA Detection Stage, the jth RNA target is detected with a jth fractional-initiator probe set that colocalizes a jth initiator when hybridized specifically to the cognate binding sites on the jth RNA target. During the Linear Amplification Stage, signal amplification for the jth target is provided by a jth first HCR amplifier labeled with a jth reporter. Bridging between the linear and nonlinear amplification stages for the jth target is provided by a jth anti-reporter primary antibody bridging probe labeled with a jth initiator. During the Nonlinear Amplification Stage, signal amplification for the jth target is provided by a jth second HCR amplifier labeled with a jth fluorophore.

Figure 71:
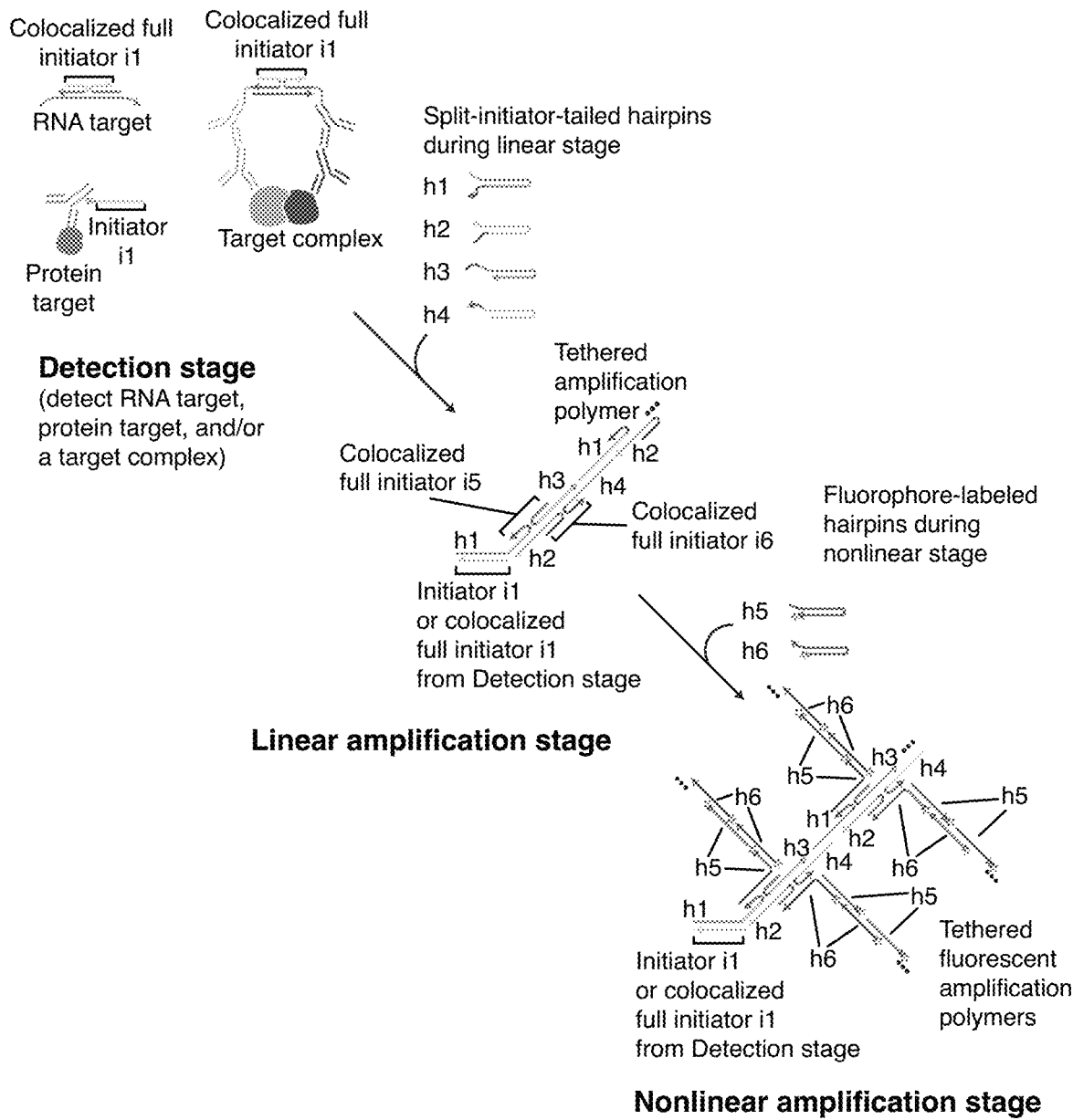
FIG. 71 depicts some embodiments of HCR imaging for RNA targets, protein targets, and/or target complexes using enzyme-free nonlinear HCR signal amplification with a 4-hairpin amplifier with split-initiator tails during the linear stage and a 2-hairpin fluorophore-labeled amplifier during the nonlinear stage.

FIGS. 16C and 71 depict enzyme-free nonlinear HCR signal amplification for detection of an RNA target, protein target, and/or a target complex. During the Detection stage, the target is detected with either fractional-initiator probes (and optionally proximity probes) or initiator-labeled probes. During the linear amplification stage, signal amplification is provided by a self-bridging 4-hairpin HCR amplifier (comprising hairpins h1, h2, h3, and h4) with each hairpin comprising a single split-initiator tail such that initiation by HCR initiator i1 triggers growth of an amplification polymer comprising periodic h1, h2, h3, and h4 hairpins such that h1 and h3 colocalize a full HCR initiator i5 tethered to the HCR amplification polymer and h2 and h4 colocalize a full HCR initiator i6 tethered to the HCR amplification polymer. During the nonlinear amplification stage, signal amplification is performed with a fluorophore-labeled HCR amplifier (comprising hairpins h5 and h6) that is initiated by colocalized full HCR initiators i5 and i6 located periodically along the HCR amplification polymer comprising periodically repeating h1, h2, h3, and h4 hairpins, leading to growth of a new HCR amplification polymer comprising periodically repeating h5 and h6 hairpins tethered to each colocalized full HCR initiator i5 or i6 along the HCR amplification polymer comprising periodically repeating h1, h2, h3, and h4 hairpins.

Figure 72A:
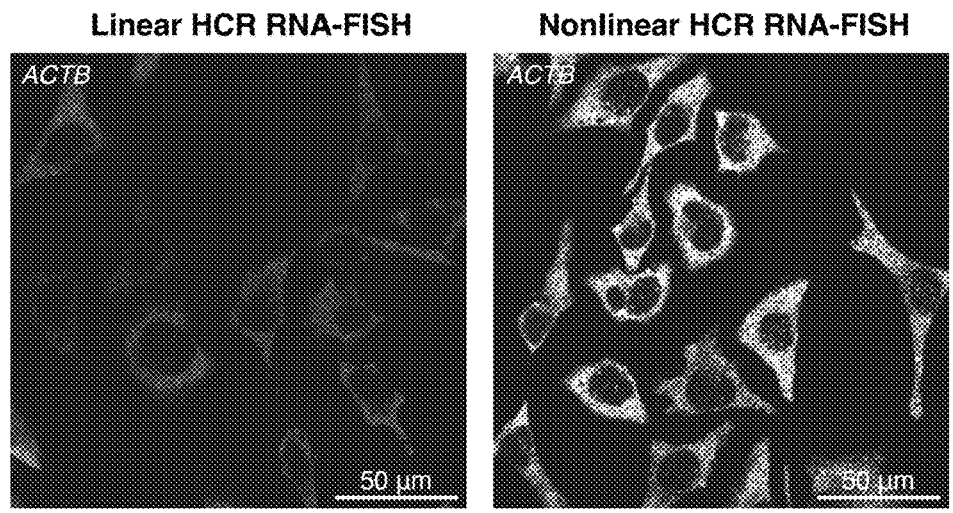
FIGS. 72A-72C depict enhanced sensitivity for HCR RNA-FISH using ultrasensitive nonlinear HCR signal amplification (using the approach of FIG. 71) relative to linear HCR signal amplification.
Figure 72B:
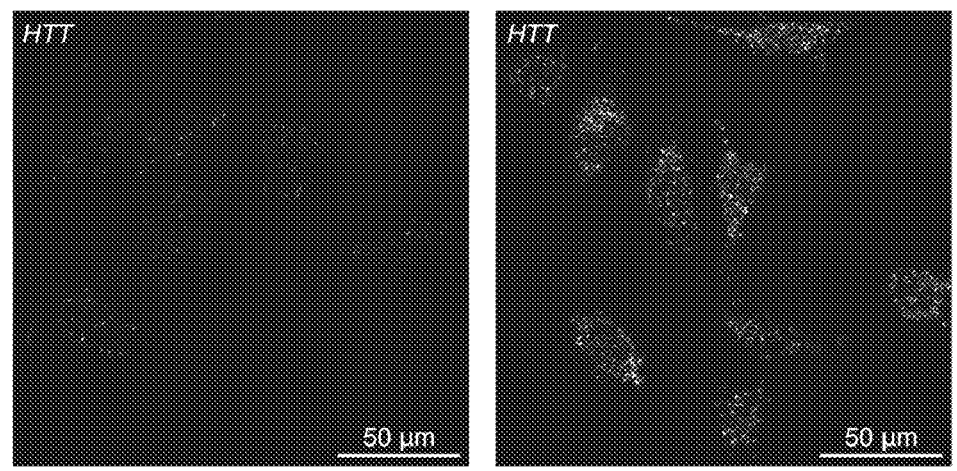
Figure 72C:
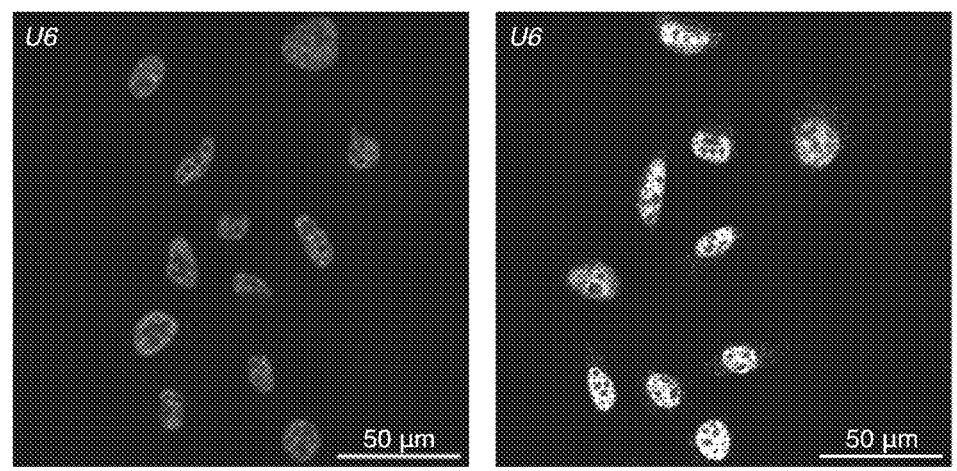

FIGS. 72A-72C demonstrate the enhanced sensitivity for HCR RNA-FISH achieved using nonlinear HCR signal amplification (right; following the approach of FIG. 71) compared to linear HCR signal amplification (left) for three different RNA targets in HeLa cells. ACTB target (high-expression mRNA): 10 fractional-initiator probe pairs. HTT target (low-expression mRNA): 30 fractional-initiator probe pairs. U6 (high-expression small nuclear RNA): 2 fractional-initiator probe pairs.

FIG. 73 depicts detection of a target with enzyme-free nonlinear HCR signal amplification involving three rounds of HCR signal amplification. The target is detected with an anti-target initiator-labeled probe. The 1 round of HCR signal amplification (also known as the linear amplification stage) is performed using a reporter-labeled HCR amplifier. Bridging to the $2^{nd}$ round of HCR signal amplification is performed using an anti-reporter initiator-labeled bridging probe. The $2^{nd}$ round of HCR signal amplification (also known as the first nonlinear amplification stage or the quadratic amplification stage) is performed using the same reporter-labeled HCR amplifier used for the $1^{st}$ round of HCR signal amplification. Bridging to the $3^{rd}$ round of HCR signal amplification is performed suing the same anti-reporter initiator-labeled bridging probe used to bridge between the $1^{st}$ and $2^{nd}$ rounds of HCR signal amplification. The $3^{rd}$ round of HCR signal amplification (also known as the $2^{nd}$ round of nonlinear signal amplification or the cubic amplification stage) is performed using a fluorophore-labeled HCR amplifier that has the same sequence as the reporter-labeled HCR amplifier used for the $1^{st}$ and $2^{nd}$ rounds of HCR signal amplification.

Additional Arrangements

Arrangement 1. A method of hybridization chain reaction (HCR) comprising: a) providing a sample containing a target; b) contacting the sample with a probe set comprising one or more probe units each comprising two or more fractional-initiator probes; c) contacting the sample with an HCR amplifier labeled with a reporter; d) detecting a signal directly or indirectly from the reporter; and wherein each of the two or more fractional-initiator probes comprises: a target-binding region, a linker region, and a fractional initiator, wherein the target-binding regions on the two or more fractional initiator probes are configured to bind to different binding sites on the target, wherein the linker regions on the two or more fractional initiator probes are configured to bind to each other, wherein the fractional initiators on the two or more fractional initiator probes are configured to bind to different binding sites on an HCR hairpin, and wherein the probes within each probe unit are configured to form a cooperative probe junction when they bind the target, each other, and an HCR hairpin; wherein the HCR amplifier comprises two or more HCR hairpins; wherein an HCR hairpin comprises an input domain comprising a single-stranded toehold and a stem section and further comprises an output domain comprising a single-stranded loop and a complement to the stem section; and wherein at least one HCR hairpin further comprises a reporter.

Arrangement 2: The method of Arrangement 1, wherein a wash step is performed between any of steps (b)-(d).

Arrangement 3: The method of any of the prior arrangements, wherein each of the two or more fractional-initiator probes further comprises a proximity domain.

Arrangement 4: The method of any of the prior arrangements, wherein the proximity domains are configured to bind to a proximity probe.

Arrangement 5: The method of any of the prior arrangements, further comprising contacting the sample with one or more proximity probes following step (b) and before (c).

Arrangement 6: The method of any of the prior arrangements, wherein a wash step is performed following the providing of one or more proximity probes to remove unbound proximity probes.

Arrangement 7: The method of any of the prior arrangements, wherein the cooperative probe junction further comprises the one or more proximity probes.

Arrangement 8: The method of any of the prior arrangements, wherein one or more auxiliary-reporter-labeled readout probes are provided following step (c).

Arrangement 9: The method of any of the prior arrangements, wherein a wash step is performed following the providing of one or more auxiliary-reporter-labeled readout probes to remove unbound auxiliary-reporter-labeled readout probes.

Arrangement 10: The method of any of the prior arrangements, further comprising detecting a signal from the auxiliary reporter.

Arrangement 11: The method of any of the prior arrangements, wherein after step (d), the method further comprises a step (e) wherein the signal is removed.

Arrangement 12: The method of any of the prior arrangements, further comprising repeating any of the steps of the method to detect another target in the sample, wherein the target binding domains are for a different target.

Arrangement 13: The method of any of the prior arrangements, wherein the target-binding regions on the two or more fractional initiator probes are configured to bind overlapping binding sites on the target.

Arrangement 14: The method of any of the prior arrangements, wherein the target-binding regions on the two or more fractional initiator probes are configured to bind non-overlapping binding sites on the target.

Arrangement 15: The method of any of the prior arrangements, wherein the fractional initiators on the two or more fractional initiator probes are configured to bind overlapping binding sites on the HCR hairpin.

Arrangement 16: The method of any of the prior arrangements, wherein the fractional initiators on the two or more fractional initiator probes are configured to bind non-overlapping binding sites on the HCR hairpin.

Arrangement 17: The method of any of the prior arrangements, wherein the target comprises an RNA molecule, a DNA molecule, a protein, a small molecule, a chemical, a biological molecule, a pathogen, a complex of molecules, or a set of molecules in proximity.

Arrangement 18: The method of any of the prior arrangements, wherein the reporter and the auxiliary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

Arrangement 19: A composition for detecting a target within a sample, comprising: An anti-target signal probe comprising a reporter and configured to bind to the target; An anti-reporter signal probe labeled with an initiator and configured to bind to the reporter; An HCR amplifier labeled with an auxiliary-reporter and configured to be triggered by the initiator to grow an auxiliary-reporter-decorated HCR amplification polymer tethered to the target; wherein the auxiliary reporter directly or indirectly mediates generation of a signal.

Arrangement 20: The composition of Arrangement 19, further comprising an anti-auxiliary-reporter tertiary-reporter-labeled readout probe configured to bind to the auxiliary-reporter-decorated amplification polymer.

Arrangement 21: The composition of any one of the prior aspects of Arrangements 19 or 20, wherein the tertiary reporter directly or indirectly mediates generation of a signal.

Arrangement 22: The composition of any one of the prior aspects of Arrangements 19-21, wherein the target comprises an RNA molecule, a DNA molecule, a protein, a small molecule, a chemical, a biological molecule, a pathogen, a complex of molecules, or a set of molecules in proximity.

Arrangement 23: The composition of any one of the prior aspects of Arrangements 19-22, wherein the reporter, the auxiliary reporter, and the tertiary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

Arrangement 24: A composition for detection of N targets within a sample, wherein N is a positive integer, comprising: A jth anti-target signal probe comprising a jth reporter and configured to bind to the jth target (for j=1, . . . , N, wherein j is a positive integer); A jth anti-reporter signal probe comprising a jth HCR initiator and configured to bind to the jth reporter; A jth HCR amplifier comprising a jth auxiliary reporter and configured to be triggered by the jth HCR initiator to grow a jth auxiliary-reporter-decorated HCR amplification polymer tethered to the jth target; and wherein the jth auxiliary reporters directly or indirectly mediate generation of a signal for the jth target.

Arrangement 25: The composition of Arrangement 24, further comprising a jth anti-auxiliary-reporter readout probe comprising a jth tertiary reporter and configured to bind to the jth auxiliary-reporter-decorated amplification polymer.

Arrangement 26: The composition of any one of the prior aspects of Arrangements 24 or 25, wherein the jth tertiary reporter directly or indirectly mediates generation of a signal for the jth target.

Arrangement 27: The composition of any one of the prior aspects of Arrangements 24-26, wherein the jth target comprises an RNA molecule, a DNA molecule, a protein, a small molecule, a chemical, a biological molecule, a pathogen, a complex of molecules, or a set of molecules in proximity.

Arrangement 28: The composition of any one of the prior aspects of Arrangements 24-27, wherein the jth reporter, the jth auxiliary reporter, and the jth tertiary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

Arrangement 29: A method of hybridization chain reaction (HCR), comprising: providing a sample containing a target; contacting the sample with at least one reporter-labeled signal probe comprising a target-binding region and at least one reporter; contacting the sample with at least one anti-reporter initiator-labeled signal probe comprising: a reporter-binding region and at least one initiator contacting the sample with a first HCR hairpin, comprising: a first input domain comprising a first toehold and a first stem section, a first output domain comprising a first hairpin loop and a complement to the first stem section; contacting the sample with a second HCR hairpin, comprising: a second input domain, comprising a second toehold and a second stem section, a second output domain, comprising a second hairpin loop and a complement to the second stem section; wherein at least one of the first HCR hairpin and the second HCR hairpin further comprises an auxiliary reporter; and detecting a signal directly or indirectly from the reporter and/or the auxiliary reporter.

Arrangement 30: The method of Arrangement 29, wherein a wash step is performed between any of the above steps.

Arrangement 31: The method of any one of the prior aspects of Arrangements 29 or 30, wherein the signal is removed following detection.

Arrangement 32: The method of any one of the prior aspects of Arrangements 29-31, wherein the first HCR hairpin comprises a first auxiliary reporter.

Arrangement 33: The method of any one of the prior aspects of Arrangements 29-32, wherein the first auxiliary reporter directly or indirectly mediates generation of a signal.

Arrangement 34: The method of any one of the prior aspects of Arrangements 29-33, wherein the second HCR hairpin comprises a second auxiliary reporter.

Arrangement 35: The method of any one of the prior aspects of Arrangements 29-34, wherein the second auxiliary reporter directly or indirectly mediates generation of a signal.

Arrangement 36: The method of any one of the prior aspects of Arrangements 29-35, wherein: the reporter-labeled signal probe comprises an anti-target primary antibody or nanobody, the reporter comprises a hapten, and the anti-reporter initiator-labeled signal probe comprises an anti-hapten primary antibody or nanobody.

Arrangement 37: The method of any one of the prior aspects of Arrangements 29-36, further comprising: binding the first HCR hairpin to the at least one initiator; binding the second HCR hairpin to the first HCR hairpin; contacting the sample with an anti-auxiliary-reporter readout probe comprising an enzyme that mediates CARD; contacting the sample with one or more CARD-substrates; and measuring a signal from one or more deposited CARD-reporters generated from the CARD-substrate by the enzyme that mediates CARD.

Arrangement 38: The method of any one of the prior aspects of Arrangements 29-37, wherein the anti-auxiliary-reporter readout probe comprises a primary antibody or nanobody that binds the auxiliary reporter and further comprises a secondary antibody or nanobody (labeled with one or more enzymes that mediate CARD) that binds the primary antibody or nanobody.

Arrangement 39: The method of any one of the prior aspects of Arrangements 29-38, further comprising repeating any of the steps of the method to detect another target in the sample.

Arrangement 40: The method of any one of the prior aspects of Arrangements 29-39, wherein the target comprises an RNA molecule, a DNA molecule, a protein, a small molecule, a chemical, a biological molecule, a pathogen, a complex of molecules, or a set of molecules in proximity.

Arrangement 41: The method of any one of the prior aspects of Arrangements 29-40, wherein the reporter and the auxiliary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

Arrangement 42: A composition for nonlinear hybridization chain reaction (HCR) signal amplification comprising: A first HCR initiator; A first HCR amplifier comprising two or more HCR hairpins, at least one of which comprises a reporter; An anti-reporter bridging probe comprising a reporter-binding domain and a second HCR initiator; A second HCR amplifier comprising two or more HCR hairpins, at least one of which comprises an auxiliary reporter; wherein the first HCR initiator is configured to trigger the HCR hairpins of the first HCR amplifier to grow a reporter-decorated first HCR amplification polymer tethered to the first HCR initiator; wherein the anti-reporter bridging probe is configured to bind the reporters decorating the first HCR amplification polymer so as to decorate it with second HCR initiators; wherein the second HCR initiator is configured to trigger the HCR hairpins of the second HCR amplifier to grow an auxiliary-reporter decorated second HCR amplification polymer tethered to the first HCR amplification polymer, and wherein the reporters and/or auxiliary reporters are configured to directly or indirectly mediate generation of an amplified signal.

Arrangement 43: The composition of Arrangement 42, wherein the first HCR initiator is attached to a signal probe configured to bind directly or indirectly to a target.

Arrangement 44: The composition of any one of the prior aspects of Arrangements 42 or 43, wherein the first HCR initiator is a colocalized full first HCR initiator formed when two or more fractional-initiator probes are bound specifically to their cognate binding sites on a target.

Arrangement 45: The composition of any one of the prior aspects of Arrangements 42-44, wherein the first HCR initiator is a colocalized full first HCR initiator formed when two or more fractional-initiator probes are bound specifically to their cognate binding sites on two targets that are complexed or are in proximity.

Arrangement 46: The composition of any one of the prior aspects of Arrangements 42-45, wherein the composition additionally comprises one or more proximity probes configured to bind to the two or more fractional-initiator probes.

Arrangement 47: The composition of any one of the prior aspects of Arrangements 42-46, wherein the auxiliary reporter is the same as the reporter.

Arrangement 48: The composition of any one of the prior aspects of Arrangements 42-47, wherein the first HCR initiator has the same sequence as the second HCR initiator and the first HCR amplifier has the same sequence as the second HCR amplifier.

Arrangement 49: The composition of any one of the prior aspects of Arrangements 42-48, wherein the reporter and the auxiliary reporter can be the same or different, each comprising a hapten, a fluorophore, a chromophore, or a rare-earth element or compound.

Arrangement 50: The composition of any one of the prior aspects of Arrangements 42-49, wherein the auxiliary reporter is configured to mediate catalytic reporter deposition (CARD).

Arrangement 51: The composition of any one of the prior aspects of Arrangements 42-50, further comprising an anti-auxiliary-reporter readout probe comprising a tertiary reporter.

Arrangement 52: The composition of any one of the prior aspects of Arrangements 42-51, wherein the tertiary reporter comprises an enzyme.

Arrangement 53: The composition of any one of the prior aspects of Arrangements 42-52, wherein the enzyme is configured to act on CARD-substrates to catalytically deposit CARD-reporters that directly or indirectly generate a fluorescent or chromogenic signal.

Arrangement 54: The composition of any one of the prior aspects of Arrangements 42-53, wherein the target comprises an RNA molecule, a DNA molecule, a protein, a small molecule, a chemical, a biological molecule, a pathogen, a complex of molecules, or a set of molecules in proximity.

Arrangement 55: The composition of any one of the prior aspects of Arrangements 42-54, wherein the reporter, the auxiliary reporter, and the tertiary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

Arrangement 56: A composition for detection of N targets in a sample using nonlinear HCR signal amplification, wherein N is a positive integer, comprising: a) A jth signal probe set (for j=1, . . . , N, wherein j is a positive integer) configured to bind the jth target, comprising: i. A jth initiator-labeled signal probe comprising a jth first HCR initiator, or ii. A jth fractional-initiator signal probe set configured to colocalize a jth full first HCR initiator when the probes within a probe unit bind specifically to their cognate binding sites on the jth target, or iii. A jth fractional-initiator signal probe set configured to colocalize a jth full first HCR initiator when the probes within a probe unit bind specifically to the jth target complex or jth set of proximal targets and are bound by one or more jth proximity probes, or iv. A jth anti-target reporter-labeled primary signal probe comprising a jth reporter; and a jth anti-reporter initiator-labeled secondary signal probe comprising a jth first HCR initiator; b) A jth first HCR amplifier comprising two or more HCR hairpins, at least one of which comprises a jth auxiliary reporter; c) A jth anti-auxiliary-reporter bridging probe comprising a jth auxiliary-reporter-binding domain and a jth second HCR initiator; d) A jth second HCR amplifier comprising two or more HCR hairpins, at least one of which comprises a jth tertiary reporter; wherein the jth first HCR initiator is configured to trigger the HCR hairpins comprising the jth first HCR amplifier to grow a jth auxiliary-reporter-decorated first HCR amplification polymer tethered to the jth target; wherein the jth anti-auxiliary-reporter bridging probe is configured to bind the jth auxiliary reporters decorating the jth first HCR amplification polymer so as to decorate it with jth second HCR initiators; wherein the jth second HCR initiator decorating the jth first HCR amplification polymer is configured to trigger the HCR hairpins comprising the jth second HCR amplifier to grow a jth tertiary-reporter decorated second HCR amplification polymer tethered to the jth first HCR amplification polymer; and wherein the jth reporters, jth auxiliary reporters, and/or the jth tertiary reporters are configured to directly or indirectly mediate generation of a jth amplified signal at the site of the jth target.

Arrangement 57: The composition of Arrangement 56, wherein the jth target comprises an RNA molecule, a DNA molecule, a protein, a small molecule, a chemical, a biological molecule, a pathogen, a complex of molecules, or a set of molecules in proximity.

Arrangement 58: The composition of any one of the prior aspects of Arrangements 56 or 57, wherein the jth reporter, the jth auxiliary reporter, and the jth tertiary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

Arrangement 59: A composition for nonlinear HCR signal amplification comprising: A first HCR initiator; A self-bridging first HCR amplifier comprising two or more HCR hairpins each comprising one split-initiator tail; A second HCR amplifier comprising two or more HCR hairpins, at least one of which comprises a reporter; wherein the first HCR initiator is configured to trigger the HCR hairpins comprising the self-bridging first HCR amplifier to form a first HCR amplification polymer tethered to the first HCR initiator; wherein the split-initiator tails on the two or more HCR hairpins comprising the self-bridging first HCR amplification polymer are configured to colocalize a full second HCR initiator within the polymer; wherein each colocalized full second HCR initiator within the first HCR amplification polymer is configured to trigger the HCR hairpins comprising the second HCR amplifier to grow a reporter-decorated second HCR amplification polymer tethered to the first HCR amplification polymer, and wherein the reporters are configured to directly or indirectly mediate generation of an amplified signal.

Arrangement 60: The composition of Arrangement 59, wherein the target comprises an RNA molecule, a DNA molecule, a protein, a small molecule, a chemical, a biological molecule, a pathogen, a complex of molecules, or a set of molecules in proximity.

Arrangement 61: The composition of any one of the prior aspects of Arrangements 59 or 60, wherein the reporter comprises a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

Arrangement 62: A method for target detection with nonlinear hybridization chain reaction (HCR) signal amplification, the method comprising: providing a sample containing one or more targets; contacting the sample with a probe set comprising one or more initiator-labeled probes or one or more probe units each comprising two or more fractional-initiator probes, such that the target is bound by a target-binding region of the probe set; c) contacting the sample with a reporter-labeled first HCR amplifier, such that a linear HCR amplification stage is initiated; d) contacting the sample with an anti-reporter initiator-labeled bridging probe comprising one or more HCR initiators; e) contacting the sample with an auxiliary-reporter-labeled second HCR amplifier, such that a nonlinear HCR amplification stage is initiated; f) detecting one or more signals from the reporter and/or the auxiliary reporter.

Arrangement 63: The method of Arrangement 62, wherein the probe set comprises one or more initiator-labeled probes, wherein an initiator-labeled probe comprises a target-binding region and one or more HCR initiators.

Arrangement 64: The method of any one of the prior aspects of Arrangements 62 or 63, wherein the probe set comprises one or more probe units each comprising two or more fractional-initiator probes, wherein a fractional-initiator probe comprises a target-binding region and a fractional initiator.

Arrangement 65: The method of any one of the prior aspects of Arrangements 62-64, comprising additional rounds of HCR signal amplification, each additional round comprising repeating steps (c) through (d).

Arrangement 66: The method of any one of the prior aspects of Arrangements 62-65, wherein the reporter comprises a hapten and the bridging probe comprises an anti-hapten primary antibody or nanobody.

Arrangement 67: The method of any one of the prior aspects of Arrangements 62-66, wherein the auxiliary reporter is a fluorophore, a chromophore, or a rare-earth element or compound.

Arrangement 68: The method of any one of the prior aspects of Arrangements 62-67, wherein the anti-reporter bridging probe comprises a primary antibody or nanobody that binds the reporter and further comprises an initiator-labeled secondary antibody or nanobody that binds the primary antibody or nanobody.

Arrangement 69: The method of any one of the prior aspects of Arrangements 62-68, wherein the first HCR amplifier and the second HCR amplifier have the same sequence.

Arrangement 70: The method of any one of the prior aspects of Arrangements 62-69, wherein the reporter and the auxiliary reporter are the same.

Arrangement 71: The method of any one of the prior aspects of Arrangements 62-70, further comprising: contacting the sample with an anti-auxiliary-reporter readout probe comprising an enzyme that mediates CARD; contacting the sample with one or more CARD-substrates; and measuring a signal from one or more catalytically deposited CARD-reporters.

Arrangement 72: The method of any one of the prior aspects of Arrangements 62-71, wherein a wash step is performed between any of steps (b)-(f).

Arrangement 73: The method of any one of the prior aspects of Arrangements 62-72, wherein after step (f), the method further comprises a step (g) wherein the signal is removed.

Arrangement 74: The method of any one of the prior aspects of Arrangements 62-73, wherein the auxiliary-reporter molecules directly or indirectly mediate generation of a signal.

Arrangement 75: The method of any one of the prior aspects of Arrangements 62-74, wherein an HCR amplifier comprises two or more HCR hairpins.

Arrangement 76: The method of any one of the prior aspects of Arrangements 62-75, wherein an HCR hairpin comprises an input domain comprising a single-stranded toehold and a stem section.

Arrangement 77: The method of any one of the prior aspects of Arrangements 62-76, wherein an HCR hairpin comprises an output domain comprising a single-stranded loop and a complement to the stem section.

Arrangement 78: The method of any one of the prior aspects of Arrangements 62-77, wherein at least one HCR hairpin of the first HCR amplifier further comprises one or more reporters, and at least one HCR hairpin of the second HCR amplifier further comprises one or more auxiliary reporters.

Arrangement 79: The method of any one of the prior aspects of Arrangements 62-78, further comprising repeating any of the steps of the method to detect another target in the sample.

Arrangement 80: The method of any one of the prior aspects of Arrangements 62-79, wherein the target comprises an RNA molecule, a DNA molecule, a protein, a small molecule, a chemical, a biological molecule, a pathogen, a complex of molecules, or a set of molecules in proximity.

Arrangement 81: The method of any one of the prior aspects of Arrangements 62-80, wherein the reporter and the auxiliary reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

Arrangement 82: A method for nonlinear hybridization chain reaction (HCR) signal amplification, the method comprising: contacting a sample with a first HCR initiator or two or more fractional initiators that together comprise a full first HCR initiator; contacting the sample with a first HCR amplifier labeled with a first reporter and incubating to initiate growth of a first-reporter-decorated HCR amplification polymer tethered to the first HCR initiator; contacting the sample with an anti-first-reporter bridging probe comprising a second HCR initiator and incubating so that the first HCR amplification polymer is decorated with second HCR initiators; contacting the sample with a second-reporter-labeled HCR amplifier and incubating to initiate growth of a second-reporter-decorated HCR amplification polymer tethered to each second HCR initiator decorating the first HCR amplification polymer tethered to the first HCR initiator; detecting a signal generated directly or indirectly by the first reporter and/or the second reporter; wherein at least one HCR hairpin of the first-reporter-labeled HCR amplifier comprises one or more first reporters, and wherein at least one HCR hairpin of the second-reporter-labeled HCR amplifier comprises one or more second reporters.

Arrangement 83: The method of Arrangement 82, further comprising providing an anti-second-reporter bridging probe comprising a third HCR initiator and incubating so that the second HCR amplification polymer is decorated with third HCR initiators.

Arrangement 84: The method of any one of the prior aspects of Arrangements 82 or 83, further comprising providing a third-reporter-labeled HCR amplifier and incubating to initiate growth of a third-reporter-decorated HCR amplification polymer tethered to each third HCR initiator decorating the second HCR amplification polymer tethered to a second HCR initiator decorating the first HCR amplification polymer tethered to the first HCR initiator, wherein at least one HCR hairpin of the third-reporter-labeled HCR amplifier comprises one or more third reporters.

Arrangement 85: The method of any one of the prior aspects of Arrangements 82-84, wherein the third reporter directly or indirectly mediates generation of a signal.

Arrangement 86: The method of any one of the prior aspects of Arrangements 82-85, wherein some or all of the first reporter, the second reporter, and the third reporter are the same.

Arrangement 87: The method of any one of the prior aspects of Arrangements 82-86, wherein some or all of the first-reporter-decorated HCR amplifier, the second-reporter-decorated HCR amplifier, and the third-reporter-decorated HCR amplifier have the same sequence.

Arrangement 88: The method of any one of the prior aspects of Arrangements 82-87, wherein the first, second and third reporters can be the same or different, each comprising a hapten, fluorophore, a chromophore, or a rare-earth element or compound.

Arrangement 89: The method of any one of the prior aspects of Arrangements 82-88, wherein the third reporter is used to mediate CARD signal amplification.

Arrangement 90: The method of any one of the prior aspects of Arrangements 82-89, wherein the anti-reporter initiator-labeled bridging probes used to bridge between different rounds of HCR signal amplification are the same.

Arrangement 91: The method of any one of the prior aspects of Arrangements 82-90, further comprising performing a wash between any of steps (a)-(e).

Arrangement 92: The method of any one of the prior aspects of Arrangements 82-91, wherein after step (e), the method further comprises a step (f) in which the signal is removed.

Arrangement 93: The method of any one of the prior aspects of Arrangements 82-92, wherein any of steps (a)-(f) are repeated.

Arrangement 94: The method of any one of the prior aspects of Arrangements 82-93, wherein an HCR amplifier comprises two or more HCR hairpins.

Arrangement 95: The method of any one of the prior aspects of Arrangements 82-94, wherein an HCR hairpin comprises an input domain comprising a single-stranded toehold and a stem section.

Arrangement 96: The method of any one of the prior aspects of Arrangements 82-95, wherein an HCR hairpin further comprises an output domain comprising a single-stranded loop and a complement to the stem section.

Arrangement 97: The method of any one of the prior aspects of Arrangements 82-96, wherein the target comprises an RNA molecule, a DNA molecule, a protein, a small molecule, a chemical, a biological molecule, a pathogen, a complex of molecules, or a set of molecules in proximity.

Arrangement 98: The method of any one of the prior aspects of Arrangements 82-97, wherein the first reporter, the second reporter, and the third reporter can be the same or different, each comprising a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

Although the foregoing invention has been described in terms of certain preferred embodiments, other embodiments will be apparent to those of ordinary skill in the art. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims.

Any of the embodiments, compositions, and/or methods provided herein can be employed with, or in the alternative form of, any of the following. Thus, for example, the above noted compositions and/or methods can employ any of the compositions or methods noted below. Similarly, the above noted compositions and/or methods should be understood to also provide methods employing the methods below or as being part of the methods noted below.

Similarly, the embodiments and/or methods provided herein should also be understood to provide embodiments involved in the method, e.g., compositions, components of the method, kits, etc. In some embodiments, any of the ingredients in one or more of the methods and/or steps provided herein can be provided as a kit including one or more of the noted ingredients (and optionally the target or target sequence or sample).

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive. Unless defined otherwise, technical and scientific terms used herein have the same meaning as commonly understood by one of ordinary skill in the art to which this invention belongs. See, for example Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). It is to be understood that both the general description and the detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

In some embodiments, any one or more of the optional elements of any one or more of the figures herein can be combined with any one or more of the other optional elements of any one or more of the figures herein. In some embodiments, any one or more of the compositions or steps provided in any of the figures provided herein can be combined with any of the other compositions or steps provided herein. As used herein, a generic reference to a set of figures (for example, FIG. 24) denotes all of the different figures contained within that number (for example, FIGS. 24A-24R), each combined together, one or more of them, or each in the alternative, unless otherwise denoted.

REFERENCES (1) Dirks, R. M.; Pierce, N. A. Triggered Amplification by Hybridization Chain Reaction. *Proc. Natl. Acad. Sci. U.S.A* 2004, 101 (43), 15275-15278.

(2) Choi, H. M. T.; Chang, J. Y.; Trinh, L. A.; Padilla, J. E.; Fraser, S. E.; Pierce, N. A. Programmable in Situ Amplification for Multiplexed Imaging of mRNA Expression. *Nat. Biotechnol.* 2010, 28 (11), 1208-1212.

(3) Choi, H. M. T.; Beck, V. A.; Pierce, N. A. Next-Generation in Situ Hybridization Chain Reaction: Higher Gain, Lower Cost, Greater Durability. *ACS Nano* 2014, 8 (5), 4284-4294.

(4) Choi, H. M. T.; Schwarzkopf, M.; Fornace, M. E.; Acharya, A.; Artavanis, G.; Stegmaier, J.; Cunha, A.; Pierce, N. A. Third-Generation in Situ Hybridization Chain Reaction: Multiplexed, Quantitative, Sensitive, Versatile, Robust. *Development* 2018, 145, dev165753.

(5) Schwarzkopf, M.; Liu, M. C.; Schulte, S. J.; Ives, R.; Husain, N.; Choi, H. M. T.; Pierce, N. A. Hybridization Chain Reaction Enables a Unified Approach to Multiplexed, Quantitative, High-Resolution Immunohistochemistry and in Situ Hybridization. *Development* 2021, 148 (22), dev199847.

(6) Choi, H. M. T.; Calvert, C. R.; Husain, N.; Huss, D.; Barsi, J. C.; Deverman, B. E.; Hunter, R. C.; Kato, M.; Lee, S. M.; Abelin, A. C. T.; Rosenthal, A. Z.; Akbari, O. S.; Li, Y.; Hay, B. A.; Sternberg, P. W.; Patterson, P. H.; Davidson, E. H.; Mazmanian, S. K.; Prober, D. A.; van de Rijn, M.; Leadbetter, J. R.; Newman, D. K.; Readhead, C.; Bronner, M. E.; Wold, B.; Lansford, R.; Sauka-Spengler, T.; Fraser, S. E.; Pierce, N. A. Mapping a Multiplexed Zoo of mRNA Expression. *Development* 2016, 143, 3632-3637.

(7) Schulte, S. J.; Shin, B.; Rothenberg, E. V.; Pierce, N. A. Multiplex, Quantitative, High-Resolution Imaging of Protein: Protein Complexes via Hybridization Chain Reaction. *ACS Chem. Biol.* 2024, 19 (2), 280-288.

(8) Schulte, S. J.; Fornace, M. E.; Hall, J. K.; Shin, G. J.; Pierce, N. A. HCR Spectral Imaging: 10-Plex, Quantitative, High-Resolution RNA and Protein Imaging in Highly Autofluorescent Samples. *Development* 2024, 151, dev202307.

(9) Tao, Y.; Zhou, X.; Sun, L.; Lin, D.; Cai, H.; Chen, X.; Zhou, W.; Yang, B.; Hu, Z.; Yu, J.; Zhang, J.; Yang, X.; Yang, F.; Shen, B.; Qi, W.; Fu, Z.; Dai, J.; Cao, G. Highly Efficient and Robust π-FISH Rainbow for Multiplexed in Situ Detection of Diverse Biomolecules. *Nat. Commun.* 2023, 14 (1), 443.

(10) Player, A. N.; Shen, L. P.; Kenny, D.; Antao, V. P.; Kolberg, J. A. Single-Copy Gene Detection Using Branched DNA (bDNA) in Situ Hybridization. *J. Histochem. Cytochem.* 2001, 49 (5), 603-611.

(11) Wang, F.; Flanagan, J.; Su, N.; Wang, L. C.; Bui, S.; Nielson, A.; Wu, X. Y.; Vo, H. T.; Ma, X. J.; Luo, Y. L. RNAscope: A Novel in Situ RNA Analysis Platform for Formalin-Fixed, Paraffin-Embedded Tissues. *J. Mol. Diagn.* 2012, 14 (1), 22-29.

(12) Kenny, D.; Shen, L. P.; Kolberg, J. A. Detection of Viral Infection and Gene Expression in Clinical Tissue Specimens Using Branched DNA (bDNA) in Situ Hybridization. *J. Histochem. Cytochem.* 2002, 50 (9), 1219-1227.

(13) Zadeh, J. N.; Steenberg, C. D.; Bois, J. S.; Wolfe, B. R.; Pierce, M. B.; Khan, A. R.; Dirks, R. M.; Pierce, N. A. NUPACK: Analysis and Design of Nucleic Acid Systems. *J. Comput. Chem.* 2011, 32 (1), 170-173.

(14) Wolfe, B. R.; Porubsky, N. J.; Zadeh, J. N.; Dirks, R. M.; Pierce, N. A. Constrained Multistate Sequence Design for Nucleic Acid Reaction Pathway Engineering. *J. Am. Chem. Soc.* 2017, 139, 3134-3144. ADDIN ZOTERO_BIBL {"uncited":[ ],"omitted":[ ],"custom":[ ]} CSL_BIBLIOGRAPHY

What is claimed is:

1. A method for nonlinear hybridization chain reaction (HCR) signal amplification, the method comprising:
   a) contacting a sample with a first HCR initiator;
   b) contacting the sample with a first HCR amplifier labeled with a first reporter and incubating to initiate growth of a first-reporter-decorated HCR amplification polymer tethered to the first HCR initiator;
   c) contacting the sample with an anti-first-reporter bridging probe comprising a second HCR initiator and incubating so that the first HCR amplification polymer is decorated with second HCR initiators;
   d) contacting the sample with a second-reporter-labeled HCR amplifier and incubating to initiate growth of a second-reporter-decorated HCR amplification polymer tethered to each second HCR initiator decorating the first HCR amplification polymer tethered to the first HCR initiator; and
   e) detecting a signal generated directly or indirectly by the first reporter and/or the second reporter;
   wherein the first-reporter-labeled HCR amplifier and the second-reporter-labeled HCR amplifier each comprise two or more HCR hairpins;
   wherein at least one HCR hairpin of the first-reporter-labeled HCR amplifier comprises one or more first reporters, and wherein at least one HCR hairpin of the second-reporter-labeled HCR amplifier comprises one or more second reporters.

2. The method of claim 1, further comprising providing an anti-second-reporter bridging probe comprising a third HCR initiator and incubating so that the second HCR amplification polymer is decorated with third HCR initiators.

3. The method of claim 2, further comprising providing a third-reporter-labeled HCR amplifier and incubating to initiate growth of a third-reporter-decorated HCR amplification polymer tethered to each third HCR initiator decorating the second HCR amplification polymer tethered to a second HCR initiator decorating the first HCR amplification polymer tethered to the first HCR initiator, wherein at least one HCR hairpin of the third-reporter-labeled HCR amplifier comprises one or more third reporters, wherein the third-reporter-labeled HCR amplifier comprises two or more HCR hairpins.

4. The method of claim 3, wherein the third reporter directly or indirectly mediates generation of the signal.

5. The method of claim 3, wherein some or all of the first reporter, the second reporter, and the third reporter are the same.

6. The method of claim 3, wherein some or all of the first-reporter-labeled HCR amplifier, the second-reporter-labeled HCR amplifier, and the third-reporter-labeled HCR amplifier have the same sequence.

7. The method of claim 3, wherein the anti-reporter bridging probes used to bridge between different rounds of HCR signal amplification are the same.

8. The method of claim 1, wherein the second reporter is used to mediate CARD signal amplification.

9. The method of claim 1, further comprising performing a wash between any of steps (a)-(e).

10. The method of claim 1, wherein after step (e), the method further comprises a step (f) in which the signal is removed.

11. The method of claim 10, wherein any of steps (a)-(f) are repeated.

12. The method of claim 1, wherein each HCR hairpin comprises an input domain comprising a single-stranded toehold and a stem section, and wherein each HCR hairpin further comprises an output domain comprising a single-stranded loop and a complement to the stem section.

13. The method of claim 1, wherein the first HCR initiator is a colocalized full first HCR initiator comprising two or more fractional initiators.

14. The method of claim 1, wherein the sample comprises a target comprising an RNA molecule, a DNA molecule, a protein, a small molecule, a chemical, a biological molecule, a pathogen, a complex of molecules, or a set of molecules in proximity.

15. The method of claim 14, wherein the target binds to a probe set comprising the first HCR initiator.

16. The method of claim 3, wherein the first reporter, the second reporter, and the third reporter each independently comprise a fluorophore, a chromophore, a luminophore, a phosphor, a FRET pair, a member of a FRET pair, a quencher, a fluorophore/quencher pair, a rare earth element or compound, a radioactive molecule, a nucleotide, an amino acid, an oligonucleotide, DNA, RNA, 2'OMe-RNA, a chemically modified nucleic acid, a synthetic nucleic acid analog, a chemically modified protein, a synthetic protein analog, a peptide, a binding substrate, a carbon atom, a chemical linker, a magnetic molecule, carbon black (CB), carbon nanotubes, magnetized carbon nanotubes, gold nanoparticles (AuNP), gold nanoshells, gold nanorods, silver-shelled gold nanoparticles, latex, magnetic nanoparticles, silica nanoparticles, fluorophore-loaded nanoparticles, dye-loaded nanoparticles, a hapten, a ligand, digoxigenin (DIG), fluorescein isothiocyanate (FITC), biotin, dinitrophenol, aniline, an enzyme, any combination thereof, or a molecule that directly or indirectly mediates generation of a signal.

17. The method of claim 2, wherein the anti-first-reporter bridging probe and anti-second-reporter bridging probe each independently comprise an antibody, a nanobody, a nucleic acid, or any molecule or complex comprising a reporter-binding domain.

\* \* \* \* \*

SEQUENCE LISTING

```
Sequence total quantity: 4
SEQ ID NO: 1          moltype = DNA  length = 78
FEATURE               Location/Qualifiers
```

```
source                  1..78
                        mol_type = other DNA
                        organism = synthetic construct
SEQUENCE: 1
cgggttaaag ttgagtggag atatagaggc agggacaaag tctaatccgt ccctgcctct   60
atatctccac tctatcat                                                 78

SEQ ID NO: 2            moltype = DNA  length = 72
FEATURE                 Location/Qualifiers
source                  1..72
                        mol_type = other DNA
                        organism = synthetic construct
SEQUENCE: 2
gtccctgcct ctatatctcc actcaacttt aacccggagt ggagatatag aggcagggac   60
ggattagact tt                                                       72

SEQ ID NO: 3            moltype = DNA  length = 36
FEATURE                 Location/Qualifiers
source                  1..36
                        mol_type = other DNA
                        organism = synthetic construct
SEQUENCE: 3
gtccctgcct ctatatctcc actcaacttt aacccg                             36

SEQ ID NO: 4            moltype = DNA  length = 42
FEATURE                 Location/Qualifiers
source                  1..42
                        mol_type = other DNA
                        organism = synthetic construct
SEQUENCE: 4
atgatagagt ggagatatag aggcagggac ggattagact tt                      42
```